(12) United States Patent
Barten et al.

(10) Patent No.: US 11,627,736 B2
(45) Date of Patent: Apr. 18, 2023

(54) MANAGEMENT OF CORN THROUGH SEMI-DWARF SYSTEMS

(71) Applicant: Monsanto Technology LLC, St. Louis, MO (US)

(72) Inventors: Ty J. Barten, Ankeny, IA (US); David V. Butruille, Des Moines, IA (US); Edward J. Cargill, Chesterfield, MO (US); Charles Dietrich, Chesterfield, MO (US); Jose R. Gomez, Zapopan (MX); Michael A. Hall, Wildwood, MO (US); Manuel Oyervides Garcia, El Palomar (MX)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 984 days.

(21) Appl. No.: 16/276,617

(22) Filed: Feb. 15, 2019

(65) Prior Publication Data

US 2019/0246619 A1    Aug. 15, 2019

Related U.S. Application Data

(60) Provisional application No. 62/775,346, filed on Dec. 4, 2018, provisional application No. 62/631,181, filed on Feb. 15, 2018.

(51) Int. Cl.
  *C12N 15/00* (2006.01)
  *A01M 7/00* (2006.01)
  *B05B 1/20* (2006.01)
  *A01C 21/00* (2006.01)
  *A01H 3/04* (2006.01)

(52) U.S. Cl.
  CPC ........... *A01M 7/0071* (2013.01); *A01C 21/00* (2013.01); *A01H 3/04* (2013.01); *B05B 1/20* (2013.01); *C12N 15/00* (2013.01)

(58) Field of Classification Search
  CPC .. A01H 6/4684; A01H 1/121; C12N 15/8241; A01M 7/0042
  See application file for complete search history.

(56) References Cited

U.S. PATENT DOCUMENTS

| | | | |
|---|---|---|---|
| 4,368,592 A * | 1/1983 | Welch | A01H 1/02 800/275 |
| 5,939,539 A | 8/1999 | Lange et al. | |
| 6,198,021 B1 * | 3/2001 | Lange | C12Y 114/11015 800/298 |
| 6,380,467 B1 | 4/2002 | Duclos | |
| 6,765,133 B2 | 7/2004 | Koehring | |
| 7,041,874 B2 | 5/2006 | Johal et al. | |
| 10,724,047 B2 * | 7/2020 | Allen | C12N 15/8297 |
| 10,881,057 B2 | 1/2021 | Cannon et al. | |
| 2002/0162142 A1 * | 10/2002 | Johal | C12N 15/8261 536/23.6 |
| 2003/0172409 A1 | 9/2003 | Horn | |
| 2009/0070898 A1 | 3/2009 | Allen et al. | |
| 2011/0035839 A1 | 2/2011 | Lutfitta et al. | |
| 2011/0126310 A1 | 5/2011 | Feng et al. | |
| 2011/0296555 A1 | 12/2011 | Ivashuta et al. | |
| 2013/0121101 A1 | 5/2013 | Ochampaugh et al. | |
| 2013/0345937 A1 * | 12/2013 | Strelioff | A01D 41/141 701/50 |
| 2014/0013464 A1 | 1/2014 | Davie | |
| 2014/0074360 A1 | 3/2014 | Rosa et al. | |
| 2015/0201619 A1 | 7/2015 | Annigeri et al. | |
| 2016/0050865 A1 | 2/2016 | Morse et al. | |
| 2016/0319375 A1 * | 11/2016 | Barten | A01H 6/4684 |
| 2017/0079224 A1 | 3/2017 | Jolliffe et al. | |
| 2018/0051295 A1 * | 2/2018 | Allen | C12N 15/8261 |
| 2019/0014730 A1 | 1/2019 | Dong et al. | |
| 2019/0014731 A1 | 1/2019 | Ovadya et al. | |
| 2019/0241903 A1 | 8/2019 | Ellis et al. | |
| 2019/0246586 A1 | 8/2019 | Cannon et al. | |
| 2022/0039320 A1 | 2/2022 | Barten et al. | |

FOREIGN PATENT DOCUMENTS

| | | |
|---|---|---|
| WO | WO 2016/176286 A1 | 11/2016 |
| WO | WO 2017/011791 A1 | 1/2017 |
| WO | WO 2018/035354 A1 | 2/2018 |
| WO | WO 2018/119225 A1 | 6/2018 |
| WO | WO 2018/129302 A1 | 7/2018 |
| WO | WO 2019/161143 A1 | 8/2019 |
| WO | WO 2019/161149 A1 | 8/2019 |

OTHER PUBLICATIONS

"Corn Herbicide Application Timings", 2015, published online by PennState Extension; obtained from https://extension.psu.edu/corn-herbicide-application-timings (Year: 2015).*
Qiao, Feng, and Kai-Jun Zhao. "The influence of RNAi targeting of OsGA20ox2 gene on plant height in rice." Plant Molecular Biology Reporter 29.4 (2011): 952-960. (Year: 2011).*
Amanullah, et al. "Phenology, growth, and grain yield of maize as influenced by foliar applied urea at different growth stages." Journal of plant nutrition 33.1 (2009): 71-79. (Year: 2009).*
"4 Series Sprayers", published in May 2016, obtained from https://www.deere.com/en_CAF/docs/product/equipment/4_Series_Sprayers.pdf (Year: 2016).*
Crommelinck et al., "Simulating an Autonomously Operating Low-Cost Static Terrestrial LiDAR for Multitemporal Maize Crop Height Measurements," *Remote Sensing*, 8(3):205, pp. 1-17 (2016).
D'Andrea et al., "Genotypic Variability in Morphological and Physiological Traits among Maize Inbred Lines—Nitrogen Responses," *Crop Sci.*, 46:1266-1276 (2006).

(Continued)

*Primary Examiner* — Weihua Fan
(74) *Attorney, Agent, or Firm* — Dentons US LLP; David Lanzotti

(57) ABSTRACT

Methods for providing compositions to corn fields prior to harvesting are provided herein. These methods provide an extended time period for the use of lower height or standard height farm equipment in-season in corn fields, while reducing the risk of damage to the corn plants. These methods also allow for late season access with lower height or standard height farm equipment, while reducing the risk of damage to the corn plants.

37 Claims, 2 Drawing Sheets
Specification includes a Sequence Listing.

(56) References Cited

OTHER PUBLICATIONS

GenBank Accession No. AY366085, "*Zea mays* cultivar B73 PGP1 (pgp1) gene, complete cds" (2003).
International Search Report and Written Opinion dated Aug. 8, 2019, in International Application No. PCT/US2019/018129.
International Search Report and Written Opinion dated May 10, 2019, in International Application No. PCT/US2019/018127.
Kempton, "Heritable Characters of Maize, III. Brachytic Culms," *Jour. Hered.*, 11(1):111-115 (1920).
Mourtzinis et al., "Corn Grain and Stover Yield Prediction at RI Growth Stage," *Agronomy Journal*, 105(4):1045-1050 (2013).
Zaidi et al., "Phenotyping for Abiotic Stress Tolerance in Maize Heat Stress," *CIMMYT*, pp. 1-40 (2016).
International Search Report and Written Opinion dated Apr. 22, 2020, issued in International Application No. PCT/US2019/064270, pp. 1-14.
Wang et al., "Analysis of hormone sensitivity of a dwarf mutant of maize," Journal of Northwest A&F University, Nat. Sci. Ed., 45(8) (2017).
Weng et al., "Genome-Wide Association Study Identifies Candidate Genes That Affect Plant Height in Chinese Elite Maize (*Zea mays* L.) Inbred Lines," PLOS One, 6(12) (2011).
Butzen, "Timing Corn Harvest," *Crop Insights*, (Sep. 2018).
Chen et al., "Identification and genetic mapping for rht-DM, a dominant dwarfing gene in mutant semi-dwarf maize using QTL-seq approach," *Genes & Genomics* 40, pp. 1091-1099 (Jun. 2018) (electronic publication).
Elmore et al., "In-Field Drydown Rates and Harvest," Iowa State University Extension and Outreach, https://crops.extension.iastate.edu/cropnews/2010/09/field-drydown-rates-and-harvest (Sep. 28, 2010).
Lu, "Chapter 3 Research on Production Increase Technology in Late Harvesting of Maize in Optimum Period," Theory and Technology of Maize High Yield (2015).
Spelhaug, "Predicting Your Corn Harvest Date," *Peterson Farms Seed* (2013).
Supplementary European Search Report dated Oct. 11, 2022 in EP 19 89 2688.
Thomison et al., "Corn Response to Harvest Date a Affected by Plant Population and Hybrid," *Agron J.* 103, pp. 1765-1772 (Sep. 2011) (electronic publication).
GenBank Accession No. AY366085.
Kempton, J.H., "Heritable Characters of Maize: III. Brachytic Culms," *Journal of Heredity*, 11(3):111-115 (1920).
Multani et al., "Loss of an MDR Transporter in Compact Stalks of Maize br2 and Sorghum dw3 Mutants," *Science*, 302:81-84 (2003).
Pilu et al., "Isolation and characterization of a new mutant allele of brachytic 2 maize gene," *Molecular Breeding*, 20:83-91 (2007).

\* cited by examiner

SEQUENCE LISTING

<160> NUMBER OF SEQ ID NOS: 131

<210> SEQ ID NO 1
<211> LENGTH: 1741
<212> TYPE: DNA
<213> ORGANISM: Zea mays

<400> SEQUENCE: 1

```
gacggtagtt ttcatctaaa gtttattctt cgtcacatgg gatggccgtt tgcttgtttg      60
ttgcttccgg gaggcggtgg tgaattgaag cagatcgaca agcatggctg cccactggtc     120
tcgatcgatc ggcctgccat gccatgccat gccactagag tccgtcctga ctggccgccc     180
gttcccccgt ataaaaaggc aggcaggcag gcagagcggg gacgagcaag caagcagttg     240
cagttgcagc ggcctcctcc tctgcttcct ccctcctcct cctcaccatg gtgctggctg     300
cgcacgatcc ccctcccctt gtgttcgacg ctgcccgcct gagcggcctc tccgacatcc     360
cgcagcagtt catctggccg gcggacgaga gccccacccc ggactccgcc gaggagctgg     420
ccgtgccgct catcgacctc tccggggacg ccgccgaggt ggtccggcag gtccggcgcg     480
cctgcgacct gcacggcttc ttccaggtgg tggggcacgg catcgacgcg gcgctgacgg     540
cggaggccca ccgctgcatg gacgccttct tcacgctgcc gctcccggac aagcagcgcg     600
cgcagcgccg ccaggggggac agctgcgggct acgccagcag cttcacgggc cggttcgcgt     660
ccaagctgcc ctggaaggag acgctgtcgt tccgctacac cgacgacgac gacggcgaca     720
agtccaagga cgtcgtggcg tcctacttcg tggacaagct gggcgagggg taccggcacc     780
acggggaggt gtacgggcgc tactgctctg agatgagccg tctgtcgctg gagctcatgg     840
aggtgctagg cgagagcctg ggcgtggggcc ggcgccactt ccggcgcttc ttccagggga     900
acgactccat catgcgcctc aactactacc cgccgtgcca gcggccctac gacacgctgg     960
gcacggggcc gcattgcgac cccacgtcgc tcaccatcct gcaccaggac gacgtgggcg    1020
gactccaggt gttcgacgcc gccacgctcg cgtggcgctc catcaggccc cgcccgggcg    1080
```

-continued

```
ccttcgtcgt caacatcggc gacaccttca tggcgctctc caacgggcgc tacaggagct    1140
gcctccaccg cgccgtcgtc aacagccggg tggcacgccg ctcgctcgcc ttcttcctgt    1200
gcccggagat ggacaaggtg gtcaggccgc ccaaggagct ggtggacgac gccaacccga    1260
gggcgtaccc ggacttcacg tggaggacgc tgctggactt caccatgagg cactacaggt    1320
cggacatgag gacgctcgag gccttctcca actggctcag caccagtagc aatggcggac    1380
agcacctgct ggagaagaag taggcatgct atttgggtat ggaagatggt ggatgtaagc    1440
aaacaaagcc aaattaagca gagtaggtta attaaggttg gctgatgatc catttaggga    1500
aggagctgat ctccctgact ccctcctcca attttctcaa ccaaatttat atagtataat    1560
aataataata aaatagcaag taatagttgt atcgtattat tattaattaa tttattagct    1620
ggtaggcaag tagtattaaa taccatttgt agtacgatgg gcgtatttct attttggcgt    1680
tttgctctgt gttttttgac gtttcctttg gatttggggg gacctcagat cagctcggcc    1740
t                                                                    1741

<210> SEQ ID NO 2
<211> LENGTH: 1116
<212> TYPE: DNA
<213> ORGANISM: Zea mays

<400> SEQUENCE: 2
atggtgctgg ctgcgcacga tcccctccc cttgtgttcg acgctgcccg cctgagcggc      60
ctctccgaca tccgcagca gttcatctgg ccggcggacg agagccccac cccggactcc     120
gccgaggagc tggccgtgcc gctcatcgac ctctccgggg acgccgccga ggtggtccgg    180
caggtccggc gcgcctgcga cctgcacggc ttcttccagg tggtggggca cggcatcgac    240
gcggcgctga cggcggaggc ccaccgctgc atggacgcct tcttcacgct gccgctcccg    300
gacaagcagc gcgcgcagcg ccgccagggg gacagctgcg gctacgccag cagcttcacg    360
ggccggttcg cgtccaagct gccctggaag gagacgctgt cgttccgcta caccgacgac    420
gacgacggcg acaagtccaa ggacgtcgtg gcgtcctact tcgtggacaa gctgggcgag    480
gggtaccggc accacgggga ggtgtacggg cgctactgct ctgagatgag ccgtctgtcg    540
ctggagctca tggaggtgct aggcgagagc tgggcgtgg gccggcgcca cttccggcgc    600
ttcttccagg ggaacgactc catcatgcgc ctcaactact acccgccgtg ccagcggccc    660
tacgacacgc tgggcacggg gccgcattgc gaccccacgt cgctcaccat cctgcaccag    720
gacgacgtgg gcggactcca ggtgttcgac gccgccacgc tcgcgtggcg ctccatcagg    780
ccccgcccgg gcgccttcgt cgtcaacatc ggcgacacct tcatggcgct ctccaacggg    840
cgctacagga gctgcctcca ccgcgccgtc gtcaacagcc gggtggcacg ccgctcgctc    900
gccttcttcc tgtgcccgga gatggacaag gtggtcaggc cgcccaagga gctggtggac    960
gacgccaacc cgagggcgta cccggacttc acgtggagga cgctgctgga cttcaccatg   1020
aggcactaca ggtcggacat gaggacgctc gaggccttct ccaactggct cagcaccagt   1080
agcaatggcg gacagcacct gctggagaag aagtag                            1116

<210> SEQ ID NO 3
<211> LENGTH: 371
<212> TYPE: PRT
<213> ORGANISM: Zea mays
```

```
<400> SEQUENCE: 3

Met Val Leu Ala Ala His Asp Pro Pro Leu Val Phe Asp Ala Ala
1               5                   10                  15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Leu Ala Val Pro Leu
        35                  40                  45

Ile Asp Leu Ser Gly Asp Ala Ala Glu Val Val Arg Gln Val Arg Arg
50                  55                  60

Ala Cys Asp Leu His Gly Phe Phe Gln Val Val Gly His Gly Ile Asp
65              70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Gln Gly Asp Ser
            100                 105                 110

Cys Gly Tyr Ala Ser Ser Phe Thr Gly Arg Phe Ala Ser Lys Leu Pro
            115                 120                 125

Trp Lys Glu Thr Leu Ser Phe Arg Tyr Thr Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Arg Phe Phe Gln Gly Asn Asp Ser Ile
        195                 200                 205

Met Arg Leu Asn Tyr Tyr Pro Pro Cys Gln Arg Pro Tyr Asp Thr Leu
210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
            245                 250                 255

Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
    275                 280                 285

Ala Val Val Asn Ser Arg Val Ala Arg Arg Ser Leu Ala Phe Phe Leu
290                 295                 300

Cys Pro Glu Met Asp Lys Val Val Arg Pro Pro Lys Glu Leu Val Asp
305                 310                 315                 320

Asp Ala Asn Pro Arg Ala Tyr Pro Asp Phe Thr Trp Arg Thr Leu Leu
            325                 330                 335

Asp Phe Thr Met Arg His Tyr Arg Ser Asp Met Arg Thr Leu Glu Ala
            340                 345                 350

Phe Ser Asn Trp Leu Ser Thr Ser Ser Asn Gly Gly Gln His Leu Leu
        355                 360                 365

Glu Lys Lys
    370

<210> SEQ ID NO 4
<211> LENGTH: 1517
<212> TYPE: DNA
<213> ORGANISM: Zea mays
```

<400> SEQUENCE: 4

```
caggaataaa ataagcctcc gcccggcttc gttgcatcca cgcacgcagc aagcgatcgg      60
atttcgccag catggcggcg gcggccgtgg tgttcgacgc cgaggcgctg agccgggagg     120
agcacatccc ggcgcagttc gtgtggccca ccgaggagcg ggcgccggcg gcggcgtgg      180
aggaggtcgc catccccgtg gtcgacctcg gcgagttcct ccgccgcggg gtgctcccgc     240
gcggcgtggc ggaggcgtgc gagcgccacg cgtcttcca ggtggtgaac acggcgtgg       300
gcgccgcgct gctcgccgag gcctaccgct gttgcgacgc ctttacgcg ctcccgctcg      360
cggacaagca gcgcgcgcag cgccggcacg gggagaacca cggctacgcc agcagcttca     420
cgggccgctt ccactgctgc ctgccgtgga aggagacgct gtccttcaac tgccccgccg     480
gtgccgggac tgcgcgcgcc gtcgtcggct acttcgtcga cgtcctcggc gaggactacc     540
gccacatggg ggaggtgtac caggagtact gcgacgcgat gacgcgtctg gcgctggacg     600
tgacggaggt gctggcggca cgctggggc tggaccgcgg cgcactgcgc ggcttcttcg      660
agggcggcga ctccgtcatg cggctgaacc actaccggc gtgccggcag ccgcacctga     720
cgctggggac gggcccgcac cgggacccga cgtcgctgac gctgctgcac caggacgacg     780
tgggcgggct gcaggtgcgc gccggcggcg ggccgtggcg cgcggtgcgg ccccgcgcg      840
acgcgttcgt ggtcaacatt ggcgacacct tcgccgcgct caccgacggg cgtcacacca     900
gctgcctgca ccgcgccgtg gtgaccggcg gcggctcccg ccggtcgctc gccttcttcc     960
tcaacccgcc gctggaccgc gtcgtccgcc cgccgggcgc gctcctccag gagaacaagc    1020
aggcgggccg cccgcgcgcg ttcccggact tcacgtggcg cgagttcctc gagttcacgc    1080
agaagcacta ccggtcggac gcgggcacca tggacgcctt cgtgtcgtgg atcgcgggag    1140
gccgccgcca ccatggcgga caggaggagg gcaactgaga tcgatgcatc tctagctgta    1200
ggcagcagcg cagcagctac caagaataat ggccggcgac ggagatgcag ctacgacgca    1260
caaataaatt gagtgtttgt ggtacaataa ggacaggac gatcaatggc gacctgtaac     1320
cggtgcagtt ttagttaatc tttcatggcg atatggcatt aaccaatcgt tggtgtaaaa    1380
tgcgtgcatg ctttgcatgc caatgttggc catgtgatgg cacagcgtga gtgtagctca    1440
cccaccgtga caacgtgcta atttcgtgtg gtcctagata ccaaggtcgt ctaatgaact    1500
tgatggattg atgattt                                                  1517
```

<210> SEQ ID NO 5
<211> LENGTH: 1107
<212> TYPE: DNA
<213> ORGANISM: Zea mays

<400> SEQUENCE: 5

```
atggcggcgg cggccgtggt gttcgacgcc gaggcgctga gccgggagga gcacatcccg      60
gcgcagttcg tgtggcccac cgaggagcgg gcgccggcgg cggcgtgga ggaggtcgcc      120
atccccgtgg tcgacctcgg cgagttcctc cgccgcgggg tgctcccgcg cggcgtggcg     180
gaggcgtgcg agcgccacgg cgtcttccag gtggtgaacc acggcgtggg cgccgcgctg     240
ctcgccgagg cctaccgctg ttgcgacgcc ttttacgcgc tcccgctcgc ggacaagcag     300
cgcgcgcagc gccggcacgg ggagaaccac ggctacgcca gcagcttcac gggccgcttc     360
cactgctgcc tgccgtggaa ggagacgctg tccttcaact gccccgccgg tgccgggact     420
gcgcgcgccc tcgtcggcta cttcgtcgac gtcctcggcg aggactaccg ccacatgggg     480
gaggtgtacc aggagtactg cgacgcgatg acgcgtctgg cgctggacgt gacggaggtg     540
```

```
ctggcggcag cgctggggct ggaccgcggc gcactgcgcg gcttcttcga gggcggcgac     600
tccgtcatgc ggctgaacca ctacccggcg tgccggcagc cgcacctgac gctggggacg     660
ggcccgcacc gggacccgac gtcgctgacg ctgctgcacc aggacgacgt gggcgggctg     720
caggtgcgcg ccggcggcgg gccgtggcgc gcggtgcggc cccgcgcgga cgcgttcgtg     780
gtcaacattg gcgacacctt cgccgcgctc accgacgggc gtcacaccag ctgcctgcac     840
cgcgccgtgg tgaccggcgg cggctcccgc cggtcgctcg ccttcttcct caacccgccg     900
ctggaccgcg tcgtccgccc gccgggcgcg ctcctccagg agaacaagca ggcgggccgc     960
ccgcgcgcgt tcccggactt cacgtggcgc gagttcctcg agttcacgca gaagcactac    1020
cggtcggacg cgggcaccat ggacgccttc gtgtcgtgga tcgcgggagg ccgccgccac    1080
catggcggac aggaggaggg caactga                                        1107
```

<210> SEQ ID NO 6
<211> LENGTH: 368
<212> TYPE: PRT
<213> ORGANISM: Zea mays

<400> SEQUENCE: 6

Met Ala Ala Ala Val Val Phe Asp Ala Glu Ala Leu Ser Arg Glu
1               5                   10                  15

Glu His Ile Pro Ala Gln Phe Val Trp Pro Thr Glu Arg Ala Pro
            20                  25                  30

Ala Gly Gly Val Glu Glu Val Ala Ile Pro Val Val Asp Leu Gly Glu
        35                  40                  45

Phe Leu Arg Arg Gly Val Leu Pro Arg Gly Val Ala Glu Ala Cys Glu
    50                  55                  60

Arg His Gly Val Phe Gln Val Val Asn His Gly Val Gly Ala Ala Leu
65                  70                  75                  80

Leu Ala Glu Ala Tyr Arg Cys Cys Asp Ala Phe Tyr Ala Leu Pro Leu
                85                  90                  95

Ala Asp Lys Gln Arg Ala Gln Arg Arg His Gly Glu Asn His Gly Tyr
            100                 105                 110

Ala Ser Ser Phe Thr Gly Arg Phe His Cys Cys Leu Pro Trp Lys Glu
        115                 120                 125

Thr Leu Ser Phe Asn Cys Pro Ala Gly Ala Gly Thr Ala Arg Ala Val
    130                 135                 140

Val Gly Tyr Phe Val Asp Val Leu Gly Glu Asp Tyr Arg His Met Gly
145                 150                 155                 160

Glu Val Tyr Gln Glu Tyr Cys Asp Ala Met Thr Arg Leu Ala Leu Asp
                165                 170                 175

Val Thr Glu Val Leu Ala Ala Ala Leu Gly Leu Asp Arg Gly Ala Leu
            180                 185                 190

Arg Gly Phe Phe Glu Gly Gly Asp Ser Val Met Arg Leu Asn His Tyr
        195                 200                 205

Pro Ala Cys Arg Gln Pro His Leu Thr Leu Gly Thr Gly Pro His Arg
    210                 215                 220

Asp Pro Thr Ser Leu Thr Leu Leu His Gln Asp Asp Val Gly Gly Leu
225                 230                 235                 240

Gln Val Arg Ala Gly Gly Pro Trp Arg Ala Val Arg Pro Arg Ala
                245                 250                 255

Asp Ala Phe Val Val Asn Ile Gly Asp Thr Phe Ala Ala Leu Thr Asp
            260                 265                 270

```
Gly Arg His Thr Ser Cys Leu His Arg Ala Val Val Thr Gly Gly Gly
            275                 280                 285

Ser Arg Arg Ser Leu Ala Phe Phe Leu Asn Pro Pro Leu Asp Arg Val
        290                 295                 300

Val Arg Pro Pro Gly Ala Leu Leu Gln Glu Asn Lys Gln Ala Gly Arg
305                 310                 315                 320

Pro Arg Ala Phe Pro Asp Phe Thr Trp Arg Glu Phe Leu Glu Phe Thr
                325                 330                 335

Gln Lys His Tyr Arg Ser Asp Ala Gly Thr Met Asp Ala Phe Val Ser
            340                 345                 350

Trp Ile Ala Gly Gly Arg Arg His His Gly Gly Gln Glu Glu Gly Asn
        355                 360                 365

<210> SEQ ID NO 7
<211> LENGTH: 1522
<212> TYPE: DNA
<213> ORGANISM: Zea mays

<400> SEQUENCE: 7
gcacactcgc agctcgcaca tctcatggtg tcctaagaac ggcaagagcc agctctgcct      60
agcagcagcg cacagccaca tccatggacg ccagcccgac cccaccgctc ccctccgcg     120 ccccaactcc cagcattgac ctccccgctg caaggacag ggccgacgcg gcggctaaca     180
aggccgcggc tgtgttcgac ctgcgccggg agcccaagat cccggagcca ttcctgtggc     240
cgcacgaaga ggcgcggccg acctcggccg cggagctgga ggtgccggtg gtggacgtgg     300
gcgtgctgcg caatggcgac ggcgcggggc tccgccgcgc gcggcgcaa gtggcggcgg     360 cgtgcgcgac gcacgggttc ttccaggtgt gcgggcacgg cgtggacgcg cgctggggc     420 gcgccgcgct ggacggcgcc agcgacttct tccggctgcc gctggctgag aagcagcggg     480
cccggcgcgt ccccggcacc gtgtccgggt acacgagcgc gcacgccgac cggttcgcgt     540
ccaagctccc ctggaaggag accctgtcct tcggcttcca cgacggcgcc gcggcgcccg     600
tcgtcgtgga ctacttcacc ggcaccctcg gccaagattt cgagccagtg gggcgggtgt     660
accagaggta ctgcgaggag atgaaggagc tgtcgctgac gatcatggag ctgctggagc     720
tgagcctggg cgtggagcgc ggctactacc gggagttctt cgaggacagc cgctccatca     780
tgcggtgcaa ctactacccg ccgtgccegg tgccggagcg cacgctgggc acgggccgc     840 actgcgaccc cacggcgctg accatcctcc tgcaggacga cgtcggcggg ctggaggtcc     900
tggtggacgg cgagtggcgc cccgtccggc ccgtcccagg cgccatggtc atcaacatcg     960
gcgacacctt catggcgctg tccaacgggc ggtacaagag ctgcctgcac cgcgcggtgg    1020
tgaaccggcg gcaggagcgg caatcgctgg ccttcttcct gtgcccgcgc gaggaccggg    1080
tggtgcgccc gccggccagc gccgcgccgc ggcagtaccc ggacttcacc tgggccgacc    1140
tcatgcgctt cacgcagcgc cactaccgcg ccgacacccg cacgctggac gccttcaccc    1200
gctggctctc ccacggcccg gcggcggcgg ctccctgcac ctaacgagcc ggccgtctct    1260
ttcgccgggg cccgcgcggg gttcgcccac gtggtgatca ggtggcagac atgtgggcca    1320
cgggccccgc gccgccttcc ccattttttgg acgaccctac tgctactact actagtgtac    1380
atatgcaaaa aaatacatat atatataggt actttctcta atattttttat atataagcaa    1440 ggcggcctgg tgttcttttc tttgtttttgt cgacaactgt ttgatcccat cctatggacg    1500
atggatagtt caatgtttgt ac                                              1522
```

-continued

<210> SEQ ID NO 8
<211> LENGTH: 1161
<212> TYPE: DNA
<213> ORGANISM: Zea mays

<400> SEQUENCE: 8

| | | | | | |
|---|---|---|---|---|---|
| atggacgcca | gcccgacccc | accgctcccc | ctccgcgccc | caactcccag | cattgacctc | 60 |
| cccgctggca | aggacagggc | cgacgcggcg | gctaacaagg | ccgcggctgt | gttcgacctg | 120 |
| cgccgggagc | ccaagatccc | ggagccattc | ctgtggccgc | acgaagaggc | gcggccgacc | 180 |
| tcggccgcgg | agctggaggt | gccggtggtg | gacgtgggcg | tgctgcgcaa | tggcgacggc | 240 |
| gcggggctcc | gccgcgccgc | ggcgcaagtg | gcggcggcgt | gcgcgacgca | cgggttcttc | 300 |
| caggtgtgcg | gcacggcgt | ggacgcggcg | ctggggcgcg | ccgcgctgga | cggcgccagc | 360 |
| gacttcttcc | ggctgccgct | ggctgagaag | cagcgggccc | ggcgcgtccc | cggcaccgtg | 420 |
| tccgggtaca | cgagcgcgca | cgccgaccgg | ttcgcgtcca | agctcccctg | gaaggagacc | 480 |
| ctgtccttcg | gcttccacga | cggcgccgcg | gcgcccgtcg | tcgtggacta | cttcaccggc | 540 |
| accctcggcc | aagatttcga | gccagtgggg | cgggtgtacc | agaggtactg | cgaggagatg | 600 |
| aaggagctgt | cgctgacgat | catggagctg | ctggagctga | gctgggcgt | ggagcgcggc | 660 |
| tactaccggg | agttcttcga | ggacagccgc | tccatcatgc | ggtgcaacta | ctacccgccg | 720 |
| tgcccggtgc | cggagcgcac | gctgggcacg | ggcccgcact | cgaccccac | ggcgctgacc | 780 |
| atcctcctgc | aggacgacgt | cggcgggctg | gaggtcctgg | tggacggcga | gtggcgcccc | 840 |
| gtccggcccg | tcccaggcgc | catggtcatc | aacatcggcg | acaccttcat | ggcgctgtcc | 900 |
| aacgggcggt | acaagagctg | cctgcaccgc | gcggtggtga | accggcggca | ggagcggcaa | 960 |
| tcgctggcct | tcttcctgtg | cccgcgcgag | gaccgggtgg | tgcgcccgcc | ggccagcgcc | 1020 |
| gcgccgcggc | agtacccgga | cttcacctgg | gccgacctca | tgccgcttcac | gcagcgccac | 1080 |
| taccgcgccg | acacccgcac | gctggacgcc | ttcacccgct | ggctctccca | cggcccggcg | 1140 |
| gcggcggctc | cctgcaccta | a | | | | 1161 |

<210> SEQ ID NO 9
<211> LENGTH: 386
<212> TYPE: PRT
<213> ORGANISM: Zea mays

<400> SEQUENCE: 9

Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

Ala Gly Leu Arg Arg Ala Ala Ala Gln Val Ala Ala Cys Ala Thr
                85                  90                  95

His Gly Phe Phe Gln Val Cys Gly His Gly Val Asp Ala Ala Leu Gly
            100                 105                 110

Arg Ala Ala Leu Asp Gly Ala Ser Asp Phe Phe Arg Leu Pro Leu Ala
        115                 120                 125

```
Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Pro Val Val Asp
                165                 170                 175

Tyr Phe Thr Gly Thr Leu Gly Gln Asp Phe Glu Pro Val Gly Arg Val
                180                 185                 190

Tyr Gln Arg Tyr Cys Glu Glu Met Lys Glu Leu Ser Leu Thr Ile Met
            195                 200                 205

Glu Leu Leu Glu Leu Ser Leu Gly Val Glu Arg Gly Tyr Tyr Arg Glu
    210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
                260                 265                 270

Leu Val Asp Gly Glu Trp Arg Pro Val Arg Pro Val Pro Gly Ala Met
    275                 280                 285

Val Ile Asn Ile Gly Asp Thr Phe Met Ala Leu Ser Asn Gly Arg Tyr
290                 295                 300

Lys Ser Cys Leu His Arg Ala Val Val Asn Arg Gln Glu Arg Gln
305                 310                 315                 320

Ser Leu Ala Phe Phe Leu Cys Pro Arg Glu Asp Arg Val Val Arg Pro
                325                 330                 335

Pro Ala Ser Ala Ala Pro Arg Gln Tyr Pro Asp Phe Thr Trp Ala Asp
                340                 345                 350

Leu Met Arg Phe Thr Gln Arg His Tyr Arg Ala Asp Thr Arg Thr Leu
    355                 360                 365

Asp Ala Phe Thr Arg Trp Leu Ser His Gly Pro Ala Ala Ala Ala Pro
370                 375                 380

Cys Thr
385

<210> SEQ ID NO 10
<211> LENGTH: 1457
<212> TYPE: DNA
<213> ORGANISM: Zea mays

<400> SEQUENCE: 10
taatcacctc atcacaggtc cccccagcct cactctcgcg ccggctcaag gtacattgcg      60
tgtcctagcc aagacacgca gctcatctca gcctcacacg cacagcaaga gcgaggcgtg     120
attcgccatg ggcggcctca ctatggacca ggccttcgtg caggcccccg agcaccgccc     180
caagcccatc gtcaccgagg ccaccggcat ccctctcatc gacctctcgc ctctggccgc     240
cagcggcggc gccgtggacg cgctggccgc cgaggtgggc gcggcgagcc gggactgggg     300
cttcttcgtg gtcgtgggcc acggcgtgcc cgcagagacc gtggcgcgcg cgacggaggc     360
gcagcgagcg ttcttcgcgc tgccggcaga gcggaaggcc gccgtgcgga ggaacgaggc     420
ggagccgctc gggtactacg agtcggagca caccaagaac gtgagggact ggaaggaggt     480
gtacgacctc gtgccgcgcg agccgccgcc gccggcagcc gtggccgacg cgagcttgt      540 gttcgataac aagtggcccc aggatctacc gggcttcaga gaggcgctgg aggagtacgc     600
```

```
gaaagcgatg gaagagctgg cgttcaagct gctggagctg atcgcccgga gcctgaagct    660
gaggcccgac cggctgcacg gcttcttcaa ggaccagacg accttcatcc ggctgaacca    720
ctaccctcct tgcccgagcc ccgacctggc cctcggcgtg gggcggcaca aggacgccgg    780
cgccctgacc atcctgtacc aggacgacgt cgggggctc gacgtccggc ggcgctccga    840
cggcgagtgg gtccgcgtca ggcccgtgcc cgactcgttc atcatcaacg tcggcgacct    900
catccaggta cgagagcgcg gagcaccggg tgtcggtgaa ctcggcgagg agaggttct    960 ccatgcccta cttcttcaac ccggcgacct acaccatggt ggagccggtg gaggagctgg   1020
tgagcaagga cgatccgccc aggtacgacg cctacaactg gggcgacttc ttcagcacca   1080
ggaagaacag caacttcaag aagctcaacg tggagaacat tcagatcgcg catttcaaga   1140
agagcctcgt cctcgcctaa ctactgctac tgctaggatc catgccattg ccatgtcgtc   1200
ttcagattca gagcacgcca tgtcgtcgct agcttcgtgg tagaacaaat aatgatgtgc   1260
gtgctgtgtg taagcatgga tatggatgtg aatatgtaat atgatgagca ctcctactt    1320 ggtatgtttg ggataacag acttgtgttg gtctggttca ttatttgtaa gaaaatcaaa   1380
aagagttagt agggcaggag gctaaccaca gtcatgctgc accacatccc tggtggaaag   1440
ctggccgggt tacgcta                                                  1457

<210> SEQ ID NO 11
<211> LENGTH: 1116
<212> TYPE: DNA
<213> ORGANISM: Zea mays

<400> SEQUENCE: 11
atgggcggcc tcactatgga ccaggccttc gtgcaggccc ccgagcaccg ccccaagccc     60
atcgtcaccg aggccaccgg catccctctc atcgacctct cgcctctggc cgccagcggc    120
ggcgccgtgg acgcgctggc cgccgaggtg ggcgcggcga ccgggactg gggcttcttc    180 gtggtcgtgg ccacggcgt gcccgcagag accgtggcgc gcgcgacgga ggcgcagcga    240
gcgttcttcg cgctgccggc agagcggaag gccgccgtgc ggaggaacga ggcggagccg    300
ctcgggtact acgagtcgga gcacaccaag aacgtgaggg actggaagga ggtgtacgac    360
ctcgtgccgc gcgagccgcc gccgccggca gccgtggccg acggcgagct tgtgttcgat    420
aacaagtggc cccaggatct accgggcttc agagaggcgc tggaggagta cgcgaaagcg    480
atggaagagc tggcgttcaa gctgctggag ctgatcgccc ggagcctgaa gctgaggccc    540
gaccggctgc acggcttctt caaggaccag acgaccttca tccggctgaa ccactaccct    600
ccttgcccga gccccgacct ggccctcggc gtgggcggc acaaggacgc cggcgccctg    660
accatcctgt accaggacga cgtcgggggg ctcgacgtcc ggcggcgctc cgacggcgag    720
tgggtccgcg tcaggcccgt gcccgactcg ttcatcatca acgtcggcga cctcatccag    780
gtacgagagc gcggagcacc gggtgtcggt gaactcggcg agggagaggt tctccatgcc    840
ctacttcttc aacccggcga cctacaccat ggtggagccg gtggaggagc tggtgagcaa    900
ggacgatccg cccaggtacg acgcctacaa ctggggcgac ttcttcagca ccaggaagaa    960
cagcaacttc aagaagctca acgtggagaa cattcagatc gcgcatttca agaagagcct   1020
cgtcctcgcc taactactgc tactgctagg atccatgcca ttgccatgtc gtcttcagat   1080
tcagagcacg ccatgtcgtc gctagcttcg tggtag                             1116
```

```
<210> SEQ ID NO 12
<211> LENGTH: 371
<212> TYPE: PRT
<213> ORGANISM: Zea mays

<400> SEQUENCE: 12

Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
            20                  25                  30

Leu Ser Pro Leu Ala Ala Ser Gly Ala Val Asp Ala Leu Ala Ala
        35                  40                  45

Glu Val Gly Ala Ala Ser Arg Asp Trp Gly Phe Phe Val Val Gly
50                  55                  60

His Gly Val Pro Ala Glu Thr Val Ala Arg Ala Thr Glu Ala Gln Arg
65                  70                  75                  80

Ala Phe Phe Ala Leu Pro Ala Glu Arg Lys Ala Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro Pro
        115                 120                 125

Pro Ala Val Ala Asp Gly Glu Leu Val Phe Asp Asn Lys Trp Pro
    130                 135                 140

Gln Asp Leu Pro Gly Phe Arg Glu Ala Leu Glu Glu Tyr Ala Lys Ala
145                 150                 155                 160

Met Glu Glu Leu Ala Phe Lys Leu Leu Glu Leu Ile Ala Arg Ser Leu
                165                 170                 175

Lys Leu Arg Pro Asp Arg Leu His Gly Phe Phe Lys Asp Gln Thr Thr
            180                 185                 190

Phe Ile Arg Leu Asn His Tyr Pro Pro Cys Pro Ser Pro Asp Leu Ala
        195                 200                 205

Leu Gly Val Gly Arg His Lys Asp Ala Gly Ala Leu Thr Ile Leu Tyr
    210                 215                 220

Gln Asp Asp Val Gly Gly Leu Asp Val Arg Arg Arg Ser Asp Gly Glu
225                 230                 235                 240

Trp Val Arg Val Arg Pro Val Pro Asp Ser Phe Ile Ile Asn Val Gly
                245                 250                 255

Asp Leu Ile Gln Val Arg Glu Arg Gly Ala Pro Gly Val Gly Glu Leu
            260                 265                 270

Gly Glu Gly Glu Val Leu His Ala Leu Leu Leu Gln Pro Gly Asp Leu
        275                 280                 285

His His Gly Gly Ala Gly Gly Gly Ala Gly Glu Gln Gly Arg Ser Ala
    290                 295                 300

Gln Val Arg Arg Leu Gln Leu Gly Arg Leu Leu Gln His Gln Glu Glu
305                 310                 315                 320

Gln Gln Leu Gln Glu Ala Gln Arg Gly Glu His Ser Asp Arg Ala Phe
                325                 330                 335

Gln Glu Glu Pro Arg Pro Arg Leu Thr Thr Ala Thr Ala Arg Ile His
            340                 345                 350

Ala Ile Ala Met Ser Ser Ser Asp Ser Glu His Ala Met Ser Ser Leu
        355                 360                 365

Ala Ser Trp
    370
```

<210> SEQ ID NO 13
<211> LENGTH: 1733
<212> TYPE: DNA
<213> ORGANISM: Zea mays

<400> SEQUENCE: 13

| | | | | | |
|---|---|---|---|---|---|
| atgaggccgc | gcctccctcc | aaatgttccc | tccctgcctt | cgtctttgtc | gttgctcgca | 60 |
| aactccctgt | cctcccctgt | tacaaatacc | cccacccgcc | cggacagctt | ccctgcatac | 120 |
| ttgcagctcg | cacatctcat | ggtgtcgcag | gaacgacaag | agccagctgt | gcctagcagc | 180 |
| agcagcagca | gcgccaagcg | cgcagccacg | tccatggacg | ccagcccggc | ccgccgctc | 240 |
| ctcctccgcg | cccccactcc | cagcccccagc | attgacctcc | ccgctggcaa | ggacaaggcc | 300 |
| gacgcggcgg | ccagcaaggc | cggcgcggcc | gtgttcgacc | tgcgccggga | gcccaagatc | 360 |
| cccgcgccat | tcctgtggcc | gcaggaagag | gcgcggccgt | cctcggccgc | ggagctggag | 420 |
| gtgccgatgg | tggacgtggg | cgtgctgcgc | aatggcgacc | gcgcggggct | gcggcgcgcc | 480 |
| gcggcgcagg | tggccgcggc | gtgcgcgacg | cacgggttct | tccaggtgtg | cgggcacggc | 540 |
| gtggacgcgg | cgctggggcg | cgccgcgctg | gacgcgcca | gcgacttctt | ccggctgccg | 600 |
| ctcgccgaga | agcagcgcgc | ccggcgcgtc | ccggcaccg | tgtccgggta | cacgagcgcg | 660 |
| cacgccgacc | ggttcgcggc | caagctcccc | tggaaggaga | ccctgtcgtt | cggctaccac | 720 |
| gacggcgccg | cgtcgcctgt | cgtcgtggac | tacttcgtcg | gcaccctcgg | ccaggatttc | 780 |
| gagccaatgg | ggtgggtgta | ccagaggtac | tgcgaggaga | tgaaggagct | gtcgctgacg | 840 |
| atcatggagc | tgctggagct | gagcctgggc | gtggagctgc | gcggctacta | ccggagttc | 900 |
| ttcgaggaca | gccggtccat | catgcggtgc | aactactacc | gccgtgccc | ggagccggag | 960 |
| cgcacgctgg | gcacgggccc | gcactgcgac | cccacggcgc | tcaccatcct | cctgcaggac | 1020 |
| gacgtgggcg | ggctggaggt | gctggtgac | ggtgagtggc | gccccgtccg | gcccgtcccg | 1080 |
| ggcgccatgg | tcatcaacat | cggcgacacc | ttcatggcgc | tgtcgaacgg | gaggtacaag | 1140 |
| agctgcctgc | accgcgcggt | ggtgaaccag | cggcgggcgc | ggcggtcgct | ggccttcttc | 1200 |
| ctgtgcccgc | gcgaggaccg | ggtggtgcgc | ccgccggcca | gtgctgcgcc | gcggcgctac | 1260 |
| ccggacttca | cctgggccga | cctcatgcgc | ttcacgcagc | gccactaccg | cgccgacacc | 1320 |
| cgcacgctgg | acgccttcac | ccgctggctc | tcccacggcc | cggcccaggc | ggcggcgcct | 1380 |
| ccctgcacct | agcgagccgg | gccaaggccg | tctctttcgc | cccacgtgcg | cgcccagctg | 1440 |
| ggcaggtggc | cagacacgcg | gcccgcgggc | ccgcgccgc | cttgccattt | tttgacgctg | 1500 |
| gccctactgc | tgtgctacta | gtgtacatat | gcaagagtac | atatatatat | atatatatac | 1560 |
| gtattttcta | tatattatat | ataaaagcaa | ggcggcccgg | tgcccttctc | ttgttttgtc | 1620 |
| cacaactgtt | tgatcccatt | attctatgga | ccatggatac | ttcaatgttt | gtactaagac | 1680 |
| cgtgaacgtg | ggattctttt | ccttcctctg | tgttttttct | gagaaaaatt | aaa | 1733 |

<210> SEQ ID NO 14
<211> LENGTH: 1392
<212> TYPE: DNA
<213> ORGANISM: Zea mays

<400> SEQUENCE: 14

| | | | | | |
|---|---|---|---|---|---|
| atgaggccgc | gcctccctcc | aaatgttccc | tccctgcctt | cgtctttgtc | gttgctcgca | 60 |
| aactccctgt | cctcccctgt | tacaaatacc | cccacccgcc | cggacagctt | ccctgcatac | 120 |
| ttgcagctcg | cacatctcat | ggtgtcgcag | gaacgacaag | agccagctgt | gcctagcagc | 180 |

-continued

```
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgg cgctggggcg cgccgcgctg gacgcgccga gcgacttctt ccggctgccg    600
ctcgccgaga gcagcgcgc ccggcgcgtc cccggcaccg tgtccgggta cacgagcgcg    660
cacgccgacc ggttcgcggc caagctcccc tggaaggaga ccctgtcgtt cggctaccac    720
gacggcgccg cgtcgcctgt cgtcgtggac tacttcgtcg gcaccctcgg ccaggatttc    780
gagccaatgg ggtgggtgta ccagaggtac tgcgaggaga tgaaggagct gtcgctgacg    840
atcatggagc tgctggagct gagcctgggc gtggagctgc gcggctacta ccggagttc    900 ttcgaggaca gccggtccat catgcggtgc aactactacc gccgtgccc ggagccggag    960 cgcacgctgg gcacgggccc gcactgcgac cccacggcgc tcaccatcct cctgcaggac   1020
gacgtgggcg gctggaggt gctggtgac ggtgagtgg ccccgtccg gcccgtcccg   1080 ggcgccatgg tcatcaacat cggcgacacc ttcatggcgc tgtcgaacgg gaggtacaag   1140
agctgcctgc accgcgcgt ggtgaaccag cggcgggcg ggcggtcgct ggccttcttc   1200
ctgtgcccgc gcgaggaccg ggtggtgcgc ccgccggcca tgctgcgcc cggcgctac   1260 ccggacttca cctgggccga cctcatgcgc ttcacgcagc gccactaccg cgccgacacc   1320
cgcacgctgg acgccttcac ccgctggctc tcccacggcc cggcccaggc ggcggcgcct   1380
ccctgcacct ag                                                       1392
```

<210> SEQ ID NO 15
<211> LENGTH: 463
<212> TYPE: PRT
<213> ORGANISM: Zea mays

<400> SEQUENCE: 15

```
Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ala Ser Lys Ala Gly Ala Ala Val Phe
            100                 105                 110

Asp Leu Arg Arg Glu Pro Lys Ile Pro Ala Pro Phe Leu Trp Pro Gln
        115                 120                 125

Glu Glu Ala Arg Pro Ser Ser Ala Ala Glu Leu Glu Val Pro Met Val
    130                 135                 140

Asp Val Gly Val Leu Arg Asn Gly Asp Arg Ala Gly Leu Arg Arg Ala
145                 150                 155                 160
```

Ala Ala Gln Val Ala Ala Ala Cys Ala Thr His Gly Phe Phe Gln Val
            165                 170                 175

Cys Gly His Gly Val Asp Ala Ala Leu Gly Arg Ala Ala Leu Asp Gly
        180                 185                 190

Ala Ser Asp Phe Phe Arg Leu Pro Leu Ala Glu Lys Gln Arg Ala Arg
    195                 200                 205

Arg Val Pro Gly Thr Val Ser Gly Tyr Thr Ser Ala His Ala Asp Arg
210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Val Asp Tyr Phe Val Gly Thr Leu
                245                 250                 255

Gly Gln Asp Phe Glu Pro Met Gly Trp Val Tyr Gln Arg Tyr Cys Glu
                260                 265                 270

Glu Met Lys Glu Leu Ser Leu Thr Ile Met Glu Leu Leu Glu Leu Ser
            275                 280                 285

Leu Gly Val Glu Leu Arg Gly Tyr Tyr Arg Glu Phe Phe Glu Asp Ser
        290                 295                 300

Arg Ser Ile Met Arg Cys Asn Tyr Tyr Pro Cys Pro Glu Pro Glu
305                 310                 315                 320

Arg Thr Leu Gly Thr Gly Pro His Cys Asp Pro Thr Ala Leu Thr Ile
                325                 330                 335

Leu Leu Gln Asp Asp Val Gly Gly Leu Glu Val Leu Val Asp Gly Glu
            340                 345                 350

Trp Arg Pro Val Arg Pro Val Pro Gly Ala Met Val Ile Asn Ile Gly
        355                 360                 365

Asp Thr Phe Met Ala Leu Ser Asn Gly Arg Tyr Lys Ser Cys Leu His
370                 375                 380

Arg Ala Val Val Asn Gln Arg Arg Ala Arg Arg Ser Leu Ala Phe Phe
385                 390                 395                 400

Leu Cys Pro Arg Glu Asp Arg Val Val Arg Pro Pro Ala Ser Ala Ala
                405                 410                 415

Pro Arg Arg Tyr Pro Asp Phe Thr Trp Ala Asp Leu Met Arg Phe Thr
                420                 425                 430

Gln Arg His Tyr Arg Ala Asp Thr Arg Thr Leu Asp Ala Phe Thr Arg
            435                 440                 445

Trp Leu Ser His Gly Pro Ala Gln Ala Ala Pro Pro Cys Thr
        450                 455                 460

<210> SEQ ID NO 16
<211> LENGTH: 1510
<212> TYPE: DNA
<213> ORGANISM: Zea mays

<400> SEQUENCE: 16
aaagagcgcg cgacggcggc ccctgggaga gccatgcgag actggaggcg gaaccgcgca    60
cgacaccaag ctgccgcgcc ggactgctgc acgcaagcgc agcgcaggac cgaccgacct   120
ccgtaggcac gcacggcgcc ggcggcatgg cggagcacct cctgtcgacg gccgtgcacg   180
acacgctgcc ggggagctac gtgcggccgg agccggagcg cccgcgcctc gcggaggtcg   240
tgaccggcgc gcgcatcccc gtcgtggacc tgggcagccc cgaccgcggc gcggtcgtgg   300
ccgccgtcgg cgacgcctgc cgctcgcacg gcttcttcca ggtcgtcaac cacgggatac   360
acgccgccct ggtcgcggcg gtgatggccg cggggcgcgg cttcttccgg ctgcccccg    420

```
aggagaaggc caagctctac tccgacgacc ccgccaggaa gatccggctg tccaccagct      480
tcaacgtgcg caaggagacg gtgcacaact ggcgcgacta cctccgcctg cactgccatc      540
ccctcgacga gttcctgccc gattggccgt ccaacccgcc cgatttcaag gagaccatgg      600
gcacctactg caaggaggtc cgggagctcg ggttcaggct gtacgccgcg atctcggaga      660
gcctgggcct agaggcgagc tacatgaagg aagcgctggg ggagcaggag cagcacatgg      720
cggtcaactt ctacccgccg tgcccggagc cggagctcac ctacggcctc ccggcgcaca      780
ccgaccccaa cgcgctcacc atcctgctca tggacccgga cgtcgccggc ctgcaggtgc      840
tccacgccgg ccagtgggtc gccgtcaacc cgcagcccgg cgcgctcatc atcaacatcg      900
gcgaccagct gcaggcgctg agcaacgggc agtaccggag cgtgtggcac cgcgcggtgg      960
tgaactcgga ccgggagcgc atgtccgtgg cgtcgttcct gtgcccgtgc aaccacgtcg     1020
tgctcggccc cgcgcggaag ctcgtcaccg aggacacccc ggccgtgtac aggaactaca     1080
cgtacgacaa gtactacgcc aagttctgga gcaggaacct ggaccaggag cactgcctcg     1140
agctcttcag aacctagcga atcggatacg gatggatgga tacattacat acgcgccctc     1200 tgttttctc catgacgtta gaagaacacg ttctgcaatg tttgtccatt caaggtggta     1260
tcaatcaagg ctgtggtcgt tgcaattctt ccgctccata tacatgatta aatgctttga     1320
aagaaaaaga aaaaaagaa acacaagtat tatggcacta ctagtgtttt taggaacaag     1380
gaaagagggg ttgcccctgc tggctatata tattaaatat aaataaaggt aaggctgtag     1440
acattggtga ataagagaaa gtatttgagt ttctctattg tcactccaga acagactcct     1500
ttgcctcgat                                                           1510
```

<210> SEQ ID NO 17
<211> LENGTH: 1011
<212> TYPE: DNA
<213> ORGANISM: Zea mays

<400> SEQUENCE: 17

```
atggcggagc acctcctgtc gacggccgtg cacgacacgc tgccggggag ctacgtgcgg       60
ccggagccgg agcgcccgcg cctcgcggag gtcgtgaccg cgcgcgcat ccccgtcgtg      120 gacctgggca gccccgaccg cggcgcggtc gtggccgccg tcggcgacgc ctgccgctcg      180
cacggcttct tccaggtcgt caaccacggg atacacgccg ccctggtcgc ggcggtgatg      240
gccgcggggc gcggcttctt ccggctgccc cccgaggaga aggccaagct ctactccgac      300
gaccccgcca ggaagatccg gctgtccacc agcttcaacg tgcgcaagga cacggtgcac      360
aactggcgcg actacctccg cctgcactgc catcccctcg acgagttcct gcccgattgg      420
ccgtccaacc cgcccgattt caaggagacc atgggcacct actgcaagga ggtccgggag      480
ctcgggttca ggctgtacgc cgcgatctcg gagagcctgg gcctagaggc gagctacatg      540
aaggaagcgc tggggggagca ggagcagcac atggcggtca acttctaccc gccgtgcccg      600
gagccggagc tcacctacgg cctccgccgcg cacaccgacc caacgcgct caccatcctg      660 ctcatggacc cggacgtcgc cggcctgcag gtgctccacg ccggccagtg ggtcgccgtc      720
aacccgcagc ccgcgcgct catcatcaac atcggcgacc agctgcaggc gctgagcaac      780
gggcagtacc ggagcgtgtg gcaccgcgcg gtggtgaact cggaccggga gcgcatgtcc      840
gtggcgtcgt tcctgtgccc gtgcaaccac gtcgtgctcg gccccgcgcg gaagctcgtc      900
accgaggaca ccccggccgt gtacaggaac tacacgtacg acaagtacta cgccaagttc      960
tggagcagga acctggacca ggagcactgc ctcgagctct tcagaaccta g             1011
```

<210> SEQ ID NO 18
<211> LENGTH: 336
<212> TYPE: PRT
<213> ORGANISM: Zea mays

<400> SEQUENCE: 18

Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
            20                  25                  30

Thr Gly Ala Arg Ile Pro Val Val Asp Leu Gly Ser Pro Asp Arg Gly
        35                  40                  45

Ala Val Val Ala Ala Val Gly Asp Ala Cys Arg Ser His Gly Phe Phe
    50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Leu Pro Asp Trp Pro Ser Asn Pro
    130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Pro
    210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Arg Lys Leu Val Thr Glu Asp Thr
    290                 295                 300

Pro Ala Val Tyr Arg Asn Tyr Thr Tyr Asp Lys Tyr Ala Lys Phe
305                 310                 315                 320

Trp Ser Arg Asn Leu Asp Gln Glu His Cys Leu Glu Leu Phe Arg Thr
                325                 330                 335

<210> SEQ ID NO 19
<211> LENGTH: 1387
<212> TYPE: DNA
<213> ORGANISM: Zea mays

<400> SEQUENCE: 19

```
gttttctttt tgaacgtaac tgacagaagc tatctgccta gctacggcgt gtcggttgct      60
tgtctcacca aagcagcgac atggaagcct gacagctcgt cgcgtcgcgc catttccacc     120
caacaaagcg gcggcgccag cacgcactgc ttctgcttgt gcgtgctcct ccgttccggg     180
cacgcctcta aagtctatac agcctcgaat ccatcccggc cgccgctcct ggggatact     240
acagcgagcc gaagcgggga tggcggagat ccctgtgatc gacctgcgcg tcgccggctc     300
ggcggccgag gagtccgcgc ggctgcgggc cgcgtgcgag cgcctgggct gcttccgggt     360
gaccggccac ggcgtgccct cggtgctcct ggcagagatg aaggccgccg tgcgcgcgct     420
cttcgacctc cccgacgacg ccaagcgccg caacgccgac gtcatcaccg gcagcggcta     480
cgtcgccccc agcccgacca acccgctcta cgaggccttc gggctcctcg acgccgccgt     540
gcccaccgac gtcgacgcct tttgcgcgct cctcgacgcg ccgcccaaca tcagggagac     600
cgtcaaggcc tacgcggaga agatgcacga tgtgatcgtt ggcgtcgccc gcgagctggc     660
gtctagcctg gggctagtcg aggagcactc gttccaggac tggccgtgcc agttccgcat     720
caacaggtac aactacacgc gggagacggt gggctcctcc ggcgtgcaga cccacacgga     780
ctcgggcttc ctcaccgtgc tccatgagga cgagtgtgtc ggcggcctcg aggtcctgga     840
cccgggcacc ggcgagttcg tgcccgtgga ccccgtcgcg ggctcctttc tcgtaaacat     900
cggcgacgtc ggcacggcgt ggagcaacgg gaggctgcac aacgtgaagc accgggtgcg     960
gtgcgtcgca cccgtgccgc gcatctccat cgccatgttc ctgctcgcac ccaaggacga    1020
cagcgtgagc gcaccggcgg cgttcgtgga cgcggaccac ccgcgcaggt acaaggtgtt    1080
caactacaac gactatcgga ggctcagact gtccaccggc gagcacgcag gcgaggcgct    1140
cgcacggatg gcggcgtgac gtggctggag ctgcaaattg gattggaagc cgagacaagc    1200
cgttagttat ttaccatgcc cgtgcgttca ccgcacacaa tcatattcaa aagccataaa    1260
ataaaaaata attttaatat cagtcaacat atggtttaaa tatcatatgg agtacaatat    1320
tccgaatttt tttttgtaat ttagtctgtc ttttgaaaaa aatgcacatc tagacctccg    1380
gatgact                                                              1387
```

<210> SEQ ID NO 20
<211> LENGTH: 900
<212> TYPE: DNA
<213> ORGANISM: Zea mays

<400> SEQUENCE: 20

```
atggcggaga tccctgtgat cgacctgcgc gtcgccggct cggcggccga ggagtccgcg      60
cggctgcggg ccgcgtgcga gcgcctgggc tgcttccggg tgaccggcca cggcgtgccc     120
tcggtgctcc tggcagagat gaaggccgcc gtgcgcgcgc tcttcgacct ccccgacgac     180
gccaagcgcc gcaacgccga cgtcatcacc ggcagcggct acgtcgcccc cagcccgacc     240
aacccgctct acgaggcctt cgggctcctc gacgccgccg tgcccaccga cgtcgacgcc     300
ttttgcgcgc tcctcgacgc gccgcccaac atcagggaga ccgtcaaggc ctacgcggag     360
aagatgcacg atgtgatcgt tggcgtcgcc cgcgagctgg cgtctagcct ggggctagtc     420
gaggagcact cgttccagga ctggccgtgc cagttccgca tcaacaggta caactacacg     480
cgggagacgg tgggctcctc cggcgtgcag acccacacgg actcgggctt cctcaccgtg     540
ctccatgagg acgagtgtgt cggcggcctc gaggtcctgg acccgggcac cggcgagttc     600
gtgcccgtgg accccgtcgc gggctccttt ctcgtaaaca tcggcgacgt cggcacggcg     660
```

```
tggagcaacg ggaggctgca caacgtgaag caccgggtgc ggtgcgtcgc acccgtgccg      720
cgcatctcca tcgccatgtt cctgctcgca cccaaggacg acagcgtgag cgcaccggcg      780
gcgttcgtgg acgcggacca cccgcgcagg tacaaggtgt tcaactacaa cgactatcgg      840
aggctcagac tgtccaccgg cgagcacgca ggcgaggcgc tcgcacggat ggcggcgtga      900
```

<210> SEQ ID NO 21
<211> LENGTH: 299
<212> TYPE: PRT
<213> ORGANISM: Zea mays

<400> SEQUENCE: 21

```
Met Ala Glu Ile Pro Val Ile Asp Leu Arg Val Ala Gly Ser Ala Ala
1               5                   10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95

Asp Val Asp Ala Phe Cys Ala Leu Leu Asp Ala Pro Pro Asn Ile Arg
            100                 105                 110

Glu Thr Val Lys Ala Tyr Ala Glu Lys Met His Asp Val Ile Val Gly
        115                 120                 125

Val Ala Arg Glu Leu Ala Ser Ser Leu Gly Leu Val Glu Glu His Ser
    130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175

Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
    210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
            260                 265                 270

Val Phe Asn Tyr Asn Asp Tyr Arg Arg Leu Arg Leu Ser Thr Gly Glu
        275                 280                 285

His Ala Gly Glu Ala Leu Ala Arg Met Ala Ala
    290                 295
```

<210> SEQ ID NO 22
<211> LENGTH: 1496
<212> TYPE: DNA
<213> ORGANISM: Zea mays

<400> SEQUENCE: 22

```
gtcggtctct tgtctcacca aaccggcgac atggtacatg gaggccagcc cgtcgcttgg      60
cgccacaagt ctcggtgccg tccgtccgac aagcggcgcc agcgcacgct ggctgctcgt     120
gcacgcctct aaatacggcc ccggacccgc caccaagcga aggccaatcc cgtccgccgc     180
cccccaccaa ccacgaacca cgcaagcgaa cccggccggc gcggggcagc ggcgatggcg     240
gagatcccgg tgatcgacct cgcctcgcc ggctcgtcgc ccgacgagtc ggcgcggctg      300
cgcgacgcgt gcgagcgcct gggctgcttt cgggtgaccg ccacggcgc gcccgcgggg     360
ctcctggccg acatgaaggc cgccgtgcgc gcgctcttcg acctccccga cgacgccaag     420
cgccgcaacg ccgacgtcat ccccggcagc ggctacgtcg cgccctgccc cgccaacccg     480
ctctacgagg ccttcgggct cctcgacgcc gccgcgcccg ccgacgtcga cgccttctgc     540
gcgcgcctcg acgcgccgcc caaagtcagg gagaccgtca agacctacgc ggagaagatg     600
cacgacgtga tcgtcggcgt cgccggcgag ctggccacca gcctgggggct gggcctggag    660
gagcactcgt tccaggactg gccgtgccag ttccgcatca acaggtacaa ctacacgcag     720
gagacggtgg gctcctccgg cgtgcagacc cacacggact cgggcttcct caccgtgctc     780
caggaggacg agtgcgtcgg cggcctcgag gtgctggacc ccgccgccgg tgagttcgtg     840
cccgtggacc ccgtcgccgg ctccttcctc gtcaacatcg cgacgtcgg cacggcgtgg     900
agcaacggga ggctccacaa cgtgaagcac cgggtgcggt cgtcgcgcc cgtgccgcgc     960
atctccatcg ccatgttcct gctggcgccc aaggacgacc gcgtgagcgc cccggaggcg    1020
ttggtcgacg cgggccaccc cgtcggtac aagccgttca actacgacga ctaccggagg      1080
ctccggctgt ccaccggcga gcgcgcaggc gaggcgctcg cgcggatggc ggcgtgatgt     1140
cgtcacgcac gtgcaagccg ttaattatag gctcgcgcat gcatacgcct acacgagagg     1200
ttgtctcgtt aagccgttct attaaaatgt gtgggggaga agatgactag ccgtggtgcc     1260
atgtggattg ctatcgggtc tgatcaataa aatcttgcaa cacttgcacg tgcgattcca     1320
tatcctagca cgggtgggcg ccacgctagt aggtagagac cggagcggcc aaaaaatggc     1380
tacagcacca gtaggtgaac tctcaagcaa cactggctat cccacttctg acgttgtctc     1440
tctcatcact atgtatgacc agcgaatgaa gtgtttaaaa atctgacgcc gtgaaa         1496
```

<210> SEQ ID NO 23
<211> LENGTH: 903
<212> TYPE: DNA
<213> ORGANISM: Zea mays

<400> SEQUENCE: 23

```
atggcggaga tcccggtgat cgacctgcgc ctcgccggct cgtcgcccga cgagtcggcg      60
cggctgcgcg acgcgtgcga gcgcctgggc tgctttcggg tgaccggcca cggcgcgccc    120
gcggggctcc tggccgacat gaaggccgcc gtgcgcgcgc tcttcgacct ccccgacgac    180
gccaagcgcc gcaacgccga cgtcatcccc ggcagcggct acgtcgcgcc ctgccccgcc    240
aacccgctct acgaggcctt cgggctcctc gacgccgccg cgcccgccga cgtcgacgcc    300
ttctgcgcgc gcctcgacgc gccgcccaaa gtcaggggaga ccgtcaagac ctacgcggag    360
aagatgcacg acgtgatcgt cggcgtcgcc ggcgagctgg ccaccagcct ggggctgggc    420
ctggaggagc actcgttcca ggactggccg tgccagttcc gcatcaacag gtacaactac    480
acgcaggaga cggtgggctc ctccggcgtg cagacccaca cggactcggg cttcctcacc    540
gtgctccagg aggacgagtg cgtcggcggc ctcgaggtgc tggaccccgc cgccggtgag    600
```

```
ttcgtgcccg tggaccccgt cgccggctcc ttcctcgtca acatcggcga cgtcggcacg    660
gcgtggagca acgggaggct ccacaacgtg aagcaccggg tgcggtgcgt cgcgcccgtg    720
ccgcgcatct ccatcgccat gttcctgctg gcgcccaagg acgaccgcgt gagcgccccg    780
gaggcgttgg tcgacgcggg ccacccgcgt cggtacaagc cgttcaacta cgacgactac    840
cggaggctcc ggctgtccac cggcgagcgc gcaggcgagg cgctcgcgcg gatggcggcg    900
tga                                                                  903
```

<210> SEQ ID NO 24
<211> LENGTH: 300
<212> TYPE: PRT
<213> ORGANISM: Zea mays

<400> SEQUENCE: 24

```
Met Ala Glu Ile Pro Val Ile Asp Leu Arg Leu Ala Gly Ser Ser Pro
1               5                   10                  15

Asp Glu Ser Ala Arg Leu Arg Asp Ala Cys Glu Arg Leu Gly Cys Phe
            20                  25                  30

Arg Val Thr Gly His Gly Ala Pro Ala Gly Leu Leu Ala Asp Met Lys
        35                  40                  45

Ala Ala Val Arg Ala Leu Phe Asp Leu Pro Asp Asp Ala Lys Arg Arg
    50                  55                  60

Asn Ala Asp Val Ile Pro Gly Ser Gly Tyr Val Ala Pro Cys Pro Ala
65                  70                  75                  80

Asn Pro Leu Tyr Glu Ala Phe Gly Leu Leu Asp Ala Ala Ala Pro Ala
                85                  90                  95

Asp Val Asp Ala Phe Cys Ala Arg Leu Asp Ala Pro Pro Lys Val Arg
            100                 105                 110

Glu Thr Val Lys Thr Tyr Ala Glu Lys Met His Asp Val Ile Val Gly
        115                 120                 125

Val Ala Gly Glu Leu Ala Thr Ser Leu Gly Leu Gly Leu Glu Glu His
    130                 135                 140

Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
                165                 170                 175

Gly Phe Leu Thr Val Leu Gln Glu Asp Glu Cys Val Gly Gly Leu Glu
            180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
    210                 215                 220

Gly Arg Leu His Asn Val Lys His Arg Val Arg Cys Val Ala Pro Val
225                 230                 235                 240

Pro Arg Ile Ser Ile Ala Met Phe Leu Leu Ala Pro Lys Asp Asp Arg
                245                 250                 255

Val Ser Ala Pro Glu Ala Leu Val Asp Ala Gly His Pro Arg Arg Tyr
            260                 265                 270

Lys Pro Phe Asn Tyr Asp Asp Tyr Arg Arg Leu Arg Leu Ser Thr Gly
        275                 280                 285

Glu Arg Ala Gly Glu Ala Leu Ala Arg Met Ala Ala
    290                 295                 300
```

<210> SEQ ID NO 25
<211> LENGTH: 1614
<212> TYPE: DNA
<213> ORGANISM: Zea mays

<400> SEQUENCE: 25

```
accacacgaa ttgcacatct ccacagctca cgattccaac actagctaca tatatatgta     60
gctttctagg ctactatata cactcaccac caagtgtgaa gtgtgtatat atagtgacag    120
ctactgcaat atatacatac gcgtcaccta tatattagcc aagctagcta tatgagcttg    180
gttgcggcgc caatggcgat cgtcgacgtg gccaacgccc agctgcagca agcagcagca    240
gcagctgcca agaaagacga ggacggccat gagcagcagg agtcgtccta cgactacggc    300
gcgctgatga aggcgtgagg gcacctgtcg gacagcggca ttaccaggct gcccgacagg    360
tacgtcctgc ccgcgtccga ccgccccggc gtccttgccg tctcgtcgtc cgtggcgggc    420
agcggcaggg tcaagctccc tgtcgtcaac ctcgccggcc tccgcgaccc ctgccagcgc    480
gccgccgtgc tggccacgct cgacgccgcg tgccgggagt acggcttctt tcaggtggta    540
aaccacgggt tcgggagcga cgtgagcggc gggatgctgg acgtggcgca gcgcttcttc    600
gagctgccgc tggccgagcg agcgcggcac atgtcggcgg acgtgcgggc gccggtgcgc    660
tacggcacca gcttcaacca ggccaaggac gacgtgctct gctggcgcga cttcctcaag    720
ctcgtctgcc agccgctgca ggcggtgctc ccgtactggc cccagcagcc ggcggacctc    780
agggacgtgg ccaccaggta cgccacggcg agccaccggc tgttcatgga ggtcatggag    840
gcggcgctgg aggccctggg catccccacg gccggcggcg tgctcgggga gctggcagcg    900
tcgtcgtcgc acatgatgac ggtgaactgc tacccggcgt gcccgcagcc tgagctcacg    960
ctggggatgc cctcgcactc ggactacggc ctcttcacgt tcgtcctgca ggaccacgtc   1020
gagggcctcc aggtcatgca cgacggccgc tggctcacca tcgaccccat cccgggatcg   1080
ttcgtcgtca cgtcggcga ccacctagag atctacagca cgggcggta caagagcgcg   1140 ctgcaccggg tgcacgtgaa ctccacgcgg ccgcgcatct cggtggcgtc gttccacagc   1200
ctgccggcgg agcgagtgat cgggccggcg ccggagctgg tggacgacga ggccggcaac   1260
ccgcggcggt acatggacac cgacttcgct accttcctcg cctacctcgc atccgcggac   1320
ggcaagaaca agaccttcct ccagtcaagg aagctgcctg ctgctgctcc tccatgcctc   1380
tagctaacta gatagctgct tattaatctg acagaataaa attaatcagt tcagcgcaca   1440
attccacaag cgaaaacaaa cctggatttg ttttaattag ctctgccctt cattattaca   1500
ttcaagctag ctcttggtca acgcatgcac acaagcttga gcattgactg gtcccttttc   1560
aatcggttgc attgtactcc ctccgtacca aaattggttg tcgctatagt attt         1614
```

<210> SEQ ID NO 26
<211> LENGTH: 1212
<212> TYPE: DNA
<213> ORGANISM: Zea mays

<400> SEQUENCE: 26

```
atgagcttgg ttgcggcgcc aatggcgatc gtcgacgtgg ccaacgccca gctgcagcaa     60
gcagcagcag cagctgccaa gaaagacgag gacggccatg agcagcagga gtcgtcctac    120
gactacggcg cgctgatgaa ggcgtgaggg cacctgtcgg acagcggcat taccaggctg    180
cccgacaggt acgtcctgcc cgcgtccgac cgccccggcg tccttgccgt ctcgtcgtcc    240
gtggcgggca gcggcagggt caagctccct gtcgtcaacc tcgccggcct ccgcgacccc    300
```

-continued

```
tgccagcgcg ccgccgtgct ggccacgctc gacgccgcgt gccgggagta cggcttcttt      360
caggtggtaa accacgggtt cgggagcgac gtgagcggcg ggatgctgga cgtggcgcag      420
cgcttcttcg agctgccgct ggccgagcga gcgcggcaca tgtcggcgga cgtgcgggcg      480
ccggtgcgct acggcaccag cttcaaccag gccaaggacg acgtgctctg ctggcgcgac      540
ttcctcaagc tcgtctgcca gccgctgcag gcggtgctcc cgtactggcc ccagcagccg      600
gcggacctca gggacgtggc caccaggtac gccacggcga ccaccggct gttcatggag       660 gtcatggagg cggcgctgga ggccctgggc atccccacgg ccgcggcgt gctcggggag       720 ctggcagcgt cgtcgtcgca catgatgacg gtgaactgct accgcgtg cccgcagcct        780 gagctcacgc tggggatgcc ctcgcactcg gactacggcc tcttcacgtt cgtcctgcag      840
gaccacgtcg agggcctcca ggtcatgcac gacggccgct ggctcaccat cgaccccatc      900
ccgggatcgt tcgtcgtcaa cgtcggcgac cacctagaga tctacagcaa cgggcggtac      960
aagagcgcgc tgcaccgggt gcacgtgaac tccacgcggc cgcgcatctc ggtggcgtcg     1020
ttccacagcc tgccggcgga gcgagtgatc gggccgcgc cggagctggt ggacgacgag      1080
gccggcaacc cgcggcggta catggacacc gacttcgcta ccttcctcgc ctacctcgca     1140
tccgcggacg gcaagaacaa gaccttcctc cagtcaagga agctgcctgc tgctgctcct     1200
ccatgcctct ag                                                        1212
```

```
<210> SEQ ID NO 27
<211> LENGTH: 403
<212> TYPE: PRT
<213> ORGANISM: Zea mays

<400> SEQUENCE: 27
```

| | | | | | | | | | | | | | | |
|---|---|---|---|---|---|---|---|---|---|---|---|---|---|---|
| Met | Ser | Leu | Val | Ala | Ala | Pro | Met | Ala | Ile | Val | Asp | Val | Ala | Asn | Ala |
| 1 | | | | 5 | | | | | 10 | | | | | 15 | |

Gln Leu Gln Gln Ala Ala Ala Ala Ala Lys Lys Asp Glu Asp Gly
                20                  25                  30

His Glu Gln Gln Glu Ser Ser Tyr Asp Tyr Gly Ala Leu Met Lys Gly
                35                  40                  45

Val Arg His Leu Ser Asp Ser Gly Ile Thr Arg Leu Pro Asp Arg Tyr
 50                  55                  60

Val Leu Pro Ala Ser Asp Arg Pro Gly Val Leu Ala Val Ser Ser Ser
 65                  70                  75                  80

Val Ala Gly Ser Gly Arg Val Lys Leu Pro Val Asn Leu Ala Gly
                85                  90                  95

Leu Arg Asp Pro Cys Gln Arg Ala Ala Val Leu Ala Thr Leu Asp Ala
                100                 105                 110

Ala Cys Arg Glu Tyr Gly Phe Phe Gln Val Val Asn His Gly Phe Gly
                115                 120                 125

Ser Asp Val Ser Gly Gly Met Leu Asp Val Ala Gln Arg Phe Phe Glu
                130                 135                 140

Leu Pro Leu Ala Glu Arg Ala Arg His Met Ser Ala Asp Val Arg Ala
145                 150                 155                 160

Pro Val Arg Tyr Gly Thr Ser Phe Asn Gln Ala Lys Asp Asp Val Leu
                165                 170                 175

Cys Trp Arg Asp Phe Leu Lys Leu Val Cys Gln Pro Leu Gln Ala Val
                180                 185                 190

Leu Pro Tyr Trp Pro Gln Gln Pro Ala Asp Leu Arg Asp Val Ala Thr
                195                 200                 205

```
Arg Tyr Ala Thr Ala Ser His Arg Leu Phe Met Glu Val Met Glu Ala
            210                 215                 220
Ala Leu Glu Ala Leu Gly Ile Pro Thr Ala Gly Val Leu Gly Glu
225                 230                 235                 240
Leu Ala Ala Ser Ser His Met Met Thr Val Asn Cys Tyr Pro Ala
                245                 250                 255
Cys Pro Gln Pro Glu Leu Thr Leu Gly Met Pro Ser His Ser Asp Tyr
                260                 265                 270
Gly Leu Phe Thr Phe Val Leu Gln Asp His Val Glu Gly Leu Gln Val
            275                 280                 285
Met His Asp Gly Arg Trp Leu Thr Ile Asp Pro Ile Pro Gly Ser Phe
290                 295                 300
Val Val Asn Val Gly Asp His Leu Glu Ile Tyr Ser Asn Gly Arg Tyr
305                 310                 315                 320
Lys Ser Ala Leu His Arg Val His Val Asn Ser Thr Arg Pro Arg Ile
                325                 330                 335
Ser Val Ala Ser Phe His Ser Leu Pro Ala Glu Arg Val Ile Gly Pro
                340                 345                 350
Ala Pro Glu Leu Val Asp Asp Glu Ala Gly Asn Pro Arg Arg Tyr Met
                355                 360                 365
Asp Thr Asp Phe Ala Thr Phe Leu Ala Tyr Leu Ala Ser Ala Asp Gly
            370                 375                 380
Lys Asn Lys Thr Phe Leu Gln Ser Arg Lys Leu Pro Ala Ala Ala Pro
385                 390                 395                 400
Pro Cys Leu

<210> SEQ ID NO 28
<211> LENGTH: 1863
<212> TYPE: DNA
<213> ORGANISM: Zea mays

<400> SEQUENCE: 28
tgccaccata ccactagtgc aaggtcctag atttacactt ggtgctacac cttgcttcgc      60
cccttccttc cttccttcc ttccttccct ccttccttgg tctctaggca gctagcagtg      120
tggtgctgct gccggccgcc tattggccgc ctgggactgg gatccattaa ttactgcgcg      180
cgcgcggcta accaaccaat cccagcgtgc gtaatctatt gcccacatgc cgacgccgtc      240
gcacctcaac aagaacccgc gctacctgga cttccgggcg gcgcggcggg tgccggagtc      300
gcacgcctgg ccgggcctgc acgaccaccc cgtcgtggac ggcggcgcgc cgggcccccga     360
cgccgtgccg gtggtggacc tgggcgccgc ggacccggcg ccggcgccgg cggcggcggt      420
ggcccgcgcc gccgagcaat ggggcgcgtt cctgctcacg ggccacgcg tccccgcgga      480
cctgctggcg cgcgtggagg accggatcgc caccatgttc gcgctgccgg ccgacgacaa      540
gatgcgcgcc gtgcgcgggc ccggcgacgc ctgcggctac ggctcccgc ccatctcctc      600
cttcttctcc aagtgcatgt ggtccgaggg ctacaccttc cgccggcct ccctccgcgc      660
cgacctccgc aagctctggc ccaaggccgg cgacgactac accagcttct gtgatgtgat      720
ggaggagttc cacaagcaca tgcgcgccct cgcggacaag ctgctggagc tgttcctcat      780
ggcgctgggg ctcaccgacg agcaggccag cgccgtcgag gccgagcgga ggatcgccga      840
gacgatgacc gccaccatgc atctcaactg gtacccgagg tgcccggacc cgcggcgcgc      900
gctgggcct atcgcgcaca ccgactcggg cttcttcacc ttcgtgatgc agagcctcgt      960
gcccgggctg cagctcttcc gccacgcccc ggaccggtgg gtggcggtgc cggccgtgcc     1020
```

```
gggcgccttc gtcgtcaacg tgggcgacct cttccacatc ctcaccaacg gccggttcca    1080
cagcgtgtac caccgcgccg tcgtgaaccg ggacctcgac aggatctcgc tcggctactt    1140
cctcggcccg ccgccgcacg ccaaggtggc gccgctgcgc gaggccgtgc cgcccggccg    1200
ggcccccgcg taccgcgccg tcacgtggcc cgagtacatg ggcgtccgca agaaggcctt    1260
caccaccggc gcctccgcgc tcaagatggt cgccctcgcc gccgccgccg acctcgacga    1320
cgacggcgac gccgccgtcg tccatcagca gcagcagcta gtcgtctcgt cgtagccgag    1380
accgatcgcc ggagactgat gctgatgatg atgcatatat acatgagaga aatcgtcgag    1440
tagactagcc gattgcaaaa gcaaccccag ctgccgaaac ctggcatatc gatcccattc    1500
tctgctgcgc acatgtatgc atgcatgcgc ttcgtccgtt cgactcgtgt gtgcttgctt    1560
gcttgcgcgt gcagcagaac taattccgtt ccgcagctag ctgctctgct ctgctctgct    1620
ggaatgtaat taagtagtag tatatggtag tagagaaaag attagctagg cgatcgatat    1680
agatgacggg ccggggaaga agacgaatta attaagatcg atcgacgacg acgagctgtg    1740
cgtggctggc tgtgttcttc tctagcctag ttacagaggc cggctgctgc tgcttccaat    1800
cgggctgctt gtcgctactg acgatcgtta gtggatccat taactaatct ggaattctgg    1860
att                                                                  1863

<210> SEQ ID NO 29
<211> LENGTH: 1149
<212> TYPE: DNA
<213> ORGANISM: Zea mays

<400> SEQUENCE: 29
atgccgacgc cgtcgcacct caacaagaac ccgcgctacc tggacttccg ggcggcgcgg      60
cgggtgccgg agtcgcacgc ctggccgggc ctgcacgacc accccgtcgt ggacggcggc     120
gcgccgggcc ccgacgccgt gccggtggtg gacctgggcg ccgcggaccc ggcgccggcg     180
ccggcggcgg cggtggcccg cgccgccgag caatggggcg cgttcctgct cacgggccac     240
ggcgtccccg cggacctgct ggcgcgcgtg gaggaccgga tcgccaccat gttcgcgctg     300
ccggccgaca caagatgcg cgccgtgcgc gggcccggcg acgcctgcgg ctacggctcc     360
ccgcccatct cctccttctt ctccaagtgc atgtggtccg agggctacac cttctcgccg     420
gcctccctcc gcgccgacct ccgcaagctc tggcccaagg ccggcgacga ctacaccagc     480
ttctgtgatg tgatggagga gttccacaag cacatgcgcg ccctcgcgga caagctgctg     540
gagctgttcc tcatggcgct ggggctcacc gacgagcagg ccagcgccgt cgaggccgag     600
cggaggatcg ccgagacgat gaccgccacc atgcatctca actggtaccc gaggtgcccg     660
gacccgcggc gcgcgctggg gctgatcgcg cacaccgact cgggcttctt caccttcgtg     720
atgcagagcc tcgtgcccgg gctgcagctc ttccgccacg ccccggaccg gtgggtggcg     780
gtgccggccg tgccgggcgc cttcgtcgtc aacgtgggcg acctcttcca catcctcacc     840
aacggccggt tccacagcgt gtaccaccgc gccgtcgtga accgggacct cgacaggatc     900
tcgctcggct acttcctcgg cccgccgccg cacgccaagg tggcgccgct gcgcgaggcc     960
gtgccgcccg gccgggcccc cgcgtaccgc gccgtcacgt ggcccgagta catgggcgtc    1020
cgcaagaagg ccttcaccac cggcgcctcc gcgctcaaga tggtcgccct cgccgccgcc    1080
gccgacctcg acgacgacgg cgacgccgcc gtcgtccatc agcagcagca gctagtcgtc    1140
tcgtcgtag                                                            1149
```

```
<210> SEQ ID NO 30
<211> LENGTH: 382
<212> TYPE: PRT
<213> ORGANISM: Zea mays

<400> SEQUENCE: 30
```

| | | | | | | | | | | | | | | |
|---|---|---|---|---|---|---|---|---|---|---|---|---|---|---|
| Met<br>1 | Pro | Thr | Pro | Ser<br>5 | His | Leu | Asn | Lys | Asn<br>10 | Pro | Arg | Tyr | Leu | Asp Phe<br>15 |
| Arg | Ala | Ala | Arg<br>20 | Arg | Val | Pro | Glu | Ser<br>25 | His | Ala | Trp | Pro | Gly<br>30 | Leu His |
| Asp | His | Pro<br>35 | Val | Val | Asp | Gly | Gly<br>40 | Ala | Pro | Gly | Pro | Asp<br>45 | Ala | Val Pro |
| Val<br>50 | Val | Asp | Leu | Gly | Ala<br>55 | Ala | Asp | Pro | Ala | Pro<br>60 | Ala | Pro | Ala | Ala Ala |
| Val<br>65 | Ala | Arg | Ala | Ala | Glu<br>70 | Gln | Trp | Gly | Ala | Phe<br>75 | Leu | Leu | Thr | Gly His<br>80 |
| Gly | Val | Pro | Ala | Asp<br>85 | Leu | Leu | Ala | Arg | Val<br>90 | Glu | Asp | Arg | Ile | Ala Thr<br>95 |
| Met | Phe | Ala | Leu<br>100 | Pro | Ala | Asp | Asp | Lys<br>105 | Met | Arg | Ala | Val | Arg<br>110 | Gly Pro |
| Gly | Asp | Ala<br>115 | Cys | Gly | Tyr | Gly | Ser<br>120 | Pro | Pro | Ile | Ser | Ser<br>125 | Phe | Phe Ser |
| Lys<br>130 | Cys | Met | Trp | Ser | Glu<br>135 | Gly | Tyr | Thr | Phe | Ser<br>140 | Pro | Ala | Ser | Leu Arg |
| Ala<br>145 | Asp | Leu | Arg | Lys | Leu<br>150 | Trp | Pro | Lys | Ala | Gly<br>155 | Asp | Asp | Tyr | Thr Ser<br>160 |
| Phe | Cys | Asp | Val | Met<br>165 | Glu | Glu | Phe | His | Lys<br>170 | His | Met | Arg | Ala | Leu Ala<br>175 |
| Asp | Lys | Leu | Leu<br>180 | Glu | Leu | Phe | Leu | Met<br>185 | Ala | Leu | Gly | Leu | Thr<br>190 | Asp Glu |
| Gln | Ala | Ser<br>195 | Ala | Val | Glu | Ala | Glu<br>200 | Arg | Arg | Ile | Ala | Glu<br>205 | Thr | Met Thr |
| Ala<br>210 | Thr | Met | His | Leu | Asn<br>215 | Trp | Tyr | Pro | Arg | Cys<br>220 | Pro | Asp | Pro | Arg Arg |
| Ala<br>225 | Leu | Gly | Leu | Ile | Ala<br>230 | His | Thr | Asp | Ser | Gly<br>235 | Phe | Phe | Thr | Phe Val<br>240 |
| Met | Gln | Ser | Leu | Val<br>245 | Pro | Gly | Leu | Gln | Leu<br>250 | Phe | Arg | His | Ala | Pro Asp<br>255 |
| Arg | Trp | Val | Ala<br>260 | Val | Pro | Ala | Val | Pro<br>265 | Gly | Ala | Phe | Val | Val<br>270 | Asn Val |
| Gly | Asp | Leu<br>275 | Phe | His | Ile | Leu | Thr<br>280 | Asn | Gly | Arg | Phe | His<br>285 | Ser | Val Tyr |
| His<br>290 | Arg | Ala | Val | Val | Asn<br>295 | Arg | Asp | Leu | Asp | Arg<br>300 | Ile | Ser | Leu | Gly Tyr |
| Phe<br>305 | Leu | Gly | Pro | Pro | His<br>310 | Ala | Lys | Val | Ala | Pro<br>315 | Leu | Arg | Glu | Ala<br>320 |
| Val | Pro | Pro | Gly | Arg<br>325 | Ala | Pro | Ala | Tyr | Arg<br>330 | Ala | Val | Thr | Trp | Pro Glu<br>335 |
| Tyr | Met | Gly | Val<br>340 | Arg | Lys | Lys | Ala | Phe<br>345 | Thr | Thr | Gly | Ala | Ser<br>350 | Ala Leu |
| Lys | Met | Val<br>355 | Ala | Leu | Ala | Ala | Ala<br>360 | Ala | Asp | Leu | Asp | Asp<br>365 | Asp | Gly Asp |
| Ala<br>370 | Ala | Val | Val | His | Gln<br>375 | Gln | Gln | Gln | Leu | Val<br>380 | Val | Ser | Ser | |

```
<210> SEQ ID NO 31
<211> LENGTH: 1439
<212> TYPE: DNA
<213> ORGANISM: Zea mays

<400> SEQUENCE: 31
gacctccatt tgattatct ctatcctgta cgtgccgaga gtccttcaaa gccgacgacg      60
agacgacgat gcagtcgtcg tcgtcatcag cctcgacgcc ggctgccgct tccggcctcg    120
tcttcgatct cgggtctgcg gcgggcgtgc cggagacaca cgcgtggccg ggggtgaacg    180
agtacccgtc ggtggagtcc gctggccgcg acgtggtccc ggtggtggac atggggtgg     240 cctgccggga cgcgacgcgg gcgttggcgc gcgccgcaga cgagtggggc gtgtttctgc    300
tcgtcggcca cggcgtgccc cgggaagtgg cggcgcgtgc cgaggagcag gtcgcgcgcc    360
tgttcgtgct cccggctcct gacaaggccc gcgcggggcg ccgccccggg agcccacgg     420 ccaccggcta cggcaggccg cccctggcac tccgcttctc caagctcatg tggtccgagg    480
ggtacacgtt ccgcgccgcc accgtccgcg aagagttccg ccgcgtctgg cccgacggcg    540
gcgacgacta cctccgcttc tgcgacgtga tggaggagta cgacagagag atgagggctc    600
tcggtggcag gctgctcgac ctcttcttca tggcgctcgg cctcaccgac gtccagttcg    660
ccaccggcga gacggagcgg aggatccgcg agacctggac ggcgacgatg cacccaatcc    720
tgtgtccgga accggagcgc gccatcgggc tgacggcgca cacggactcg ggcttcatca    780
cgctcatcat gcagagcccc gtgccgggc tgcagctgct ccgccgcggg ccggaccggt    840
gggtgacggt gccggcgccg ccgggcgcgc tcatcgtcat gctcggcgac ctgttccagg    900
tgctcacgaa cggccgcttc cggagcccta tccaccgcgc cgtcgtaagc cgagagcgcg    960
agcggatctc cgtgccctac ttcctctgcc cgccggagga catgacggtg gcgccgctcg   1020
cgtccgctct gctgccgggg aggaaggccg tgttccgggc cgtgacgtgg ccagagtaca   1080
tggaggtcaa gcacaaggtg ttcggcacg atgcgccggc cctggagatg ctgcagctgc   1140
aggtggatga ggaagaacaa ggtgaaaggg ccgccaccac ctaagcccta aggaactact   1200
agctgaatcc ataaactaat aaagaattcg tgaataaggg cgttggaaga ctggacacaa   1260
cacaagagag ttgctatata tcgtatttct gaaatttaag gcaaatatct tagttaaaaa   1320
actggtatat ttaaatagac aatatatatc taaaataaag atagttcacc atttttacgg   1380
tcgaacaatg ataaagttat atattgtctg aatagtaaca aattaaagat ttccaggag    1439

<210> SEQ ID NO 32
<211> LENGTH: 1116
<212> TYPE: DNA
<213> ORGANISM: Zea mays

<400> SEQUENCE: 32
atgcagtcgt cgtcgtcatc agcctcgacg ccggctgccg cttccggcct cgtcttcgat     60
ctcgggtctg cggcgggcgt gccggagaca cacgcgtggc cggggtgaa cgagtacccg    120 tcggtggagt ccgctggccg cgacgtggtc ccggtggtgg acatgggggt ggcctgcccg    180
gacgcgacgc gggcgttggc gcgcgccgca gacgagtggg gcgtgtttct gctcgtcggc    240
cacggcgtgc ccgggaagt ggcggcgcgt gccgaggagc aggtcgcgcg cctgttcgtg    300
ctcccggctc ctgacaaggc ccgcgcgggg cgccgccccg gggagcccac ggccaccggc    360 tacgcaggc cgcccctggc actccgcttc tccaagctca tgtggtccga ggggtacacg    420
ttccgcgccg ccaccgtccg cgaagagttc cgccgcgtct ggcccgacgg cggcgacgac    480
```

| | | |
|---|---|---|
| tacctccgct tctgcgacgt gatggaggag tacgacagag agatgagggc tctcggtggc | 540 |
| aggctgctcg acctcttctt catggcgctc ggcctcaccg acgtccagtt cgccaccggc | 600 |
| gagacggagc ggaggatccg cgagacctgg acggcgacga tgcacccaat cctgtgtccg | 660 |
| gaaccggagc gcgccatcgg gctgacggcg cacacggact cgggcttcat cacgctcatc | 720 |
| atgcagagcc ccgtgcccgg gctgcagctg ctccgccgcg ggccggaccg gtgggtgacg | 780 |
| gtgccggcgc cgccgggcgc gctcatcgtc atgctcggcg acctgttcca ggtgctcacg | 840 |
| aacggccgct ccggagcccc tatccaccgc gccgtcgtaa gccgagagcg cgagcggatc | 900 |
| tccgtgccct acttcctctg cccgccggag gacatgacgg tggcgccgct cgcgtccgct | 960 |
| ctgctgccgg ggaggaaggc cgtgttccgg gccgtgacgt ggccagagta catggaggtc | 1020 |
| aagcacaagg tgttcggcac ggatgcgccg gccctggaga tgctgcagct gcaggtggat | 1080 |
| gaggaagaac aaggtgaaag ggccgccacc acctaa | 1116 |

<210> SEQ ID NO 33
<211> LENGTH: 371
<212> TYPE: PRT
<213> ORGANISM: Zea mays

<400> SEQUENCE: 33

```
Met Gln Ser Ser Ser Ser Ala Ser Thr Pro Ala Ala Ala Ser Gly
1               5                  10                  15

Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
        35                  40                  45

Val Val Pro Val Val Asp Met Gly Val Ala Cys Pro Asp Ala Thr Arg
    50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
                85                  90                  95

Arg Leu Phe Val Leu Pro Ala Pro Asp Lys Ala Arg Ala Gly Arg Arg
            100                 105                 110

Pro Gly Glu Pro Thr Ala Thr Gly Tyr Gly Arg Pro Leu Ala Leu
            115                 120                 125

Arg Phe Ser Lys Leu Met Trp Ser Glu Gly Tyr Thr Phe Arg Ala Ala
        130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Arg Glu Met Arg
                165                 170                 175

Ala Leu Gly Gly Arg Leu Leu Asp Leu Phe Phe Met Ala Leu Gly Leu
            180                 185                 190

Thr Asp Val Gln Phe Ala Thr Gly Glu Thr Glu Arg Arg Ile Arg Glu
        195                 200                 205

Thr Trp Thr Ala Thr Met His Pro Ile Leu Cys Pro Glu Pro Glu Arg
    210                 215                 220

Ala Ile Gly Leu Thr Ala His Thr Asp Ser Gly Phe Ile Thr Leu Ile
225                 230                 235                 240

Met Gln Ser Pro Val Pro Gly Leu Gln Leu Leu Arg Arg Gly Pro Asp
                245                 250                 255
```

Arg Trp Val Thr Val Pro Ala Pro Gly Ala Leu Ile Val Met Leu
            260                 265                 270

Gly Asp Leu Phe Gln Val Leu Thr Asn Gly Arg Phe Arg Ser Pro Ile
        275                 280                 285

His Arg Ala Val Val Ser Arg Glu Arg Glu Arg Ile Ser Val Pro Tyr
        290                 295                 300

Phe Leu Cys Pro Pro Glu Asp Met Thr Val Ala Pro Leu Ala Ser Ala
305                 310                 315                 320

Leu Leu Pro Gly Arg Lys Ala Val Phe Arg Ala Val Thr Trp Pro Glu
                325                 330                 335

Tyr Met Glu Val Lys His Lys Val Phe Gly Thr Asp Ala Pro Ala Leu
            340                 345                 350

Glu Met Leu Gln Leu Gln Val Asp Glu Glu Gln Gly Glu Arg Ala
            355                 360                 365

Ala Thr Thr
    370

<210> SEQ ID NO 34
<211> LENGTH: 4095
<212> TYPE: DNA
<213> ORGANISM: Zea mays

<400> SEQUENCE: 34

```
taaatttgtg atccttgtga agttgttata tcatgaattg tgaacttgtt gcatttgtga      60
tcttttgtca actttgttgt attgtgaagt ttgatatgtt taccgatcgt attttagatt     120
tcgatcgtta ccggtgtatt ttccgcacca aacttttgtt tccgatgttt tcgaaatacc     180
gatatcgttt ccgtttctat agttacccct ttcaattttta tttccgatta aaaatatgaa     240
aacggtaatg gttttagtgt ttatcgaccg ttttcatctc taatcatccc tgccggtgaa     300
gtttaattt tcccttggct aaagagatgc aagctgctgt aaaatacgtt aaaacaggca      360
aggcagcccc agcagccagc atcgcgtgcc cgtctatgta catcagtgga tacgtagcat     420
ctctagtgag taatataacg attgcatttg gctggaggac gtatgttata aagtatgtc     480
atttaccagt tgcattagta tcttccctaa ctcctataat aactctcttc gtggaatgga     540
cgtagacgta tgctatataa gtattaaaaa atagtttttt aagctggtgt cctcaattt      600
gctattgttc tcgttttat ctttagttgt gtcacaaatt taatccgtac aacaaatcaa      660
aaataccata cccttcttat attaattttc taacataaca tttgtttaga tattttcagt     720
cgtgaaaata caattctaat tctaacgtcg tagtatcaaa tcaaaccatc cagaatttga     780
ccaagcttaa ttataaaaaa tataaaattt atgatactga atagatagca ttagatttgt     840
tatataaatat atttttataa aataccattt ttatggtata aatattggta ctcctttact     900
ttaaactata gatagttttg actaaggatg caactagaat tgcatcctct tttcactgca     960
ccttcattag ttttaatatt tatttagatg ggcccttgca aactgtagat atcatctctt    1020
gcaacattct ttctatagca ccacgaaaat gtattgcggc tttgaaatta taattgaatt    1080
agttgtatca tttctttcac cgatgcgtta aattcaaaat taagtgttat atttcttcat    1140
aatttgttaa atatatagac cctataatcc accattattt actataatag catacattaa    1200
cattggtttt agcctacact acgacactcg aggcattgaa ttttcctcta tcaaagaatt    1260
atatgtgtag tagtattgtt cttgacaaaa agggggatta aaattaaact accaatattg    1320
atacttatct tatcacatcc atgaatacaa tcaacactct tacaaaagat aagatacaag    1380
attaaaaagt accatgataa tacattaaga ttattagcaa tgcattaaat taaataaatg    1440
```

```
tgcaagtgaa tcatgatttt agttttatct attttacttt taaaatatga tattctctga    1500
ctacttctaa gcataaatgt gattctaagt catgaccgat cgtgcttatt cagaaaaatg    1560
aaggagacac agatttctat aaaaaaaggt tgtcatggga ctattgggtc aaccatctta    1620
ttcatttggg aaaataagtt tagaacacat caacccattt tagatgttga gtttggccct    1680
aatggtccat tgaccttact tttgtgggtt gacatagacc atctatccca agttattgtt    1740
gtgtcacatt ccctgatatc atgaatctat attttagctt tccgttttca tattttagt    1800
cgttacatat ttttatccg cgtactagat taaaactcta gttgttgcaa tacattttgt    1860
tcattttttt ctatttcttc tttactaaca acatattcta gttcctagct acattcttaa    1920
gtaccatagt gctataaaca ttttttatcc tacattattc cacttaagaa attgaatttt    1980
ctgcataaaa aaattatatg tccagtagtg ttgtcttata aaagcataaa gtgattaaaa    2040
ttaaaaccat tattgatatc ttatttttca aaaaaaaata aagcttata gaaagtgaat    2100
taatttcatg gtaaattaat atagtttaaa ttgaattatt agtgttatta ctatgtttat    2160
tatcaatgaa acattttca tggttgatat aacttagtgt tacttatttt agtattttt    2220
atataattct agttaacttt tagttttga tttaaaaaaa cgagaattgt gtccttttgt    2280
ggagtgagta taaagaaagt aatatctgtt catcataatt tggttttta aggtacgtga    2340
aacttgcttt atatttggac tcaagctatg tctaaataca tagtaaaaaa gcaatatttc    2400
tagaaaagac aaaacatctt ataatttaga atcaaggaaa tatatagatt ttatgtgcag    2460
tgagaagcca tttacaatgg aacgttcaac gttgggccaa tagatatttt gcgatatgat    2520
gatgggcata ttttgcatg gttgtccctc cactagctat agtttgatga tacgatacgc    2580
tgcacacacc attgggttgt accatgttag tgtagcaaca gtagaaaccc aattgtggcc    2640
gtgaaccatg ataatactag gtagagtgct agctagaggt ttcaggctat tgatgcgtga    2700
attaaacttt ctgttgtgtt gcgaggaaac gagtattgtg aaatatttga aacggttttt    2760
tttgtgaaag atttgaaacg gtattttgt tgtgaaataa agatcaaggc taaataaatt    2820
caaactaata aaacatatta attgacggcc tgaagccccc gcccccatgg ccccatgcca    2880
tagcatcagg tcccacatga catgaggccg cgcctccctc tatgttggct ccctgccttc    2940
gccgttgtcg tcgctcccga actccctctc ctccctgtt acaaataccc ccacccgccc    3000
ggacagcttc cctgcacact cgcagctcgc acatctcatg gtgtcctaag aacggcaaga    3060
gccagctctg cctagcagca gcgcacagcc acatccatgg acgccagccc gaccccaccg    3120
ctcccctcc gcgccccaac tcccagcatt gacctcccg ctggcaagga cagggccgac    3180
gcggcggcta acaaggccgc ggctgtgttc gacctgcgcc gggagcccaa gatcccggag    3240
ccattcctgt ggccgcacga agaggcgcgg ccgacctcgg ccgcggagct ggaggtgccg    3300
gtggtggacg tgggcgtgct gcgcaatggc gacggcgcgg ggctccgccg cgccgcggcg    3360
caagtggcgg cggcgtgcgc gacgcacggg ttcttccagg tgtgcgggca cggcgtggac    3420
gcggcgctgg ggcgcgccgc gctggacggc gccagcgact tcttccggct gccgctggct    3480
gagaagcagc gggcccggcg cgtccccggc accgtgtccg ggtacacgag cgcgcacgcc    3540
gaccggttcg cgtccaagct cccctggaag gagaccctgt ccttcggctt ccacgacggc    3600
gccgcggcgc ccgtcgtcgt ggactacttc accggcaccc tcggccaaga tttcgagcca    3660
gtggggtgag taaagaagaa gatggcgccg aatttacatt tataagtagg accagcagaa    3720
gcccctgccc ctgggggcct tagcattgca ttcgactgat gaatacgcat ggcaggcggg    3780
tgtaccagag gtactgcgag gagatgaagg agctgtcgct gacgatcatg gagctgctgg    3840
```

```
agctgagcct gggcgtggag cgcggctact accgggagtt cttcgaggac agccgctcca    3900
tcatgcggtg caactactac ccgccgtgcc cggtgccgga gcgcacgctg ggcacgggcc    3960
cgcactgcga ccccacggcg ctgaccatcc tcctgcagga cgacgtcggc gggctggagg    4020
tcctggtgga cggcgagtgg cgccccgtcc ggcccgtccc aggcgccatg gtcatcaaca    4080
tcggcgacac cttca                                                     4095

<210> SEQ ID NO 35
<211> LENGTH: 7404
<212> TYPE: DNA
<213> ORGANISM: Zea mays

<400> SEQUENCE: 35
cctattttgt gtctaatact cttcttatat taattgtttg gtcaaacttt agataaattt      60
gactaatgat gcaattaaaa ctgcatcacc tttactaagg tactgcttta tatgtttcga     120
caaaattttc aattattctc tatgtgtttt aatctttgcg ctacacctcc attgatttaa     180
atactcattt attttaaacc ataacttaaa ttatatcgga tctttgcatc ctttctatgg     240
caccatacat gaatcgatat tttggctgca aatttttaat catgttagtt ttagcatttt     300
ttcatatcca tgtgttaagt ttgaatcatg tgttgttttt atataattta ttgaaaatat     360
agatcctaaa cttcactaat acttacaaca atagcatcat catgtgtttt aatccacgcc     420
acaacactca aggcattgaa ttttcttcta ccaaagagtt gtatgtgtgt attgttcttt     480
aaaaaataga gtgattataa ttaaactacc agtattcata tgtaaaatgt atagacatct     540
aaaataaaat ttgcaaaaaa cattgttgca gactttcaat ataattaaga atgggtttta     600
gggtcatgat atatggtttg ttaaagaaac ttgtttttt ttgcaattga taaactataa     660
aatacatttt cactattgtg tgcatatgta cttggtatac atagtggcat atatcatttt     720
tgtttacttt gaggtttgaa ttatctatgt taaaattgga taacatagat acattggtgt     780
gcgtcctttg gcccatttac ttgactgagg agcaatacta taaagtaaaa catatttgga     840
tattttatct taaactccta gcataatatt gatttaatta tgaacaaata tatgtttagg     900
tgatagtttc atgggtggta aactatataa gaaggcttac catgatcttt gcaaactcta     960
ggctatgaaa gagttccatg atttgtctta gaagcataga caaaacagtg ataatgatct    1020
aaatcacact tatggcactg atgaccatat atgcaaagct aaatgcatgt taagttgtat    1080
tatatcatat gtttacaatg actatcgcat ataacgagga atacattgtc tatatagata    1140
gctattactg tagtagtgcc aaatgttgga caacatgaat cataatcttc aaacctagag    1200
aaattgtagt cagtcgtaca catatcgtct agtaagttgt ctatactttt tatttattgt    1260
atcaaatttt attgttatct tgcttgcttg tttgtttgta ccatagacac aatatggtca    1320
aaaagtggtc aatcgattcg aagaagattg caattgacga gtgctaacag ttgatccttt    1380
tgttgtgcac gctagcggag tagcatgaaa agagtaaaat atgaaattag cgttctaaac    1440
tgtttgtgct ataggtactt cgtatttaat ggagtgacta actataggaa ggtgagagct    1500
cagaagtcag caccctcaca cagagttcta gagttagtgg tcatcgaacc acgacaaact    1560
acatgatgag cagaagaggc aacatcaaga ctatgatcaa tagtttcggg tcaatgaatg    1620
acatcgtgat gagtatttat ctaactatat agaacaacaa cacatgatgt tttaagtaag    1680
ttcaactgat cttctattgc tatctttaag tatttaacgt agcgaataat gtttatctca    1740
tttcattcat aaataatgtt gtgacaaaag gggataacca tcacttttac catgttctag    1800
ataccacaac catctccacc atcataatgg gttcttcatt ggtgcttgga cctcaaataa    1860
```

```
tcatatctat agccaactta gctcaattct aataaaatta ggcaacttgg cttcattgta    1920
gcaaaaatag ccaacttagc tcaattttat ctaaacttag ctaatctagc acaacttaga    1980
tcaatattag gaaaaactaa tcaatctaat ctagctcaac tatagcgaaa gatagatatt    2040
gtagcataac ttagtagatc tatctcaaat tttagcaaaa actaatcaat ttagataaac    2100
tctataaaat tttaatcatt atgacttatt ccaactaat tgtaacttgc atgatttta     2160 tgttccttct ttataattag caacacctaa agacacgaat gatgagggt ctaacgcatt     2220 cattaaccag ttgttaaata atactctagg tagatgataa gaactctaat tattctatga    2280
atctaagcta aaagatgttt aatatttaag tattggtgtt tattatgtta tttagaacga    2340
ttcatgttac ttaaagattt gttatgattt ttaaatatga ttatgataat ttatgtggtg    2400
tggattaact tgtgaacata tgtgatgtag atgaatatgt atgttgtgga tggaaccata    2460
tgaatatata tacacactca tatactattc gttggtgtag gtaaagcttc atccatcggt    2520
aattactaaa tggtcttcag tcattaccac taggtgaagc ttcacacgac cgataaattat   2580 tgaagaacgc tcattaattt ccggtaatgg cttattggcc ttcactagtc ggtgaaaatt    2640
agctattttt ataccaataa aaattagcta atatatgtaa accaggtcta atttttatgg    2700
gcctcttacc gaccaaaatt gattagatta ttgttacaat agttttagtc aaaagctagc    2760
tatgctataa aaattttgaa ttaaagtgag tttcgtaata aaaattgcat acttttaaaa    2820
taaaataatt aaaaaacagt ttttagaaat acaatcaaac accttatgct ataaaaaat    2880 tgtaatgtac ctacaaatat ataatacttt actttaaaat aggcctgtgc cttctcggct    2940
ctatatgggc tgcctccaac gaagcgccat ggccatgggc tccactgtgt cgggtcccac    3000
atgaggccgc gcctccctcc aaatgttccc tccctgcctt cgtctttgtc gttgctcgca    3060
aactccctgt cctcccctgt tacaaatacc cccacccgcc cggacagctt ccctgcatac    3120
ttgcagctcg cacatctcat ggtgtcgcag gaacgacaag agccagctgt gcctagcagc    3180
agcagcagca gcgccaagcg cgcagccacg tccatggacg ccagcccggc cccgccgctc    3240
ctcctccgcg cccccactcc cagccccagc attgacctcc ccgctggcaa ggacaaggcc    3300
gacgcggcgg ccagcaaggc cggcgcggcc gtgttcgacc tgcgccggga gcccaagatc    3360
cccgcgccat tcctgtggcc gcaggaagag gcgcggccgt cctcggccgc ggagctggag    3420
gtgccgatgg tggacgtggg cgtgctgcgc aatggcgacc gcgcggggct gcggcgcgcc    3480
gcggcgcagg tggccgcggc gtgcgcgacg cacgggttct tccaggtgtg cgggcacggc    3540
gtggacgcgg cgctggggcg cgccgcgctg gacggcgcca cgacttctt ccggctgccg     3600 ctcgccgaga agcagcgcgc ccggcgcgtc cccggcaccg tgtccgggta cacgagcgcg    3660
cacgccgacc ggttcgcggc caagctcccc tggaaggaga ccctgtcgtt cggctaccac    3720
gacggcgccg cgtcgcctgt cgtcgtggac tacttcgtcg gcaccctcgg ccaggatttc    3780
gagccaatgg ggtaagtaag gtagtaagaa ggagcgccgg tttacattta ccgcacgtcg    3840
gcgtgcggtc gagtcgggac tcgggagacg tatgaacccc cgtcccgtcc catgcatgtg    3900
tggcaggtgg gtgtaccaga ggtactgcga ggagatgaag gagctgtcgc tgacgatcat    3960
ggagctgctg gagctgagcc tgggcgtgga gctgcgcggc tactaccggg agttcttcga    4020
ggacagccgg tccatcatgc ggtgcaacta ctacccgccg tgcccggagc cggagcgcac    4080
gctgggcacg ggcccgcact gcgaccccac ggcgctcacc atcctcctgc aggacgacgt    4140
gggcgggctg gaggtgctgg tggacggtga gtggcgcccc gtccgcccg tcccgggcgc     4200 catggtcatc aacatcggcg acaccttcat ggtaacgaaa cgaaagcgct cgctcctctg    4260
```

```
ttttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacgggggac gtggcgggga gacgatacga    4680
tgggtgccgg gcaggtttcc gaattccaaa cgttttttgtg gcgtgcgtcc atggggcgcc    4740
cccaaacttc ggacgtttcc ggcgctccaa caaatcttct cgcttcacac gtcaccgtcg    4800
tcccggattc atttgcctcg tcgctccacc attcgctgct ctcctctcca cgtactctta    4860
ccctgacctt tgggaaagaa ctgaacattc gagatgcaca acagttcaaa tataacatat    4920
gcagcacaag atcgttcgac tgctatccga caagccaaca acgtgcccag tagaactgaa    4980
tgtacctgtg atttccagca ctaacttaca gcaacgttgt gaaaaacaa aaacgaaaac      5040
aaacggcaga aaaaacagat gtattgttct acagttacac caaatatttt ctggtccttt    5100
cagcaccaac aagagccata cgcatatcta gaagacaaaa ttcctctaat ttcacccta     5160
cgtggtagca gttcctcctc aacacagttc acgtgctagc gtcgagttct ttgggccgcc    5220
acatcgactt ctcgacgcag agcaggccct cgctgcccct tggtgtaggtc atccgcacct   5280
cccactgcac ggacttggcc atgctctcca gctcatttat cgtgtccgcg gtgtccctca    5340
cgatcagctt gccctgtggc ctcagtacac ggtcgacctc ggcgaaaact gcagccagtt    5400
tgcatctgta aacaggcaac acagattttt agtatctaaa acactgcagg caaacgccac    5460
aggttttagt cgcaagaagc aataaaaagca tgcaaacaat gctacgtgta cgtatcaaag   5520
gaacatgtca aaactcgttg catgaacgat cattgatgtt tccttgctga actagtcaca    5580
tcagtctgct tcaacttctg ggtttcacta gtagatatac cagaagggta gaataatgtg    5640
aagagcaaga aatacagacc tctttctgag ctttgagaac agatggtccg cgtgcagaag    5700
gtcatacgtt cttgggtaag tgctgaaaga ctcgcaccag tcatggtaca tgccaaacaa    5760
accgcgctcg tagatgatgg gcagcgtgtc tggtgaatcg atcggcacga tattcatgac    5820
ccagacctttt tggtccctca gagctgcagc aaaaactgcca tgcaacaatg taaagcatta   5880
gtcaagaaga aggtgtacag tgcatttctc cttgtcaaca gtcttcagta acaaaaaaaa    5940
agtgttatgc ttgactgaat cttttcaaaga aatatgcttg atgacttatg gtggacaagt    6000
tgcctgttat agtgttatgt tttaattaac tatgtgccag cttgggtaac tagtagttat    6060
gtagtgtgat ctgaattacc aaaatataaa taaataaata aacatgccca agaaaactacg    6120
aaaaccattt acttaccctc catagacagc tctcatgtcc atgacatttc tcactttgga    6180
ccagtcaatt cccatgccat tcacatacga tttacttaca acccgtttcc agtgggcatt    6240
atctgcctca aaatcttcat ttgcaggctt tccatagaca ccaaccttgg aaccatcaat    6300
ccagaaaggg gtcttctcaa gcctttgcgg ccataactct ggccattttg atcctcggac    6360
ttttgagcca ccaggcagtt tgtgcatgca tgcttccaac ggtacattcc tgcaaatcaa    6420
aaggctgtgt aagcaaagca gagaagcact tttctccatt gaaaatatac tcttctcaaa    6480
gaaccgaaac cataccaagc agcatctgca tcatcagatt ccttgcacaa tggcgggctg    6540
ttttcagatc ttttctcata gcaaatattg tccattggtt tctgatatat gaccatacca    6600
acttggttta acttatcctt agtcttgttg accatcttcc agcacatgga ctttgtcaaa    6660
```

-continued

| | |
|---|---|
| gtagacatgg ctgaaaaggg tatgtggcca catgttatgt tagaaataaa attcaatttt | 6720 |
| gaacagttgg tccatagcat gtattttgaa caaatgcaat ccttctccat ccatgaaaga | 6780 |
| agttgaccct tcatacttag gattattcag tactttcact catgtctgct gaatttgttc | 6840 |
| tcttggtagt tgctatacaa gaaagggga agtacagagt agctaaactt atacaagcta | 6900 |
| tagtctgata tttgtatgaa acataaattt tggtatggat gtcttattaa aatgggaggt | 6960 |
| tgtataatat ttttctagcc tacctcaact tgcttgagac taaaaggctt tgttgttgtt | 7020 |
| gttgaggctg tatggtgctt tgactttaca aatcaagtta tcagctaccc tacttatgga | 7080 |
| tatacacctc tcataaaatg atggtaagaa gtttcgatat gtcacattaa cataagaact | 7140 |
| tcattcagtt agggtacaac gaagttaagt agttacggaa ataccattcc aaatctcaac | 7200 |
| atcctctggg agcttttggt aaacaggagt ggcagaccag acaaagtaac caccagggcg | 7260 |
| taacaagcgg ttcaattcca gcaaaagcat gccacctaaa agtagcgagc cagcaataag | 7320 |
| attcagttct atagcaaatc aataaatgaa aggaggacat gtcaatatgt aaccagcagg | 7380 |
| acaaaccttc gatgtgccaa ggga | 7404 |

<210> SEQ ID NO 36
<211> LENGTH: 1788
<212> TYPE: DNA
<213> ORGANISM: Zea mays

<400> SEQUENCE: 36

| | |
|---|---|
| aatcccagcg tgcgtaatct attgcccaca tgccgacgcc gtcgcacctc aacaagaacc | 60 |
| cgcgctacct ggacttccgg gcggcgcggc gggtgccgga gtcgcacgcc tggccgggcc | 120 |
| tgcacgacca ccccgtcgtg gacggcggcg cgccgggccc cgacgccgtg ccggtggtgg | 180 |
| acctgggcgc gcggacccg gcgcggcgc cggcggcggc ggtggcccgc gccgccgagc | 240 |
| aatggggcgc gttcctgctc acgggccacg gcgtccccgc ggacctgctg gcgcgcgtgg | 300 |
| aggaccggat cgccaccatg ttcgcgctgc cggccgacga caagatgcgc gccgtgcgcg | 360 |
| ggcccggcga cgcctgcggc tacggctccc cgcccatctc ctccttcttc tccaagtgca | 420 |
| tgtggtccga gggctacacc ttctcgccgg cctcccctcc gcgccgacctc cgcaagctct | 480 |
| ggcccaaggc cggcgacgac tacaccagct tctggtacgt tgcgttgcgt gcttgtgtgc | 540 |
| gcgcacacct gccgaccgcg gccacaccgt acgcaaccca cgcgtacgta cgtgcgctag | 600 |
| ctacctgctt cgctcgcttc gctcctctcg cctcgccatg catatgcacg tacggccgta | 660 |
| caggtacagc agcaggtcac acgcacgaac gcacgcacgc accagcaccg atatgataca | 720 |
| tcatcgacgt gtcgtccccc cgtctaaggc catgcatgca tgcaagcacg cctagctagc | 780 |
| ccttttggct tgctagctga cgaggggagc taggacgagc atacttactg tgcgcgtcat | 840 |
| gctcaattgc tcacactata ctactacttg ttactacagt gatgtgatgg aggagttcca | 900 |
| caagcacatg cgcgccctcg cggacaagct gctggagctg ttcctcatgg cgctggggct | 960 |
| caccgacgag caggccagcg ccgtcgaggc cgagcggagg atcgccgaga cgatgaccgc | 1020 |
| caccatgcat ctcaactggt gggtatatat tattgtctgt catgttgtcg tcgtcgtacg | 1080 |
| cgttgcggtt gggtgtacat gtatataaca caaacaacaa aaaactaacg ccgtgccgac | 1140 |
| gacgacgacg atcatcaggt acccgaggtg cccggacccg cggcgcgcgc tggggctgat | 1200 |
| cgcgcacacc gactcgggct tcttcacctt cgtgatgcag agcctcgtgc ccgggctgca | 1260 |
| gctcttccgc cacgccccgg accggtgggt ggcggtgccg gccgtgccgg cgccttcgt | 1320 |
| cgtcaacgtg ggcgacctct tccacatcct caccaacggc cggttccaca cgtgtaccca | 1380 |

```
ccgcgccgtc gtgaaccggg acctcgacag gatctcgctc ggctacttcc tcggcccgcc    1440
gccgcacgcc aaggtggcgc cgctgcgcga ggccgtgccg cccggccggg ccccgcgta     1500 ccgcgccgtc acgtggcccg agtacatggg cgtccgcaag aaggccttca ccaccggcgc    1560
ctccgcgctc aagatggtcg ccctcgccgc cgccgccgac ctcgacgacg acggcgacgc    1620
cgccgtcgtc catcagcagc agcagctagt cgtctcgtcg tagccgagac cgatcgccgg    1680
agactgatgc tgatgatgat gcatatatac atgagagaaa tcgtcgagta gactagccga    1740
ttgcaaaagc aacccagct gccgaaacct ggcatatcga tcccattc                  1788

<210> SEQ ID NO 37
<211> LENGTH: 1698
<212> TYPE: DNA
<213> ORGANISM: Zea mays

<400> SEQUENCE: 37
cgtgccgaga gtccttcaaa gccgacgacg agacgacgat gcagtcgtcg tcgtcatcag      60
cctcgacgcc ggctgccgct tccggcctcg tcttcgatct cgggtctgcg gcgggcgtgc    120
cggagacaca cgcgtggccg ggggtgaacg agtacccgtc ggtggagtcc gctggccgcg    180
acgtggtccc ggtggtggac atgggggtgg cctgcccgga cgcgacgcgg gcgttggcgc    240
gcgccgcaga cgagtggggc gtgtttctgc tcgtcggcca cggcgtgccc cgggaagtgg    300
cggcgcgtgc cgaggagcag gtcgcgcgcc tgttcgtgct cccggctcct gacaaggccc    360
gcgcggggcg ccgccccggg gagcccacgg ccaccggcta cggcaggccg cccctggcac    420
tccgcttctc caagctcatg tggtccgagg gtacgcgtt ccgcgccgcc accgtccgcg     480
aagagttccg ccgcgtctgg cccgacggcg gcgacgacta cctccgcttc tggtacgtac    540
gagcgccatg tcacgtgctt gtgctttcat gcctcgtacc gtcgtcgtgc tgtacgtgtt    600
atgtttatcg gccggtacgt cacgcgtgct acactggtta acgacgtgag cgtgcccacg    660
ttgactgcat gcatgtgcat gcgcgcgccc agcgacgtga tggaggagta cgacagagag    720
atgagggctc tcggtggcag gctgctcgac ctcttcttca tggcgctcgg cctcaccgac    780
gtccagttcg ccaccggcga gacggagcgg aggatccgcg agacctggac ggcgacgatg    840
cacccaatcc tgtacgtacg tcaaaaacga atatctgacc aatgcaaacg ttttctgca    900 atgccagtca tccactcatc ctgtacgtac ctctggactc tgcttgtcca tctactgatg    960
acacgtatgg taggtaccc aggtgtccgg aaccggagcg cgccatcggg ctgacggcgc   1020
acacggactc gggcttcatc acgctcatca tgcagagccc cgtgcccggg ctgcagctgc   1080
tccgccgcgg gccggaccgg tgggtgacgg tgccggcgcc gccgggcgcg ctcatcgtca   1140
tgctcggcga cctgttccag gtgctcacga acggccgctt ccggagccct atccaccgcg   1200
ccgtcgtaag ccgagagcgc gagcggatct ccgtgcccta cttcctctgc ccgccggagg   1260
acatgacggt ggcgccgctc gcgtccgctc tgctgccggg gaggaaggcc gtgttccggg   1320
ccgtgacgtg gccagagtac atggaggtca agcacaaggt gttcggcacg gatgcgccgg   1380
ccctggagat gctgcagctg caggtggatg aggaagaaca aggtgaaagg gccgccacca   1440
cctaagccct aaggaactac tagctgaatc cataaactaa taagaattc gtgaataagg     1500 gcgttggaag actggacaca acacaagaga gttgctatat atcgtatttc tgaaatttaa   1560
ggcaaatatc ttagttaaaa aactggtata tttaaataga caatatatat ctaaaataaa   1620
gatagttcac catttttacg gtcgaacaat gataaagtta tatattgtct gaatagtaac   1680
aaattaaaga tttccagg                                                 1698
```

<210> SEQ ID NO 38
<211> LENGTH: 4095
<212> TYPE: DNA
<213> ORGANISM: Zea mays

<400> SEQUENCE: 38

| | | | | | | |
|---|---|---|---|---|---|---|
| cggtctaagt | gaccgtttga | gagaggaaaa | gggttgaaag | agacccggtc | tttgtgacca | 60 |
| cctcaacggg | gagtaggttt | ataagaaccg | aacctcggta | aaacgaatca | ccgtgtcatc | 120 |
| cgccttattt | gcttgtgatt | tgttttcgcc | ctctctttcg | gactcgttta | tatttctaac | 180 |
| gctaaccccg | acttgtagtt | gtgcttaaag | tttgtaaatt | tcagattcgc | cctattcacc | 240 |
| ccctctaggc | gactttcata | taaatattgg | gagaaatatg | aaaacaaat | gaaggtcgaa | 300 |
| cgagtcagag | acaccataaa | aaagaggtcg | tcttaactag | ggtgctaaac | ctcaacattg | 360 |
| tagtagatct | tagtactgag | tttgacatct | ttgacaccaa | caagatggtg | atacgttact | 420 |
| ttctacgtta | acttgggtag | gtatatcgac | tatagtggcc | tataacacta | ggctatgtaa | 480 |
| tatgatattg | tgttgagtct | ttataaacat | gattttttt | aaaaaaaga | gctaaaataa | 540 |
| aaaatagaaa | tcgacggtac | gatgcaagtt | cttctcaaga | caaccaaacg | caccccttgcc | 600 |
| cctttattga | aattgaagta | tgtgcttat | caaatgttta | aatactaatt | ataagtatta | 660 |
| aatataattt | aattataata | ctaattatat | agataaagac | taaataacaa | gacaaattta | 720 |
| ttaaatataa | ttaattcatt | attaacaaat | acttaatgta | gcacgatcga | atcatggact | 780 |
| aattagtctt | gatagactcg | tcttaccatt | taatcataat | tagttttgta | tactgtttat | 840 |
| aatatttcta | actagctagt | attaaacttt | tgatgtaacc | taactaaagt | ttagtcacgc | 900 |
| caatacataa | ggactcggat | cgttcgatca | cccatgacat | cacgtatact | aagagcatct | 960 |
| ccaaaagctc | tccagaagtc | tcccctaaat | ctattttttt | gggaaaaaca | caaaaacatg | 1020 |
| tctccaacag | ttcccttaaa | gcgcccccaa | cttttttcata | gcccttaaaa | ctccctcatt | 1080 |
| tgtagctaca | aatgaggggt | tttttgggct | ccccagaaac | aaactgttga | tttaagggat | 1140 |
| ctgttggaga | aaggattaaa | atttaccctc | acttattatt | tagatgtccc | ttaaaactga | 1200 |
| ttttgaggag | tcgttttatg | tagagctctt | ggagatgctc | taacacaccg | agcacaaccg | 1260 |
| catcatcaat | caaaacaacc | caagtttgt | tcggtacaag | tcatcagcct | gtgtacacac | 1320 |
| atcagcctcg | gccccgggag | aagcgctagc | aaacaaggtt | cacctaaaaa | tccatccaga | 1380 |
| ttcattgaat | ccaaccagca | caaacgtccc | atttattaat | cacctcatca | caggtccccc | 1440 |
| cagcctcact | ctcgcgccgg | ctcaaggtac | attgcgtgtc | ctagccaaga | cacgcagctc | 1500 |
| atctcagcct | cacacgcaca | gcaagagcga | ggcgtgattc | gccatgggcg | gcctcactat | 1560 |
| ggaccaggcc | ttcgtgcagg | cccccgagca | ccgccccaag | cccatcgtca | ccgaggccac | 1620 |
| cggcatccct | ctcatcgacc | tctcgcctct | ggccgccagc | ggcggcgccg | tggacgcgct | 1680 |
| ggccgccgag | gtgggcgcgg | cgagccggga | ctggggcttc | ttcgtggtcg | tgggccacgg | 1740 |
| cgtgcccgca | gagaccgtgg | cgcgcgcgac | ggaggcgcag | cgagcgttct | tcgcgctgcc | 1800 |
| ggcagagcgg | aaggccgccg | tgcggaggaa | cgaggcggag | ccgctcgggt | actacgagtc | 1860 |
| ggagcacacc | aagaacgtga | gggactggaa | ggaggtgtac | gacctcgtgc | cgcgcgagcc | 1920 |
| gccgccgccg | gcagccgtgg | ccgacggcga | gcttgtgttc | gataacaagt | ggcccccagga | 1980 |
| tctaccgggc | ttcaggtgac | gaaattaact | atatatccct | ttcgatcata | gttgcgttaa | 2040 |
| taaattaagg | gaatcgtgag | cgtacgtacg | taagtttccg | cagagaggcg | ctggaggagt | 2100 |
| acgcgaaagc | gatggaagag | ctggcgttca | agctgctgga | gctgatcgcc | cggagcctga | 2160 |

```
agctgaggcc cgaccggctg cacggcttct tcaaggacca gacgaccttc atccggctga    2220
accactaccc tccttgcccg agccccgacc tggccctcgg cgtggggcgg cacaaggacg    2280
ccggcgccct gaccatcctg taccaggacg acgtcggggg gctcgacgtc cggcggcgct    2340
ccgacggcga gtgggtccgc gtcaggcccg tgcccgactc gttcatcatc aacgtcggcg    2400
acctcatcca ggtacgtgcc cacctgatga actgagctga acgtaggttg catgcactgc    2460
atgtgtatag gcttctcaga tcgcttcgtg tggcgtaagg tgtggagcaa cgacaggtac    2520
gagagcgcgg agcaccgggt gtcggtgaac tcggcgaggg agaggttctc catgccctac    2580
ttcttcaacc cggcgaccta caccatggtg gagccggtgg aggagctggt gagcaaggac    2640
gatccgccca ggtacgacgc ctacaactgg ggcgacttct tcagcaccag gaagaacagc    2700
aacttcaaga agctcaacgt ggagaacatt cagatcgcgc atttcaagaa gagcctcgtc    2760
ctcgcctaac tactgctact gctaggatcc atgccattgc catgtcgtct tcagattcag    2820
agcacgccat gtcgtcgcta gcttcgtggt agaacaaata atgatgtgcg tgctgtgtgt    2880
aagcatggat atggatgtga atatgtaata tgatgagcac tcctactttg gtatgtttgg    2940
gaataacaga cttgtgttgg tctggttcat tatttgtaag aaaatcaaaa agagttagta    3000
gggcaggagg ctaaccacag tcatgctgca ccacatccct ggtggaaagc tggccggggtt   3060 acgctacgct cgtgcagcca gattactgca gggccgggat atgcttccgg tggaaggaag    3120
gggacggtgg ctgaggacca tggggctgga gcctgggaga gaggtcgagc tagaagaaag    3180
ggggagagag aagacgcaca acgaagatgg gtcagccagg gatttcgacc caaggggggag   3240 ctagtggatt tgggagaaa acagaaaaga gaaagagaa aagaagaaaa atttgttggt     3300
gtgaacacaa ggttgatttg tcttttctta tttggattga tgatgagtcg tggactaacc    3360
gacccgtgag ctattgtgtc gtataatcat gtctctcggt ttctggtgtg caggtttgaa    3420
gcacagagac ggtggtcgac gcaaaggtga acgtcatgca ggttcgtgcc gatggaccgg    3480
gagcagtgaa agacgagcgt tgggacttga acaagggacc agagtcgccg gatgactagc    3540
cgcagtggct gacgcctgga acacgcatag acgtgaggac gtggtagagc aggtgaaaat    3600
cgcctagagg ggggggggggt gaatagacaa aacctaaaaa ttataaactt tgaacacaaa    3660 cttttacctga ggttaccgtt agaacgagta ttaatgaaat cggagtgcgg aaggcaagtt    3720
cttcttgcta cgagttgctt aatcaatatt gataactttg ggagtcaact caaaatgatc    3780
acaagcaaaa gaactagaga gagaggagag gaagaatcaa ctcgcaaagt aatgatcaac    3840
acaaatgaac acaatgattt atttctcgag gtttggttcc gaagaaccta ctccccgttc    3900
aggagtccac ataggacatg tctctttcaa ccctttctct ctctcaaatg gtcacataga    3960
ctggttcagt tgagagcacc tagaggggggg tgaataggtg atcttgtaaa atcaaacact    4020
aatagccaca aaacttagtt taaagtgtta gtacggctaa gtagctttga agcgagttat    4080
tgtgaacaca acaat                                                   4095
```

<210> SEQ ID NO 39  
<211> LENGTH: 726  
<212> TYPE: DNA  
<213> ORGANISM: Rice tungro bacilliform virus

<400> SEQUENCE: 39

```
tcctacaaaa gggagtagta atatttaatg agcttgaagg aggatatcaa ctctctccaa      60
ggtttattgg agacctttat gctcatggtt ttattaaaca aataaacttc acaaccaagg     120
ttcctgaagg gctaccgcca atcatagcgg aaaaacttca agactataag ttccctggat     180
```

| | |
|---|---|
| caaataccgt cttaatagaa cgagagattc ctcgctggaa cttcaatgaa atgaaaagag | 240 |
| aaacacagat gaggaccaac ttatatatct tcaagaatta tcgctgtttc tatggctatt | 300 |
| caccattaag gccatacgaa cctataactc ctgaagaatt tgggtttgat tactacagtt | 360 |
| gggaaaatat ggttgatgaa gacgaaggag aagttgtata catctccaag tatactaaga | 420 |
| ttatcaaagt cactaaagag catgcatggg cttggccaga acatgatgga gacacaatgt | 480 |
| cctgcaccac atcaatagaa gatgaatgga tccatcgtat ggacaatgct taaagaagct | 540 |
| ttatcaaaag caactttaag tacgaatcaa taaagaagga ccagaagata taaagcggga | 600 |
| acatcttcac atgctaccac atggctagca tctttacttt agcatctcta ttattgtaag | 660 |
| agtgtataat gaccagtgtg ccccctggact ccagtatata aggagcacca gagtagtgta | 720 |
| atagat | 726 |

<210> SEQ ID NO 40
<211> LENGTH: 165
<212> TYPE: DNA
<213> ORGANISM: Rice tungro bacilliform virus

<400> SEQUENCE: 40

| | |
|---|---|
| acgaatcaat aaagaaggac cagaagatat aaagctggaa catcttcaca tgctaccaca | 60 |
| tggctagcat ctttacttta gcatctctat tattgtaaga gtgtataatg accagtgtgc | 120 |
| ccctggactc cagtatataa ggagcaccag agtagtgtaa tagat | 165 |

<210> SEQ ID NO 41
<211> LENGTH: 2000
<212> TYPE: DNA
<213> ORGANISM: Zea mays

<400> SEQUENCE: 41

| | |
|---|---|
| ctgcaatata tacaccaaaa gtattataaa ctgtcatata tatgaccaaa acctttttat | 60 |
| tttagaaaag tatattaatc atggtatatt aatcaaagtt gttgttgggg ctgcaaaaat | 120 |
| cataccctttc ttccacaagc tgttccttga actgcaggta ctcaggaact ctcagctcct | 180 |
| caacagcgag ctcactgacg ttgaccctca catactccca gacaccaggc ctagggcgga | 240 |
| tggcaagtgc aacccatggg gggatgacaa tcgcctcctg taagataata gagctagaat | 300 |
| gattaaagaa ggtgcacact acaaaaggaa cagtgctgtc cagcgagatc tgaatctgat | 360 |
| gcaaacctga gctgccctca ggacatcctc aaaagcacca tccttgagct tctcgcgctc | 420 |
| agcctcaggg atcgcattgt tgtactcggc aatgatctgg tggggctgca gcataccctt | 480 |
| tccaaggttt ttcagcctgc gcaaaacgat gtgccaaata acatcagact atgccagatc | 540 |
| tataaactca tcaaacatat acaattcaa gaaatagttt agacgtatga tcagcagtca | 600 |
| gtagcgtggg aacatatgca acatagcgaa gaggcacaac agcaaattca ttcgaaaaaa | 660 |
| tgaaaacaaa gattcctctc ttttaactga acttctcgaa accccttca tgcctacaca | 720 |
| tccgatctag tcagatgcct atgcgttcat gctgaacaga acgtgtcaga actaagcata | 780 |
| aactggttag caagcattat cgtattcgat agacccttta gtaacaagct atacattggg | 840 |
| taagttcaga ctccaatcat tctgttcaga aacatcgtat tgaatataaa actaaagaac | 900 |
| acacatgcag gtgcagccag atctaacagc agtttacagt cggtactaaa aaaagcatgg | 960 |
| tgtatgtatg tatcatcagt atccagtact aggtttcgac aaaatcctgg atgctaatta | 1020 |
| aatactcatc ttattaggga acacaggaac attatgtcta cagcattgaa tgatggccac | 1080 |
| atcatgctag atctaacaat acataatatg atggaactgg tcttaaaaag tcgcattcgc | 1140 |

```
tcaaataata cccgtagcaa aataaatgta aacttgcaga cgaagcgggg gaaatgaggg      1200
cagacctggt gaagacggcg acaagctcat tggggtgggc agagagtgag tcgccaatgc      1260
gctccctgac gctgtggagg cggctcagga cacggtcacc tgcaccttcc cccattgctg      1320
tcctcttcct ggatcctcag gcctgcacag cgaaaccgaa acggaagcgg aagcttcagt      1380
cagcagagaa aactgaaacc gaaaacggt tcagatccgt tgacataaaa gctgcgatga      1440
catcctaaaa ctaaaacccc tccagcaaga cataaaccca actgccaaca accagtcttt      1500
taagtctcga cacacccttg acgctgcgcc acgaaactat attgcaggca agaaaccaac      1560
agaacctaac tctggaaggg gggaaagaaa cggcagacag gagcaagacc caaaaaaaaa      1620
cgactcagat cctggtacta tagtcctagt acctagacca gaaagaagaa acaaccaata      1680
caacaagagg catacaagaa ctgaatcgat gaactgaaac gcttcagagg accgaggaat      1740
ggcggagaag ggaggcgcct atttatacag atctgacgag agaaccgaac aaaaacacat      1800
cgatgggaac catggagaag aaaagggctg gccgcatggc accatggcc tcggcctcca      1860 aaaagccgtt gaatcaaag caggcgagga cgaagcgtga cgcggcaggg tacttctcta      1920
gaaaagcacg gcatcagcaa ggtgggggg ctggggttcc ttattgcagg caatcacgag      1980
gtgattagca caaacggaag                                                  2000

<210> SEQ ID NO 42
<211> LENGTH: 2000
<212> TYPE: DNA
<213> ORGANISM: Oryza sativa

<400> SEQUENCE: 42
ctgaaatata catcagagat attacaatga catatatatc gataaaagaa aaataataaa       60
attaagtttt aaattttaag aatatatgtt tttagtatcc caattatgca gatttcatac      120
ccttcttcca caagctgttc cttgaactgc aagtactcgg ggactgtcag caactcaaca      180
gcgagctcgc tcacattgac cctcacatac tcccagacac cgggcctcgg gcggatggca      240
agggcaaccc atggggagat aacaatcccc tcctgcatga taaaaacaa ttacaagtta      300 agttagagca agcggtagag taaagatgga tctctgtgat gcaatgaaat ctgaatctga      360
ttcaaacctg tgcactcctc aggacatcct caaaagcacc gtccttcagc ttctcacgat      420
cagcctcaga gattgcgttg ttgtactcag caatgatctg gtgggcctga agcattccct      480
ttccgaggtt aaccagcctg cgcaaataac agtgtcaaca aaaatatcag gccagatcta      540
tcaactcagc ctataaatat tcaataaga taatttttagc acttgagcat ttgcgcataa      600
taagaaaatt tgctattagc cacttaaaaa gaccatatat gatctgtttg cattgagatg      660
aattaaaaat ttcattgtag atatgaaatg attagttttg accatttaat tggacttaat      720
gaaatatgcg cgataatcag atctacgcgc tcgcgccaat agatctagta agatgtaggt      780
tttttatttt ttttgtgaaa ctttgctacc acaacaagca tctgtaccag tgcagaattc      840
attacttgta ttcagtttgt aaaccgtata tataatataa ataacatgca catgcagtca      900
gatctagcac taccagtcca cagtaatcca aaactacatt tgtatatttc atcattattc      960
agtagtacta ggtttgtaca aaatcttggc tgcagaaggc cgcacttaaa tattcattct     1020
aatcagaaac ttaaaaaaaa agtgactaca aaatgattgc atccaattca gtaaatatga     1080
gccattcctg gccagatcta acaatctcaa caacaaagat cctatatgaa catctccttc     1140 taaagaaaa tacagtaaca tctgaaggca gtagactaga aaccaacaaa atctaatgct     1200
gggaaatcac taaatcagca cgaacctggt gaagacggcg acgagctcat tggggtgggc     1260
```

```
ggagagggag tcgccgatgc gctccctgac gctgtggagg cggctcagga cgcggtcgcc    1320
ggcagcttcc cccattgctc tcctcttcct cttggctcct caagcctgcg tgcacaacca    1380
accaccatca tcagatacat ccagacccag tcaacacaat cactccagga aaaaaaaag    1440 tcaagccata aacccccaacc aaaaaccacg cctttgacaa acactggaag aaaaagaaaa    1500
tcgcagcttt ttcacaagca atctagaaga aaagaaaaag aaaagactac atagcagcta    1560
taattgactg agaagcatac aggaatcaaa caatggagaa ggggagggag gaagaacaat    1620
gatgctccag gctgaggacc gaggaactgg gtgaagcggg gtaggcgcgt atttatgcag    1680
atctgaggag agaaaccacc aaaacaatcc gatggtttca acgaaaaaga tcgtcgcttc    1740
ttgctgcacc agctcaccca tagccgttga gatcgaagct aagctagcag cagcaaagct    1800
ggaacgaaga gtgacgcatt caagctcctc tcctctcctc tcctctcctc cggagcacga    1860
ggccagcatg ggatggattg gggtttcttg ttggccatgg caaggagga ggtcattaac    1920 gttgacacgg cgtaatttaa ttaaatctta tcttaaaata tgatttaagt ggtagtaaca    1980
aggaagatta atactatgaa                                                2000

<210> SEQ ID NO 43
<211> LENGTH: 2000
<212> TYPE: DNA
<213> ORGANISM: Oryza sativa

<400> SEQUENCE: 43
gctgtttaag aaaaacagaa gtaaaattca gtcactgtta ttttgcttca gttataatct      60
gcaaatcgtc gttctggtac ttactgtcca tcaacaagct gttccttgaa tgccaagtac     120
tcagaaacac tcagctcttc cactgccaac tcacttacat tcacccgaat gtagtcccag     180
acaccaggcc ttggcctgat ggccagtgca acccagggcg gcagcacaat ggcttcctac     240
atacagtcaa ggaagtaagt tagaaagact ggtatttgac tttgagttga ctatcataac     300
catcctggct cattgccaaa tttacctgag cagcccggag aatgtcttca aagggagcat     360
atttctcttt gtcagcttcg atcaaggcat cgaactccgc aagcagctgg tgacgctgga     420
gcattccctt tccctggtta acatacctgc atagagtgat atttaagaaa tagaaccaat     480
gcttagatct cacatccttt ctgcggctga actatgttaa tggcactacc acataaaacct    540 gatttttact tcttattttt aagaccacat gatctgtact taatctagct atgaacaaac     600
aatatttcaa catcatctaa gattcatgac tcaagacaaa aatgttagag ctcatcacag     660
attattatag ataccatcat taaaactaaa gagatgcata accttgtcag ctaagaattt     720
gtaacatact aacatgttat cgtttcacat ctgggttgac taagaactaa ccaactgtat     780
ggataaaatc attgaaaact caaaacaatt agtagcaggt tccaagaaga cacaagatat     840
tatattgaga tcttcaccta gaagagtg caatcaactc attgggatga dacgagaagg       900
tggcaccgag gcgttcgcgg agactgtgga ggcgagctag cttggcagcc atgactcaat    960
ttcaggaact gcaaagaaag gttacactta gcaacacgta ccaaaaccac tcacttgcac   1020
aagaataatt agtcaacagc catcactaag cattgcaaga ctatctctga acaggaaagc   1080
catgctaaat caaacactaat aacatcacac aaaagcattg gaagatcaaa acataactaa  1140
aaacagctgt ttcatctaca caactgaaag catctatggt ttacgaagca gagtgcgagt    1200
actgattcaa aataaatcaa cctgaaccaa tatactctga caatgttttc aaagggataa    1260
aagaaccagc tttatcaaat ggatttgttg ggttttagta agtatcattg agataccgat    1320
ggcatatctc aaactttgca aaattataat ggcatggttc caaattaccc tttagtatta    1380
```

-continued

| | |
|---|---|
| gcaccagtta gatcctaatt cctaaatccg ataggacaga gcgaaagatc cctggagata | 1440 |
| tgaagatttg gctacagatt aagcagagcc aacatgaagt tccgaatatt atgaatccgc | 1500 |
| aagcggggag atcaaagaga agaatacgga aggtcgcgac tccatgaaag aatccaacca | 1560 |
| aaaacccaaa gattttctc agttcaaaaa aaaaaaccc ttcatttttg gttcgccatc | 1620 |
| caccgacagg caccaagaca ttcctcagga agcaaaaaag attaagcaga acaagtgata | 1680 |
| agcaagacac agtatcaacg gactacgagt cgagaaaatc actgaggcgc gattcttact | 1740 |
| gcaccaagta aaaaaaaatt tgggggcaaa aagaactctg caatggggcg gagcaacgtg | 1800 |
| gcagcaaaac taaggtcga ggatttgagg ttttttgccg gttttcctcg aaaccccgaa | 1860 |
| tccgctcata gtaaacccac taaactgcag cagaaacccc cctcttggtt cagatttacc | 1920 |
| gaaagcagta aacccaagaa catgtcagca aaaactcctg caagattcag ctgacgaccc | 1980 |
| accaaagaat cgcaagaaat | 2000 |

<210> SEQ ID NO 44
<211> LENGTH: 2000
<212> TYPE: DNA
<213> ORGANISM: Oryza sativa

<400> SEQUENCE: 44

| | |
|---|---|
| tggcggacgc gccacgcaca aacacaaacc tgcacacccc tgtgtcagag gaggagaggc | 60 |
| caagaaagga aatcgagtgg aggaagtgag gagcggcgga gacgtaggag gaggagggg | 120 |
| agatggaaat ggaaagccgc gcgagagagg aggcgcgtgc tggatgggag gaggaggagg | 180 |
| aggtggtggg tttgtgtttg gagagacgag cgagagaggc gaagcattta aaggaggaa | 240 |
| gaggggggaga gagagagaga gagagagaga gagagagaga gagagagaaa ggaggaatat | 300 |
| aataaagggt ggtgcacctg ccaactgcta tgctcaccaa cactttgtac acacccagtt | 360 |
| acacccccct gcctttatta tttccagtgc agtaataact tcaacaatta ttgaaatgaa | 420 |
| aatggaatta atggagttag tatcggatta gcgacacgct tgccgagctt ctagacggtg | 480 |
| cgattatttc agcgggaacg acttctgta ggtgaattta atagaggagt gttttaaatc | 540 |
| cactcgacgt tgtaatagct ggtttaattc gtttgtactg tcgagtagtt atccaaaatc | 600 |
| aattttggat atttaaaaga aaaaaaaaca gatccgaagt attggaccta ctggcaaata | 660 |
| ggaattttgc tatatatagg tgtgcgttca tttataatgg agtagcatgg agttttatta | 720 |
| atccagtaaa tgttttcatt gatttaatta atataacgaa tttcgcttga ggccatattt | 780 |
| gttaaacgct tttatctcta tcatcattca tcctaccagt aaagagcacc ggagatcgca | 840 |
| cttcatttaa atatatgtcc atgttggata aaccatagtt tattatagtg ttctttttata | 900 |
| tgttttgtgg ggaatttaga ttgtttaata tggcatacat atccatccat cattattata | 960 |
| ttctaacaca actggataag tgttctaaac tattgtagaa taactttgta gtatgatcga | 1020 |
| tcttgtggaa taaaaaagt ctgacaataa cctttcataa aggaatatga ataccgtaa | 1080 |
| tcaacgcatc aaatcattca cggtgtacgc ctagcgaatt cgttggcgag tgctcgtgcg | 1140 |
| gccgtgggct cgctgtgatg catgcatggc tctctggcta cgtcgagata gcgattagta | 1200 |
| gcaaaattaa gcaagccact tattaattaa tctttggaga tatcatatga ttaaggcatt | 1260 |
| aattcgtacg tactcgtcgt cagcgttttc tgcaaagtcc actacagttt tttctttctt | 1320 |
| tgctgaaaat gctgatgtgt tggagatgga gtgacgtgca caacctgccg ccacgtggat | 1380 |
| ggttgctgga gcctacgtgt catcttaatt tgaacaaaaa aaaagagga ataatacatc | 1440 |
| aatacatttt cgaatttcag ttctgccatt gaccagtaat acacatgtcg gcctcacatt | 1500 |

```
ttaccctgat cttagtaacg ggtggtcgcc tggtcggtca ctgaaaaaag ttcaggaaat    1560
tatagtcaaa ctgaaacgaa catattcact ccttaaaaaa actaaatctt tttatatatt    1620
tgtgatattg taaaatagct acgggataat gatatagata tatatagtga taagggatag    1680
atggatcgag atatggagtt gtgctttctt taatttccac tacttgggct accatattat    1740
ggtagttggt atgaaaagat acacagcagt atagtgatgt gatcaatgac atgtatatct    1800
cacatgctcc catgttggag tcaaattttg ctagactaaa atccaattcc aagcagtccc    1860
tagccaagaa caaacaaaat tcagtgaggt cactgctgca ccaaggactg catgcatgca    1920
ggagaagggc atttctctt ttttctttg gagactcgat tcaattcggt cggtcggtcg    1980
caatggtcag cttaattaaa                                                2000

<210> SEQ ID NO 45
<211> LENGTH: 2000
<212> TYPE: DNA
<213> ORGANISM: Oryza sativa

<400> SEQUENCE: 45
tgtgaaaggt ggcggcacca gcttagccgc agcttctctc gtcgtctccc tgaaacgaga      60
gggaggaagt tggtagcgtg atatatttag gcatgtcatc tcttgtataa gaagtcttat     120
ctgtgctaat tcacacggtt ctctaatctc tctccattct gttttttgtaa attggttcag    180 tagatagcgt agggttatgc ttatatatac tccgtgaagt atatatttaa aaattagtca     240
cacgtaaagt actatacatg ttttatcgtc taataacaat aaaaacacta atcataaaat     300
ttttttaaat aatacgaatg gttaaacgtt gaatatgaac cgtgcaaaac tatatttatt    360
ttgtaacaga gaaaatattt cacattaatt agattgttgt tttatggaag gttggagagc    420
tgcgccgccg ttgcgcagac ctaggaggct gcttataagt tataatcaat caattcacgg    480
atgccggctg ggacgcggcc catcgtccgg gaagacgaca actcaacgca aaaagccgat    540
atgcctccaa attgccattg ccacctctac ggctgtttat actgctccaa atcaaaagcg    600
tccatggaag aatctagtat ttcccgcaaa gacgatgatg atatgcagga ttggatatat    660
agggggttgt tgcatgattg ctagaactcc cgtttccgaa gttgttcgtc catttttaaa    720
gctgccaaat aggaatttat tttgttttca agtgtaatag agttctgtcc agatgagtga    780
attataattt ggttcacatt ttatttgcta agtttcagtt tgaacattct caaataactt    840
ttttcttcac ttttttaaccg agtaacttag ttattttttc cgtttggacc acccaacaat    900
ttgttgctaa gtgcatctca cccgtcaaat aattcctttg aatccaaatt caattatatc    960
ccaaaaataa aaaacttctg aattccacat caattcaaac cccaaccatt ttaatttctc   1020
tccatatttt ccatttctct attttttacct ttctctttt tccatctatt tattttttc    1080 cttttctatt tctttctttc tccttccttt ctctgtttcc ttcttcttct cctcggctag    1140
gcccgagcca gccgtgccg cctcgcgcca accctgtgcc gccttacgcc gcgcttgcgt    1200
gcgctcgcgc ccacctcgtg cccaacccgc gcacgccaca cgcacacacg aggacgatcg    1260
acggacgaat gcaatcatat ccccttcctt actcagctag aaggctcaag aaccgcaact    1320
ttgatctctt ccaccctctc aaatccgccc caaccctgc tgactcaatc gccattaccg    1380
gaggaaaaat ccccgaaacc ctattaccgg cgccactaac agagctccaa aattcgtcgc    1440
ataattcgaa aatattctga aattgaaggt aaaaatggaa tctacatgcg aagtactccc    1500
tttcccctcc aatccgtcac tggaacgccg ccggcgccgc ctcccgctgc cactgccctg    1560
tttggccgcc gacagccgca cggcgcgccg ctgctccagg ccgccctagc ttcaaccacc    1620
```

```
gccacctttg gctccgcctc cctcctctta tgctcaccaa gcccgcctcc ctcgccggag    1680
atcgccggaa ccaccgccgc catggccgcc accgcctcct gcttctggcc gccgccgcca    1740
gcctcgccac cggcgcctat gccaccgccg accacggaaa cggagtccct acaccttggg    1800
gaccacaaaa ccggcggcat ccctcccaaa accggcctcc tccaccgccg gcgttcgtgg    1860
gattccggcc agttctgtgc agagcgagag aagaagagga aaaatagatt ttcctattga    1920
aagataaatc agaaaattcc tttttctttt cctatcaagt tgaccatccg tttgacctca    1980
aaatcaaaat ctgagaccta                                                2000

<210> SEQ ID NO 46
<211> LENGTH: 786
<212> TYPE: DNA
<213> ORGANISM: Zea mays

<400> SEQUENCE: 46
gacatggagg tggaaggcct gacgtagata gagaagatgc tcttagcttt cattgtcttt      60
cttttgtagt catctgattt acctctctcg tttatacaac tggtttttta aacactcctt     120
aacttttcaa attgtctctt tctttaccct agactagata attttaatgg tgattttgct     180
aatgtggcgc catgttagat agaggtaaaa tgaactagtt aaaagctcag agtgataaat     240
caggctctca aaaattcata aactgttttt taaatatcca aatattttta catggaaaat     300
aataaaattt agtttagtat taaaaaattc agttgaatat agttttgtct tcaaaaatta     360
tgaaactgat cttaattatt tttccttaaa accgtgctct atctttgatg tctagtttga     420
gacgattata taatttttttt tgtgcttaac tacgacgagc tgaagtacgt agaaatacta    480
gtggagtcgt gccgcgtgtg cctgtagcca ctcgtacgct acagcccaag cgctagagcc     540
caagaggccg gaggtggaag gcgtcgcggc actatagcca ctcgccgcaa gagcccaaga    600
gaccggagct ggaaggatga gggtctgggt gttcacgaat tgcctggagg caggaggctc     660
gtcgtccgga gccacaggcg tggagacgtc cgggataagg tgagcagccg ctgcgatagg    720
ggcgcgtgtg aaccccgtcg cgccccacgg atggtataag aataaaggca ttccgcgtgc    780
aggatt                                                                786

<210> SEQ ID NO 47
<211> LENGTH: 1160
<212> TYPE: DNA
<213> ORGANISM: Zea mays

<400> SEQUENCE: 47
atgtgctggt gccccataag gtaggcacct aggtctgtgt ttgaagcatc gacagatttg      60
taaacatgtt cctatgaacc tatttctgat tgataatttg tcaaaactca tcatttgtct     120
tcatccttgc ctgcttgcgt tcacgtgaca agtacgtgta atgtcttcgg cctttgctgt     180
gtatgtttcg cattgcttag atgtggtgaa agaacatcag aagatgcatt gatggcgtgc     240
ttaaaccagt gatgtgctcc aggtgttcct gcagtctgca gagatattta ctcttgtagt     300
cttgttgaca gcacagttgt atgtgatttc ttggatgtaa tgtaaaccaa atgaaagata     360
ggaacagttc gtcctcttcc gtatacgaag gtcactgtat catttgtcgt ggcacaagat     420
gatctgcagg caggactgca acatggtttc ttggactgtc ctgaatgccc gttcttgttc     480
tttagttgag ccagagcagc agcctggtgt cggtgcctga cctgacga agcacacggc      540 aaacaaacaa gtcgcagcag ctagcagggg cgttgccatc gccacaagcc cccaagagac    600
ccgccgagga aaagaaaaaa aaactacggc cgccgttgcc aagccgagcg tgcgaaccga    660
```

```
tccacggatg ggagatcaga gatcacccac cgcaggcggg cggcagtggc tggcgaggtg      720
cgtccacaga acctgctgca ggtccctgtc cgtcccggcg acccctttc taggcgagca       780 actccccatg gcagagctgc acgcagcagg gcccgtcgtt ggttgcagct ttaacccttt      840
ttgttttaac catacaatgc agagtcgcag aggtgaaaca ggacgaaat tacagaaaag       900 atggtggtgt gccagcagcc ccagcatgaa gaagatcagg acaaaagaaa agcttgtgat     960
tggtgacagc aacaggattg gattggagcc aagctaggca gtgagaggca ggcagcaaga    1020
cgcgtcagcc actgaaatcc agagggcaac ctcggcctca caactcatat ccccttgtgc    1080
tgttgcgcgc cgtggttagc caggtgtgct gcaggcctcc tccttgttta tatatgggag    1140
atgctctcac cctctaaggt                                                 1160

<210> SEQ ID NO 48
<211> LENGTH: 1532
<212> TYPE: DNA
<213> ORGANISM: Oryza sativa

<400> SEQUENCE: 48
tagtcctcta atatatgaaa ttttgatata ggtaaagaag ggtattgcaa ggataagaat       60 gtaaaagaa ataagagtaa tccttaccga taatagtatt ccttctctac cgttaaaagt      120
taaacctgtg cgtgtagcat tttaatccag gatctatcga atccgtccct cgttggcgtg    180
ggcgacgaac acgtgcagaa gaagctttcc ccagaaagca cctcaccgcc tcgccgtctg    240
gcagactggc acgcggggcc ctaccctcgc tgcgcctggg cccgtccgcc ttctgcacac    300
tgtcacgccc ccacccgctc gccgcctcgc gcctctctct ccgcctccgc cgcggccgcc    360
cgacgtgata gcgacacgta ggactcgcca aacacaaaaa atccatcgcg attttttggaa   420 ttttgttaca aaccaaatcc cgcattagag atttaatttg atttaattta attacgtagg   480
agtaccagat aaggagatcg agttaaaaaa gctaacggcg cggcgtggtt atctccgaat    540
cggctgtggc tccccgcgtc ggcgtcggcg cggcggcggc gcgccggccg aaccctggcc    600
gtcggatcgg gcgtcgtcct gggcccacg cgccacgggc ggctgtcgtt tgctcctcgg     660
agcggggtgg gcccaccatg gccaccacca caggtcgcgg tcgcggctga cctggcggtg    720
gtcccgtgct cgcggtgttt ttttttttc actctctttc tctcggtgga cagtagcggg    780
ggccgcggcc cgcgggggca gagattgcaa aacagcgga aacggaagat tgcaaaattg     840
caactgcttt cctgtttta attcgggatc aaaaagattc tttcgtcggg gtccccgtgc     900
cattgttgta ttgcgcgtag gtccttgctt gtaaagata atctccttaa ttttttcttt    960
gtactactag tgtatatgca gtaagaatat accatgagta aaatgaacca caaaactaat   1020
tacgatatac cattctcatg tagacgttct ctttttcttt gctagtcata cgtgcatata   1080
taaccaaaca aaaaaatgtt tgaagtactc ctatccaatt tattactcca gtagacaaca   1140
aaagaaaatg tttgaagtaa taactgatcc atggtacagt agggttgtcg tcaatcttgt   1200
gtttctttca ttccattgta cttacaatcg tactccagct agcacagcac aatgggctta   1260
agctttggac cccaaattct gatcttgtcg gggacccgta cgaaaatact cccgtagaga   1320
tgcagatacc gtcacaacct acaaccaacg aatgttaaga aaacaaaggg aaaaaaaaag   1380
aggcgaattc ggaggagaaa aaacggtggc taaaatatag tgcgggtgtg gggacgcgac   1440
gcgagcgacg aaagaggaga gaggatgggt tggcctgccc ccccctcccc tgtctataaa   1500
tgcagaggcg ccgagtgccc tagtcgccgc tc                                  1532
```

```
<210> SEQ ID NO 49
<211> LENGTH: 841
<212> TYPE: DNA
<213> ORGANISM: Oryza sativa

<400> SEQUENCE: 49
tcgaggtcat tcatatgctt gagaagagag tcgggatagt ccaaaataaa acaaaggtaa      60
gattacctgg tcaaaagtga aaacatcagt taaaaggtgg tataaagtaa aatatcggta     120 ataaaggtg gcccaaagtg aaatttactc ttttctacta ttataaaaat tgaggatgtt     180
tttgtcggta ctttgatacg tcatttttgt atgaattggt ttttaagttt attcgctttt     240
ggaaatgcat atctgtattt gagtcgggtt ttaagttcgt ttgcttttgt aaatacagag     300
ggatttgtat aagaaatatc tttagaaaaa cccatatgct aatttgacat aattttttgag    360 aaaaatatat attcaggcga attctcacaa tgaacaataa taagattaaa atagcttttcc    420 cccgttgcag cgcatgggta ttttttctag taaaaataaa agataaactt agactcaaaa    480
catttacaaa acaaccccct aaagttccta aagcccaaag tgctatccac gatccatagc    540
aagcccagcc caacccaacc caacccaacc caccccagtc cagccaactg gacaatagtc    600
tccacacccc cccactatca ccgtgagttg tccgcacgca ccgcacgtct cgcagccaaa    660 aaaaaaaga agaaaaaaa agaaaaagaa aaaacagcag gtgggtccgg gtcgtggggg       720
ccggaaacgc gaggaggatc gcgagccagc gacgaggccg gccctccctc cgcttccaaa    780
gaaacgcccc ccatcgccac tatatacata cccccccctc tcctcccatc cccccaaccc    840
t                                                                    841

<210> SEQ ID NO 50
<211> LENGTH: 1392
<212> TYPE: DNA
<213> ORGANISM: Oryza sativa

<400> SEQUENCE: 50
ctcgaggtca ttcatatgct tgagaagaga gtcgggatag tccaaaataa aacaaaggta     60
agattacctg gtcaaaagtg aaaacatcag ttaaaaggtg gtataagtaa aatatcggta     120 ataaaggtg gcccaaagtg aaatttactc ttttctacta ttataaaaat tgaggatgtt     180
ttgtcggtac tttgatacgt cattttttgta tgaattggtt tttaagttta ttcgcgattt     240
tggaaatgca tatctgtatt tgagtcgggt tttaagttcg tttgcttttg taaatacaga     300
gggatttgta taagaaatat ctttaaaaaa acccatatgc taatttgaca taattttttga    360 gaaaaatata tattcaggcg aattctcaca atgaacaata ataagattaa aatagcttgc     420
ccccgttgca gcgatgggta ttttttctag taaaataaaa gataaactta gactcaaaac    480
atttacaaaa acaaccccta aagtcctaaa gcccaaagtg ctatgcacga tccatagcaa    540
gcccagccca acccaaccca acccaaccca cccccagtgca gccaactggc aaatagtctc    600 cacacccgg cactatcacc gtgagttgtc cgcaccaccg cacgtctcgc agccaaaaaa    660 aaaaaagaa agaaaaaaa gaaaaagaaa aaacagcagg tgggtccggg tcgtggggc       720 cggaaagcg aggaggatcg cgagcagcga cgaggccggc cctccctccg cttccaaaga    780 aacgccccc atcgccacta tatataccc cccctctc tcccatccc cccaaccct         840 ccaccaccac caccaccacc tcctcccccc tcgctgccgg acgacgagct cctcccccct    900 cccctccgc cgccgccggt aaccacccg cgtccctctc tctttctttt ctccgttttt      960 ttttttccgtc tcgtctcgat ctttggcctt ggtagtttgg gggcgagagg cggcttcgtc   1020
```

```
gcccagatcg gtgcgcggga ggggcgggat ctcgcggctg ggtctcggcg tgcggccgga   1080
tcctcgcggg gaatgggget ctcggatgta gatctgatcc gccgttgttg ggggagatga   1140
tggggcgttt aaaatttcgc catgctaaac aagatcagga agaggggaaa agggcactat   1200
ggtttatatt tttatatatt tctgctgctg ctcgtcaggc ttagatgtgc tagatctttc   1260
tttcttcttt ttgtgggtag aatttgaatc cctcagcatt gttcatcggt agttttcctt   1320
ttcatgattt gtgacaaatg cagcctcgtg cggagctttt ttgtaggtag aagatggctg   1380
acgccgagga ta                                                       1392
```

<210> SEQ ID NO 51
<211> LENGTH: 743
<212> TYPE: DNA
<213> ORGANISM: Oryza sativa

<400> SEQUENCE: 51

```
gaattcccgg acctccatgc ctacatcaac taatttgatt ccttgagttt acgtttagtg     60
atatgtctat ttttagagct tgttggggct tcggcctcag ctctagccag ccaaacatgt    120
tctaccaagt accctatgtt ggcatgatat agtgatgcat tataacaata aatgagcgag    180
ggattgctgg ctgaaaaagc tatactagct gcatttggtt atagttaacc gaactattaa    240
ttgcgtgtac aacaaaataa aaaaaatgca tgttgcacat tctttcatta acattatgtt    300
ttggtagtgt gaattagaaa tttgattgac agtagatcga caaacatagt ttcaatatgc    360
ttaagttagt tatgacttta acatatcagt ctccttgata ttttcgtttt agattcgtct    420
ctctactagt gtgtatgtcc accttccata gcagtgaagg gttccattcc atccctggta    480
aaaaaaaatc aaccactact atttatttcc taaaaagcaa aatgataaaa tatcatttt     540 ttaataaaaa taaaaaaatt tggggtaca taattgatgt tgccccttgg gattaacctt     600
aaaaaagggc gaattttcta gggtttggcc aagttttgca atgcaccaaa ttattcccct    660
tgggccggcc gccaccccaa aaaaaacccc aaccccaac tttccattga aggccgggcc    720
cccttaaatc ctcatccccc caa                                           743
```

<210> SEQ ID NO 52
<211> LENGTH: 144
<212> TYPE: DNA
<213> ORGANISM: Oryza sativa

<400> SEQUENCE: 52

```
taaaaagggg cgaattttct agggtttggc caagttttgc aatgcaccaa attattcccc     60
ttgggccggc cgccacccca aaaaaaaccc caacccccaa ctttccattg aaggccgggc    120
ccccttaaat cctcatcccc ccaa                                          144
```

<210> SEQ ID NO 53
<211> LENGTH: 612
<212> TYPE: DNA
<213> ORGANISM: Cauliflower mosaic virus

<400> SEQUENCE: 53

```
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg gaaaagaag acgttccaac cacgtcttca    240
aagcaagtgg attgatgtga tggtccgatt gagactttc aacaaagggt aatatccgga    300
```

```
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaagaa     480 gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga gg                                                        612

<210> SEQ ID NO 54
<211> LENGTH: 837
<212> TYPE: DNA
<213> ORGANISM: Coix lacryma-jobi

<400> SEQUENCE: 54
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180 tagggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaattttt gcgtattcga     360 gaaaaaaga agattctatc tgttttttt ttgaaatggc tccaatttat aggaggagcc     420
cgtttaacgg cgtcgacaaa tctaacggac accaaccagc gaatgagcga acccaccagc    480
gccaagctag ccaagcgaag cagacggccg agacgctgac acccttgcct ggcgcggca    540 tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc cacccctccc agcttccttc gccacat       837

<210> SEQ ID NO 55
<211> LENGTH: 947
<212> TYPE: DNA
<213> ORGANISM: Oryza sativa

<400> SEQUENCE: 55
aatccgaaaa gtttctgcac cgttttcacg tcctaactaa caatataggg aacgtgtgct     60
aaatataaaa tgagacctta tatgtagc gctgataact agaactatgt aagaaaaact      120
catccaccta ctttagtggc aatcgggcta aataaaaaag agtcgctaca ctagtttcgt    180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagat atttttttt aaaaaaaat      360 agaatgaaga tattctgaac gtatcggcaa agattaaac atataattat ataatttat     420 agtttgtgca ttcgttatat cgcacgtcat taaggacatg tcttactcca tctcaatttt    480
tatttagtaa ttaaagacaa ttgacttatt tttattattt atcttttttc gattagatgc    540
aaggtactta cgcacacact ttgtgctcat gtgcatgtgt gagtgcacct cctcaataca    600
cgttcaacta gcgacacatc tccaatatca ctcgcctatt taatacattt aggtagcaat    660
atctgaattc aagcactcca ccatcaccag accacttta ataatatcta aaatacaaaa     720
```

| | |
|---|---|
| aataatttta cagaatagca tgaaaagtat gaaacgaact atttaggttt ttcacataca | 780 |
| aaaaaaaaaa gaattttgct cgtgcgcgag cgccaatctc ccatattggg cacacaggca | 840 |
| acaacagagt ggctgcccac agaacaaccc acaaaaaacg atgatctaac ggaggacagc | 900 |
| aagtccgcaa caacctttta acagcaggct ttgcggccag agagag | 947 |

<210> SEQ ID NO 56
<211> LENGTH: 721
<212> TYPE: DNA
<213> ORGANISM: Mirabilis mosaic caulimovirus

<400> SEQUENCE: 56

| | |
|---|---|
| tggagattca gaaaaatctc catcaacaaa taatccaagt aaggattaat ggattgatca | 60 |
| acatccttac cgctatgggt aagattgatg aaaagtcaaa acaaaaaatc aattatgcac | 120 |
| accagcatgt gttgatcacc agctattgtg ggacaccaat ttcgtccaca gacatcaaca | 180 |
| tcttatcgtc ctttgaagat aagataataa tgttgaagat aagagtggga gccaccacta | 240 |
| aaacattgct ttgtcaaaag ctaaaaaaga tgatgcccga cagccacttg tgtgaagcat | 300 |
| gtgaagccgg tccctccact aagaaaatta gtgaagcatc ttccagtggt ccctccactc | 360 |
| acagctcaat cagtgagcaa caggacgaag gaaatgacgt aagccatgac gtctaatccc | 420 |
| acaagaattt ccttatataa ggaacacaaa tcagaaggaa gagatcaatc gaaatcaaaa | 480 |
| tcggaatcga aatcaaaatc ggaatcgaaa tctctcatct ctctctacct tctctctaaa | 540 |
| aaacacttag atgtgtgagt aatcacccac ttggggttgt aatatgtagt agtaaataag | 600 |
| ggaaccttag ggtataccat tgttgtaata ttattttcag tatcaataaa ataatctttc | 660 |
| agtttatctt atattcattt gtgtgacacc gtattcccat aaaaccgatc ctaatctctc | 720 |
| c | 721 |

<210> SEQ ID NO 57
<211> LENGTH: 352
<212> TYPE: DNA
<213> ORGANISM: Peanut chlorotic streak caulimovirus

<400> SEQUENCE: 57

| | |
|---|---|
| acagagggat ttctctgaag atcatgtttg ccagctatgc gaacaatcat cgggagatct | 60 |
| tgagccaatc aaagaggagt gatgtagacc taaagcaata atggagccat gacgtaaggg | 120 |
| cttacgccat tacgaaataa ttaaaggctg atgtgacctg tcggtctctc agaaccttta | 180 |
| ctttttatat ttggcgtgta tttttaaatt tccacggcaa tgacgatgtg acctgtgcat | 240 |
| ccgctttgcc tataaataag ttttagtttg tattgatcga cacgatcgag aagacacggc | 300 |
| catttggacg atcatttgag agtctaaaag aacgagtctt gtaatatgtt tt | 352 |

<210> SEQ ID NO 58
<211> LENGTH: 7139
<212> TYPE: DNA
<213> ORGANISM: Zea mays

<400> SEQUENCE: 58

| | |
|---|---|
| gctctgccac tctgctgagg tgggggagga ggagctcccc ctccctcctc tcccctcctc | 60 |
| gccatgtcta gcagcgaccc ggaggagatc agggcgcgcg tcgtcgttct cggttcgccc | 120 |
| catgccgacg gcggcgacga gtgggcccgg cccgagctcg aggccttcca tctgccgtct | 180 |
| cccgcccacc agcctcctgg cttcctagcc gggcaaccgg aagcagcaga gcaacccacg | 240 |
| ctccctgctc ctgctggccg cagcagcagc agcagcaaca cgcctactac atctgccggt | 300 |

```
ggcggcgctg ctcctcctcc tccttcttcg cctcccctc cgccggcttc tctggagacc    360
gagcagccgc ccaatgccag gccagcctcc gccggcgcca atgacagcaa gaagcccacc    420
ccgcccgccg ccctgcgcga cctcttccgc ttcgccgacg gcctcgactg cgcgctcatg    480
ctcatcggca ccctcggcgc gctcgtccac gggtgctcgc tccccgtctt cctccgcttc    540
ttcgccgacc tcgtcgactc cttcggctcc cacgccgacg acccggacac catggtccgc    600
ctcgtcgtca agtacgcctt ctacttcctc gtcgtcggag cggcaatctg gcatcctcg    660 tgggcaggta cgctatccct cctcctcctg ccgccccagc ttgtgtgcgt cgcgaattgg    720
cggtcaattt ggattggatg acaaatcacg tcggtcagcc aatcgccgtg gctacaaacg    780
agatgttcaa atcgttcgcc ccgctcgcaa gagatctctt gctggatgtg gaccggcgag    840
cggcagtcga cgcggatgcg gattcggtac ctggacgcgg cgctgcggca ggacgtgtcc    900
ttcttcgaca ccgacgtgcg ggcctcggac gtgatctacg ccatcaacgc ggacgccgtg    960
gtggtgcagg acgccatcag ccagaaactg gcaacctca tccactacat ggccaccttc    1020
gtggccggct tcgtcgtggg gttcacggcc gcgtggcagc tggcgctggt cacgctggcc    1080
gtggtgccgc tcatcgccgt catcggcggg ctgagcgccg ccgcgctcgc caagctctcg    1140
tcccgcagcc aggacgcgct ctcgggcgcc agcggcatcg cggagcaggc gctcgcgcag    1200
atacggatcg tgcaggcgtt cgttggcgag gagcgcgaga tgcgggccta ctcggcggcg    1260
ctggccgtgg cgcagaggat cggctaccgc agccggcttcg ccaaggggct cggcctcggc    1320
ggcacctact tcaccgtctt ctgctgctac gggctcctgc tctggtacgg cggccacctc    1380
gtgcgcgccc agcacaccaa cggcgggctc gccatcgcca ccatgttctc cgtcatgatc    1440
ggcggactgt aaggcccacc acaccacgca ctctctcctt ctgctgtcct cggccgcccc    1500
cgtcgtcatt gctgctgacg gtatctgtgg atcgcgtgca ggcctcggca gtcggcgccg    1560
agcatggccg cgttcgccaa ggcgcgtgtg gcggctgcca agatcttccg catcatcgac    1620
cacaggccgg gcatctcctc gcgcgacggc gcggagccag agtcggtgac ggggcgggtg    1680
gagatgcggg gcgtggactt cgcgtacccg tcgcggccgg acgtccccat cctgcgcggc    1740
ttctcgctga gcgtgcccgc cgggaagacc atcgcgctgg tgggcagctc cggctccggg    1800
aagagcacgg tggtgtcgct catcgagaga ttctacgacc ccagcgcagg tatacctagt    1860
actgttacta cttttagcgc attaatctga ggatgtccag ttcgcttgct tgccaatcgc    1920
cattgccatc gcaacaacaa tacttcgcca actgccattg ctgggtagat tagtacagta    1980
gcagttagaa gaagcctcca ctgtacattg cattgccaaa caaaagtgaa ttgtgcagta    2040
actctgtacc accacattga catggaaatg aagtgaatgc ttggagcatg cagagctggc    2100
cggcctcatg ggctgctgct acctgctagc tagccaacca gaaccagcca tcctctttct    2160
tgcttttctt tttactttct ttggtcgtgg ctgtttgtgg tcatacatac attcacgcag    2220
agcagaagag ctagctaagc taggtgggtg tgcctgcaac gcgggacaaa gaaaactatt    2280
tgttgcctgg caagatgcta ctgttgccta gcacatgcct gccattgacc gactgctcag    2340
tgagaagtgg ttcagttgtg ctgttgacag tatagataga tatatatagt agccctgtag    2400
attttttttt cagacaaaaa aagaagaaga acgagatgaa gtctgcaatt cggttttggc    2460
agggcaaatc ctgctggacg ggcacgacct caggtcgctg gagctgcggt ggctgcggcg    2520
gcagatcggg ctggtgagcc aggagccggc gctgttcgcg acgagcatca gggagaacct    2580
gctgctgggg cgggacagcc agagcgcgac gctggcggag atggaggagg cggccagggt    2640
ggccaacgcc cactccttca tcatcaaact ccccgacggc tacgacacgc aggtccgtcc    2700
```

| | |
|---|---|
| cgtatagcta gctcactagc tgcactgcca cttctctcgc ttgctccccc accgttgctg | 2760 |
| cctgttgctc tccaatccac ttgtcggtgt ctggaccaca cgtgctgctt gcctagctgc | 2820 |
| tccacatctg cttcccctgt ccaaccttat gcaactcact ctaatactat atcaaataca | 2880 |
| tttctagagt ttaaagctta tcttagaata aatgcatctt tagctacgag acaacctaac | 2940 |
| ttcagttgtt gttgttgttt ttttttacttt ctctcttctc acaaatacta tgattacgtc | 3000 |
| tttacagcga tctttttat tccaaaccta aaaatgcatg cactcactct aaaagcgcaa | 3060 |
| agggagcatc ttttttttccc ccatcatctg cacgcagcct tttcttttcc tcatgtcacg | 3120 |
| aagggactga aggtgtgtat gcagcgtcaa gtcatccatc cgttccactc cactcactca | 3180 |
| tgcgtcgcgc actctgcgct cgtgcctgcc cggggctaaa gctttagtag ctagcctcag | 3240 |
| atcagatact gttcgtgttt gttaggccgc ggcagctgca catgagctca tgacagccgg | 3300 |
| cagcaccacc accaacgcca tggaagaggg gtcggggtcc atcacataga cataatgcct | 3360 |
| gttgtagact aggacgggag ggcaattgtt aggcgcctgt tgccatcgca tttgctgctg | 3420 |
| tgggttgcca acaagtaaca tgccaggatg ctttgctatc acgcacagga caggagaggt | 3480 |
| ccttttctc gacacaagct ctacagcctc tactaaacta gcacttgctg atgagtgcag | 3540 |
| aggatgaatg gacgatgaac atctagagtg agagagaaaa aaatgttaat aataataaaa | 3600 |
| agtagtagca ggattaagaa tcaacctggg gtacgtagga agaggtacaa tccctaggaa | 3660 |
| tctagagtat gagaagtatg ggaggagttg ggggagtgaa acgaacaaa ttccgagttg | 3720 |
| gtattttgtc gggaatgtca agttgatttt tgatcctagt gcaagcaaga attatcaatc | 3780 |
| actcagactc agcctgtctg tgtctgtcca ccccagctct tgctactcta cttactactg | 3840 |
| tgctactagt gggtagggta ggtatcttac ataaactgtt attataaact gtcatctgag | 3900 |
| aaagagagcc agtcaaaccc atgctgctgc ttattttaat cactgtcaaa tggcaggcag | 3960 |
| gcaggcagtc tggttagtta ataacatctg ggaagggttt aatcaaacca aatcaaatca | 4020 |
| gacgaaatct agaggccaca tgggatgggg ccatatgtac tgtactagca taactagcgg | 4080 |
| ctagatttta ttagaacacg gactcacact cccataacta taactgactt gatcatgatt | 4140 |
| ccttgccaag caatgctcgc atgcccatgc atgcatcatc cctggtcaaa ctcaaacact | 4200 |
| ctccaccgtc agggaataag acttattatt ttattaacaa ttcaattttt atttattaat | 4260 |
| tacgtctgga cgaggagtac tggtttattt gatgagagac atggcagtcc aagtcaaact | 4320 |
| cgtttgtctg accatggcgg tgatggccgg tgcaggttgg ggagcgcggc ctgcagctct | 4380 |
| ccggtgggca gaagcagcgc atcgccatcg cccgcgccat gctcaagaac cccgccatcc | 4440 |
| tgctgctgga cgaggccacc agcgcgctgg actccgagtc tgagaagctc gtgcaggagg | 4500 |
| cgctggaccg cttcatgatg gggcgcacca cccttggtga tcgcgcaaca ggctgtccac | 4560 |
| catccgcaaa ggccgacgtg gtggccgtgc tgcagggcgg cgccgtctcc gagatgagcg | 4620 |
| cgcacgacga gctgatggcc aagggcgaga acggcaccta cgccaagctc atccgcatgc | 4680 |
| aggagcaggc gcacgaggcg gcgctcgtca acgcccgccg cagcagcgcc aggccctcca | 4740 |
| gcgcccgcaa ctccgtcagc tcgcccatca tgacgcgcaa ctcctcctac ggccgctccc | 4800 |
| cctactcccg ccgcctctcc gacttctcca cctccgactt cacccctctc atccacgacc | 4860 |
| cgcaccacca ccaccggacc atggcggaca agcagctggc gttccgcgcc ggcgccagct | 4920 |
| ccttcctgcg cctcgccagg atgaactcgc ccgagtgggc ctacgcgctc gccggctcca | 4980 |
| tcggctccat ggtctgcggc tccttcagcg ccatcttcgc ctacatcctc agcgccgtgc | 5040 |
| tcagcgtcta ctacgcgccg gacccgcggt acatgaagcg cgagatcgca aaatactgtt | 5100 |

-continued

| | |
|---|---|
| acctgctcat cggcatgtcc tccgcggcgc tgctgttcaa cacggtgcag cacgtgttct | 5160 |
| gggacacggt gggcgagaac ttgaccaagc gggtgcgcga aagatgttc gccgccgtgt | 5220 |
| tccgcaacga gatcgcctgg ttcgacgcgg acgagaacgc cagcgcgcgc gtgaccgcca | 5280 |
| ggctagcgct ggacgcccag aacgtgcgct ccgccatcgg ggaccgcatc tccgtcatcg | 5340 |
| tccagaactc ggcgctgatg ctggtggcct gcaccgcggg gttcgtcctc cagtggcgcc | 5400 |
| tcgcgctcgt gctcctcgcc gtgttcccgc tcgtcgtggg cgccaccgtg ctgcagaaga | 5460 |
| tgttcatgaa gggcttctcg ggggacctgg aggccgcgca cgccagggcc acgcagatcg | 5520 |
| cgggcgaggc cgtggccaac ctgcgcaccg tggccgcgtt caacgcggag cgcaagatca | 5580 |
| cggggctgtt cgaggccaac ctgcgcggcc cgctccggcg ctgcttctgg aaggggcaga | 5640 |
| tcgccggcag cggctacggc gtggcgcagt tcctgctgta cgcgtcctac gcgctggggc | 5700 |
| tgtggtacgc ggcgtggctg gtgaagcacg gcgtgtccga cttctcgcgc accatccgcg | 5760 |
| tgttcatggt gctgatggtg tccgcgaacg cgccgccga cgctgacg ctggcgccgg | 5820 |
| acttcatcaa aggcgggcgc gcgatgcggt cggtgttcga caatcgac cgcaagacgg | 5880 |
| aggtggagcc ccacgacgtg gacgcggcgc cggtgccgga cggcccaggg gcgaaggtgg | 5940 |
| aacttaagca cgtggacttt ttgtacccgt cgcggccgga catccaagtg ttccgcgacc | 6000 |
| tgagcctccg tgcgcgcgcc ggaaaaaacgt tggcgctggt ggggccgagc gggtccggca | 6060 |
| agagctcggt cctggctctg gtgcagcggt tctacaagcc cacgtccggg cgcgtgctct | 6120 |
| tggacggcaa ggacgtgcgc aagtacaacc tgcgggcgct gcggcgcgtg gtggcggtgg | 6180 |
| taccgcagga gccgttcctg ttcgcggcga gcatccacga gaacatcgcg tacgggcgcg | 6240 |
| agggcgcgac ggaggcggag gtggtggagg cggcggcgca ggcgaacgcg caccggttca | 6300 |
| tcgcggcgct gccggagggg taccggacg aggtgggcga gcgcggggtg cagctgtcgg | 6360 |
| gggggcagcg gcagcggatc gcgatcgcgc gcgcgctggt gaagcaggcg gccatcgtgc | 6420 |
| tgctggacga ggcgaccagc gcgctggacg ccgagtcgga gcggtgcgtg caggaggcgc | 6480 |
| tggagcgcgc ggggtccggg cgcaccacca tcgtggtggc gcaccggctg gccacggtgc | 6540 |
| gcggcgcgca caccatcgcg gtcatcgacg acggcaaggt ggcggagcag gggtcgcact | 6600 |
| cgcacctgct caagcaccat cccgacgggt gctacgcgcg gatgctgcag cttgcagcgg | 6660 |
| ctgacgggcg cggcggccgg gcccgggccg tcgtcctcgt gcaacggggc gcgtaggac | 6720 |
| ggaatggatg gatggatggg tttggttcct cgagagattg atgggtgagg aagctgaagc | 6780 |
| tccggatcaa atggtggtac tccatgatcg caacaatgag gggaaaaaag gaaaggagaa | 6840 |
| aatacggtgg ttcatatgat tgtacaattt gacgatctgt ttgagtcggg gttttaggat | 6900 |
| gatgtaaacc ttcactcgcc tttttttac tcttgtttct catccgcatc agtatcatct | 6960 |
| atctacatac agtgtcagag atgggaactg atcccgcatc atcatctacc tcccaaggca | 7020 |
| ccccagattg tattaatgta cttagttagc ctgttttata tatacttata agtaccaaat | 7080 |
| agcagaattt tactccttat ctgcagtagc acgaaagaaa aaaaaaaaaa gctaaacct | 7139 |

<210> SEQ ID NO 59
<211> LENGTH: 143
<212> TYPE: DNA
<213> ORGANISM: Zea mays

```
<400> SEQUENCE: 59
ttgcctagca catgcctgcc attgaccgac tgctcagtga aagtggttc agttgtgctg    60 ttgacagtat atatagatat atatagtagc cctgtagatt ttttttttcag acaaaaaaag   120 aagaagaacg agatgaagtc tgc                                          143

<210> SEQ ID NO 60
<211> LENGTH: 143
<212> TYPE: DNA
<213> ORGANISM: Zea mays

<400> SEQUENCE: 60
ctagcacatg cctgccattg accgactgct cagtgagaag tggttcagtt gtgctgttga    60
cagtatagat atatatatat agtagccctg tagatttttt tttcagacaa aaaagaaga   120 agaacgagat gaagtctgca att                                          143

<210> SEQ ID NO 61
<211> LENGTH: 143
<212> TYPE: DNA
<213> ORGANISM: Zea mays

<400> SEQUENCE: 61
acatgcctgc cattgaccga ctgctcagtg agaagtggtt cagttgtgct gttgacagta    60
tagatagata tgtatagtag ccctgtagat ttttttttca gacaaaaaaa gaagaagaac   120
gagatgaagt ctgcaattcg gtt                                          143

<210> SEQ ID NO 62
<211> LENGTH: 142
<212> TYPE: DNA
<213> ORGANISM: Zea mays

<400> SEQUENCE: 62
catgcctgcc attgaccgac tgctcagtga agtggttc agttgtgctg ttgacagtat     60
agatagatat agtagccctg tagatttttt tttcagacaa aaaagaaga agaacgagat    120 gaagtctgca attcggtttt gg                                           142

<210> SEQ ID NO 63
<211> LENGTH: 140
<212> TYPE: DNA
<213> ORGANISM: Zea mays

<400> SEQUENCE: 63
gctgttgaca gtatagatag atatatatag tagccctgta gatttttttt tcagacaaaa    60 aagaagaac gagatgaagt ctgcaattcg gttttggcag ggcaaatcct gctggacggg   120
cacgacctca ggtcgctgga                                              140

<210> SEQ ID NO 64
<211> LENGTH: 141
<212> TYPE: DNA
<213> ORGANISM: Zea mays

<400> SEQUENCE: 64
tgacagtata gatagatata tatagtagcc ctgtagattt ttttttcaga caaaaaaga     60 agaagaacgg gatgaagtct gcaattcggt tttggcaggg caaatcctgc tggacgggca   120
cgacctcagg tcgctggagc t                                            141
```

```
<210> SEQ ID NO 65
<211> LENGTH: 141
<212> TYPE: DNA
<213> ORGANISM: Zea mays

<400> SEQUENCE: 65
tgacagtata gatagatata tatagtagcc ctgtagattt tttttcaga caaaaaaga      60 agaagaacgg gatgaagtct gcaattcggt tttggcaggg caaatcctgc tggacgggca   120
cgacctcagg tcgctggagc t                                             141

<210> SEQ ID NO 66
<211> LENGTH: 144
<212> TYPE: DNA
<213> ORGANISM: Zea mays

<400> SEQUENCE: 66
aggcggccag ggtggccaac gcccactcct tcatcatcaa actccccgac ggctacgaca    60
cgcaggtccg tgtccgtccc gtatagctag ctcactagct gcactgccac ttctctcgct   120
tgctccccca ccgttgctgc ctgt                                          144

<210> SEQ ID NO 67
<211> LENGTH: 136
<212> TYPE: DNA
<213> ORGANISM: Zea mays

<400> SEQUENCE: 67
caacgcccac tccttcatca tcaaactccc cgacggctac gacacgcagg tccgtcccgt    60
atagcggtag ctcactagct gcactgccac ttctctcgct tgctccccca ccgttgctgc   120
ctgttgctct ccaatc                                                   136

<210> SEQ ID NO 68
<211> LENGTH: 136
<212> TYPE: DNA
<213> ORGANISM: Zea mays

<400> SEQUENCE: 68
gcccactcct tcatcatcaa actccccgac ggctacgaca cgcaggtccg tcccgtatag    60
ctatagctca ctagctgcac tgccacttct ctcgcttgct cccccaccgt tgctgcctgt   120
tgctctccaa tccact                                                   136

<210> SEQ ID NO 69
<211> LENGTH: 133
<212> TYPE: DNA
<213> ORGANISM: Zea mays

<400> SEQUENCE: 69
ctccttcatc atcaaactcc ccgacggcta cgacacgcag gtccgtcccg tatagctagc    60
taactagctg cactgccact tctctcgctt gctcccccac cgttgctgcc tgttgctctc   120
caatccactt gtc                                                      133

<210> SEQ ID NO 70
<211> LENGTH: 141
<212> TYPE: DNA
<213> ORGANISM: Zea mays
```

```
<400> SEQUENCE: 70
cacacgcaca cacacagatc gcctgacaag ccagccattg cttcagatca aagaaactgc    60
gtaataattt ctttctttct ttctttcttt ctttccagag cacaagggag gggggttata   120
atggctagta cctgactgac t                                             141

<210> SEQ ID NO 71
<211> LENGTH: 143
<212> TYPE: DNA
<213> ORGANISM: Zea mays

<400> SEQUENCE: 71
agccagccat tgcttcagat caaagaaact gcgtaataat tcctttcttt ctttctttct    60
ttctttccag atcacaaggg agggggggtta taatggctag tacctgactg actgtacgag   120
ccgagattaa cggcagtcac ctc                                           143

<210> SEQ ID NO 72
<211> LENGTH: 143
<212> TYPE: DNA
<213> ORGANISM: Zea mays

<400> SEQUENCE: 72
atcgccctgc tggccatttg gcaccaccta gtcgtacatg tgttcagtca tttccgtcca    60
ttactactac ggccgtgctc acccgtgccg acgcgccgtg catggtcccc gtcccggctg   120
gaacgcgtcc tcggaagaga gag                                           143

<210> SEQ ID NO 73
<211> LENGTH: 143
<212> TYPE: DNA
<213> ORGANISM: Zea mays

<400> SEQUENCE: 73
ccattactac tacgaccgtg ctcacccgtg ccgacgcgcc gtgcatggtc cccgtcccgg    60
ctggaacgcg tgctcggaag agagagatag agcacagcag acaggagac agggatggaa   120 ggatggcgtt cgcccggtac agg                                           143

<210> SEQ ID NO 74
<211> LENGTH: 143
<212> TYPE: DNA
<213> ORGANISM: Zea mays

<400> SEQUENCE: 74
cattactact acgaccgtgc tcacccgtgc cgacgcgccg tgcatggtcc ccgtcccggc    60
tggaacgcgt catcggaaga gagagataga gcacagcaga cagggagaca gggatggaag   120
gatggcgttc gcccggtaca ggt                                           143

<210> SEQ ID NO 75
<211> LENGTH: 143
<212> TYPE: DNA
<213> ORGANISM: Zea mays

<400> SEQUENCE: 75
attactacta cgaccgtgct cacccgtgcc gacgcgccgt gcatggtccc cgtcccggct    60
ggaacgcgtc cccggaagag agagatagag cacagcagac aggagacag ggatggaagg   120 atggcgttcg cccggtacag gtt                                           143
```

```
<210> SEQ ID NO 76
<211> LENGTH: 143
<212> TYPE: DNA
<213> ORGANISM: Zea mays

<400> SEQUENCE: 76
ttactactac gaccgtgctc acccgtgccg acgcgccgtg catggtcccc gtcccggctg       60
gaacgcgtcc tgggaagaga gagatagagc acagcagaca gggagacagg gatggaagga      120
tggcgttcgc ccggtacagg ttg                                              143

<210> SEQ ID NO 77
<211> LENGTH: 143
<212> TYPE: DNA
<213> ORGANISM: Zea mays

<400> SEQUENCE: 77
tactactacg accgtgctca cccgtgccga cgcgccgtgc atggtccccg tcccggctgg       60
aacgcgtcct ccgaagagag agatagagca cagcagacag ggagacaggg atggaaggat      120
ggcgttcgcc cggtacaggt tgc                                              143

<210> SEQ ID NO 78
<211> LENGTH: 143
<212> TYPE: DNA
<213> ORGANISM: Zea mays

<400> SEQUENCE: 78
ctactacgac cgtgctcacc cgtgccgacg cgccgtgcat ggtccccgtc ccggctggaa       60
cgcgtcctcg gtagagagag atagagcaca gcagacaggg agacagggat ggaaggatgg      120
cgttcgcccg gtacaggttg cta                                              143

<210> SEQ ID NO 79
<211> LENGTH: 143
<212> TYPE: DNA
<213> ORGANISM: Zea mays

<400> SEQUENCE: 79
tactacgacc gtgctcaccc gtgccgacgc gccgtgcatg gtccccgtcc cggctggaac       60
gcgtcctcgg acgagagaga tagagcacag cagacaggga gacagggatg gaaggatggc      120
gttcgcccgg tacaggttgc tag                                              143

<210> SEQ ID NO 80
<211> LENGTH: 146
<212> TYPE: DNA
<213> ORGANISM: Zea mays

<400> SEQUENCE: 80
actacgaccg tgctcacccg tgccgacgcg ccgtgcatgg tccccgtccc ggctggaacg       60
cgtcctcgga actcggagag agatagagca cagcagacag ggagacaggg atggaaggat      120
ggcgttcgcc cggtacaggt tgctag                                           146

<210> SEQ ID NO 81
<211> LENGTH: 143
<212> TYPE: DNA
<213> ORGANISM: Zea mays
```

<400> SEQUENCE: 81
caggaggcgc tggaccgctt catgatcggg cgcaccaccc tggtgatcgc gcacaggctg     60
tccaccatcc gcaaggccga cgtggtggcc gtgctgcagg gcggcgccgt ctccgagatg    120
ggcgcgcacg acgagctgat ggc                                            143

<210> SEQ ID NO 82
<211> LENGTH: 143
<212> TYPE: DNA
<213> ORGANISM: Zea mays

<400> SEQUENCE: 82
tccatcggct ccatggtctg cggctccttc agcgccatct tcgcctacat cctcagcgcc     60
gtgctcagcg tctactacgc gccggacccg cggtacatga agcgcgagat cgcaaaatac    120
tgctacctgc tcatcggcat gtc                                            143

<210> SEQ ID NO 83
<211> LENGTH: 143
<212> TYPE: DNA
<213> ORGANISM: Zea mays

<400> SEQUENCE: 83
gcctacatcc tcagcgccgt gctcagcgtc tactacgcgc cggacccgcg gtacatgaag     60
cgcgagatcg caaaatactg ctacctgctc atcggcatgt cctccgcggc gctgctgttc    120
aacacggtgc agcacgtgtt ctg                                            143

<210> SEQ ID NO 84
<211> LENGTH: 143
<212> TYPE: DNA
<213> ORGANISM: Zea mays

<400> SEQUENCE: 84
ctggttcgac gcggacgaga acgccagcgc gcgcgtggcc gccaggctag cgctggacgc     60
ccagaacgtg cgctccgcca tcggggaccg catctccgtc atcgtccaga actcggcgct    120
gatgctggtg gcctgcaccg cgg                                            143

<210> SEQ ID NO 85
<211> LENGTH: 143
<212> TYPE: DNA
<213> ORGANISM: Zea mays

<400> SEQUENCE: 85
cagaacgtgc gctccgccat cggggaccgc atctccgtca tcgtccagaa ctcggcgctg     60
atgctggtgg cctgcaccgc ggggttcgtc ctccagtggc gcctcgcgct cgtgctcctc    120
gccgtgttcc cgctcgtcgt ggg                                            143

<210> SEQ ID NO 86
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 86
ttgcctagca catgcctgcc attgaccgac tgctcagtga gaagtggttc agttgtgctg    60
ttgacagtat anatagatat atatagtagc cctgtagatt ttttttttcag acaaaaaaag   120 aagaagaacg agatgaagtc tgc                                           143

<210> SEQ ID NO 87
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 87
ctagcacatg cctgccattg accgactgct cagtgagaag tggttcagtt gtgctgttga    60
cagtatagat anatatatat agtagccctg tagatttttt tttcagacaa aaaagaaga   120 agaacgagat gaagtctgca att                                           143

<210> SEQ ID NO 88
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 88
acatgcctgc cattgaccga ctgctcagtg agaagtggtt cagttgtgct gttgacagta    60
tagatagata tntatagtag ccctgtagat tttttttttca gacaaaaaaa gaagaagaac   120
gagatgaagt ctgcaattcg gtt                                           143

<210> SEQ ID NO 89
<211> LENGTH: 146
<212> TYPE: DNA
<213> ORGANISM: Zea mays
<220> FEATURE:
<221> NAME/KEY: modified_base
<222> LOCATION: (72)..(75)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 89
catgcctgcc attgaccgac tgctcagtga gaagtggttc agttgtgctg ttgacagtat    60
agatagatat annnngtagc cctgtagatt ttttttcag acaaaaaaag aagaagaacg    120
agatgaagtc tgcaattcgg ttttgg                                        146

<210> SEQ ID NO 90
<211> LENGTH: 143
<212> TYPE: DNA
<213> ORGANISM: Zea mays

-continued

```
<220> FEATURE:
<221> NAME/KEY: modified_base
<222> LOCATION: (70)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 90
gctgttgaca gtatagatag atatatatag tagccctgta gattttttt tcagacaaaa      60 aaagaagaan nncgagatga agtctgcaat tcggttttgg cagggcaaat cctgctggac    120
gggcacgacc tcaggtcgct gga                                             143

<210> SEQ ID NO 91
<211> LENGTH: 141
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 91
tgacagtata gatagatata tatagtagcc ctgtagattt tttttcaga caaaaaaga       60 agaagaacgn gatgaagtct gcaattcggt tttggcaggg caaatcctgc tggacgggca   120
cgacctcagg tcgctggagc t                                              141

<210> SEQ ID NO 92
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 92 ttttttttc agacaaaaaa agaagaagaa cgagatgaag tctgcaattc ggttttggca      60
gggcaaatcc tnctggacgg gcacgacctc aggtcgctgg agctgcggtg gctgcggcgg   120
cagatcgggc tggtgagcca gga                                            143

<210> SEQ ID NO 93
<211> LENGTH: 144
<212> TYPE: DNA
<213> ORGANISM: Zea mays
<220> FEATURE:
<221> NAME/KEY: modified_base
<222> LOCATION: (72)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 93
aggcggccag ggtggccaac gcccactcct tcatcatcaa actccccgac ggctacgaca     60
cgcaggtccg tnnnnnnccc gtatagctag ctcactagct gcactgccac ttctctcgct   120 tgctcccca ccgttgctgc ctgt                                            144
```

<210> SEQ ID NO 94
<211> LENGTH: 136
<212> TYPE: DNA
<213> ORGANISM: Zea mays
<220> FEATURE:
<221> NAME/KEY: modified_base
<222> LOCATION: (66)..(67)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 94
caacgcccac tccttcatca tcaaactccc cgacggctac gacacgcagg tccgtcccgt    60
atagcnntag ctcactagct gcactgccac ttctctcgct tgctcccccca ccgttgctgc   120 ctgttgctct ccaatc                                                    136

<210> SEQ ID NO 95
<211> LENGTH: 136
<212> TYPE: DNA
<213> ORGANISM: Zea mays
<220> FEATURE:
<221> NAME/KEY: modified_base
<222> LOCATION: (64)..(65)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 95
gcccactcct tcatcatcaa actccccgac ggctacgaca cgcaggtccg tcccgtatag    60
ctanngctca ctagctgcac tgccacttct ctcgcttgct cccccaccgt tgctgcctgt   120
tgctctccaa tccact                                                    136

<210> SEQ ID NO 96
<211> LENGTH: 133
<212> TYPE: DNA
<213> ORGANISM: Zea mays
<220> FEATURE:
<221> NAME/KEY: modified_base
<222> LOCATION: (62)..(62)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 96
ctccttcatc atcaaactcc ccgacggcta cgacacgcag gtccgtcccg tatagctagc    60
tnactagctg cactgccact tctctcgctt gctcccccac cgttgctgcc tgttgctctc   120
caatccactt gtc                                                       133

<210> SEQ ID NO 97
<211> LENGTH: 141
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 97
cacacgcaca cacacagatc gcctgacaag ccagccattg cttcagatca aagaaactgc    60
gtaataattn ctttctttct ttctttcttt ctttccagag cacaagggag gggggttata   120
atggctagta cctgactgac t                                             141

<210> SEQ ID NO 98
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 98
agccagccat tgcttcagat caaagaaact gcgtaataat tcctttcttt ctttctttct    60
ttctttccag ancacaaggg aggggggtta taatggctag tacctgactg actgtacgag   120
ccgagattaa cggcagtcac ctc                                           143

<210> SEQ ID NO 99
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 99
atcgccctgc tggccatttg gcaccaccta gtcgtacatg tgttcagtca tttccgtcca    60
ttactactac gnccgtgctc acccgtgccg acgcgccgtg catggtcccc gtcccggctg   120
gaacgcgtcc tcggaagaga gag                                           143

<210> SEQ ID NO 100
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 100
ccattactac tacgaccgtg ctcacccgtg ccgacgcgcc gtgcatggtc cccgtcccgg    60
ctggaacgcg tnctcggaag agagagatag agcacagcag acagggagac agggatggaa   120
ggatggcgtt cgcccggtac agg                                           143

<210> SEQ ID NO 101
<211> LENGTH: 143
<212> TYPE: DNA
<213> ORGANISM: Zea mays

```
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 101
cattactact acgaccgtgc tcacccgtgc cgacgcgccg tgcatggtcc ccgtcccggc    60
tggaacgcgt cntcggaaga gagagataga gcacagcaga cagggagaca gggatggaag   120
gatggcgttc gcccggtaca ggt                                          143

<210> SEQ ID NO 102
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 102
attactacta cgaccgtgct cacccgtgcc gacgcgccgt gcatggtccc cgtcccggct    60
ggaacgcgtc cncggaagag agagatagag cacagcagac agggagacag ggatggaagg   120
atggcgttcg cccggtacag gtt                                          143

<210> SEQ ID NO 103
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 103
ttactactac gaccgtgctc acccgtgccg acgcgccgtg catggtcccc gtcccggctg    60
gaacgcgtcc tnggaagaga gagatagagc acagcagaca gggagacagg gatggaagga   120
tggcgttcgc ccggtacagg ttg                                          143

<210> SEQ ID NO 104
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 104
ttactactac gaccgtgctc acccgtgccg acgcgccgtg catggtcccc gtcccggctg    60
gaacgcgtcc tnggaagaga gagatagagc acagcagaca gggagacagg gatggaagga   120
tggcgttcgc ccggtacagg ttg                                          143
```

<210> SEQ ID NO 105
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 105
ctactacgac cgtgctcacc cgtgccgacg cgccgtgcat ggtccccgtc ccggctggaa     60
cgcgtcctcg gnagagagag atagagcaca gcagacaggg agacagggat ggaaggatgg    120
cgttcgcccg gtacaggttg cta                                            143

<210> SEQ ID NO 106
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 106
tactacgacc gtgctcaccc gtgccgacgc gccgtgcatg gtccccgtcc cggctggaac     60
gcgtcctcgg angagagaga tagagcacag cagacaggga gacagggatg gaaggatggc    120
gttcgcccgg tacaggttgc tag                                            143

<210> SEQ ID NO 107
<211> LENGTH: 146
<212> TYPE: DNA
<213> ORGANISM: Zea mays
<220> FEATURE:
<221> NAME/KEY: modified_base
<222> LOCATION: (72)..(75)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 107
actacgaccg tgctcacccg tgccgacgcg ccgtgcatgg tccccgtccc ggctggaacg     60
cgtcctcgga annnngagag agatagagca cagcagacag ggagacaggg atggaaggat    120
ggcgttcgcc cggtacaggt tgctag                                         146

<210> SEQ ID NO 108
<211> LENGTH: 143
<212> TYPE: DNA
<213> ORGANISM: Zea mays
<220> FEATURE:
<221> NAME/KEY: modified_base
<222> LOCATION: (72)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 108
ttgcctagca catgcctgcc attgaccgac tgctcagtga gaagtggttc agttgtgctg    60
ttgacagtat annnnnntat atatagtagc cctgtagatt ttttttttcag acaaaaaaag   120 aagaagaacg agatgaagtc tgc                                           143

<210> SEQ ID NO 109
<211> LENGTH: 148
<212> TYPE: DNA
<213> ORGANISM: Zea mays
<220> FEATURE:
<221> NAME/KEY: modified_base
<222> LOCATION: (76)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 109
catgcctgcc attgaccgac tgctcagtga gaagtggttc agttgtgctg ttgacagtat    60
agatagatat atatanngta gccctgtaga ttttttttc agacaaaaaa agaagaagaa    120
cgagatgaag tctgcaattc ggttttgg                                      148

<210> SEQ ID NO 110
<211> LENGTH: 142
<212> TYPE: DNA
<213> ORGANISM: Zea mays
<220> FEATURE:
<221> NAME/KEY: modified_base
<222> LOCATION: (66)..(69)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 110
caacgcccac tccttcatca tcaaactccc cgacggctac gacacgcagg tccgtcccgt    60
atagcnnnnt agctcactag ctgcactgcc acttctctcg cttgctcccc caccgttgct   120
gcctgttgct ctccaatcca ct                                            142

<210> SEQ ID NO 111
<211> LENGTH: 146
<212> TYPE: DNA
<213> ORGANISM: Zea mays
<220> FEATURE:
<221> NAME/KEY: modified_base
<222> LOCATION: (71)..(76)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 111
tttctagagt ttaaagctta tcttagaata aatgcatctt tagctacgag acaacctaac    60
ttcagttgtt nnnnnngttt tttttacttt ctctcttctc acaaatacta tgattacgtc   120
tttacagcga tctttttat tccaaa                                         146

<210> SEQ ID NO 112
<211> LENGTH: 146
<212> TYPE: DNA
<213> ORGANISM: Zea mays

```
<220> FEATURE:
<221> NAME/KEY: modified_base
<222> LOCATION: (77)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 112
tttctagagt ttaaagctta tcttagaata aatgcatctt tagctacgag acaacctaac      60
ttcagttgtt gttgttnttt tttttacttt ctctcttctc acaaatacta tgattacgtc     120
tttacagcga tctttttat tccaaa                                           146

<210> SEQ ID NO 113
<211> LENGTH: 105
<212> TYPE: DNA
<213> ORGANISM: Zea mays
<220> FEATURE:
<221> NAME/KEY: modified_base
<222> LOCATION: (60)..(61)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 113
attccaaacc taaaaatgca tgcactcact ctaaaagcgc aaagggagca tctttttttn      60 nccccccatca tctgcacgca gccttttctt ttcctcatgt cacga                    105

<210> SEQ ID NO 114
<211> LENGTH: 181
<212> TYPE: DNA
<213> ORGANISM: Zea mays
<220> FEATURE:
<221> NAME/KEY: modified_base
<222> LOCATION: (63)..(111)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 114
tcggtgctgg ctctggtgca gcggttctac gagcccacgt ccgggcgcgt gctcctggac      60
ggnnnnnnnn nnnnnnnnnn nnnnnnnnnn nnnnnnnnnn nnnnnnnnnn ncaaggacgt     120
gcgcaagtac aacctgcggg cgctgcggcg cgtggtggcg gtggtaccgc aggagccgtt     180
c                                                                    181

<210> SEQ ID NO 115
<211> LENGTH: 185
<212> TYPE: DNA
<213> ORGANISM: Zea mays
<220> FEATURE:
<221> NAME/KEY: modified_base
<222> LOCATION: (51)..(135)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 115
agaacacgga ctcacactcc cataactata actgacttga tcatgattcc nnnnnnnnnn      60
nnnnnnnnnn nnnnnnnnnn nnnnnnnnnn nnnnnnnnnn nnnnnnnnnn nnnnnnnnnn    120
```

```
nnnnnnnnnn nnnnnatttt attaacaatt caatttttat ttattaatta cgtctggacg    180
aggag                                                                185
```

<210> SEQ ID NO 116
<211> LENGTH: 140
<212> TYPE: DNA
<213> ORGANISM: Zea mays
<220> FEATURE:
<221> NAME/KEY: modified_base
<222> LOCATION: (52)..(69)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 116

```
ccaccgtcag ggaataagac ttattatttt attaacaatt caatttttat tnnnnnnnnn     60
nnnnnnnnnt attaattacg tctggacgag gagtactggt ttatttgatg agagacatgg    120
cagtccaagt caaactcgtt                                                140
```

<210> SEQ ID NO 117
<211> LENGTH: 711
<212> TYPE: DNA
<213> ORGANISM: Zea mays
<220> FEATURE:
<221> NAME/KEY: modified_base
<222> LOCATION: (66)..(644)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 117

```
actgaaggtg tgtatgcagc gtcaagtcat ccatccgttc cactccactc actcatgcgt     60
cgcgcnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnactctg cgctcgtgcc    660
tgcccggggc taaagcttta gtagctagcc tcagatcaga tactgttcgt g             711
```

<210> SEQ ID NO 118
<211> LENGTH: 114
<212> TYPE: DNA
<213> ORGANISM: Zea mays
<220> FEATURE:
<221> NAME/KEY: modified_base
<222> LOCATION: (68)..(80)
<223> OTHER INFORMATION: a, c, t, g, or absent
<220> FEATURE:
<223> OTHER INFORMATION: See specification as filed for detailed
      description of substitutions and preferred embodiments

```
<400> SEQUENCE: 118
gcactcagga ctcgcagcga gagaattttt ttaatcaagc ctaaaattca ctttcggaca      60
aatcgaannn nnnnnnnnnn ctactcataa atattaacca tgagacccttt tcgc          114

<210> SEQ ID NO 119
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 119
ttagcgcatt aatctgagga tgtccagttc gcttgcttgc caatcgccat tgccatcgca      60
acaacaatac ntcgccaact gccattgctg ggtagactag tacagtagca gttagaagaa    120
gcctccactg tacattgcat t                                              141

<210> SEQ ID NO 120
<211> LENGTH: 141
<212> TYPE: DNA
<213> ORGANISM: Zea mays
<220> FEATURE:
<221> NAME/KEY: modified_base
<222> LOCATION: (73)..(73)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 120
ttagcgcatt aatctgagga tgtccagttc gcttgcttgc caatcgccat tgccatcgca      60
acaacaatac ttngccaact gccattgctg ggtagactag tacagtagca gttagaagaa    120
gcctccactg tacattgcat t                                              141

<210> SEQ ID NO 121
<211> LENGTH: 144
<212> TYPE: DNA
<213> ORGANISM: Zea mays
<220> FEATURE:
<221> NAME/KEY: modified_base
<222> LOCATION: (72)..(73)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 121
ccatcctctt tcttgctttt cttttactt tctttggtcg tggctgtttg tggtcataca      60
tacattcacg cnnagagcag aagagctagc taagctaggt gggtgtgcct gcaacgcggg    120
acaaagaaaa ctatttgttg cctg                                           144

<210> SEQ ID NO 122
<211> LENGTH: 138
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
```

```
<220> FEATURE:
<223> OTHER INFORMATION: See specification as filed for detailed
      description of substitutions and preferred embodiments

<400> SEQUENCE: 122
tgtgtctgtc cacccccagct cttgctactc tacttactac tgtgctacta gtggtagggt    60
aggtatcttn cataaactgt tattataaac tgtcatctga gaaagagagc cagtcaaacc   120
catgctgctg cttattt                                                  138

<210> SEQ ID NO 123
<211> LENGTH: 142
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 123
tcttacataa actgttatta taaactgtca tctgagaaag agagccagtc aaacccatgc    60
tgctgcttan ttttaatcac tgtcaaatgg caggcaggca ggcagtctgg ttagttaata   120
acatctggga agggtttaat ca                                           142

<210> SEQ ID NO 124
<211> LENGTH: 141
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 124
ggcaggcagg caggcagtct ggttagttaa taacatctgg gaagggttta atcaaaccaa    60
atcaaatcan acgaaatcta gaggccacat gggatggggc catatgtact gtactagcat   120
aactagcggc tagattttat t                                            141

<210> SEQ ID NO 125
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 125
caaaccaaat caaatcagac gaaatctaga ggccacatgg gatggggcca tatgtactgt    60
actagcataa ntagcggcta gattttatta gaacacggac tcacactccc ataactataa   120
ctgacttgat catgattcct t                                            141
```

```
<210> SEQ ID NO 126
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 126
tactgtacta gcataactag cggctagatt ttattagaac acggactcac actcccataa      60
ctataactga cnttgatcat gattccttgc caagcaatgc tcgcatgccc atgcatgcat     120
catccctggt caaactcaaa cac                                             143

<210> SEQ ID NO 127
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 127
catcatccct ggtcaaactc aaacactctc caccgtcagg gaataagact tattattta      60 ttaacaattc nattttatt tattaattac gtctggacga ggagtactgg tttatttgat     120
gagagacatg gcagtccaag t                                              141

<210> SEQ ID NO 128
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 128
aacactctcc accgtcaggg aataagactt attatttat taacaattca attttattt      60 attaattacg nctggacgag gagtactggt ttatttgatg agagacatgg cagtccaagt    120
caaactcgtt tgtctgacca t                                              141

<210> SEQ ID NO 129
<211> LENGTH: 139
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments
```

-continued

```
<400> SEQUENCE: 129
gggaataaga cttattattt tattaacaat tcaatttta tttattaatt acgtctggac      60
gaggagtact ngtttatttg atgagagaca tggcagtcca agtcaaactc gtttgtctga    120
ccatggcggt gatggccgg                                                 139

<210> SEQ ID NO 130
<211> LENGTH: 134
<212> TYPE: DNA
<213> ORGANISM: Zea mays
<220> FEATURE:
<221> NAME/KEY: modified_base
<222> LOCATION: (68)..(68)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 130
tttatttgat gagagacatg gcagtccaag tcaaactcgt ttgtctgacc atggcggtga     60
tggccggntg caggttgggg agcgcggcct gcagctctcc ggtgggcaga agcagcgcat   120
cgccatcgcc cgcg                                                     134

<210> SEQ ID NO 131
<211> LENGTH: 141
<212> TYPE: DNA
<213> ORGANISM: Zea mays
<220> FEATURE:
<221> NAME/KEY: modified_base
<222> LOCATION: (65)..(74)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 131
gtcgtacatg tgttcagtca tttccgtcca ttactactac gaccgtgctc acccgtgccg     60
acgcnnnnnn nnnngccgtg catggtcccc gtcccggctg gaacgcgtcc tcggaagaga   120
gagatagagc acagcagaca g                                             141
```

MANAGEMENT OF CORN THROUGH SEMI-DWARF SYSTEMS

CROSS REFERENCE TO RELATED APPLICATIONS

This application claims the benefit of U.S. Provisional Patent Application No. 62/631,181, filed Feb. 15, 2018; and U.S. Provisional Patent Application No. 62/775,346, filed Dec. 4, 2018, both of which are incorporated herein by reference in their entireties.

FIELD OF THE INVENTION

The present disclosure relates to methods of applying compositions to corn fields prior to harvesting.

INCORPORATION OF SEQUENCE LISTING

A sequence listing contained in the filed named P34578US02_SEQ.txt, which is 172,032 bytes (measured in MS-Windows®) and created on Feb. 15, 2018, comprises 131 sequences, and is filed electronically herewith and incorporated by reference in its entirety.

BACKGROUND

Hybrid corn plants often reach heights over 6 feet (1.83 meters) during the growing season, particularly during later stages of development. However, standard agricultural sprayers and other mechanized applicators typically have an above-ground clearance of 6 feet or less (e.g., due to the height of the spray or applicator arms or booms and/or the bottom of the cabin). An above-ground sprayer or equipment clearance that is shorter than the height of the crop precludes farmers from accessing their agricultural fields to spray fertilizers or pesticides or conduct other over-the-top applications using standard vehicular equipment without risking significant damage to the crop. Thus, a need exists in the art to develop methods that allow in-season or late-season access to corn fields with standard farm equipment while reducing the risk of damaging the corn plants.

SUMMARY

In an aspect, this disclosure provides a method of providing an agricultural composition to a corn field comprising applying said agricultural composition on said corn field from above using a ground-based agricultural vehicle comprising an applicator for applying said agricultural composition, wherein the corn plants of said corn field comprise an average height of less than or equal to 1.8 meters, and wherein at least 50% of said corn plants are at V12 stage or later.

In an aspect, this disclosure provides a method of providing an agricultural composition to a corn field, comprising applying said agricultural composition to said corn field from above using a ground-based agricultural vehicle with an applicator for applying said agricultural composition, wherein said ground-based agricultural vehicle comprises a main body, and wherein said applicator is attached to said main body, wherein the lower exterior surface of said main body is positioned at a height equal to or less than 1.8 meters above soil level, and wherein at least 50% of said corn plants are at V12 stage or later.

In an aspect, this disclosure provides a method of providing an agricultural composition to a plurality of corn plants in a corn field, comprising applying the agricultural composition to said corn plants of said corn field from above using a ground-based agricultural vehicle comprising an applicator arm or boom for applying said agricultural composition, wherein the lower surface of said applicator arm or boom is at a height equal to or less than 1.8 meters above the soil level and is equal to or less than 15 centimeters shorter than average height of said corn plants, and wherein the corn plants are at V12 stage or later.

In an aspect, this disclosure provides a method of providing an agricultural composition to a corn plant comprising applying said agricultural composition on said corn plant from above using a ground-based agricultural vehicle, wherein said corn plant is not damaged by said ground-based agricultural vehicle, wherein said corn plant comprises a height of equal to or less than 1.8 meters, and wherein said corn plant is at V12 stage or later.

In an aspect, this disclosure provides a method of providing an agricultural composition to a corn field comprising applying the agricultural composition on the corn field from above using a ground-based agricultural vehicle comprising an applicator for applying the agricultural composition, where the corn plants of the corn field comprise an average height of less than or equal to 1.0 meters, and where at least 50% of the corn plants are at V6 stage or later.

In an aspect, this disclosure provides a method of providing an agricultural composition to a corn field, comprising applying the agricultural composition to the corn field from above using a ground-based agricultural vehicle with an applicator for applying the agricultural composition, where the ground-based agricultural vehicle comprises a main body, and where the applicator is attached to the main body, where the lower exterior surface of the main body and/or applicator is positioned at a height equal to or less than 1.6 meters above soil level, and where at least 50% of the corn plants of the corn field are at V8 stage or later.

In an aspect, this disclosure provides a method of providing an agricultural composition to a plurality of corn plants in a corn field, comprising applying the agricultural composition to the corn plants of the corn field from above using a ground-based agricultural vehicle comprising an applicator arm or boom for applying the agricultural composition, where the lower exterior surface of the applicator arm or boom is at a height equal to or less than 1.6 meters above the soil level and is equal to or less than 15 centimeters shorter than average height of the corn plants, and where the corn plants are at V8 stage or later.

In an aspect, this disclosure provides a method of providing an agricultural composition to a corn plant comprising applying the agricultural composition on the corn plant from above using a ground-based agricultural vehicle, where the corn plant is not damaged by the ground-based agricultural vehicle, where the corn plant comprises a height of equal to or less than 1.6 meters, and where the corn plant is at V8 stage or later.

BRIEF DESCRIPTION OF THE DRAWINGS

In FIG. 2, "short" plants refer to semi-dwarf BR plants, and "tall" plants refer to wild-type control plants.

DETAILED DESCRIPTION

Figure 1:
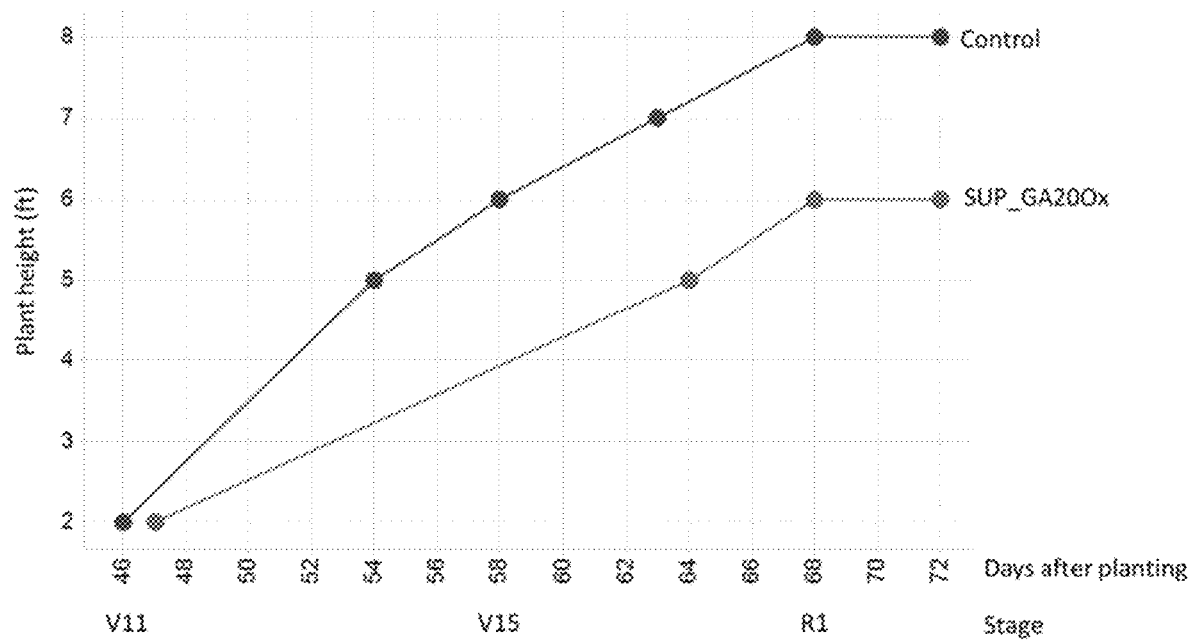
FIG. 1 depicts the height of wild-type control (WT) corn plants and semi-dwarf corn plants comprising a GA20 oxidase suppression construct (SUP_GA20 oxidase). Height is measured in feet (ft) and growth time is indicated by both date (Jun: June; Jul: July) and growth stage (V11, V15, and R1).

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; And C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

As well understood in the art, metric measurement values provided herein can be easily converted to standard (S.I.) units and vice versa.

As used herein, a "plant" includes an explant, plant part, seedling, plantlet or whole plant at any stage of regeneration or development. As commonly understood, a "corn plant" or "maize plant" refers to any plant of species *Zea mays* and includes all plant varieties that can be bred with corn, including wild maize species.

In an aspect, corn plants disclosed herein are selected from the subspecies *Zea mays* L. ssp. *mays*. In an additional aspect, corn plants disclosed herein are selected from the group *Zea mays* L. subsp. *mays* Indentata, otherwise known as dent corn. In another aspect, corn plants disclosed herein are selected from the group *Zea mays* L. subsp. *mays* Indurata, otherwise known as flint corn. In an aspect, corn plants disclosed herein are selected from the group *Zea mays* L. subsp. *mays* Saccharata, otherwise known as sweet corn. In another aspect, corn plants disclosed herein are selected from the group *Zea mays* L. subsp. *mays* Amylacea, otherwise known as flour corn. In a further aspect, corn plants disclosed herein are selected from the group *Zea mays* L. subsp. *mays* Everta, otherwise known as popcorn. Plants disclosed herein also include hybrids, inbreds, partial inbreds, or members of defined or undefined populations.

As used herein, the term "inbred" means a line that has been bred for genetic homogeneity. As used herein, the term "hybrid" means a progeny of mating between at least two genetically dissimilar parents or inbreds.

As used herein, a "field" or a "corn field" refers to an outdoor location that is suitable for growing corn. The location can be irrigated or non-irrigated. A corn field can comprise a land area planted with corn seed and/or at least one corn plant or a plurality of corn plants, which can be at one or more stages of development. According to some aspects, a plurality of corn plants in a field can be at a homogeneous or the same (or nearly homogeneous or nearly the same) stage of development, such that the plurality of corn plants have approximately the same height. In an aspect, a corn plant provided herein is planted in a field.

In another aspect, a corn plant provided herein is not planted in the field, but is planted indoors, such as in a greenhouse, and/or in a container holding a growth medium or soil.

A corn field can comprise one or more rows of corn plants of the same or different lengths. As used herein, a "row" comprises at least one corn plant. In an aspect, a row comprises at least two corn plants. Without being limiting, a row of corn plants is planted in a line, and if a corn field comprises two or more rows, they are typically planted parallel to each other. A corn field can comprise one or more rows of corn plants where the rows are of the same or different lengths. Without being limiting, a corn field comprises at least 1 row of corn plants. In another aspect, a corn field comprises at least 10 rows of corn plants. In another aspect, a corn field comprises at least 50 rows of corn plants. In another aspect, a corn field comprises at least 500 rows of corn plants. In another aspect, a corn field comprises at least 1,000 rows of corn plants. In another aspect, a corn field comprises at least 5,000 rows of corn plants. In another aspect, a corn field comprises at least 10,000 rows of corn plants.

In an aspect, a corn field comprises rows that are spaced at least 5 inches apart. In another aspect, a corn field comprises rows that are spaced at least 10 inches apart. In a further aspect, a corn field comprises rows that are spaced at least 15 inches apart. In an aspect, a corn field comprises rows of corn plants that are spaced at least 20 inches apart. In another aspect, a corn field comprises rows of corn that are spaced at least 25 inches apart. In another aspect, a corn field comprises rows of corn that are spaced at least 30 inches apart. According to some aspects, a corn field can comprise two or more pluralities of corn plants with the pluralities of corn plants being planted with different corn varieties, at different times, at different densities, in different arrangements (e.g., in rows or scattered or random placement), and/or at different row spacings and/or row lengths, such that the pluralities of corn plants have different heights, spacings, etc., at different time points during the growing season, although each plurality of corn plants can be relatively uniform with respect to plant height and other growth metrics.

In an aspect, a field comprises a single plot. In another aspect, a field comprises multiple plots. In another aspect, one or more edges of a field are bordered by a fence. In another aspect, one or more edges of a field are unfenced. In another aspect, one or more edges of a field are bordered by hedges. In an aspect, a field comprises a physically contiguous space. In another aspect, the field comprises a physically non-contiguous space. In still another aspect, the field comprises a biologically contiguous space. As used herein, a "biologically contiguous space" refers to a space where the pollen can move from one section of a field to another. In an aspect, a biologically contiguous field is physically contiguous. In another aspect, a biologically contiguous field is physically non-contiguous (e.g., plots within the field or a single plot within the field can be separated by a structure, without being limiting, such as a road, creek, irrigation ditch, trail, hedgerow, fence, irrigation pipes, fallow field, empty field, non-corn plants).

In an aspect, a field comprises at least 0.5 acres. In an aspect, a field comprises at least 1 acre. In another aspect, a field comprises at least 5 acres. In another aspect, a field comprises at least 10 acres. In another aspect, a field comprises at least 15 acres. In another aspect, a field comprises at least 20 acres. In another aspect, a field comprises at least 25 acres. In another aspect, a field comprises at least 30 acres. In another aspect, a field comprises at least 35 acres. In another aspect, a field comprises at least 40 acres. In another aspect, a field comprises at least 45 acres. In another aspect, a field comprises at least 50 acres. In another aspect, a field comprises at least 75 acres. In another aspect, a field comprises at least 100 acres. In another aspect, a field comprises at least 150 acres. In another aspect, a field comprises at least 200 acres. In another aspect, a field comprises at least 250 acres. In another aspect, a field comprises at least 300 acres. In another aspect, a field comprises at least 350 acres. In another aspect, a field comprises at least 400 acres. In another aspect, a field comprises at least 450 acres. In another aspect, a field comprises at least 500 acres. In another aspect, a field comprises at least 750 acres. In another aspect, a field comprises at least 1000 acres. In another aspect, a field comprises at least 1500 acres. In another aspect, a field comprises at least 2000 acres. In another aspect, a field comprises at least 2500 acres. In another aspect, a field comprises at least 3000 acres. In another aspect, a field comprises at least 4000 acres. In another aspect, a field comprises at least 5000 acres. In another aspect, a field comprises at least 10,000 acres.

In an aspect, a field comprises between 0.5 acres and 10,000 acres. In another aspect, a field comprises between 1 acre and 10,000 acres. In another aspect, a field comprises between 5 acres and 10,000 acres. In another aspect, a field comprises between 10 acres and 10,000 acres. In another aspect, a field comprises between 15 acres and 10,000 acres. In another aspect, a field comprises between 20 acres and 10,000 acres. In another aspect, a field comprises between 25 acres and 10,000 acres. In another aspect, a field comprises between 30 acres and 10,000 acres. In another aspect, a field comprises between 35 acres and 10,000 acres. In another aspect, a field comprises between 40 acres and 10,000 acres. In another aspect, a field comprises between 45 acres and 10,000 acres. In another aspect, a field comprises between 50 acres and 10,000 acres. In another aspect, a field comprises between 75 acres and 10,000 acres. In another aspect, a field comprises between 100 acres and 10,000 acres. In another aspect, a field comprises between 150 acres and 10,000 acres. In another aspect, a field comprises between 200 acres and 10,000 acres. In another aspect, a field comprises between 250 acres and 10,000 acres. In another aspect, a field comprises between 300 acres and 10,000 acres. In another aspect, a field comprises between 350 acres and 10,000 acres. In another aspect, a field comprises between 400 acres and 10,000 acres. In another aspect, a field comprises between 450 acres and 10,000 acres. In another aspect, a field comprises between 500 acres and 10,000 acres. In another aspect, a field comprises between 750 acres and 10,000 acres. In another aspect, a field comprises between 1000 acres and 10,000 acres. In another aspect, a field comprises between 1500 acres and 10,000 acres. In another aspect, a field comprises between 2000 acres and 10,000 acres. In another aspect, a field comprises between 2500 acres and 10,000 acres. In another aspect, a field comprises between 3000 acres and 10,000 acres. In another aspect, a field comprises between 4000 acres and 10,000 acres. In another aspect, a field comprises between 5000 acres and 10,000 acres. In another aspect, a field comprises between 1 acre and 5000 acres. In another aspect, a field comprises between 1 acre and 2500 acres. In another aspect, a field comprises between 1 acre and 1000 acres. In another aspect, a field comprises between 1 acre and 500 acres. In another aspect, a field comprises between 1 acre and 250 acres. In another aspect, a field comprises between 1 acre and 100 acres. In another aspect, a field comprises between 1 acre and 75 acres. In another aspect, a field comprises between 1 acre and 50 acres. In another aspect, a field comprises between 1 acre and 25 acres. In another aspect, a field comprises between 1 acre and 10 acres.

In an aspect, a corn field can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds. In another aspect, a greenhouse and/or in a container holding a growth medium or soil can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds.

In an aspect, a corn field comprises a density of at least 10,000 corn plants per acre. In another aspect, a corn field comprises a density of at least 15,000 corn plants per acre. In another aspect, a corn field comprises a density of at least 20,000 corn plants per acre. In another aspect, a corn field comprises a density of at least 22,000 corn plants per acre. In another aspect, a corn field comprises a density of at least 24,000 corn plants per acre. In another aspect, a corn field comprises a density of at least 26,000 corn plants per acre. In another aspect, a corn field comprises a density of at least 28,000 corn plants per acre. In another aspect, a corn field comprises a density of at least 30,000 corn plants per acre. In another aspect, a corn field comprises a density of at least 32,000 corn plants per acre. In another aspect, a corn field comprises a density of at least 34,000 corn plants per acre. In another aspect, a corn field comprises a density of at least 36,000 corn plants per acre. In another aspect, a corn field comprises a density of at least 38,000 corn plants per acre. In another aspect, a corn field comprises a density of at least 40,000 corn plants per acre. In another aspect, a corn field comprises a density of at least 42,000 corn plants per acre. In another aspect, a corn field comprises a density of at least 44,000 corn plants per acre. In another aspect, a corn field comprises a density of at least 46,000 corn plants per acre. In another aspect, a corn field comprises a density of at least 48,000 corn plants per acre. In another aspect, a corn field comprises a density of at least 50,000 corn plants per acre. In another aspect, a corn field comprises a density of at least 52,000 corn plants per acre. In another aspect, a corn field comprises a density of at least 54,000 corn plants per acre. In another aspect, a corn field comprises a density of at least 56,000 corn plants per acre. In another aspect, a corn field comprises a density of at least 58,000 corn plants per acre. In another aspect, a corn field comprises a density of at least 60,000 corn plants per acre.

In an aspect, a corn field comprises a density of between 10,000 and 50,000 corn plants per acre. In an aspect, a corn field comprises a density of between 10,000 and 40,000 corn plants per acre. In an aspect, a corn field comprises a density of between 10,000 and 30,000 corn plants per acre. In an aspect, a corn field comprises a density of between 10,000 and 25,000 corn plants per acre. In an aspect, a corn field comprises a density of between 10,000 and 20,000 corn plants per acre. In an aspect, a corn field comprises a density of between 20,000 corn plants and 60,000 corn plants per acre. In an aspect, a corn field comprises a density of between 20,000 corn plants and 58,000 corn plants per acre. In an aspect, a corn field comprises a density of between 20,000 corn plants and 55,000 corn plants per acre. In an aspect, a corn field comprises a density of between 20,000 corn plants and 50,000 corn plants per acre. In an aspect, a corn field comprises a density of between 20,000 corn plants and 45,000 corn plants per acre. In an aspect, a corn field comprises a density of between 20,000 corn plants and 42,000 corn plants per acre. In an aspect, a corn field comprises a density of between 20,000 corn plants and 40,000 corn plants per acre. In an aspect, a corn field comprises a density of between 20,000 corn plants and 38,000 corn plants per acre. In an aspect, a corn field comprises a density of between 20,000 corn plants and 36,000 corn plants per acre. In an aspect, a corn field comprises a density of between 20,000 corn plants and 34,000 corn plants per acre. In an aspect, a corn field comprises a density of between 20,000 corn plants and 32,000 corn plants per acre. In an aspect, a corn field comprises a density of between 20,000 corn plants and 30,000 corn plants per acre. In an aspect, a corn field comprises a density of between 24,000 corn plants and 58,000 corn plants per acre. In an aspect, a corn field comprises a density of between 38,000 corn plants and 60,000 corn plants per acre. In an aspect, a corn field comprises a density of between 38,000 corn plants and 50,000 corn plants per acre.

In an aspect, a corn field comprises at least 10 corn plants. In another aspect, a corn field comprises at least 10 corn plants per acre. In an aspect, a corn field comprises at least 100 corn plants. In another aspect, a corn field comprises at least 100 corn plants per acre. In an aspect, a corn field comprises at least 500 corn plants. In another aspect, a corn field comprises at least 500 corn plants per acre. In an aspect, a corn field comprises at least 1000 corn plants. In another aspect, a corn field comprises at least 1000 corn plants per acre. In an aspect, a corn field comprises at least 5000 corn plants. In another aspect, a corn field comprises at least 5000 corn plants per acre. In an aspect, a corn field comprises at least 10,000 corn plants. In an aspect, a corn field comprises at least 10,000 corn plants per acre. In an aspect, a corn field comprises at least 12,000 corn plants. In an aspect, a corn field comprises at least 12,000 corn plants per acre. In an aspect, a corn field comprises at least 15,000 corn plants. In an aspect, a corn field comprises at least 15,000 corn plants per acre. In an aspect, a corn field comprises at least 18,000 corn plants. In an aspect, a corn field comprises at least 18,000 corn plants per acre. In an aspect, a corn field comprises at least 20,000 corn plants. In an aspect, a corn field comprises at least 20,000 corn plants per acre. In an aspect, a corn field comprises at least 22,000 corn plants. In an aspect, a corn field comprises at least 22,000 corn plants per acre. In an aspect, a corn field comprises at least 24,000 corn plants. In an aspect, a corn field comprises at least 24,000 corn plants per acre. In an aspect, a corn field comprises at least 26,000 corn plants. In an aspect, a corn field comprises at least 26,000 corn plants per acre. In an aspect, a corn field comprises at least 28,000 corn plants. In an aspect, a corn field comprises at least 28,000 corn plants per acre. In an aspect, a corn field comprises at least 30,000 corn plants. In an aspect, a corn field comprises at least 30,000 corn plants per acre. In an aspect, a corn field comprises at least 32,000 corn plants. In an aspect, a corn field comprises at least 32,000 corn plants per acre. In an aspect, a corn field comprises at least 34,000 corn plants. In an aspect, a corn field comprises at least 34,000 corn plants per acre. In an aspect, a corn field comprises at least 36,000 corn plants. In an aspect, a corn field comprises at least 36,000 corn plants per acre. In an aspect, a corn field comprises at least 38,000 corn plants. In an aspect, a corn field comprises at least 38,000 corn plants per acre. In an aspect, a corn field comprises at least 40,000 corn plants. In an aspect, a corn field comprises at least 40,000 corn plants per acre. In an aspect, a corn field comprises at least 42,000 corn plants. In an aspect, a corn field comprises at least 42,000 corn plants per acre. In an aspect, a corn field comprises at least 44,000 corn plants. In an aspect, a corn field comprises at least 44,000 corn plants per acre. In an aspect, a corn field comprises at least 46,000 corn plants. In an aspect, a corn field comprises at least 46,000 corn plants per acre. In an aspect, a corn field comprises at least 48,000 corn plants. In an aspect, a corn field comprises at least 48,000 corn plants per acre. In an aspect, a corn field comprises at least 50,000 corn plants. In an aspect, a corn field comprises at least 50,000 corn plants per acre. In an aspect, a corn field comprises at least 52,000 corn plants. In an aspect, a corn field comprises at least 52,000 corn plants per acre. In an aspect, a corn field comprises at least 54,000 corn plants. In an aspect, a corn field comprises at least 54,000 corn plants per acre. In an aspect, a corn field comprises at least 56,000 corn plants. In an aspect, a corn field comprises at least 56,000 corn plants per acre. In an aspect, a corn field comprises at least 58,000 corn plants. In an aspect, a corn field comprises at least 58,000 corn plants per acre. In an aspect, a corn field comprises at least 60,000 corn plants. In an aspect, a corn field comprises at least 60,000 corn plants per acre.

In an aspect, a corn field comprises between 10,000 corn plants per acre and 50,000 corn plants per acre. In an aspect, a corn field comprises between 10,000 corn plants per acre and 40,000 corn plants per acre. In an aspect, a corn field comprises between 10,000 corn plants per acre and 30,000 corn plants per acre. In an aspect, a corn field comprises between 10,000 corn plants per acre and 25,000 corn plants per acre. In an aspect, a corn field comprises between 10,000 corn plants per acre and 20,000 corn plants per acre. In an aspect, a corn field comprises between 20,000 corn plants per acre and 60,000 corn plants per acre. In an aspect, a corn field comprises between 20,000 corn plants per acre and 58,000 corn plants per acre. In an aspect, a corn field comprises between 20,000 corn plants per acre and 55,000 corn plants per acre. In an aspect, a corn field comprises between 20,000 corn plants per acre and 50,000 corn plants per acre. In an aspect, a corn field comprises between 20,000 corn plants per acre and 45,000 corn plants per acre. In an aspect, a corn field comprises between 20,000 corn plants per acre and 42,000 corn plants per acre. In an aspect, a corn field comprises between 20,000 corn plants per acre and 40,000 corn plants per acre. In an aspect, a corn field comprises between 20,000 corn plants per acre and 38,000 corn plants per acre. In an aspect, a corn field comprises between 20,000 corn plants per acre and 36,000 corn plants per acre. In an aspect, a corn field comprises between 20,000 corn plants per acre and 34,000 corn plants per acre. In an aspect, a corn field comprises between 20,000 corn plants per acre and 32,000 corn plants per acre. In an aspect, a corn field comprises between 20,000 corn plants per acre and 30,000 corn plants per acre. In an aspect, a corn field comprises between 24,000 corn plants per acre and 58,000 corn plants per acre. In an aspect, a corn field comprises between 38,000 corn plants per acre and 60,000 corn plants per acre. In an aspect, a corn field comprises between 38,000 corn plants per acre and 50,000 corn plants per acre.

In an aspect, a corn field comprises at least 0.5 acres. In another aspect, a corn field comprises at least 1 acre. In another aspect, a corn field comprises at least 3 acres. In another aspect, a corn field comprises at least 5 acres. In another aspect, a corn field comprises at least 10 acres. In another aspect, a corn field comprises at least 15 acres. In another aspect, a corn field comprises at least 20 acres. In another aspect, a corn field comprises at least 25 acres. In another aspect, a corn field comprises at least 50 acres. In another aspect, a corn field comprises at least 75 acres. In another aspect, a corn field comprises at least 100 acres. In another aspect, a corn field comprises at least 150 acres. In another aspect, a corn field comprises at least 200 acres. In another aspect, a corn field comprises at least 250 acres. In another aspect, a corn field comprises at least 300 acres. In another aspect, a corn field comprises at least 350 acres. In another aspect, a corn field comprises at least 400 acres. In another aspect, a corn field comprises at least 500 acres. In another aspect, a corn field comprises at least 750 acres. In another aspect, a corn field comprises at least 1000 acres. In another aspect, a corn field comprises at least 2500 acres. In another aspect, a corn field comprises at least 5 acres. In another aspect, a corn field comprises at least 5000 acres.

In an aspect, a corn field comprises between 0.5 acres and 5000 acres. In another aspect, a corn field comprises between 1 acre and 5000 acres. In another aspect, a corn field comprises between 5 acres and 5000 acres. In another aspect, a corn field comprises between 10 acres and 5000 acres. In another aspect, a corn field comprises between 25 acres and 5000 acres. In another aspect, a corn field comprises between 50 acres and 5000 acres. In another aspect, a corn field comprises between 100 acres and 5000 acres. In another aspect, a corn field comprises between 200 acres and 5000 acres. In another aspect, a corn field comprises between 500 acres and 5000 acres. In another aspect, a corn field comprises between 1000 acres and 5000 acres. In another aspect, a corn field comprises between 1 acre and 500 acres. In another aspect, a corn field comprises between 1 acre and 400 acres. In another aspect, a corn field comprises between 1 acre and 300 acres. In another aspect, a corn field comprises between 1 acre and 250 acres. In another aspect, a corn field comprises between 1 acre and 200 acres. In another aspect, a corn field comprises between 1 acre and 150 acres. In another aspect, a corn field comprises between 1 acre and 100 acres. In another aspect, a corn field comprises between 1 acre and 75 acres. In another aspect, a corn field comprises between 1 acre and 50 acres. In another aspect, a corn field comprises between 1 acre and 25 acres. In another aspect, a corn field comprises between 10 acres and 25 acres. In another aspect, a corn field comprises between 10 acres and 50 acres. In another aspect, a corn field comprises between 10 acres and 100 acres. In another aspect, a corn field comprises between 10 acres and 250 acres. In another aspect, a corn field comprises between 10 acres and 500 acres. In another aspect, a corn field comprises between 100 acres and 250 acres. In another aspect, a corn field comprises between 100 acres and 500 acres.

Due to the height of modern corn plants, often between 1.9 meters and 2.7 meters, most standard farm equipment is unable to access a corn field through the entire growing season, particularly late season, to apply fertilizers, pesticides, cover crop seeds or other applications to corn fields without risking significant damage to the corn plants. Most standard farm equipment has a maximum above-ground clearance of between approximately 1.52 meters (5 feet) and 1.83 meters (6 feet). However, if the heights of the corn plants (e.g., dwarf or semi-dwarf corn) were relatively shorter during later stages of vegetative growth of development and/or at maturity, a longer (or potentially unlimited) window may be provided for farm equipment to access the field for over-the-top applications without significantly damaging the crop. In addition, farm equipment and applicators at a lower height may typically have limited access into the field during earlier stages of the growing season without damaging the corn plants once the corn plants reach a certain height. For example, it may be desirable to have a wider window of application during V8-V12 stages of corn development with equipment, such as a tractor and toolbar (or other lower height sprayer or dry spreader), having a relatively lower clearance height. In some embodiments, for example, a toolbar for spray applications having a height of about 30 inches above the ground may have an extra six days of field access (e.g., 46 days vs. 40 days after planting with some hybrids), or possibly longer in colder climates due to different growing degree units (GDUs) per calendar day, with short stature semi-dwarf hybrid corn as compared to typical corn hybrids.

As used herein, an "agricultural composition" refers to any composition that can be applied to a corn field. In an aspect, an agricultural composition comprises a fertilizer. In another aspect, an agricultural composition comprises a pesticide. In an aspect, an agricultural composition comprises an herbicide. In an aspect, an agricultural composition comprises a fungicide. In an aspect, an agricultural composition comprises an insecticide. In an aspect, an agricultural composition comprises a nematicide. In an aspect, an agricultural composition comprises water. In an aspect, an agricultural composition comprises a cover crop seed. In an aspect, an agricultural composition comprises a seed. In an aspect, an agricultural composition comprises a polynucleotide. In an aspect, an agricultural composition comprises pollen.

As used herein, "applying" refers to any application or method known in the art for providing, applying, delivering, or administering an agricultural composition to a plant or an agricultural field including an agricultural soil or growth medium, which can be carried out with a ground-based agricultural vehicle. Non-limiting examples of "applying" include spraying, dripping, dropping, blowing, casting, pouring, dusting, shaking, sprinkling, squirting, splashing, and topically coating an agricultural composition on or to a plant or agricultural field.

In an aspect, this disclosure provides a method of providing an agricultural composition, such as water and/or a fertilizer, a pesticide, an insecticide, an herbicide, a fungicide, and/or a cover crop seed, to a corn field comprising applying the agricultural composition, such as water and/or a fertilizer, a pesticide, an insecticide, an herbicide, a fungicide, and/or a cover crop seed, on or to the corn field from above using a ground-based agricultural vehicle comprising an applicator for applying the agricultural composition, such as water and/or a fertilizer, a pesticide, an insecticide, an herbicide, a fungicide, and/or a cover crop seed, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V6 stage or later, V7 stage or later, V8 stage or later, V9 stage or later, V10 stage or later, V11 stage or later, V12 stage or later, V13 stage or late, V14 stage or later, V15 stage or later, or R1 stage or later. In an aspect, this disclosure provides a method of providing an agricultural composition, such as water and/or a fertilizer, a pesticide, an insecticide, an herbicide, a fungicide, and/or a cover crop seed, to a corn field comprising applying the agricultural composition, such as water and/or a fertilizer, a pesticide, an insecticide, an herbicide, a fungicide, and/or a cover crop seed, on or to the corn field from above using a ground-based agricultural vehicle comprising an applicator for applying the agricultural composition, such as water and/or a fertilizer, a pesticide, an insecticide, an herbicide, a fungicide, and/or a cover crop seed, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V6 stage or later, V7 stage or later, V8 stage or later, V9 stage or later, V10 stage or later, or V11 stage or later.

In an aspect, this disclosure provides a method of providing an agricultural composition to a corn field comprising applying the agricultural composition, such as water and/or a fertilizer, pesticide, insecticide, herbicide, fungicide, or cover crop seed, on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 0.5 meters, and where at least 50%, at least 60%, at least 70%, at least 80%, at least 85%, at least 90%, at least 95%, at least 99%, or 100% of the corn plants are at V6 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, less than or equal to 0.2 meters, or less than or equal to 0.1 meters, and where at least 50%, at least 60%, at least 70%, at least 80%, at least 85%, at least 90%, at least 95%, at least 99%, or 100% of the corn plants are at V6 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, less than or equal to 0.2 meters, or less than or equal to 0.1 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V6 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 0.5 meters, less than or equal to 0.4 meters, less than or equal to 0.3 meters, less than or equal to 0.2 meters, less than or equal to 0.1 meters, less than or equal to 0.09 meters, less than or equal to 0.08 meters, or less than or equal to 0.07 meters where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V6 stage or later.

In a further aspect, this disclosure provides a method of providing an agricultural composition, such as water and/or a fertilizer, pesticide, insecticide, herbicide, fungicide, or cover crop seed, to a corn field, comprising applying the agricultural composition to the corn field from above using a ground-based agricultural vehicle comprising an applicator for applying the agricultural composition, where at least 50% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, 0.4 meters or less, 0.3 meters or less, 0.2 meters or less, or 0.1 meters or less, and where at least 50%, at least 60%, at least 70%, at least 80%, at least 85%, at least 90%, at least 95%, at least 99%, or 100% of the corn plants are at V6 stage or later. According to some of these embodiments, the lower exterior surface of the main body and/or applicator of the ground-based agricultural vehicle is at a height above ground between 0.09 meters and 2.0 meters, 0.09 meters and 1.8 meters, 0.09 meters and 1.5 meters, 0.09 meters and 1.0 meter, 0.09 meters and 0.9 meters, 0.09 meters and 0.8 meters, 0.09 meters and 0.7 meters, 0.09 meters and 0.6 meters, 0.09 meters and 0.5 meters, 0.09 meters and 0.4 meters, 0.09 meters and 0.3 meters, 0.09 meters and 0.2 meters, 0.1 meters and 2.0 meters, 0.1 meters and 1.8 meters, 0.1 meters and 1.5 meters, 0.1 meters and 1.0 meter, 0.1 meters and 0.9 meters, 0.1 meters and 0.8 meters, 0.1 meters and 0.7 meters, 0.1 meters and 0.6 meters, 0.1 meters and 0.5 meters, 0.1 meters and 0.4 meters, 0.1 meters and 0.3 meters, 0.1 meters and 0.2 meters, 0.2 meters and 2.0 meters, 0.2 meters and 1.8 meters, 0.2 meters and 1.5 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, or 0.4 meters and 0.5 meters, or at a height above ground of about 0.1 meters, 0.2 meters, 0.3 meters, 0.4 meters, 0.5 meters, 0.6 meters, 0.7 meters, 0.8 meters, 0.9 meters, 1.0 meter, 1.1 meters, or 1.2 meters, such as at about 6 inches, 8 inches, 10 inches, 12 inches, 18 inches, 24 inches, 30 inches, 36 inches, 42 inches, or 48 inches, or any other height therebetween. According to some of these embodiments, the lower exterior surface of the main body and/or applicator of the ground-based agricultural vehicle is at least 0.09 meters above ground, at least 0.1 meters above ground, at least 0.2 meters above ground, at least 0.3 meters above ground, at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, or at least 2.0 meters above ground.

As used herein, "about" refers to within (e.g., plus or minus) 10% of a stated value. For example, "about 100" refers to between 90 and 110.

In an aspect, this disclosure provides a method of providing an agricultural composition to a corn field comprising applying the agricultural composition, such as water and/or a fertilizer, pesticide, insecticide, herbicide, fungicide, or cover crop seed, on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 0.7 meters, and where at least 50%, at least 60%, at least 70%, at least 80%, at least 85%, at least 90%, at least 95%, at least 99%, or 100% of the corn plants are at V7 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V7 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V7 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 0.7 meters, less than or equal to 0.6 meters, less than or equal to 0.5 meters, less than or equal to 0.4 meters, less than or equal to 0.3 meters, less than or equal to 0.2 meters, less than or equal to 0.1 meters, less than or equal to 0.09 meters, or less than or equal to 0.08 meters where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V7 stage or later.

In a further aspect, this disclosure provides a method of providing an agricultural composition, such as water and/or a fertilizer, pesticide, insecticide, herbicide, fungicide, or cover crop seed, to a corn field, comprising applying the agricultural composition to the corn field from above using a ground-based agricultural vehicle comprising an applicator for applying the agricultural composition, where at least 50% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, 0.4 meters or less, 0.3 meters or less, or 0.2 meters or less, and where at least 50%, at least 60%, at least 70%, at least 80%, at least 85%, at least 90%, at least 95%, at least 99%, or 100% of the corn plants are at V7 stage or later. According to some of these embodiments, the lower exterior surface of the main body and/or applicator of the ground-based agricultural vehicle is at a height above ground between 0.1 meters and 2.0 meters, 0.1 meters and 1.8 meters, 0.1 meters and 1.5 meters, 0.1 meters and 1.0 meter, 0.1 meters and 0.9 meters, 0.1 meters and 0.8 meters, 0.1 meters and 0.7 meters, 0.1 meters and 0.6 meters, 0.1 meters and 0.5 meters, 0.1 meters and 0.4 meters, 0.1 meters and 0.3 meters, 0.1 meters and 0.2 meters, 0.2 meters and 2.0 meters, 0.2 meters and 1.8 meters, 0.2 meters and 1.5 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, or 0.6 meters and 0.7 meters, or at a height above ground of about 0.2 meters, 0.3 meters, 0.4 meters, 0.5 meters, 0.6 meters, 0.7 meters, 0.8 meters, 0.9 meters, 1.0 meter, 1.1 meters, or 1.2 meters, such as at about 6 inches, 8 inches, 10 inches, 12 inches, 18 inches, 24 inches, 30 inches, 36 inches, 42 inches, or 48 inches, or any other height therebetween. According to some of these embodiments, the lower exterior surface of the main body and/or applicator of the ground-based agricultural vehicle is at least 0.09 meters above ground, at least 0.1 meters above ground, at least 0.2 meters above ground, at least 0.3 meters above ground, at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, or at least 2.0 meters above ground.

In an aspect, this disclosure provides a method of providing an agricultural composition to a corn field comprising applying the agricultural composition, such as water and/or a fertilizer, pesticide, insecticide, herbicide, fungicide, or cover crop seed, on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.0 meter, and where at least 50%, at least 60%, at least 70%, at least 80%, at least 85%, at least 90%, at least 95%, at least 99%, or 100% of the corn plants are at V8 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, or less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V8 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, or less than or equal to 0.3 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V8 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, less than or equal to 0.2 meters, or less than or equal to 0.1 meters where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V8 stage or later.

In a further aspect, this disclosure provides a method of providing an agricultural composition, such as water and/or a fertilizer, pesticide, insecticide, herbicide, fungicide, or cover crop seed, to a corn field, comprising applying the agricultural composition to the corn field from above using a ground-based agricultural vehicle comprising an applicator for applying the agricultural composition, where at least 50% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, 0.4 meters or less, 0.3 meters or less, or 0.2 meters or less, and where at least 50%, at least 60%, at least 70%, at least 80%, at least 85%, at least 90%, at least 95%, at least 99%, or 100% of the corn plants are at V8 stage or later. According to some of these embodiments, the lower exterior surface of the main body and/or applicator of the ground-based agricultural vehicle is at a height above ground between 0.2 meters and 2.0 meters, 0.2 meters and 1.8 meters, 0.2 meters and 1.5 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, or at a height above ground of about 0.2 meters, 0.3 meters, 0.4 meters, 0.5 meters, 0.6 meters, 0.7 meters, 0.8 meters, 0.9 meters, 1.0 meter, 1.1 meters, or 1.2 meters, such as at about 6 inches, 8 inches, 10 inches, 12 inches, 18 inches, 24 inches, 30 inches, 36 inches, 42 inches, or 48 inches, or any other height therebetween. According to some of these embodiments, the lower exterior surface of the main body and/or applicator of the ground-based agricultural vehicle is at least 0.2 meters above ground, at least 0.3 meters above ground, at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, or at least 2.0 meters above ground.

In an aspect, this disclosure provides a method of providing an agricultural composition to a corn field comprising applying the agricultural composition, such as water and/or a fertilizer, pesticide, insecticide, herbicide, fungicide, or cover crop seed, on the corn field from above using a ground-based agricultural vehicle comprising an applicator for applying the agricultural composition, where at least 50% of the corn plants within the corn field are not damaged by the applicator, where the corn plants comprise an average height of less than or equal to 1.3 meters, and where at least 50%, at least 60%, at least 70%, at least 80%, at least 85%, at least 90%, at least 95%, at least 99%, or 100% of the corn plants are at V9 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V9 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V9 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V9 stage or later.

In a further aspect, this disclosure provides a method of providing an agricultural composition, such as water and/or a fertilizer, pesticide, insecticide, herbicide, fungicide, or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, 0.4 meters or less, 0.3 meters or less, or 0.2 meters or less, and where at least 50%, at least 60%, at least 70%, at least 80%, at least 85%, at least 90%, at least 95%, at least 99%, or 100% of the corn plants are at V9 stage or later. According to some of these embodiments, the lower exterior surface of the main body and/or applicator of the ground-based agricultural vehicle is at a height above ground between 0.2 meters and 2.0 meters, 0.2 meters and 1.8 meters, 0.2 meters and 1.5 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, or at a height above ground of about 0.2 meters, 0.3 meters, 0.4 meters, 0.5 meters, 0.6 meters, 0.7 meters, 0.8 meters, 0.9 meters, 1.0 meter, 1.1 meters, 1.2 meters, 1.3 meters, 1.4 meters, or 1.5 meters, such as at about 6 inches, 8 inches, 10 inches, 12 inches, 18 inches, 24 inches, 30 inches, 36 inches, 42 inches, 48 inches, 54 inches, 60 inches, or any other height therebetween. According to some of these embodiments, the lower exterior surface of the main body and/or applicator of the ground-based agricultural vehicle is at least 0.2 meters above ground, at least 0.3 meters above ground, at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, or at least 2.0 meters above ground.

In an aspect, this disclosure provides a method of providing an agricultural composition to a corn field comprising applying the agricultural composition, such as water and/or a fertilizer, pesticide, insecticide, herbicide, fungicide, or cover crop seed, on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.4 meters, and where at least 50%, at least 60%, at least 70%, at least 80%, at least 85%, at least 90%, at least 95%, at least 99%, or 100% of the corn plants are at V10 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V10 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, or less than or equal to 0.7 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V10 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters where the height is measured as the distance between the soil and the ligule of the uppermost fully-expanded leaf, and where at least 50%, at least 60%, at least 70%, at least 80%, at least 85%, at least 90%, at least 95%, at least 99%, or 100% of the corn plants are at V10 stage or later.

In a further aspect, this disclosure provides a method of providing an agricultural composition, such as water and/or a fertilizer, pesticide, insecticide, herbicide, fungicide, or cover crop seed, to a corn field, comprising applying the agricultural composition to the corn field from above using a ground-based agricultural vehicle comprising an applicator for applying the agricultural composition, where at least 50% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, 0.4 meters or less, or 0.3 meters or less, and where at least 50%, at least 60%, at least 70%, at least 80%, at least 85%, at least 90%, at least 95%, at least 99%, or 100% of the corn plants are at V10 stage or later. According to some of these embodiments, the lower exterior surface of the main body and/or applicator of the ground-based agricultural vehicle is at a height above ground between 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, 1.2 meters and 1.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, or 1.3 meters and 1.4 meters, or at a height above ground of about 0.3 meters, 0.4 meters, 0.5 meters, 0.6 meters, 0.7 meters, 0.8 meters, 0.9 meters, 1.0 meter, 1.1 meters, 1.2 meters, 1.3 meters, 1.4 meters, or 1.5 meters, such as at about 8 inches, 10 inches, 12 inches, 18 inches, 24 inches, 30 inches, 36 inches, 42 inches, 48 inches, 54 inches, or 60 inches, or any other height therebetween. According to some of these embodiments, the lower exterior surface of the main body and/or applicator of the ground-based agricultural vehicle is at least 0.3 meters above ground, at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground.

In an aspect, this disclosure provides a method of providing an agricultural composition to a corn field comprising applying the agricultural composition, such as water and/or a fertilizer, pesticide, insecticide, herbicide, fungicide, or cover crop seed, on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.5 meters, and where at least 50%, at least 60%, at least 70%, at least 80%, at least 85%, at least 90%, at least 95%, at least 99%, or 100% of the corn plants are at V11 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V11 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, or less than or equal to 0.8 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V11 stage or later. In another aspect, this disclosure provides a method of providing an agricultural composition, such as water and/or a fertilizer, pesticide, insecticide, herbicide, fungicide, or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters where the height is measured as the distance between the soil and the ligule of the uppermost fully-expanded leaf, and where at least 50%, at least 60%, at least 70%, at least 80%, at least 85%, at least 90%, at least 95%, at least 99%, or 100% of the corn plants are at V11 stage or later.

In a further aspect, this disclosure provides a method of providing an agricultural composition, such as water and/or a fertilizer, pesticide, insecticide, herbicide, fungicide, or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, 0.4 meters or less, or 0.3 meters or less, and where at least 50%, at least 60%, at least 70%, at least 80%, at least 85%, at least 90%, at least 95%, at least 99%, or 100% of the corn plants are at V11 stage or later. According to some of these embodiments, the lower exterior surface of the main body and/or applicator of the ground-based agricultural vehicle is at a height above ground 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.0 meters, 1.4 meters and 1.9 meters, 1.4 meters and 1.8 meters, 1.4 meters and 1.7 meters, 1.4 meters and 1.6 meters, or 1.4 meters and 1.5 meters, or at a height above ground of about 0.3 meters, 0.4 meters, 0.5 meters, 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, or 1.8 meters, such as at about 8 inches, 10 inches, 12 inches, 18 inches, 24 inches, 30 inches, 36 inches, 42 inches, 48 inches, 54 inches, 60 inches, or 66 inches, or any other height therebetween. According to some of these embodiments, the lower exterior surface of the main body and/or applicator of the ground-based agricultural vehicle is at least 0.3 meters above ground, at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, or at least 2.0 meters above ground.

In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.6 meters, and where at least 50%, at least 60%, at least 70%, at least 80%, at least 85%, at least 90%, at least 95%, at least 99%, or 100% of the corn plants are at V12 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V12 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, or less than or equal to 0.8 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V12 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V12 stage or later.

In a further aspect, this disclosure provides a method of providing an agricultural composition, such as water and/or a fertilizer, pesticide, insecticide, herbicide, fungicide, and/or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.1 meters or less, 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, 0.5 meters or less, or 0.4 meters or less, and where at least 50%, at least 60%, at least 70%, at least 80%, at least 85%, at least 90%, at least 95%, at least 99%, or 100% of the corn plants are at V12 stage or later. According to some of these embodiments, the lower exterior surface of the main body and/or applicator of the ground-based agricultural vehicle is at a height above ground between 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.0 meters, 1.5 meters and 1.9 meters, 1.5 meters and 1.8 meters, 1.5 meters and 1.7 meters, or 1.5 meters and 1.6 meters, or at a height above ground of about 0.4 meters, 0.5 meters, 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, or 2.0 meters, such as at about 10 inches, 12 inches, 18 inches, 24 inches, 30 inches, 36 inches, 42 inches, 48 inches, 54 inches, 60 inches, or 66 inches, or any other height therebetween. According to some of these embodiments, the lower exterior surface of the main body and/or applicator of the ground-based agricultural vehicle is at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, or at least 2.1 meters above ground.

In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.8 meters, and where at least 50%, at least 60%, at least 70%, at least 80%, at least 85%, at least 90%, at least 95%, at least 99%, or 100% of the corn plants are at V13 stage or later. In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V13 stage or later. In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, or less than or equal to 0.9 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V13 stage or later. In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters, less than or equal to 0.4 meters, less than or equal to 0.3 meters, or less than or equal to 0.2 meters, where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V13 stage or later.

In another aspect, this disclosure provides a method of providing an agricultural composition to a corn field comprising applying the agricultural composition on the corn field from above using a ground-based agricultural vehicle comprising an applicator for applying the agricultural composition, where the corn plants of the corn field comprise an average height of less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, or less than or equal to 0.5 meters, less than or equal to 0.4 meters, less than or equal to 0.3 meters, or less than or equal to 0.2 meters, and where at least 50%, at least 60%, at least 70%, at least 80%, at least 85%, at least 90%, at least 95%, at least 99%, or 100% of the corn plants are at V13 stage or later. In a further aspect, this disclosure provides a method of providing an agricultural composition, such as water and/or a fertilizer, pesticide, insecticide, herbicide, fungicide, and/or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.3 meters or less, 2.2 meters or less, 2.1 meters or less, 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, or 0.5 meters or less, and where at least 50%, at least 60%, at least 70%, at least 80%, at least 85%, at least 90%, at least 95%, at least 99%, or 100% of the corn plants are at V13 stage or later. According to some of these embodiments, the lower exterior surface of the main body and/or applicator of the ground-based agricultural vehicle is at a height above ground 0.5 meters and 2.3 meters, 0.5 meters and 2.2 meters, 0.5 meters and 2.1 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.3 meters, 0.6 meters and 2.2 meters, 0.6 meters and 2.1 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.3 meters, 0.7 meters and 2.2 meters, 0.7 meters and 2.1 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.3 meters, 0.8 meters and 2.2 meters, 0.8 meters and 2.1 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.3 meters, 0.9 meters and 2.2 meters, 0.9 meters and 2.1 meters, 0.9 meters and 2.0 meters, 0.9 meters and 1.8 meters, 0.9 meters and 1.5 meters, 0.9 meters and 1.0 meter, 1.0 meter and 2.3 meters, 1.0 meter and 2.2 meters, 1.0 meter and 2.1 meters, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.3 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.3 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.3 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.3 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.3 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.3 meters, 1.7 meters and 2.2 meters, 1.7 meters and 2.1 meters, 1.7 meters and 2.0 meters, 1.7 meters and 1.9 meters, or 1.7 meters and 1.8 meters, or at a height above ground of about 0.5 meters, 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, or 2.0 meters, such as at about 12 inches, 18 inches, 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, at least 2.1 meters above ground, at least 2.2 meters above ground, or at least 2.3 meters above ground.

In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 1.9 meters, and where at least 50%, at least 60%, at least 70%, at least 80%, at least 85%, at least 90%, at least 95%, at least 99%, or 100% of the corn plants are at V14 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, or less than or equal to 0.5 meters, and where at least 50%, at least 60%, at least 70%, at least 80%, at least 85%, at least 90%, at least 95%, at least 99%, or 100% of the corn plants are at V14 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, or less than or equal to 1.1 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V14 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, or less than or equal to 0.5 meters where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V14 stage or later.

In a further aspect, this disclosure provides a method of providing an agricultural composition, such as water and/or a fertilizer, pesticide, insecticide, herbicide, fungicide, and/or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.4 meters or less, 2.3 meters or less, 2.2 meters or less, 2.1 meters or less, 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, 0.7 meters or less, 0.6 meters or less, or 0.5 meters or less, and where at least 50%, at least 60%, at least 70%, at least 80%, at least 85%, at least 90%, at least 95%, at least 99%, or 100% of the corn plants are at V14 stage or later. According to some of these embodiments, the lower exterior surface of the main body and/or applicator of the ground-based agricultural vehicle is at a height above ground between 0.6 meters and 2.3 meters, 0.6 meters and 2.2 meters, 0.6 meters and 2.1 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.3 meters, 0.7 meters and 2.2 meters, 0.7 meters and 2.1 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.3 meters, 0.8 meters and 2.2 meters, 0.8 meters and 2.1 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.3 meters, 0.9 meters and 2.2 meters, 0.9 meters and 2.1 meters, 0.9 meters and 2.0 meters, 0.9 meters and 1.8 meters, 0.9 meters and 1.5 meters, 0.9 meters and 1.0 meter, 1.0 meter and 2.3 meters, 1.0 meter and 2.2 meters, 1.0 meter and 2.1 meters, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.3 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.3 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.3 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.3 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.3 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.3 meters, 1.7 meters and 2.2 meters, 1.7 meters and 2.1 meters, 1.7 meters and 2.0 meters, 1.7 meters and 1.9 meters, or 1.7 meters and 1.8 meters, 1.8 meters and 2.3 meters, 1.8 meters and 2.2 meters, 1.8 meters and 2.1 meters, 1.8 meters and 2.0 meters, or 1.8 meters and 1.9 meters, or at a height above ground of about 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, or 2.0 meters, such as at about 18 inches, 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, at least 2.1 meters above ground, at least 2.2 meters above ground, or at least 2.3 meters above ground.

In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.0 meters, and where at least 50%, at least 60%, at least 70%, at least 80%, at least 85%, at least 90%, at least 95%, at least 99%, or 100% of the corn plants are at V15 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.5 meters, less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, or less than or equal to 0.5 meters and where at least 50%, at least 60%, at least 70%, at least 80%, at least 85%, at least 90%, at least 95%, at least 99%, or 100% of the corn plants are at V15 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.5 meters, less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, or less than or equal to 0.7 meters where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at V15 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, or less than or equal to 0.5 meters where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at V15 stage or later.

In a further aspect, this disclosure provides a method of providing an agricultural composition, such as water and/or a fertilizer, pesticide, insecticide, herbicide, fungicide, and/or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.5 meters or less, 2.4 meters or less, 2.3 meters or less, 2.2 meters or less, 2.1 meters or less, 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, or 0.7 meters or less, and where at least 50%, at least 60%, at least 70%, at least 80%, at least 85%, at least 90%, at least 95%, at least 99%, or 100% of the corn plants are at V15 stage or later. According to some of these embodiments, the lower exterior surface of the main body and/or applicator of the ground-based agricultural vehicle is at a height above ground between 0.8 meters and 2.5 meters, 0.8 meters and 2.4 meters, 0.8 meters and 2.3 meters, 0.8 meters and 2.2 meters, 0.8 meters and 2.1 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.5 meters, 0.9 meters and 2.4 meters, 0.9 meters and 2.3 meters, 0.9 meters and 2.2 meters, 0.9 meters and 2.1 meters, 0.9 meters and 2.0 meters, 0.9 meters and 1.8 meters, 0.9 meters and 1.5 meters, 0.9 meters and 1.0 meter, 1.0 meter and 2.5 meters, 1.0 meter and 2.4 meters, 1.0 meter and 2.3 meters, 1.0 meter and 2.2 meters, 1.0 meter and 2.1 meters, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.5 meters, 1.1 meters and 2.4 meters, 1.1 meters and 2.3 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.5 meters, 1.2 meters and 2.4 meters, 1.2 meters and 2.3 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.5 meters, 1.3 meters and 2.4 meters, 1.3 meters and 2.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.5 meters, 1.4 meters and 2.4 meters, 1.4 meters and 2.3 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.5 meters, 1.5 meters and 2.4 meters, 1.5 meters and 2.3 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.5 meters, 1.6 meters and 2.4 meters, 1.6 meters and 2.3 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.5 meters, 1.7 meters and 2.4 meters, 1.7 meters and 2.3 meters, 1.7 meters and 2.2 meters, 1.7 meters and 2.1 meters, 1.7 meters and 2.0 meters, 1.7 meters and 1.9 meters, or 1.7 meters and 1.8 meters, 1.8 meters and 2.5 meters, 1.8 meters and 2.4 meters, 1.8 meters and 2.3 meters, 1.8 meters and 2.2 meters, 1.8 meters and 2.1 meters, 1.8 meters and 2.0 meters, 1.8 meters and 1.9 meters, 1.9 meters and 2.5 meters, 1.9 meters and 2.4 meters, 1.9 meters and 2.3 meters, 1.9 meters and 2.2 meters, 1.9 meters and 2.1 meters, or 1.9 meters and 2.0 meters, or at a height above ground of about 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, or 2.0 meters, such as at about 18 inches, 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, at least 2.1 meters above ground, at least 2.2 meters above ground, at least 2.3 meters above ground, or at least 2.4 meters above ground.

In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.1 meters, and where at least 50%, at least 60%, at least 70%, at least 80%, at least 85%, at least 90%, at least 95%, at least 99%, or 100% of the corn plants are at VT stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.5 meters, less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, or less than or equal to 0.8 meters, and where at least 50%, at least 60%, at least 70%, at least 80%, at least 85%, at least 90%, at least 95%, at least 99%, or 100% of the corn plants are at VT stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.5 meters, less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, or less than or equal to 1.3 meters, less than or equal to 1.2 meters, less than or equal to 1.1 meters, or less than or equal to 1.0 meter, where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at VT stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, or less than or equal to 0.8 meters, where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at VT stage or later.

In a further aspect, this disclosure provides a method of providing an agricultural composition, such as water and/or a fertilizer, pesticide, insecticide, herbicide, fungicide, and/or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.5 meters or less, 2.4 meters or less, 2.3 meters or less, 2.2 meters or less, 2.1 meters or less, 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, or 0.7 meters or less, and where at least 50%, at least 60%, at least 70%, at least 80%, at least 85%, at least 90%, at least 95%, at least 99%, or 100% of the corn plants are at VT stage or later. According to some of these embodiments, the lower exterior surface of the main body and/or applicator of the ground-based agricultural vehicle is at a height above ground between 1.1 meters and 2.5 meters, 1.1 meters and 2.4 meters, 1.1 meters and 2.3 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.5 meters, 1.2 meters and 2.4 meters, 1.2 meters and 2.3 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.5 meters, 1.3 meters and 2.4 meters, 1.3 meters and 2.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.5 meters, 1.4 meters and 2.4 meters, 1.4 meters and 2.3 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.5 meters, 1.5 meters and 2.4 meters, 1.5 meters and 2.3 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.5 meters, 1.6 meters and 2.4 meters, 1.6 meters and 2.3 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.5 meters, 1.7 meters and 2.4 meters, 1.7 meters and 2.3 meters, 1.7 meters and 2.2 meters, 1.7 meters and 2.1 meters, 1.7 meters and 2.0 meters, 1.7 meters and 1.9 meters, 1.7 meters and 1.8 meters, 1.8 meters and 2.5 meters, 1.8 meters and 2.4 meters, 1.8 meters and 2.3 meters, 1.8 meters and 2.2 meters, 1.8 meters and 2.1 meters, 1.8 meters and 2.0 meters, 1.8 meters and 1.9 meters, 1.9 meters and 2.5 meters, 1.9 meters and 2.4 meters, 1.9 meters and 2.3 meters, 1.9 meters and 2.2 meters, 1.9 meters and 2.1 meters, 1.9 meters and 2.0 meters, or at a height above ground of about 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, or 2.0 meters, such as at about 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, at least 2.1 meters above ground, at least 2.2 meters above ground, at least 2.3 meters above ground, or at least 2.4 meters above ground.

In an aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of the corn plants within the corn field are not damaged by the applicator, where the corn plants comprise an average height of less than or equal to 2.2 meters, and where at least 50%, at least 60%, at least 70%, at least 80%, at least 85%, at least 90%, at least 95%, at least 99%, or 100% of the corn plants are at R1 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.7 meters, less than or equal to 2.6 meters, less than or equal to 2.5 meters, less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, or less than or equal to 1.1 meters, less than or equal to 1.0 meter, or less than or equal to 0.9 meters, and where at least 50%, at least 60%, at least 70%, at least 80%, at least 85%, at least 90%, at least 95%, at least 99%, or 100% of the corn plants are at R1 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.7 meters, less than or equal to 2.6 meters, less than or equal to 2.5 meters, less than or equal to 2.4 meters, less than or equal to 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, or less than or equal to 1.1 meters, where the height is measured as the distance between the soil and the uppermost leaf surface of the leaf farthest from the soil, and where at least 50%, at least 60%, at least 70%, at least 80%, at least 85%, at least 90%, at least 95%, at least 99%, or 100% of the corn plants are at R1 stage or later. In another aspect, this disclosure provides a method of providing an agricultural composition, such as water and/or a fertilizer, pesticide, insecticide, herbicide, fungicide, and/or cover crop seed, to a corn field comprising applying the agricultural composition on the corn field from above using a ground-based agricultural vehicle comprising an applicator for applying the agricultural composition, where the corn plants of the corn field comprise an average height of less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, or less than or equal to 0.9 meters, where the height is measured as the distance between the soil and the ligule (or collar) of the uppermost fully-expanded leaf, and where at least 50%, at least 60%, at least 70%, at least 80%, at least 85%, at least 90%, at least 95%, at least 99%, or 100% of the corn plants are at R1 stage or later.

In a further aspect, this disclosure provides a method of providing an agricultural composition, such as water and/or a fertilizer, pesticide, insecticide, herbicide, fungicide, and/or cover crop seed, to a corn field, comprising applying the agricultural composition to the corn field from above using a ground-based agricultural vehicle comprising an applicator for applying the agricultural composition, where at least 50%, at least 60%, at least 70%, at least 80%, at least 85%, at least 90%, at least 95%, at least 99%, or 100% of said corn plants within said corn field are not damaged by the applicator, where the ground-based agricultural vehicle comprises a main body, and where the applicator is attached to the main body, where the lower exterior surface of the main body and/or applicator of the ground-based agricultural vehicle is at a height above ground of 2.5 meters or less, 2.4 meters or less, 2.3 meters or less, 2.2 meters or less, 2.1 meters or less, 2.0 meters or less, 1.9 meters or less, 1.8 meters or less, 1.7 meters or less, 1.6 meters or less, 1.5 meters or less, 1.4 meters or less, 1.3 meters or less, 1.2 meters or less, 1.1 meters or less, 1.0 meter or less, 0.9 meters or less, 0.8 meters or less, or 0.7 meters or less, and where at least 50%, at least 60%, at least 70%, at least 80%, at least 85%, at least 90%, at least 95%, at least 99%, or 100% of the corn plants are at R1 stage or later. According to some of these embodiments, the lower exterior surface of the main body and/or applicator of the ground-based agricultural vehicle is at a height above ground between 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.0 meters, 1.6 meters and 1.9 meters, 1.6 meters and 1.8 meters, 1.6 meters and 1.7 meters, 1.7 meters and 2.0 meters, 1.7 meters and 1.9 meters, 1.7 meters and 1.8 meters, 1.8 meters and 2.0 meters, 1.8 meters and 1.9 meters, 1.9 meters and 2.0 meters, 1.2 meters and 2.1 meters, 1.3 meters and 2.1 meters, 1.4 meters and 2.1 meters, 1.5 meters and 2.1 meters, 1.6 meters and 2.1 meters, 1.7 meters and 2.1 meters, 1.8 meters and 2.1 meters, 1.9 meters and 2.1 meters, or 2.0 meters and 2.1 meters, or at a height above ground of about 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, 2.0 meters, such as at about 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, at least 2.1 meters above ground, at least 2.2 meters above ground, at least 2.3 meters above ground, at least 2.4 meters above ground, or at least 2.5 meters above ground.

According to embodiments where at least 50%, at least 60%, at least 70%, at least 80%, at least 85%, at least 90%, at least 95%, at least 99%, or 100% of the corn plants are at V6 stage or later, V7 stage or later, V8 stage or later, V9 stage or later, V10 stage or later, or V11 stage or later, the lower exterior surface of the main body and/or applicator of the ground-based agricultural vehicle may be at a height above ground between 0.09 meters and 2.0 meters, 0.09 meters and 1.8 meters, 0.09 meters and 1.5 meters, 0.09 meters and 1.0 meter, 0.09 meters and 0.9 meters, 0.09 meters and 0.8 meters, 0.09 meters and 0.7 meters, 0.09 meters and 0.6 meters, 0.09 meters and 0.5 meters, 0.09 meters and 0.4 meters, 0.09 meters and 0.3 meters, 0.09 meters and 0.2 meters, 0.09 meters and 0.1 meters, 0.1 meters and 2.0 meters, 0.1 meters and 1.8 meters, 0.1 meters and 1.5 meters, 0.1 meters and 1.0 meter, 0.1 meters and 0.9 meters, 0.1 meters and 0.8 meters, 0.1 meters and 0.7 meters, 0.1 meters and 0.6 meters, 0.1 meters and 0.5 meters, 0.1 meters and 0.4 meters, 0.1 meters and 0.3 meters, 0.1 meters and 0.2 meters, 0.2 meters and 2.0 meters, 0.2 meters and 1.8 meters, 0.2 meters and 1.5 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, or at a height above ground of about 0.5 meters, 0.6 meters, 0.7 meters, 0.8 meters, 0.9 meters, 1.0 meter, 1.1 meters, 1.2 meters, 1.3 meters, 1.4 meters, 1.5 meters, 1.6 meters, 1.7 meters, 1.8 meters, 1.9 meters, or 2.0 meters, such as at about 8 inches, 10 inches, 12 inches, 18 inches, 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, or at least 2.0 meters above ground.

According to embodiments where at least 50%, at least 60%, at least 70%, at least 80%, at least 85%, at least 90%, at least 95%, at least 99%, or 100% of the corn plants are at V12 stage or later, V13 stage or later, V14 stage or later, V15 stage or later, VT stage or later, or R1 stage or later, the lower exterior surface of the main body and/or applicator of the ground-based agricultural vehicle may be at a height above ground between 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.0 meters, 0.9 meters and 1.8 meters, 0.9 meters and 1.5 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.5 meters, 1.1 meters and 2.4 meters, 1.1 meters and 2.3 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.5 meters, 1.2 meters and 2.4 meters, 1.2 meters and 2.3 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.5 meters, 1.3 meters and 2.4 meters, 1.3 meters and 2.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.5 meters, 1.4 meters and 2.4 meters, 1.4 meters and 2.3 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.5 meters, 1.5 meters and 2.4 meters, 1.5 meters and 2.3 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.5 meters, 1.6 meters and 2.4 meters, 1.6 meters and 2.3 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.5 meters, 1.7 meters and 2.4 meters, 1.7 meters and 2.3 meters, 1.7 meters and 2.2 meters, 1.7 meters and 2.1 meters, 1.7 meters and 2.0 meters, 1.7 meters and 1.9 meters, 1.7 meters and 1.8 meters, 1.8 meters and 2.5 meters, 1.8 meters and 2.4 meters, 1.8 meters and 2.3 meters, 1.8 meters and 2.2 meters, 1.8 meters and 2.1 meters, 1.8 meters and 2.0 meters, 1.8 meters and 1.9 meters, 1.9 meters and 2.5 meters, 1.9 meters and 2.4 meters, 1.9 meters and 2.3 meters, 1.9 meters and 2.2 meters, 1.9 meters and 2.1 meters, 1.9 meters and 2.0 meters, such as at about 8 inches, 10 inches, 12 inches, 18 inches, 24 inches, 30 inches, 36 inches, 42 inches, 48 inches, 54 inches, 60 inches, 66 inches, or 72 inches, or any other height therebetween. According to some of these embodiments, the lower exterior surface of the main body and/or applicator of the ground-based agricultural vehicle is at least 0.4 meters above ground, at least 0.5 meters above ground, at least 0.6 meters above ground, at least 0.7 meters above ground, at least 0.8 meters above ground, at least 0.9 meters above ground, at least 1.0 meter above ground, at least 1.1 meters above ground, at least 1.2 meters above ground, at least 1.3 meters above ground, at least 1.4 meters above ground, at least 1.5 meters above ground, at least 1.6 meters above ground, at least 1.7 meters above ground, at least 1.8 meters above ground, at least 1.9 meters above ground, at least 2.0 meters above ground, at least 2.1 meters above ground, at least 2.2 meters above ground, at least 2.3 meters above ground, at least 2.4 meters above ground, or at least 2.5 meters above ground.

In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant is not damaged by the vehicle or applicator, where the corn plant comprises a height of equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, equal to or less than 0.1 meters, and where the corn plant is at V6 stage or later, V7 stage or later, V8 stage or later, V9 stage or later, V10 stage or later, or V11 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant is not damaged by the vehicle or applicator, where the corn plant comprises a height of equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, or equal to or less than 0.2 meters meters where the height is measured as the distance between the soil and the uppermost leaf surface of the leaf farthest from the soil, and where the corn plant is at V6 stage or later, V7 stage or later, V8 stage or later, V9 stage or later, V10 stage or later, or V11 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant is not damaged by the vehicle or applicator, where the corn plant comprises a height of equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, or equal to or less than 0.1 meters where the height is measured as the distance between the soil and the ligule of the uppermost fully-expanded leaf, and where the corn plant is at V6 stage or later, V7 stage or later, V8 stage or later, V9 stage or later, V10 stage or later, or V11 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant comprises a height of equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, or equal to or less than 0.1 meters, and where the corn plant is at V6 stage or later, V7 stage or later, V8 stage or later, V9 stage or later, V10 stage or later, or V11 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant comprises a height of equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, or equal to or less than 0.2 meters where the height is measured as the distance between the soil and the uppermost leaf surface of the leaf farthest from the soil, and where the corn plant is at V6 stage or later, V7 stage or later, V8 stage or later, V9 stage or later, V10 stage or later, or V11 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant comprises a height of equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, or equal to or less than 0.1 meters where the height is measured as the distance between the soil and the ligule of the uppermost fully-expanded leaf, and where the corn plant is at V6 stage or later, V7 stage or later, V8 stage or later, V9 stage or later, V10 stage or later, or V11 stage or later.

In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant is not damaged by the vehicle or applicator, where the corn plant comprises a height of equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, or equal to or less than 0.5 meters, and where the corn plant is at V12 stage or later, V13 stage or later, V14 stage or later, V15 stage or later, VT stage or later, R1 stage or later, R2 stage or later, R3 stage or later, R4 stage or later, or R5 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant is not damaged by the vehicle or applicator, where the corn plant comprises a height of equal to or less than 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters where the height is measured as the distance between the soil and the uppermost leaf surface of the leaf farthest from the soil, and where the corn plant is at V12 stage or later, V13 stage or later, V14 stage or later, V15 stage or later, VT stage or later, R1 stage or later, R2 stage or later, R3 stage or later, R4 stage or later, or R5 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant is not damaged by the vehicle or applicator, where the corn plant comprises a height of equal to or less than 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters where the height is measured as the distance between the soil and the ligule (or collar) of the uppermost fully-expanded leaf, and where the corn plant is at V12 stage or later, V13 stage or later, V14 stage or later, V15 stage or later, R1 stage or later, R2 stage or later, R3 stage or later, R4 stage or later, or R5 stage or later.

In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant comprises a height of equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, or equal to or less than 0.5 meters, and where the corn plant is at V12 stage or later, V13 stage or later, V14 stage or later, V15 stage or later, R1 stage or later, R2 stage or later, R3 stage or later, R4 stage or later, or R5 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant comprises a height of equal to or less than 2.3 meters, less than or equal to 2.2 meters, less than or equal to 2.1 meters, less than or equal to 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters where the height is measured as the distance between the soil and the uppermost leaf surface of the leaf farthest from the soil, and where the corn plant is at V12 stage or later, V13 stage or later, V14 stage or later, V15 stage or later, VT stage or later, R1 stage or later, R2 stage or later, R3 stage or later, R4 stage or later, or R5 stage or later. In an aspect, this disclosure provides a method of providing an agricultural composition, such as water and/or a fertilizer, pesticide, insecticide, herbicide, fungicide, and/or cover crop seed, to a corn plant comprising applying the agricultural composition on the corn plant from above using a ground-based agricultural vehicle comprising an applicator for applying the agricultural composition, where the corn plant comprises a height of equal to or less than 2.0 meters, less than or equal to 1.9 meters, less than or equal to 1.8 meters, less than or equal to 1.7 meters, less than or equal to 1.6 meters, less than or equal to 1.5 meters, less than or equal to 1.4 meters, less than or equal to 1.3 meters, less than or equal to 1.2 meters, less than or equal to 1.1 meters, less than or equal to 1.0 meter, less than or equal to 0.9 meters, less than or equal to 0.8 meters, less than or equal to 0.7 meters, less than or equal to 0.6 meters, less than or equal to 0.5 meters where the height is measured as the distance between the soil and the ligule of the uppermost fully-expanded leaf, and where the corn plant is at V12 stage or later, V13 stage or later, V14 stage or later, V15 stage or later, R1 stage or later, R2 stage or later, R3 stage or later, R4 stage or later, or R5 stage or later.

Corn leaves consist of four main anatomical parts: a proximal sheath, a ligule, an auricle, and a distal blade. The sheath wraps around the stem and younger leaves, while the blade is flattened in the mediolateral axis (midrib to margin). The ligule and auricle are found at the blade/sheath boundary; the ligule is an adaxial (upper) membranous structure that acts as a collar around the stem, and the auricle is a projection on the lower surface of the blade base that connects the blade to the sheath. Stages of corn plant growth are divided into vegetative (V) stages and reproductive (R) stages. Upon germination, a corn plant is said to be in VE stage (emergence). Once the first leaf collar (e.g., the ligule) is visible, the corn plant is in the V1 stage. The emergence of the second leaf collar signifies V2 stage; the emergence of the third leaf collar signifies the V3 stage; and so on until the tassel emerges. For example, if twelve leaf collars are visible, the plant is a V12 stage plant. Once the bottom-most branch of the tassel emerges the plant is in VT stage, which is the final vegetative stage. The reproductive stage of growth occurs after the vegetative stage. The number of vegetative stages prior to VT stage can vary by environment and corn line. The first reproductive stage (R1; silking stage) occurs when silk is visible outside the husk leaves surrounding an ear of corn. R2 (blistering stage) occurs when corn kernels are white on the outside and are filled with a clear liquid inside. R3 (milk stage) occurs when the kernels are yellow on the outside and are filled with a milky white fluid inside. R4 (dough stage) occurs when the kernels are filled with a thick, or pasty, fluid. In some corn lines the cob will also turn pink or red at this stage. R5 (dent stage) occurs when a majority of the kernels are at least partially dented. The final reproductive stage, R6 (physiological maturity), occurs when the kernels have attained their maximum dry weight. According to present embodiments, corn developmental stages are defined according to the Iowa State University (ISU) method. See, e.g., Ritchie, S. W. et al., How a corn plant develops. Special Report No. 48, Iowa State University, CES, Ames, Iowa, reprinted 1996, the entire contents and disclosure of which are incorporated herein by reference.

In an aspect, at least 50% of the corn plants in a corn field provided herein are at V6 stage or later. In an aspect, at least 50% of the corn plants in a corn field provided herein are at V7 stage or later. In an aspect, at least 50% of the corn plants in a corn field provided herein are at V8 stage or later. In an aspect, at least 50% of the corn plants in a corn field provided herein are at V9 stage or later. In an aspect, at least 50% of the corn plants in a corn field provided herein are at V10 stage or later. In an aspect, at least 50% of the corn plants in a corn field provided herein are at V11 stage or later. In an aspect, at least 50% of the corn plants in a corn field provided herein are at V12 stage or later. In an aspect, at least 50% of the corn plants in a corn field provided herein are at V13 stage or later. In an aspect, at least 50% of the corn plants in a corn field provided herein are at V14 stage or later. In an aspect, at least 50% of the corn plants in a corn field provided herein are at V15 stage or later. In an aspect, at least 50% of the corn plants in a corn field provided herein are at VT stage or later. In an aspect, at least 50% of the corn plants in a corn field provided herein are at R1 stage or later. In an aspect, at least 50% of the corn plants in a corn field provided herein are at R2 stage or later. In an aspect, at least 50% of the corn plants in a corn field provided herein are at R3 stage or later. In an aspect, at least 50% of the corn plants in a corn field provided herein are at R4 stage or later. In an aspect, at least 50% of the corn plants in a corn field provided herein are at R5 stage or later. In an aspect, at least 50% of the corn plants in a corn field provided herein are at R6 stage or later.

In an aspect, at least 60% of the corn plants in a corn field provided herein are at V6 stage or later. In an aspect, at least 60% of the corn plants in a corn field provided herein are at V7 stage or later. In an aspect, at least 60% of the corn plants in a corn field provided herein are at V8 stage or later. In an aspect, at least 60% of the corn plants in a corn field provided herein are at V9 stage or later. In an aspect, at least 60% of the corn plants in a corn field provided herein are at V10 stage or later. In an aspect, at least 60% of the corn plants in a corn field provided herein are at V11 stage or later. In an aspect, at least 60% of the corn plants in a corn field provided herein are at V12 stage or later. In an aspect, at least 60% of the corn plants in a corn field provided herein are at V13 stage or later. In an aspect, at least 60% of the corn plants in a corn field provided herein are at V14 stage or later. In an aspect, at least 60% of the corn plants in a corn field provided herein are at V15 stage or later. In an aspect, at least 60% of the corn plants in a corn field provided herein are at VT stage or later. In an aspect, at least 60% of the corn plants in a corn field provided herein are at R1 stage or later. In an aspect, at least 60% of the corn plants in a corn field provided herein are at R2 stage or later. In an aspect, at least 60% of the corn plants in a corn field provided herein are at R3 stage or later. In an aspect, at least 60% of the corn plants in a corn field provided herein are at R4 stage or later. In an aspect, at least 60% of the corn plants in a corn field provided herein are at R5 stage or later. In an aspect, at least 60% of the corn plants in a corn field provided herein are at R6 stage or later.

In an aspect, at least 70% of the corn plants in a corn field provided herein are at V6 stage or later. In an aspect, at least 70% of the corn plants in a corn field provided herein are at V7 stage or later. In an aspect, at least 70% of the corn plants in a corn field provided herein are at V8 stage or later. In an aspect, at least 70% of the corn plants in a corn field provided herein are at V9 stage or later. In an aspect, at least 70% of the corn plants in a corn field provided herein are at V10 stage or later. In an aspect, at least 70% of the corn plants in a corn field provided herein are at V11 stage or later. In an aspect, at least 70% of the corn plants in a corn field provided herein are at V12 stage or later. In an aspect, at least 70% of the corn plants in a corn field provided herein are at V13 stage or later. In an aspect, at least 70% of the corn plants in a corn field provided herein are at V14 stage or later. In an aspect, at least 70% of the corn plants in a corn field provided herein are at V15 stage or later. In an aspect, at least 70% of the corn plants in a corn field provided herein are at VT stage or later. In an aspect, at least 70% of the corn plants in a corn field provided herein are at R1 stage or later. In an aspect, at least 70% of the corn plants in a corn field provided herein are at R2 stage or later. In an aspect, at least 70% of the corn plants in a corn field provided herein are at R3 stage or later. In an aspect, at least 70% of the corn plants in a corn field provided herein are at R4 stage or later. In an aspect, at least 70% of the corn plants in a corn field provided herein are at R5 stage or later. In an aspect, at least 70% of the corn plants in a corn field provided herein are at R6 stage or later.

In an aspect, at least 75% of the corn plants in a corn field provided herein are at V6 stage or later. In an aspect, at least 75% of the corn plants in a corn field provided herein are at V7 stage or later. In an aspect, at least 75% of the corn plants in a corn field provided herein are at V8 stage or later. In an aspect, at least 75% of the corn plants in a corn field provided herein are at V9 stage or later. In an aspect, at least 75% of the corn plants in a corn field provided herein are at V10 stage or later. In an aspect, at least 75% of the corn plants in a corn field provided herein are at V11 stage or later. In an aspect, at least 75% of the corn plants in a corn field provided herein are at V12 stage or later. In an aspect, at least 75% of the corn plants in a corn field provided herein are at V13 stage or later. In an aspect, at least 75% of the corn plants in a corn field provided herein are at V14 stage or later. In an aspect, at least 75% of the corn plants in a corn field provided herein are at V15 stage or later. In an aspect, at least 75% of the corn plants in a corn field provided herein are at VT stage or later. In an aspect, at least 75% of the corn plants in a corn field provided herein are at R1 stage or later. In an aspect, at least 75% of the corn plants in a corn field provided herein are at R2 stage or later. In an aspect, at least 75% of the corn plants in a corn field provided herein are at R3 stage or later. In an aspect, at least 75% of the corn plants in a corn field provided herein are at R4 stage or later. In an aspect, at least 75% of the corn plants in a corn field provided herein are at R5 stage or later. In an aspect, at least 75% of the corn plants in a corn field provided herein are at R6 stage or later.

In an aspect, at least 80% of the corn plants in a corn field provided herein are at V6 stage or later. In an aspect, at least 80% of the corn plants in a corn field provided herein are at V7 stage or later. In an aspect, at least 80% of the corn plants in a corn field provided herein are at V8 stage or later. In an aspect, at least 80% of the corn plants in a corn field provided herein are at V9 stage or later. In an aspect, at least 80% of the corn plants in a corn field provided herein are at V10 stage or later. In an aspect, at least 80% of the corn plants in a corn field provided herein are at V11 stage or later. In an aspect, at least 80% of the corn plants in a corn field provided herein are at V12 stage or later. In an aspect, at least 80% of the corn plants in a corn field provided herein are at V13 stage or later. In an aspect, at least 80% of the corn plants in a corn field provided herein are at V14 stage or later. In an aspect, at least 80% of the corn plants in a corn field provided herein are at V15 stage or later. In an aspect, at least 80% of the corn plants in a corn field provided herein are at VT stage or later. In an aspect, at least 80% of the corn plants in a corn field provided herein are at R1 stage or later. In an aspect, at least 80% of the corn plants in a corn field provided herein are at R2 stage or later. In an aspect, at least 80% of the corn plants in a corn field provided herein are at R3 stage or later. In an aspect, at least 80% of the corn plants in a corn field provided herein are at R4 stage or later. In an aspect, at least 80% of the corn plants in a corn field provided herein are at R5 stage or later. In an aspect, at least 80% of the corn plants in a corn field provided herein are at R6 stage or later.

In an aspect, at least 85% of the corn plants in a corn field provided herein are at V6 stage or later. In an aspect, at least 85% of the corn plants in a corn field provided herein are at V7 stage or later. In an aspect, at least 85% of the corn plants in a corn field provided herein are at V8 stage or later. In an aspect, at least 85% of the corn plants in a corn field provided herein are at V9 stage or later. In an aspect, at least 85% of the corn plants in a corn field provided herein are at V10 stage or later. In an aspect, at least 85% of the corn plants in a corn field provided herein are at V11 stage or later. In an aspect, at least 85% of the corn plants in a corn field provided herein are at V12 stage or later. In an aspect, at least 85% of the corn plants in a corn field provided herein are at V13 stage or later. In an aspect, at least 85% of the corn plants in a corn field provided herein are at V14 stage or later. In an aspect, at least 85% of the corn plants in a corn field provided herein are at V15 stage or later. In an aspect, at least 85% of the corn plants in a corn field provided herein are at VT stage or later. In an aspect, at least 85% of the corn plants in a corn field provided herein are at R1 stage or later. In an aspect, at least 85% of the corn plants in a corn field provided herein are at R2 stage or later. In an aspect, at least 85% of the corn plants in a corn field provided herein are at R3 stage or later. In an aspect, at least 85% of the corn plants in a corn field provided herein are at R4 stage or later. In an aspect, at least 85% of the corn plants in a corn field provided herein are at R5 stage or later. In an aspect, at least 85% of the corn plants in a corn field provided herein are at R6 stage or later.

In an aspect, at least 90% of the corn plants in a corn field provided herein are at V6 stage or later. In an aspect, at least 90% of the corn plants in a corn field provided herein are at V7 stage or later. In an aspect, at least 90% of the corn plants in a corn field provided herein are at V8 stage or later. In an aspect, at least 90% of the corn plants in a corn field provided herein are at V9 stage or later. In an aspect, at least 90% of the corn plants in a corn field provided herein are at V10 stage or later. In an aspect, at least 90% of the corn plants in a corn field provided herein are at V11 stage or later. In an aspect, at least 90% of the corn plants in a corn field provided herein are at V12 stage or later. In an aspect, at least 90% of the corn plants in a corn field provided herein are at V13 stage or later. In an aspect, at least 90% of the corn plants in a corn field provided herein are at V14 stage or later. In an aspect, at least 90% of the corn plants in a corn field provided herein are at V15 stage or later. In an aspect, at least 90% of the corn plants in a corn field provided herein are at VT stage or later. In an aspect, at least 90% of the corn plants in a corn field provided herein are at R1 stage or later. In an aspect, at least 90% of the corn plants in a corn field provided herein are at R2 stage or later. In an aspect, at least 90% of the corn plants in a corn field provided herein are at R3 stage or later. In an aspect, at least 90% of the corn plants in a corn field provided herein are at R4 stage or later. In an aspect, at least 90% of the corn plants in a corn field provided herein are at R5 stage or later. In an aspect, at least 90% of the corn plants in a corn field provided herein are at R6 stage or later.

In an aspect, at least 95% of the corn plants in a corn field provided herein are at V6 stage or later. In an aspect, at least 95% of the corn plants in a corn field provided herein are at V7 stage or later. In an aspect, at least 95% of the corn plants in a corn field provided herein are at V8 stage or later. In an aspect, at least 95% of the corn plants in a corn field provided herein are at V9 stage or later. In an aspect, at least 95% of the corn plants in a corn field provided herein are at V10 stage or later. In an aspect, at least 95% of the corn plants in a corn field provided herein are at V11 stage or later. In an aspect, at least 95% of the corn plants in a corn field provided herein are at V12 stage or later. In an aspect, at least 95% of the corn plants in a corn field provided herein are at V13 stage or later. In an aspect, at least 95% of the corn plants in a corn field provided herein are at V14 stage or later. In an aspect, at least 95% of the corn plants in a corn field provided herein are at V15 stage or later. In an aspect, at least 95% of the corn plants in a corn field provided herein are at VT stage or later. In an aspect, at least 95% of the corn plants in a corn field provided herein are at R1 stage or later. In an aspect, at least 95% of the corn plants in a corn field provided herein are at R2 stage or later. In an aspect, at least 95% of the corn plants in a corn field provided herein are at R3 stage or later. In an aspect, at least 95% of the corn plants in a corn field provided herein are at R4 stage or later. In an aspect, at least 95% of the corn plants in a corn field provided herein are at R5 stage or later. In an aspect, at least 95% of the corn plants in a corn field provided herein are at R6 stage or later.

In an aspect, 100% of the corn plants in a corn field provided herein are at V6 stage or later. In an aspect, 100% of the corn plants in a corn field provided herein are at V7 stage or later. In an aspect, 100% of the corn plants in a corn field provided herein are at V8 stage or later. In an aspect, 100% of the corn plants in a corn field provided herein are at V9 stage or later. In an aspect, 100% of the corn plants in a corn field provided herein are at V10 stage or later. In an aspect, 100% of the corn plants in a corn field provided herein are at V11 stage or later. In an aspect, 100% of the corn plants in a corn field provided herein are at V12 stage or later. In an aspect, 100% of the corn plants in a corn field provided herein are at V13 stage or later. In an aspect, 100% of the corn plants in a corn field provided herein are at V14 stage or later. In an aspect, 100% of the corn plants in a corn field provided herein are at V15 stage or later. In an aspect, 100% of the corn plants in a corn field provided herein are at VT stage or later. In an aspect, 100% of the corn plants in a corn field provided herein are at R1 stage or later. In an aspect, 100% of the corn plants in a corn field provided herein are at R2 stage or later. In an aspect, 100% of the corn plants in a corn field provided herein are at R3 stage or later. In an aspect, 100% of the corn plants in a corn field provided herein are at R4 stage or later. In an aspect, 100% of the corn plants in a corn field provided herein are at R5 stage or later. In an aspect, 100% of the corn plants in a corn field provided herein are at R6 stage or later.

The height of a corn plant can be measured using a variety of methods known in the art. The height of a corn plant can be measured at V6 stage, V7 stage, V8 stage, V9 stage, V10 stage, V11 stage, V12 stage, V13 stage, V14 stage, V15 stage, VT stage, R1 stage, R2 stage, R3 stage, R4 stage, R5 stage, or R6 stage. The height of a corn plant can also be determined based on a variety of anatomical locations on a corn plant. In an aspect, the height of a corn plant is measured as the distance between the top of the soil or ground and the ligule or collar of the uppermost fully-expanded leaf of a corn plant. As used herein, a "fully-expanded leaf" is a leaf where the leaf blade is exposed and both the ligule and auricle are visible at the blade/sheath boundary. In another aspect, the height of a corn plant is measured as the distance between the top of the soil or ground and the uppermost leaf surface of the leaf farthest from the soil or ground (i.e., of the uppermost leaf). In a further aspect, the height of a corn plant is measured as the distance between the top of the soil or ground and the arch of the highest corn leaf that is at least 50% developed. In still a further aspect, the height of a corn plant is measured as the distance between the top of the soil or ground and the anatomical part of the corn plant that is farthest from the soil or ground (i.e., from the top of the soil or ground), such as the uppermost surface of the leaf farthest away from the ground or soil. Exemplary, non-limiting methods of measuring plant height include comparing photographs of corn plants to a height reference, or physically measuring individual corn plants with a suitable ruler. If not otherwise stated, the height of a corn plant for the present disclosure is measured as the distance between the top of the soil or ground and the ligule or collar of the uppermost fully-expanded leaf of a corn plant. If not otherwise stated, all descriptions herein with regard to the plant height of a population of plants can refer to either the average plant height among the population of plants or, if stated, the percentage(s) of plants among the population of plants.

In an aspect, the corn plants of a corn field provided herein comprise an average height of less than or equal to 2.5 meters. In an aspect, the corn plants of a corn field provided herein comprise an average height of less than or equal to 2.4 meters. In an aspect, the corn plants of a corn field provided herein comprise an average height of less than or equal to 2.3 meters. In an aspect, the corn plants of a corn field provided herein comprise an average height of less than or equal to 2.2 meters. In an aspect, the corn plants of a corn field provided herein comprise an average height of less than or equal to 2.1 meters. In an aspect, the corn plants of a corn field provided herein comprise an average height of less than or equal to 2.0 meters. In another aspect, the corn plants of a corn field provided herein comprise an average height of less than or equal to 1.9 meters. In another aspect, the corn plants of a corn field provided herein comprise an average height of less than or equal to 1.8 meters. In another aspect, the corn plants of a corn field provided herein comprise an average height of less than or equal to 1.7 meters. In another aspect, the corn plants of a corn field provided herein comprise an average height of less than or equal to 1.6 meters. In another aspect, the corn plants of a corn field provided herein comprise an average height of less than or equal to 1.5 meters. In another aspect, the corn plants of a corn field provided herein comprise an average height of less than or equal to 1.4 meters. In another aspect, the corn plants of a corn field provided herein comprise an average height of less than or equal to 1.3 meters. In another aspect, the corn plants of a corn field provided herein comprise an average height of less than or equal to 1.2 meters. In another aspect, the corn plants of a corn field provided herein comprise an average height of less than or equal to 1.1 meters. In another aspect, the corn plants of a corn field provided herein comprise an average height of less than or equal to 1.0 meter. In another aspect, the corn plants of a corn field provided herein comprise an average height of less than or equal to 0.9 meters. In another aspect, the corn plants of a corn field provided herein comprise an average height of less than or equal to 0.8 meters. In another aspect, the corn plants of a corn field provided herein comprise an average height of less than or equal to 0.7 meters. In another aspect, the corn plants of a corn field provided herein comprise an average height of less than or equal to 0.6 meters. In another aspect, the corn plants of a corn field provided herein comprise an average height of less than or equal to 0.5 meters. In another aspect, the corn plants of a corn field provided herein comprise an average height of less than or equal to 0.4 meters. In another aspect, the corn plants of a corn field provided herein comprise an average height of less than or equal to 0.3 meters. In another aspect, the corn plants of a corn field provided herein comprise an average height of less than or equal to 0.3 meters. In an aspect, the corn plants of a corn field provided herein comprise an average height of less than or equal to 0.2 meters.

In an aspect, the corn plants of a corn field provided herein comprise an average height of less than or equal to 2.3 meters where the height is measured as the distance between the soil and the uppermost leaf surface of the leaf farthest from the soil. In an aspect, the corn plants of a corn field provided herein comprise an average height of less than or equal to 2.2 meters where the height is measured as the distance between the soil and the uppermost leaf surface of the leaf farthest from the soil. In an aspect, the corn plants of a corn field provided herein comprise an average height of less than or equal to 2.1 meters where the height is measured as the distance between the soil and the uppermost leaf surface of the leaf farthest from the soil. In an aspect, the corn plants of a corn field provided herein comprise an average height of less than or equal to 2.0 meters where the height is measured as the distance between the soil and the uppermost leaf surface of the leaf farthest from the soil. In another aspect, the corn plants of a corn field provided herein comprise an average height of less than or equal to 1.9 meters where the height is measured as the distance between the soil and the uppermost leaf surface of the leaf farthest from the soil. In another aspect, the corn plants of a corn field provided herein comprise an average height of less than or equal to 1.8 meters where the height is measured as the distance between the soil and the uppermost leaf surface of the leaf farthest from the soil. In another aspect, the corn plants of a corn field provided herein comprise an average height of less than or equal to 1.7 meters where the height is measured as the distance between the soil and the uppermost leaf surface of the leaf farthest from the soil. In another aspect, the corn plants of a corn field provided herein comprise an average height of less than or equal to 1.6 meters where the height is measured as the distance between the soil and the uppermost leaf surface of the leaf farthest from the soil. In another aspect, the corn plants of a corn field provided herein comprise an average height of less than or equal to 1.5 meters where the height is measured as the distance between the soil and the uppermost leaf surface of the leaf farthest from the soil. In another aspect, the corn plants of a corn field provided herein comprise an average height of less than or equal to 1.4 meters where the height is measured as the distance between the soil and the uppermost leaf surface of the leaf farthest from the soil. In another aspect, the corn plants of a corn field provided herein comprise an average height of less than or equal to 1.3 meters where the height is measured as the distance between the soil and the uppermost leaf surface of the leaf farthest from the soil. In another aspect, the corn plants of a corn field provided herein comprise an average height of less than or equal to 1.2 meters where the height is measured as the distance between the soil and the uppermost leaf surface of the leaf farthest from the soil. In another aspect, the corn plants of a corn field provided herein comprise an average height of less than or equal to 1.1 meters where the height is measured as the distance between the soil and the uppermost leaf surface of the leaf farthest from the soil. In another aspect, the corn plants of a corn field provided herein comprise an average height of less than or equal to 1.0 meter where the height is measured as the distance between the soil and the uppermost leaf surface of the leaf farthest from the soil. In another aspect, the corn plants of a corn field provided herein comprise an average height of less than or equal to 0.9 meters where the height is measured as the distance between the soil and the uppermost leaf surface of the leaf farthest from the soil. In another aspect, the corn plants of a corn field provided herein comprise an average height of less than or equal to 0.8 meters where the height is measured as the distance between the soil and the uppermost leaf surface of the leaf farthest from the soil. In another aspect, the corn plants of a corn field provided herein comprise an average height of less than or equal to 0.7 meters where the height is measured as the distance between the soil and the uppermost leaf surface of the leaf farthest from the soil. In another aspect, the corn plants of a corn field provided herein comprise an average height of less than or equal to 0.6 meters where the height is measured as the distance between the soil and the uppermost leaf surface of the leaf farthest from the soil. In another aspect, the corn plants of a corn field provided herein comprise an average height of less than or equal to 0.5 meters where the height is measured as the distance between the soil and the uppermost leaf surface of the leaf farthest from the soil. In another aspect, the corn plants of a corn field provided herein comprise an average height of less than or equal to 0.4 meters where the height is measured as the distance between the soil and the uppermost leaf surface of the leaf farthest from the soil. In another aspect, the corn plants of a corn field provided herein comprise an average height of less than or equal to 0.3 meters where the height is measured as the distance between the soil and the uppermost leaf surface of the leaf farthest from the soil. In another aspect, the corn plants of a corn field provided herein comprise an average height of less than or equal to 0.2 meters where the height is measured as the distance between the soil and the uppermost leaf surface of the leaf farthest from the soil.

In an aspect, the corn plants of a corn field provided herein comprise an average height of less than or equal to 2.0 meters where the height is measured as the distance between the soil and the ligule of the uppermost fully-expanded leaf. In another aspect, the corn plants of a corn field provided herein comprise an average height of less than or equal to 1.9 meters where the height is measured as the distance between the soil and the ligule of the uppermost fully-expanded leaf. In another aspect, the corn plants of a corn field provided herein comprise an average height of less than or equal to 1.8 meters where the height is measured as the distance between the soil and the ligule of the uppermost fully-expanded leaf. In another aspect, the corn plants of a corn field provided herein comprise an average height of less than or equal to 1.7 meters where the height is measured as the distance between the soil and the ligule of the uppermost fully-expanded leaf. In another aspect, the corn plants of a corn field provided herein comprise an average height of less than or equal to 1.6 meters where the height is measured as the distance between the soil and the ligule of the uppermost fully-expanded leaf. In another aspect, the corn plants of a corn field provided herein comprise an average height of less than or equal to 1.5 meters where the height is measured as the distance between the soil and the ligule of the uppermost fully-expanded leaf. In another aspect, the corn plants of a corn field provided herein comprise an average height of less than or equal to 1.4 meters where the height is measured as the distance between the soil and the ligule of the uppermost fully-expanded leaf. In another aspect, the corn plants of a corn field provided herein comprise an average height of less than or equal to 1.3 meters where the height is measured as the distance between the soil and the ligule of the uppermost fully-expanded leaf. In another aspect, the corn plants of a corn field provided herein comprise an average height of less than or equal to 1.2 meters where the height is measured as the distance between the soil and the ligule of the uppermost fully-expanded leaf. In another aspect, the corn plants of a corn field provided herein comprise an average height of less than or equal to 1.1 meters where the height is measured as the distance between the soil and the ligule of the uppermost fully-expanded leaf. In another aspect, the corn plants of a corn field provided herein comprise an average height of less than or equal to 1.0 meter where the height is measured as the distance between the soil and the ligule of the uppermost fully-expanded leaf. In another aspect, the corn plants of a corn field provided herein comprise an average height of less than or equal to 0.9 meters where the height is measured as the distance between the soil and the ligule of the uppermost fully-expanded leaf. In another aspect, the corn plants of a corn field provided herein comprise an average height of less than or equal to 0.8 meters where the height is measured as the distance between the soil and the ligule of the uppermost fully-expanded leaf. In another aspect, the corn plants of a corn field provided herein comprise an average height of less than or equal to 0.7 meters where the height is measured as the distance between the soil and the ligule of the uppermost fully-expanded leaf. In another aspect, the corn plants of a corn field provided herein comprise an average height of less than or equal to 0.6 meters where the height is measured as the distance between the soil and the ligule of the uppermost fully-expanded leaf. In another aspect, the corn plants of a corn field provided herein comprise an average height of less than or equal to 0.5 meters where the height is measured as the distance between the soil and the ligule of the uppermost fully-expanded leaf. In another aspect, the corn plants of a corn field provided herein comprise an average height of less than or equal to 0.4 meters where the height is measured as the distance between the soil and the ligule of the uppermost fully-expanded leaf. In another aspect, the corn plants of a corn field provided herein comprise an average height of less than or equal to 0.3 meters where the height is measured as the distance between the soil and the ligule of the uppermost fully-expanded leaf. In another aspect, the corn plants of a corn field provided herein comprise an average height of less than or equal to 0.2 meters where the height is measured as the distance between the soil and the ligule of the uppermost fully-expanded leaf. In another aspect, the corn plants of a corn field provided herein comprise an average height of less than or equal to 0.1 meters where the height is measured as the distance between the soil and the ligule of the uppermost fully-expanded leaf. In another aspect, the corn plants of a corn field provided herein comprise an average height of less than or equal to 0.09 meters where the height is measured as the distance between the soil and the ligule of the uppermost fully-expanded leaf.

In an aspect, the corn plants of a corn field provided herein comprise an average height of less than or equal to 1.0 meter at V6 stage or later. In an aspect, the corn plants of a corn field provided herein comprise an average height of less than or equal to 0.9 meters at V6 stage or later. In an aspect, the corn plants of a corn field provided herein comprise an average height of less than or equal to 0.8 meters at V6 stage or later. In an aspect, the corn plants of a corn field provided herein comprise an average height of less than or equal to 0.7 meters at V6 stage or later. In an aspect, the corn plants of a corn field provided herein comprise an average height of less than or equal to 0.6 meters at V6 stage or later. In an aspect, the corn plants of a corn field provided herein comprise an average height of less than or equal to 0.5 meters at V6 stage or later. In an aspect, the corn plants of a corn field provided herein comprise an average height of less than or equal to 0.4 meters at V6 stage or later. In an aspect, the corn plants of a corn field provided herein comprise an average height of less than or equal to 0.3 meters at V6 stage or later. In an aspect, the corn plants of a corn field provided herein comprise an average height of less than or equal to 0.2 meters at V6 stage or later. In an aspect, the corn plants of a corn field provided herein comprise an average height of less than or equal to 0.1 meters at V6 stage or later. In an aspect, the corn plants of a corn field provided herein comprise an average height of less than or equal to 0.09 meters at V6 stage or later.

In an aspect, the corn plants of a corn field provided herein comprise an average height of less than or equal to 1.0 meter at V6 stage or later where the height is measured as the distance between the soil and the uppermost leaf surface of the leaf farthest from the soil. In an aspect, the corn plants of a corn field provided herein comprise an average height of less than or equal to 0.9 meters at V6 stage or later where the height is measured as the distance between the soil and the uppermost leaf surface of the leaf farthest from the soil. In an aspect, the corn plants of a corn field provided herein comprise an average height of less than or equal to 0.8 meters at V6 stage or later where the height is measured as the distance between the soil and the uppermost leaf surface of the leaf farthest from the soil. In an aspect, the corn plants of a corn field provided herein comprise an average height of less than or equal to 0.7 meters at V6 stage or later where the height is measured as the distance between the soil and the uppermost leaf surface of the leaf farthest from the soil. In an aspect, the corn plants of a corn field provided herein comprise an average height of less than or equal to 0.6 meters at V6 stage or later where the height is measured as the distance between the soil and the uppermost leaf surface of the leaf farthest from the soil. In an aspect, the corn plants of a corn field provided herein comprise an average height of less than or equal to 0.5 meters at V6 stage or later where the height is measured as the distance between the soil and the uppermost leaf surface of the leaf farthest from the soil. In an aspect, the corn plants of a corn field provided herein comprise an average height of less than or equal to 0.4 meters at V6 stage or later where the height is measured as the distance between the soil and the uppermost leaf surface of the leaf farthest from the soil. In an aspect, the corn plants of a corn field provided herein comprise an average height of less than or equal to 0.3 meters at V6 stage or later where the height is measured as the distance between the soil and the uppermost leaf surface of the leaf farthest from the soil. In an aspect, the corn plants of a corn field provided herein comprise an average height of less than or equal to 0.2 meters at V6 stage or later where the height is measured as the distance between the soil and the uppermost leaf surface of the leaf farthest from the soil.

In an aspect, the corn plants of a corn field provided herein comprise an average height of less than or equal to 0.5 meters at V6 stage or later where the height is measured as the distance between the soil and the ligule of the uppermost fully-expanded leaf. In an aspect, the corn plants of a corn field provided herein comprise an average height of less than or equal to 0.4 meters at V6 stage or later where the height is measured as the distance between the soil and the ligule of the uppermost fully-expanded leaf. In an aspect, the corn plants of a corn field provided herein comprise an average height of less than or equal to 0.3 meters at V6 stage or later where the height is measured as the distance between the soil and the ligule of the uppermost fully-expanded leaf. In an aspect, the corn plants of a corn field provided herein comprise an average height of less than or equal to 0.2 meters at V6 stage or later where the height is measured as the distance between the soil and the ligule of the uppermost fully-expanded leaf. In an aspect, the corn plants of a corn field provided herein comprise an average height of less than or equal to 0.1 meters at V6 stage or later where the height is measured as the distance between the soil and the ligule of the uppermost fully-expanded leaf. In an aspect, the corn plants of a corn field provided herein comprise an average height of less than or equal to 0.09 meters at V6 stage or later where the height is measured as the distance between the soil and the ligule of the uppermost fully-expanded leaf.

In an aspect, the corn plants of a corn field provided herein comprise an average height of less than or equal to 1.2 meters at V7 stage or later. In an aspect, the corn plants of a corn field provided herein comprise an average height of less than or equal to 1.1 meters at V7 stage or later. In an aspect, the corn plants of a corn field provided herein comprise an average height of less than or equal to 1.0 meter at V7 stage or later. In an aspect, the corn plants of a corn field provided herein comprise an average height of less than or equal to 0.9 meters at V7 stage or later. In an aspect, the corn plants of a corn field provided herein comprise an average height of less than or equal to 0.8 meters at V8 stage or later. In an aspect, the corn plants of a corn field provided herein comprise an average height of less than or equal to 0.7 meters at V7 stage or later. In an aspect, the corn plants of a corn field provided herein comprise an average height of less than or equal to 0.6 meters at V7 stage or later. In an aspect, the corn plants of a corn field provided herein comprise an average height of less than or equal to 0.5 meters at V7 stage or later. In an aspect, the corn plants of a corn field provided herein comprise an average height of less than or equal to 0.4 meters at V7 stage or later. In an aspect, the corn plants of a corn field provided herein comprise an average height of less than or equal to 0.3 meters at V7 stage or later. In an aspect, the corn plants of a corn field provided herein comprise an average height of less than or equal to 0.2 meters at V7 stage or later. In an aspect, the corn plants of a corn field provided herein comprise an average height of less than or equal to 0.1 meters at V7 stage or later.

In an aspect, the corn plants of a corn field provided herein comprise an average height of less than or equal to 1.2 meters at V7 stage or later where the height is measured as the distance between the soil and the uppermost leaf surface of the leaf farthest from the soil. In an aspect, the corn plants of a corn field provided herein comprise an average height of less than or equal to 1.1 meters at V7 stage or later where the height is measured as the distance between the soil and the uppermost leaf surface of the leaf farthest from the soil. In an aspect, the corn plants of a corn field provided herein comprise an average height of less than or equal to 1.0 meter at V7 stage or later where the height is measured as the distance between the soil and the uppermost leaf surface of the leaf farthest from the soil. In an aspect, the corn plants of a corn field provided herein comprise an average height of less than or equal to 0.9 meters at V7 stage or later where the height is measured as the distance between the soil and the uppermost leaf surface of the leaf farthest from the soil. In an aspect, the corn plants of a corn field provided herein comprise an average height of less than or equal to 0.8 meters at V7 stage or later where the height is measured as the distance between the soil and the uppermost leaf surface of the leaf farthest from the soil. In an aspect, the corn plants of a corn field provided herein comprise an average height of less than or equal to 0.7 meters at V7 stage or later where the height is measured as the distance between the soil and the uppermost leaf surface of the leaf farthest from the soil. In an aspect, the corn plants of a corn field provided herein comprise an average height of less than or equal to 0.6 meters at V7 stage or later where the height is measured as the distance between the soil and the uppermost leaf surface of the leaf farthest from the soil. In an aspect, the corn plants of a corn field provided herein comprise an average height of less than or equal to 0.5 meters at V7 stage or later where the height is measured as the distance between the soil and the uppermost leaf surface of the leaf farthest from the soil. In an aspect, the corn plants of a corn field provided herein comprise an average height of less than or equal to 0.4 meters at V7 stage or later where the height is measured as the distance between the soil and the uppermost leaf surface of the leaf farthest from the soil. In an aspect, the corn plants of a corn field provided herein comprise an average height of less than or equal to 0.3 meters at V7 stage or later where the height is measured as the distance between the soil and the uppermost leaf surface of the leaf farthest from the soil. In an aspect, the corn plants of a corn field provided herein comprise an average height of less than or equal to 0.2 meters at V7 stage or later where the height is measured as the distance between the soil and the uppermost leaf surface of the leaf farthest from the soil.

In an aspect, the corn plants of a corn field provided herein comprise an average height of less than or equal to 0.7 meters at V7 stage or later where the height is measured as the distance between the soil and the ligule of the uppermost fully-expanded leaf. In an aspect, the corn plants of a corn field provided herein comprise an average height of less than or equal to 0.6 meters at V7 stage or later where the height is measured as the distance between the soil and the ligule of the uppermost fully-expanded leaf. In an aspect, the corn plants of a corn field provided herein comprise an average height of less than or equal to 0.5 meters at V7 stage or later where the height is measured as the distance between the soil and the ligule of the uppermost fully-expanded leaf. In an aspect, the corn plants of a corn field provided herein comprise an average height of less than or equal to 0.4 meters at V7 stage or later where the height is measured as the distance between the soil and the ligule of the uppermost fully-expanded leaf. In an aspect, the corn plants of a corn field provided herein comprise an average height of less than or equal to 0.3 meters at V7 stage or later where the height is measured as the distance between the soil and the ligule of the uppermost fully-expanded leaf. In an aspect, the corn plants of a corn field provided herein comprise an average height of less than or equal to 0.2 meters at V7 stage or later where the height is measured as the distance between the soil and the ligule of the uppermost fully-expanded leaf. In an aspect, the corn plants of a corn field provided herein comprise an average height of less than or equal to 0.1 meters at V7 stage or later where the height is measured as the distance between the soil and the ligule of the uppermost fully-expanded leaf.

In an aspect, the corn plants of a corn field provided herein comprise an average height of less than or equal to 1.5 meters at V8 stage or later. In an aspect, the corn plants of a corn field provided herein comprise an average height of less than or equal to 1.4 meters at V8 stage or later. In an aspect, the corn plants of a corn field provided herein comprise an average height of less than or equal to 1.3 meters at V8 stage or later. In an aspect, the corn plants of a corn field provided herein comprise an average height of less than or equal to 1.2 meters at V8 stage or later. In an aspect, the corn plants of a corn field provided herein comprise an average height of less than or equal to 1.1 meters at V8 stage or later. In an aspect, the corn plants of a corn field provided herein comprise an average height of less than or equal to 1.0 meter at V8 stage or later. In an aspect, the corn plants of a corn field provided herein comprise an average height of less than or equal to 0.9 meters at V8 stage or later. In an aspect, the corn plants of a corn field provided herein comprise an average height of less than or equal to 0.8 meters at V8 stage or later. In an aspect, the corn plants of a corn field provided herein comprise an average height of less than or equal to 0.7 meters at V8 stage or later. In an aspect, the corn plants of a corn field provided herein comprise an average height of less than or equal to 0.6 meters at V8 stage or later. In an aspect, the corn plants of a corn field provided herein comprise an average height of less than or equal to 0.5 meters at V8 stage or later. In an aspect, the corn plants of a corn field provided herein comprise an average height of less than or equal to 0.4 meters at V8 stage or later. In an aspect, the corn plants of a corn field provided herein comprise an average height of less than or equal to 0.3 meters at V8 stage or later. In an aspect, the corn plants of a corn field provided herein comprise an average height of less than or equal to 0.2 meters at V8 stage or later.

In an aspect, the corn plants of a corn field provided herein comprise an average height of less than or equal to 1.5 meters at V8 stage or later where the height is measured as the distance between the soil and the uppermost leaf surface of the leaf farthest from the soil. In an aspect, the corn plants of a corn field provided herein comprise an average height of less than or equal to 1.4 meters at V8 stage or later where the height is measured as the distance between the soil and the uppermost leaf surface of the leaf farthest from the soil. In an aspect, the corn plants of a corn field provided herein comprise an average height of less than or equal to 1.3 meters at V8 stage or later where the height is measured as the distance between the soil and the uppermost leaf surface of the leaf farthest from the soil. In an aspect, the corn plants of a corn field provided herein comprise an average height of less than or equal to 1.2 meters at V8 stage or later where the height is measured as the distance between the soil and the uppermost leaf surface of the leaf farthest from the soil. In an aspect, the corn plants of a corn field provided herein comprise an average height of less than or equal to 1.1 meters at V8 stage or later where the height is measured as the distance between the soil and the uppermost leaf surface of the leaf farthest from the soil. In an aspect, the corn plants of a corn field provided herein comprise an average height of less than or equal to 1.0 meter at V8 stage or later where the height is measured as the distance between the soil and the uppermost leaf surface of the leaf farthest from the soil. In an aspect, the corn plants of a corn field provided herein comprise an average height of less than or equal to 0.9 meters at V8 stage or later where the height is measured as the distance between the soil and the uppermost leaf surface of the leaf farthest from the soil. In an aspect, the corn plants of a corn field provided herein comprise an average height of less than or equal to 0.8 meters at V8 stage or later where the height is measured as the distance between the soil and the uppermost leaf surface of the leaf farthest from the soil. In an aspect, the corn plants of a corn field provided herein comprise an average height of less than or equal to 0.7 meters at V8 stage or later where the height is measured as the distance between the soil and the uppermost leaf surface of the leaf farthest from the soil. In an aspect, the corn plants of a corn field provided herein comprise an average height of less than or equal to 0.6 meters at V8 stage or later where the height is measured as the distance between the soil and the uppermost leaf surface of the leaf farthest from the soil. In an aspect, the corn plants of a corn field provided herein comprise an average height of less than or equal to 0.5 meters at V8 stage or later where the height is measured as the distance between the soil and the uppermost leaf surface of the leaf farthest from the soil.

In an aspect, the corn plants of a corn field provided herein comprise an average height of less than or equal to 1.0 meter at V8 stage or later where the height is measured as the distance between the soil and the ligule of the uppermost fully-expanded leaf. In an aspect, the corn plants of a corn field provided herein comprise an average height of less than or equal to 0.9 meters at V8 stage or later where the height is measured as the distance between the soil and the ligule of the uppermost fully-expanded leaf. In an aspect, the corn plants of a corn field provided herein comprise an average height of less than or equal to 0.8 meters at V8 stage or later where the height is measured as the distance between the soil and the ligule of the uppermost fully-expanded leaf. In an aspect, the corn plants of a corn field provided herein comprise an average height of less than or equal to 0.7 meters at V8 stage or later where the height is measured as the distance between the soil and the ligule of the uppermost fully-expanded leaf. In an aspect, the corn plants of a corn field provided herein comprise an average height of less than or equal to 0.6 meters at V8 stage or later where the height is measured as the distance between the soil and the ligule of the uppermost fully-expanded leaf. In an aspect, the corn plants of a corn field provided herein comprise an average height of less than or equal to 0.5 meters at V8 stage or later where the height is measured as the distance between the soil and the ligule of the uppermost fully-expanded leaf. In an aspect, the corn plants of a corn field provided herein comprise an average height of less than or equal to 0.4 meters at V8 stage or later where the height is measured as the distance between the soil and the ligule of the uppermost fully-expanded leaf. In an aspect, the corn plants of a corn field provided herein comprise an average height of less than or equal to 0.3 meters at V8 stage or later where the height is measured as the distance between the soil and the ligule of the uppermost fully-expanded leaf. In an aspect, the corn plants of a corn field provided herein comprise an average height of less than or equal to 0.2 meters at V8 stage or later where the height is measured as the distance between the soil and the ligule of the uppermost fully-expanded leaf.

In an aspect, the corn plants of a corn field provided herein comprise an average height of less than or equal to 1.8 meters at V9 stage or later. In an aspect, the corn plants of a corn field provided herein comprise an average height of less than or equal to 1.7 meters at V9 stage or later. In an aspect, the corn plants of a corn field provided herein comprise an average height of less than or equal to 1.6 meters at V9 stage or later. In an aspect, the corn plants of a corn field provided herein comprise an average height of less than or equal to 1.5 meters at V9 stage or later. In an aspect, the corn plants of a corn field provided herein comprise an average height of less than or equal to 1.4 meters at V9 stage or later. In an aspect, the corn plants of a corn field provided herein comprise an average height of less than or equal to 1.3 meters at V9 stage or later. In an aspect, the corn plants of a corn field provided herein comprise an average height of less than or equal to 1.2 meters at V9 stage or later. In an aspect, the corn plants of a corn field provided herein comprise an average height of less than or equal to 1.1 meters at V9 stage or later. In an aspect, the corn plants of a corn field provided herein comprise an average height of less than or equal to 1.0 meter at V9 stage or later. In an aspect, the corn plants of a corn field provided herein comprise an average height of less than or equal to 0.9 meters at V9 stage or later. In an aspect, the corn plants of a corn field provided herein comprise an average height of less than or equal to 0.8 meters at V9 stage or later. In an aspect, the corn plants of a corn field provided herein comprise an average height of less than or equal to 0.7 meters at V9 stage or later. In an aspect, the corn plants of a corn field provided herein comprise an average height of less than or equal to 0.6 meters at V9 stage or later. In an aspect, the corn plants of a corn field provided herein comprise an average height of less than or equal to 0.5 meters at V9 stage or later. In an aspect, the corn plants of a corn field provided herein comprise an average height of less than or equal to 0.4 meters at V9 stage or later. In an aspect, the corn plants of a corn field provided herein comprise an average height of less than or equal to 0.3 meters at V9 stage or later. In an aspect, the corn plants of a corn field provided herein comprise an average height of less than or equal to 0.2 meters at V9 stage or later.

In an aspect, the corn plants of a corn field provided herein comprise an average height of less than or equal to 1.8 meters at V9 stage or later where the height is measured as the distance between the soil and the uppermost leaf surface of the leaf farthest from the soil. In an aspect, the corn plants of a corn field provided herein comprise an average height of less than or equal to 1.7 meters at V9 stage or later where the height is measured as the distance between the soil and the uppermost leaf surface of the leaf farthest from the soil. In an aspect, the corn plants of a corn field provided herein comprise an average height of less than or equal to 1.6 meters at V9 stage or later where the height is measured as the distance between the soil and the uppermost leaf surface of the leaf farthest from the soil. In an aspect, the corn plants of a corn field provided herein comprise an average height of less than or equal to 1.5 meters at V9 stage or later where the height is measured as the distance between the soil and the uppermost leaf surface of the leaf farthest from the soil. In an aspect, the corn plants of a corn field provided herein comprise an average height of less than or equal to 1.4 meters at V9 stage or later where the height is measured as the distance between the soil and the uppermost leaf surface of the leaf farthest from the soil. In an aspect, the corn plants of a corn field provided herein comprise an average height of less than or equal to 1.3 meters at V9 stage or later where the height is measured as the distance between the soil and the uppermost leaf surface of the leaf farthest from the soil. In an aspect, the corn plants of a corn field provided herein comprise an average height of less than or equal to 1.2 meters at V9 stage or later where the height is measured as the distance between the soil and the uppermost leaf surface of the leaf farthest from the soil. In an aspect, the corn plants of a corn field provided herein comprise an average height of less than or equal to 1.1 meters at V9 stage or later where the height is measured as the distance between the soil and the uppermost leaf surface of the leaf farthest from the soil. In an aspect, the corn plants of a corn field provided herein comprise an average height of less than or equal to 1.0 meter at V9 stage or later where the height is measured as the distance between the soil and the uppermost leaf surface of the leaf farthest from the soil. In an aspect, the corn plants of a corn field provided herein comprise an average height of less than or equal to 0.9 meters at V9 stage or later where the height is measured as the distance between the soil and the uppermost leaf surface of the leaf farthest from the soil. In an aspect, the corn plants of a corn field provided herein comprise an average height of less than or equal to 0.8 meters at V9 stage or later where the height is measured as the distance between the soil and the uppermost leaf surface of the leaf farthest from the soil. In an aspect, the corn plants of a corn field provided herein comprise an average height of less than or equal to 0.7 meters at V9 stage or later where the height is measured as the distance between the soil and the uppermost leaf surface of the leaf farthest from the soil. In an aspect, the corn plants of a corn field provided herein comprise an average height of less than or equal to 0.6 meters at V9 stage or later where the height is measured as the distance between the soil and the uppermost leaf surface of the leaf farthest from the soil.

In an aspect, the corn plants of a corn field provided herein comprise an average height of less than or equal to 1.3 meters at V9 stage or later where the height is measured as the distance between the soil and the ligule of the uppermost fully-expanded leaf. In an aspect, the corn plants of a corn field provided herein comprise an average height of less than or equal to 1.2 meters at V9 stage or later where the height is measured as the distance between the soil and the ligule of the uppermost fully-expanded leaf. In an aspect, the corn plants of a corn field provided herein comprise an average height of less than or equal to 1.1 meters at V9 stage or later where the height is measured as the distance between the soil and the ligule of the uppermost fully-expanded leaf. In an aspect, the corn plants of a corn field provided herein comprise an average height of less than or equal to 1.0 meter at V9 stage or later where the height is measured as the distance between the soil and the ligule of the uppermost fully-expanded leaf. In an aspect, the corn plants of a corn field provided herein comprise an average height of less than or equal to 0.9 meters at V9 stage or later where the height is measured as the distance between the soil and the ligule of the uppermost fully-expanded leaf. In an aspect, the corn plants of a corn field provided herein comprise an average height of less than or equal to 0.8 meters at V9 stage or later where the height is measured as the distance between the soil and the ligule of the uppermost fully-expanded leaf. In an aspect, the corn plants of a corn field provided herein comprise an average height of less than or equal to 0.7 meters at V9 stage or later where the height is measured as the distance between the soil and the ligule of the uppermost fully-expanded leaf. In an aspect, the corn plants of a corn field provided herein comprise an average height of less than or equal to 0.6 meters at V9 stage or later where the height is measured as the distance between the soil and the ligule of the uppermost fully-expanded leaf. In an aspect, the corn plants of a corn field provided herein comprise an average height of less than or equal to 0.5 meters at V9 stage or later where the height is measured as the distance between the soil and the ligule of the uppermost fully-expanded leaf. In an aspect, the corn plants of a corn field provided herein comprise an average height of less than or equal to 0.4 meters at V9 stage or later where the height is measured as the distance between the soil and the ligule of the uppermost fully-expanded leaf. In an aspect, the corn plants of a corn field provided herein comprise an average height of less than or equal to 0.3 meters at V9 stage or later where the height is measured as the distance between the soil and the ligule of the uppermost fully-expanded leaf. In an aspect, the corn plants of a corn field provided herein comprise an average height of less than or equal to 0.2 meters at V9 stage or later where the height is measured as the distance between the soil and the ligule of the uppermost fully-expanded leaf.

In an aspect, the corn plants of a corn field provided herein comprise an average height of less than or equal to 1.9 meters at V10 stage or later. In an aspect, the corn plants of a corn field provided herein comprise an average height of less than or equal to 1.8 meters at V10 stage or later. In an aspect, the corn plants of a corn field provided herein comprise an average height of less than or equal to 1.7 meters at V10 stage or later. In an aspect, the corn plants of a corn field provided herein comprise an average height of less than or equal to 1.6 meters at V10 stage or later. In an aspect, the corn plants of a corn field provided herein comprise an average height of less than or equal to 1.5 meters at V10 stage or later. In an aspect, the corn plants of a corn field provided herein comprise an average height of less than or equal to 1.4 meters at V10 stage or later. In an aspect, the corn plants of a corn field provided herein comprise an average height of less than or equal to 1.3 meters at V10 stage or later. In an aspect, the corn plants of a corn field provided herein comprise an average height of less than or equal to 1.2 meters at V10 stage or later. In an aspect, the corn plants of a corn field provided herein comprise an average height of less than or equal to 1.1 meters at V10 stage or later. In an aspect, the corn plants of a corn field provided herein comprise an average height of less than or equal to 1.0 meter at V10 stage or later. In an aspect, the corn plants of a corn field provided herein comprise an average height of less than or equal to 0.9 meters at V10 stage or later. In an aspect, the corn plants of a corn field provided herein comprise an average height of less than or equal to 0.8 meters at V10 stage or later. In an aspect, the corn plants of a corn field provided herein comprise an average height of less than or equal to 0.7 meters at V10 stage or later. In an aspect, the corn plants of a corn field provided herein comprise an average height of less than or equal to 0.6 meters at V10 stage or later. In an aspect, the corn plants of a corn field provided herein comprise an average height of less than or equal to 0.5 meters at V10 stage or later. In an aspect, the corn plants of a corn field provided herein comprise an average height of less than or equal to 0.4 meters at V10 stage or later. In an aspect, the corn plants of a corn field provided herein comprise an average height of less than or equal to 0.3 meters at V10 stage or later.

In an aspect, the corn plants of a corn field provided herein comprise an average height of less than or equal to 1.9 meters at V10 stage or later where the height is measured as the distance between the soil and the uppermost leaf surface of the leaf farthest from the soil. In an aspect, the corn plants of a corn field provided herein comprise an average height of less than or equal to 1.8 meters at V10 stage or later where the height is measured as the distance between the soil and the uppermost leaf surface of the leaf farthest from the soil. In an aspect, the corn plants of a corn field provided herein comprise an average height of less than or equal to 1.7 meters at V10 stage or later where the height is measured as the distance between the soil and the uppermost leaf surface of the leaf farthest from the soil. In an aspect, the corn plants of a corn field provided herein comprise an average height of less than or equal to 1.6 meters at V10 stage or later where the height is measured as the distance between the soil and the uppermost leaf surface of the leaf farthest from the soil. In an aspect, the corn plants of a corn field provided herein comprise an average height of less than or equal to 1.5 meters at V10 stage or later where the height is measured as the distance between the soil and the uppermost leaf surface of the leaf farthest from the soil. In an aspect, the corn plants of a corn field provided herein comprise an average height of less than or equal to 1.4 meters at V10 stage or later where the height is measured as the distance between the soil and the uppermost leaf surface of the leaf farthest from the soil. In an aspect, the corn plants of a corn field provided herein comprise an average height of less than or equal to 1.3 meters at V10 stage or later where the height is measured as the distance between the soil and the uppermost leaf surface of the leaf farthest from the soil. In an aspect, the corn plants of a corn field provided herein comprise an average height of less than or equal to 1.2 meters at V10 stage or later where the height is measured as the distance between the soil and the uppermost leaf surface of the leaf farthest from the soil. In an aspect, the corn plants of a corn field provided herein comprise an average height of less than or equal to 1.1 meters at V10 stage or later where the height is measured as the distance between the soil and the uppermost leaf surface of the leaf farthest from the soil. In an aspect, the corn plants of a corn field provided herein comprise an average height of less than or equal to 1.0 meter at V10 stage or later where the height is measured as the distance between the soil and the uppermost leaf surface of the leaf farthest from the soil. In an aspect, the corn plants of a corn field provided herein comprise an average height of less than or equal to 0.9 meters at V10 stage or later where the height is measured as the distance between the soil and the uppermost leaf surface of the leaf farthest from the soil. In an aspect, the corn plants of a corn field provided herein comprise an average height of less than or equal to 0.8 meters at V10 stage or later where the height is measured as the distance between the soil and the uppermost leaf surface of the leaf farthest from the soil.

In an aspect, the corn plants of a corn field provided herein comprise an average height of less than or equal to 1.4 meters at V10 stage or later where the height is measured as the distance between the soil and the ligule of the uppermost fully-expanded leaf. In an aspect, the corn plants of a corn field provided herein comprise an average height of less than or equal to 1.3 meters at V10 stage or later where the height is measured as the distance between the soil and the ligule of the uppermost fully-expanded leaf. In an aspect, the corn plants of a corn field provided herein comprise an average height of less than or equal to 1.2 meters at V10 stage or later where the height is measured as the distance between the soil and the ligule of the uppermost fully-expanded leaf. In an aspect, the corn plants of a corn field provided herein comprise an average height of less than or equal to 1.1 meters at V10 stage or later where the height is measured as the distance between the soil and the ligule of the uppermost fully-expanded leaf. In an aspect, the corn plants of a corn field provided herein comprise an average height of less than or equal to 1.0 meter at V10 stage or later where the height is measured as the distance between the soil and the ligule of the uppermost fully-expanded leaf. In an aspect, the corn plants of a corn field provided herein comprise an average height of less than or equal to 0.9 meters at V10 stage or later where the height is measured as the distance between the soil and the ligule of the uppermost fully-expanded leaf. In an aspect, the corn plants of a corn field provided herein comprise an average height of less than or equal to 0.8 meters at V10 stage or later where the height is measured as the distance between the soil and the ligule of the uppermost fully-expanded leaf. In an aspect, the corn plants of a corn field provided herein comprise an average height of less than or equal to 0.7 meters at V10 stage or later where the height is measured as the distance between the soil and the ligule of the uppermost fully-expanded leaf. In an aspect, the corn plants of a corn field provided herein comprise an average height of less than or equal to 0.6 meters at V10 stage or later where the height is measured as the distance between the soil and the ligule of the uppermost fully-expanded leaf. In an aspect, the corn plants of a corn field provided herein comprise an average height of less than or equal to 0.5 meters at V10 stage or later where the height is measured as the distance between the soil and the ligule of the uppermost fully-expanded leaf. In an aspect, the corn plants of a corn field provided herein comprise an average height of less than or equal to 0.4 meters at V10 stage or later where the height is measured as the distance between the soil and the ligule of the uppermost fully-expanded leaf. In an aspect, the corn plants of a corn field provided herein comprise an average height of less than or equal to 0.3 meters at V10 stage or later where the height is measured as the distance between the soil and the ligule of the uppermost fully-expanded leaf.

In an aspect, the corn plants of a corn field provided herein comprise an average height of less than or equal to 2.0 meters at V11 stage or later. In an aspect, the corn plants of a corn field provided herein comprise an average height of less than or equal to 1.9 meters at V11 stage or later. In an aspect, the corn plants of a corn field provided herein comprise an average height of less than or equal to 1.8 meters at V11 stage or later. In an aspect, the corn plants of a corn field provided herein comprise an average height of less than or equal to 1.7 meters at V11 stage or later. In an aspect, the corn plants of a corn field provided herein comprise an average height of less than or equal to 1.6 meters at V11 stage or later. In an aspect, the corn plants of a corn field provided herein comprise an average height of less than or equal to 1.5 meters at V11 stage or later. In an aspect, the corn plants of a corn field provided herein comprise an average height of less than or equal to 1.4 meters at V11 stage or later. In an aspect, the corn plants of a corn field provided herein comprise an average height of less than or equal to 1.3 meters at V11 stage or later. In an aspect, the corn plants of a corn field provided herein comprise an average height of less than or equal to 1.2 meters at V11 stage or later. In an aspect, the corn plants of a corn field provided herein comprise an average height of less than or equal to 1.1 meters at V11 stage or later. In an aspect, the corn plants of a corn field provided herein comprise an average height of less than or equal to 1.0 meter at V11 stage or later. In an aspect, the corn plants of a corn field provided herein comprise an average height of less than or equal to 0.9 meters at V11 stage or later. In an aspect, the corn plants of a corn field provided herein comprise an average height of less than or equal to 0.8 meters at V11 stage or later. In an aspect, the corn plants of a corn field provided herein comprise an average height of less than or equal to 0.7 meters at V11 stage or later. In an aspect, the corn plants of a corn field provided herein comprise an average height of less than or equal to 0.6 meters at V11 stage or later. In an aspect, the corn plants of a corn field provided herein comprise an average height of less than or equal to 0.5 meters at V11 stage or later. In an aspect, the corn plants of a corn field provided herein comprise an average height of less than or equal to 0.4 meters at V11 stage or later. In an aspect, the corn plants of a corn field provided herein comprise an average height of less than or equal to 0.3 meters at V11 stage or later.

In an aspect, the corn plants of a corn field provided herein comprise an average height of less than or equal to 2.0 meters at V11 stage or later where the height is measured as the distance between the soil and the uppermost leaf surface of the leaf farthest from the soil. In an aspect, the corn plants of a corn field provided herein comprise an average height of less than or equal to 1.9 meters at V11 stage or later where the height is measured as the distance between the soil and the uppermost leaf surface of the leaf farthest from the soil. In an aspect, the corn plants of a corn field provided herein comprise an average height of less than or equal to 1.8 meters at V11 stage or later where the height is measured as the distance between the soil and the uppermost leaf surface of the leaf farthest from the soil. In an aspect, the corn plants of a corn field provided herein comprise an average height of less than or equal to 1.7 meters at V11 stage or later where the height is measured as the distance between the soil and the uppermost leaf surface of the leaf farthest from the soil. In an aspect, the corn plants of a corn field provided herein comprise an average height of less than or equal to 1.6 meters at V11 stage or later where the height is measured as the distance between the soil and the uppermost leaf surface of the leaf farthest from the soil. In an aspect, the corn plants of a corn field provided herein comprise an average height of less than or equal to 1.5 meters at V11 stage or later where the height is measured as the distance between the soil and the uppermost leaf surface of the leaf farthest from the soil. In an aspect, the corn plants of a corn field provided herein comprise an average height of less than or equal to 1.4 meters at V11 stage or later where the height is measured as the distance between the soil and the uppermost leaf surface of the leaf farthest from the soil. In an aspect, the corn plants of a corn field provided herein comprise an average height of less than or equal to 1.3 meters at V11 stage or later where the height is measured as the distance between the soil and the uppermost leaf surface of the leaf farthest from the soil. In an aspect, the corn plants of a corn field provided herein comprise an average height of less than or equal to 1.2 meters at V11 stage or later where the height is measured as the distance between the soil and the uppermost leaf surface of the leaf farthest from the soil. In an aspect, the corn plants of a corn field provided herein comprise an average height of less than or equal to 1.1 meters at V11 stage or later where the height is measured as the distance between the soil and the uppermost leaf surface of the leaf farthest from the soil. In an aspect, the corn plants of a corn field provided herein comprise an average height of less than or equal to 1.0 meter at V11 stage or later where the height is measured as the distance between the soil and the uppermost leaf surface of the leaf farthest from the soil. In an aspect, the corn plants of a corn field provided herein comprise an average height of less than or equal to 0.9 meters at V11 stage or later where the height is measured as the distance between the soil and the uppermost leaf surface of the leaf farthest from the soil.

In an aspect, the corn plants of a corn field provided herein comprise an average height of less than or equal to 1.5 meters at V11 stage or later where the height is measured as the distance between the soil and the ligule of the uppermost fully-expanded leaf. In an aspect, the corn plants of a corn field provided herein comprise an average height of less than or equal to 1.4 meters at V11 stage or later where the height is measured as the distance between the soil and the ligule of the uppermost fully-expanded leaf. In an aspect, the corn plants of a corn field provided herein comprise an average height of less than or equal to 1.3 meters at V11 stage or later where the height is measured as the distance between the soil and the ligule of the uppermost fully-expanded leaf. In an aspect, the corn plants of a corn field provided herein comprise an average height of less than or equal to 1.2 meters at V11 stage or later where the height is measured as the distance between the soil and the ligule of the uppermost fully-expanded leaf. In an aspect, the corn plants of a corn field provided herein comprise an average height of less than or equal to 1.1 meters at V11 stage or later where the height is measured as the distance between the soil and the ligule of the uppermost fully-expanded leaf. In an aspect, the corn plants of a corn field provided herein comprise an average height of less than or equal to 1.0 meter at V11 stage or later where the height is measured as the distance between the soil and the ligule of the uppermost fully-expanded leaf. In an aspect, the corn plants of a corn field provided herein comprise an average height of less than or equal to 0.9 meters at V11 stage or later where the height is measured as the distance between the soil and the ligule of the uppermost fully-expanded leaf. In an aspect, the corn plants of a corn field provided herein comprise an average height of less than or equal to 0.8 meters at V11 stage or later where the height is measured as the distance between the soil and the ligule of the uppermost fully-expanded leaf. In an aspect, the corn plants of a corn field provided herein comprise an average height of less than or equal to 0.7 meters at V11 stage or later where the height is measured as the distance between the soil and the ligule of the uppermost fully-expanded leaf. In an aspect, the corn plants of a corn field provided herein comprise an average height of less than or equal to 0.6 meters at V11 stage or later where the height is measured as the distance between the soil and the ligule of the uppermost fully-expanded leaf. In an aspect, the corn plants of a corn field provided herein comprise an average height of less than or equal to 0.5 meters at V11 stage or later where the height is measured as the distance between the soil and the ligule of the uppermost fully-expanded leaf. In an aspect, the corn plants of a corn field provided herein comprise an average height of less than or equal to 0.4 meters at V11 stage or later where the height is measured as the distance between the soil and the ligule of the uppermost fully-expanded leaf. In an aspect, the corn plants of a corn field provided herein comprise an average height of less than or equal to 0.3 meters at V11 stage or later where the height is measured as the distance between the soil and the ligule of the uppermost fully-expanded leaf.

In an aspect, the corn plants of a corn field provided herein comprise an average height of between 0.07 meters and 1.5 meters, 0.07 meters and 1.4 meters, 0.07 meters and 1.3 meters, 0.07 meters and 1.2 meters, 0.07 meters and 1.1 meters, 0.07 meters and 1.0 meter, 0.07 meters and 0.9 meters, 0.07 meters and 0.8 meters, 0.07 meters and 0.7 meters, 0.07 meters and 0.6 meters, 0.07 meters and 0.5 meters, 0.07 meters and 0.4 meters, 0.07 meters and 0.3 meters, 0.07 meters and 0.2 meters, 0.07 meters and 0.1 meters, 0.08 meters and 1.5 meters, 0.08 meters and 1.4 meters, 0.08 meters and 1.3 meters, 0.08 meters and 1.2 meters, 0.08 meters and 1.1 meters, 0.08 meters and 1.0 meter, 0.08 meters and 0.9 meters, 0.08 meters and 0.8 meters, 0.08 meters and 0.7 meters, 0.08 meters and 0.6 meters, 0.08 meters and 0.5 meters, 0.08 meters and 0.4 meters, 0.08 meters and 0.3 meters, 0.08 meters and 0.2 meters, 0.08 meters and 0.1 meters, 0.09 meters and 1.5 meters, 0.09 meters and 1.4 meters, 0.09 meters and 1.3 meters, 0.09 meters and 1.2 meters, 0.09 meters and 1.1 meters, 0.09 meters and 1.0 meter, 0.09 meters and 0.9 meters, 0.09 meters and 0.8 meters, 0.09 meters and 0.7 meters, 0.09 meters and 0.6 meters, 0.09 meters and 0.5 meters, 0.09 meters and 0.4 meters, 0.09 meters and 0.3 meters, 0.09 meters and 0.2 meters, 0.09 meters and 0.1 meters, 0.1 meters and 1.5 meters, 0.1 meters and 1.4 meters, 0.1 meters and 1.3 meters, 0.1 meters and 1.2 meters, 0.1 meters and 1.1 meters, 0.1 meters and 1.0 meter, 0.1 meters and 0.9 meters, 0.1 meters and 0.8 meters, 0.1 meters and 0.7 meters, 0.1 meters and 0.6 meters, 0.1 meters and 0.5 meters, 0.1 meters and 0.4 meters, 0.1 meters and 0.3 meters, 0.1 meters and 0.2 meters, 0.2 meters and 1.5 meters, 0.2 meters and 1.4 meters, 0.2 meters and 1.3 meters, 0.2 meters and 1.2 meters, 0.2 meters and 1.1 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 1.5 meters, 0.3 meters and 1.4 meters, 0.3 meters and 1.3 meters, 0.3 meters and 1.2 meters, 0.3 meters and 1.1 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 1.5 meters, 0.4 meters and 1.4 meters, 0.4 meters and 1.3 meters, 0.4 meters and 1.2 meters, 0.4 meters and 1.1 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 1.5 meters, 0.5 meters and 1.4 meters, 0.5 meters and 1.3 meters, 0.5 meters and 1.2 meters, 0.5 meters and 1.1 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 1.5 meters, 0.6 meters and 1.4 meters, 0.6 meters and 1.3 meters, 0.6 meters and 1.2 meters, 0.6 meters and 1.1 meters, 0.6 meters and 1.0 meter, 0.6 meters and 0.9 meters, 0.6 meters and 0.8 meters, 0.6 meters and 0.7 meters, 0.7 meters and 1.5 meters, 0.7 meters and 1.4 meters, 0.7 meters and 1.3 meters, 0.7 meters and 1.2 meters, 0.7 meters and 1.1 meters, 0.7 meters and 1.0 meter, 0.7 meters and 0.9 meters, 0.7 meters and 0.8 meters, 0.8 meters and 1.5 meters, 0.8 meters and 1.4 meters, 0.8 meters and 1.3 meters, 0.8 meters and 1.2 meters, 0.8 meters and 1.1 meters, 0.8 meters and 1.0 meter, 0.8 meters and 0.9 meters, 0.9 meters and 1.5 meters, 0.9 meters and 1.4 meters, 0.9 meters and 1.3 meters, 0.9 meters and 1.2 meters, 0.9 meters and 1.1 meters, 0.9 meters and 1.0 meter, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 1.5 meters, 1.1 meters and 1.4 meters, 1.1 meters and 1.3 meters, 1.1 meters and 1.2 meters, 1.2 meters and 1.5 meters, 1.2 meters and 1.4 meters, 1.2 meters and 1.3 meters, 1.3 meters and 1.5 meters, 1.3 meters and 1.4 meters, or 1.4 meters and 1.5 meters at V6 stage or later, V7 stage or later, V8 stage or later, V9 stage or later, V10 stage or later, or V11 stage or later where the height is measured as the distance between the soil and the ligule (or collar) of the uppermost fully-expanded leaf.

In an aspect, the corn plants of a corn field provided herein comprise an average height of between 0.1 meters and 2.0 meters, 0.1 meters and 1.9 meters, 0.1 meters and 1.8 meters, 0.1 meters and 1.7 meters, 0.1 meters and 1.6 meters, 0.1 meters and 1.5 meters, 0.1 meters and 1.4 meters, 0.1 meters and 1.3 meters, 0.1 meters and 1.2 meters, 0.1 meters and 1.1 meters, 0.1 meters and 1.0 meter, 0.1 meters and 0.9 meters, 0.1 meters and 0.8 meters, 0.1 meters and 0.7 meters, 0.1 meters and 0.6 meters, 0.1 meters and 0.5 meters, 0.1 meters and 0.4 meters, 0.1 meters and 0.3 meters, 0.1 meters and 0.2 meters, 0.2 meters and 2.0 meters, 0.2 meters and 1.9 meters, 0.2 meters and 1.8 meters, 0.2 meters and 1.7 meters, 0.2 meters and 1.6 meters, 0.2 meters and 1.5 meters, 0.2 meters and 1.4 meters, 0.2 meters and 1.3 meters, 0.2 meters and 1.2 meters, 0.2 meters and 1.1 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.0 meters, 0.3 meters and 1.9 meters, 0.3 meters and 1.8 meters, 0.3 meters and 1.7 meters, 0.3 meters and 1.6 meters, 0.3 meters and 1.5 meters, 0.3 meters and 1.4 meters, 0.3 meters and 1.3 meters, 0.3 meters and 1.2 meters, 0.3 meters and 1.1 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.0 meters, 0.4 meters and 1.9 meters, 0.4 meters and 1.8 meters, 0.4 meters and 1.7 meters, 0.4 meters and 1.6 meters, 0.4 meters and 1.5 meters, 0.4 meters and 1.4 meters, 0.4 meters and 1.3 meters, 0.4 meters and 1.2 meters, 0.4 meters and 1.1 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.0 meters, 0.5 meters and 1.9 meters, 0.5 meters and 1.8 meters, 0.5 meters and 1.7 meters, 0.5 meters and 1.6 meters, 0.5 meters and 1.5 meters, 0.5 meters and 1.4 meters, 0.5 meters and 1.3 meters, 0.5 meters and 1.2 meters, 0.5 meters and 1.1 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.0 meters, 0.6 meters and 1.9 meters, 0.6 meters and 1.8 meters, 0.6 meters and 1.7 meters, 0.6 meters and 1.6 meters, 0.6 meters and 1.5 meters, 0.6 meters and 1.4 meters, 0.6 meters and 1.3 meters, 0.6 meters and 1.2 meters, 0.6 meters and 1.1 meters, 0.6 meters and 1.0 meter, 0.6 meters and 0.9 meters, 0.6 meters and 0.8 meters, 0.6 meters and 0.7 meters, 0.7 meters and 2.0 meters, 0.7 meters and 1.9 meters, 0.7 meters and 1.8 meters, 0.7 meters and 1.7 meters, 0.7 meters and 1.6 meters, 0.7 meters and 1.5 meters, 0.7 meters and 1.4 meters, 0.7 meters and 1.3 meters, 0.7 meters and 1.2 meters, 0.7 meters and 1.1 meters, 0.7 meters and 1.0 meter, 0.7 meters and 0.9 meters, 0.7 meters and 0.8 meters, 0.8 meters and 2.0 meters, 0.8 meters and 1.9 meters, 0.8 meters and 1.8 meters, 0.8 meters and 1.7 meters, 0.8 meters and 1.6 meters, 0.8 meters and 1.5 meters, 0.8 meters and 1.4 meters, 0.8 meters and 1.3 meters, 0.8 meters and 1.2 meters, 0.8 meters and 1.1 meters, 0.8 meters and 1.0 meter, 0.8 meters and 0.9 meters, 0.9 meters and 2.0 meters, 0.9 meters and 1.9 meters, 0.9 meters and 1.8 meters, 0.9 meters and 1.7 meters, 0.9 meters and 1.6 meters, 0.9 meters and 1.5 meters, 0.9 meters and 1.4 meters, 0.9 meters and 1.3 meters, 0.9 meters and 1.2 meters, 0.9 meters and 1.1 meters, 0.9 meters and 1.0 meter, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, 1.2 meters and 1.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.0 meters, 1.6 meters and 1.9 meters, 1.6 meters and 1.8 meters, 1.6 meters and 1.7 meters, 1.7 meters and 2.0 meters, 1.7 meters and 1.9 meters, 1.7 meters and 1.8 meters, 1.8 meters and 2.0 meters, 1.8 meters and 1.9 meters, or 1.9 meters and 2.0 meters at V6 stage or later, V7 stage or later, V8 stage or later, V9 stage or later, V10 stage or later, or V11 stage or later where the height is measured as the distance between the soil and the uppermost leaf surface of the leaf farthest from the soil.

In an aspect, the corn plants of a corn field provided herein comprise an average height of less than or equal to 2.1 meters at V12 stage or later. In an aspect, the corn plants of a corn field provided herein comprise an average height of less than or equal to 2.0 meters at V12 stage or later. In an aspect, the corn plants of a corn field provided herein comprise an average height of less than or equal to 1.9 meters at V12 stage or later. In an aspect, the corn plants of a corn field provided herein comprise an average height of less than or equal to 1.8 meters at V12 stage or later. In an aspect, the corn plants of a corn field provided herein comprise an average height of less than or equal to 1.7 meters at V12 stage or later. In an aspect, the corn plants of a corn field provided herein comprise an average height of less than or equal to 1.6 meters at V12 stage or later. In an aspect, the corn plants of a corn field provided herein comprise an average height of less than or equal to 1.5 meters at V12 stage or later. In an aspect, the corn plants of a corn field provided herein comprise an average height of less than or equal to 1.4 meters at V12 stage or later. In an aspect, the corn plants of a corn field provided herein comprise an average height of less than or equal to 1.3 meters at V12 stage or later. In an aspect, the corn plants of a corn field provided herein comprise an average height of less than or equal to 1.2 meters at V12 stage or later. In an aspect, the corn plants of a corn field provided herein comprise an average height of less than or equal to 1.1 meters at V12 stage or later. In an aspect, the corn plants of a corn field provided herein comprise an average height of less than or equal to 1.0 meter at V12 stage or later. In an aspect, the corn plants of a corn field provided herein comprise an average height of less than or equal to 0.9 meters at V12 stage or later. In an aspect, the corn plants of a corn field provided herein comprise an average height of less than or equal to 0.8 meters at V12 stage or later. In an aspect, the corn plants of a corn field provided herein comprise an average height of less than or equal to 0.7 meters at V12 stage or later. In an aspect, the corn plants of a corn field provided herein comprise an average height of less than or equal to 0.6 meters at V12 stage or later. In an aspect, the corn plants of a corn field provided herein comprise an average height of less than or equal to 0.5 meters at V12 stage or later. In an aspect, the corn plants of a corn field provided herein comprise an average height of less than or equal to 0.4 meters at V12 stage or later.

In an aspect, the corn plants of a corn field provided herein comprise an average height of less than or equal to 2.1 meters at V12 stage or later where the height is measured as the distance between the soil and the uppermost leaf surface of the leaf farthest from the soil. In an aspect, the corn plants of a corn field provided herein comprise an average height of less than or equal to 2.0 meters at V12 stage or later where the height is measured as the distance between the soil and the uppermost leaf surface of the leaf farthest from the soil. In an aspect, the corn plants of a corn field provided herein comprise an average height of less than or equal to 1.9 meters at V12 stage or later where the height is measured as the distance between the soil and the uppermost leaf surface of the leaf farthest from the soil. In an aspect, the corn plants of a corn field provided herein comprise an average height of less than or equal to 1.8 meters at V12 stage or later where the height is measured as the distance between the soil and the uppermost leaf surface of the leaf farthest from the soil. In an aspect, the corn plants of a corn field provided herein comprise an average height of less than or equal to 1.7 meters at V12 stage or later where the height is measured as the distance between the soil and the uppermost leaf surface of the leaf farthest from the soil. In an aspect, the corn plants of a corn field provided herein comprise an average height of less than or equal to 1.6 meters at V12 stage or later where the height is measured as the distance between the soil and the uppermost leaf surface of the leaf farthest from the soil. In an aspect, the corn plants of a corn field provided herein comprise an average height of less than or equal to 1.5 meters at V12 stage or later where the height is measured as the distance between the soil and the uppermost leaf surface of the leaf farthest from the soil. In an aspect, the corn plants of a corn field provided herein comprise an average height of less than or equal to 1.4 meters at V12 stage or later where the height is measured as the distance between the soil and the uppermost leaf surface of the leaf farthest from the soil. In an aspect, the corn plants of a corn field provided herein comprise an average height of less than or equal to 1.3 meters at V12 stage or later where the height is measured as the distance between the soil and the uppermost leaf surface of the leaf farthest from the soil. In an aspect, the corn plants of a corn field provided herein comprise an average height of less than or equal to 1.2 meters at V12 stage or later where the height is measured as the distance between the soil and the uppermost leaf surface of the leaf farthest from the soil. In an aspect, the corn plants of a corn field provided herein comprise an average height of less than or equal to 1.1 meters at V12 stage or later where the height is measured as the distance between the soil and the uppermost leaf surface of the leaf farthest from the soil. In an aspect, the corn plants of a corn field provided herein comprise an average height of less than or equal to 1.0 meter at V12 stage or later where the height is measured as the distance between the soil and the uppermost leaf surface of the leaf farthest from the soil. In an aspect, the corn plants of a corn field provided herein comprise an average height of less than or equal to 0.9 meters at V12 stage or later where the height is measured as the distance between the soil and the uppermost leaf surface of the leaf farthest from the soil.

In an aspect, the corn plants of a corn field provided herein comprise an average height of less than or equal to 1.6 meters at V12 stage or later where the height is measured as the distance between the soil and the ligule of the uppermost fully-expanded leaf. In an aspect, the corn plants of a corn field provided herein comprise an average height of less than or equal to 1.5 meters at V12 stage or later where the height is measured as the distance between the soil and the ligule of the uppermost fully-expanded leaf. In an aspect, the corn plants of a corn field provided herein comprise an average height of less than or equal to 1.4 meters at V12 stage or later where the height is measured as the distance between the soil and the ligule of the uppermost fully-expanded leaf. In an aspect, the corn plants of a corn field provided herein comprise an average height of less than or equal to 1.3 meters at V12 stage or later where the height is measured as the distance between the soil and the ligule of the uppermost fully-expanded leaf. In an aspect, the corn plants of a corn field provided herein comprise an average height of less than or equal to 1.2 meters at V12 stage or later where the height is measured as the distance between the soil and the ligule of the uppermost fully-expanded leaf. In an aspect, the corn plants of a corn field provided herein comprise an average height of less than or equal to 1.1 meters at V12 stage or later where the height is measured as the distance between the soil and the ligule of the uppermost fully-expanded leaf. In an aspect, the corn plants of a corn field provided herein comprise an average height of less than or equal to 1.0 meter at V12 stage or later where the height is measured as the distance between the soil and the ligule of the uppermost fully-expanded leaf. In an aspect, the corn plants of a corn field provided herein comprise an average height of less than or equal to 0.9 meters at V12 stage or later where the height is measured as the distance between the soil and the ligule of the uppermost fully-expanded leaf. In an aspect, the corn plants of a corn field provided herein comprise an average height of less than or equal to 0.8 meters at V12 stage or later where the height is measured as the distance between the soil and the ligule of the uppermost fully-expanded leaf. In an aspect, the corn plants of a corn field provided herein comprise an average height of less than or equal to 0.7 meters at V12 stage or later where the height is measured as the distance between the soil and the ligule of the uppermost fully-expanded leaf. In an aspect, the corn plants of a corn field provided herein comprise an average height of less than or equal to 0.6 meters at V12 stage or later where the height is measured as the distance between the soil and the ligule of the uppermost fully-expanded leaf. In an aspect, the corn plants of a corn field provided herein comprise an average height of less than or equal to 0.5 meters at V12 stage or later where the height is measured as the distance between the soil and the ligule of the uppermost fully-expanded leaf. In an aspect, the corn plants of a corn field provided herein comprise an average height of less than or equal to 0.4 meters at V12 stage or later where the height is measured as the distance between the soil and the ligule of the uppermost fully-expanded leaf.

In an aspect, the corn plants of a corn field provided herein comprise an average height of less than or equal to 2.3 meters at V13 stage or later. In an aspect, the corn plants of a corn field provided herein comprise an average height of less than or equal to 2.2 meters at V13 stage or later. In an aspect, the corn plants of a corn field provided herein comprise an average height of less than or equal to 2.1 meters at V13 stage or later. In an aspect, the corn plants of a corn field provided herein comprise an average height of less than or equal to 2.0 meters at V13 stage or later. In an aspect, the corn plants of a corn field provided herein comprise an average height of less than or equal to 1.9 meters at V13 stage or later. In an aspect, the corn plants of a corn field provided herein comprise an average height of less than or equal to 1.8 meters at V13 stage or later. In an aspect, the corn plants of a corn field provided herein comprise an average height of less than or equal to 1.7 meters at V13 stage or later. In an aspect, the corn plants of a corn field provided herein comprise an average height of less than or equal to 1.6 meters at V13 stage or later. In an aspect, the corn plants of a corn field provided herein comprise an average height of less than or equal to 1.5 meters at V13 stage or later. In an aspect, the corn plants of a corn field provided herein comprise an average height of less than or equal to 1.4 meters at V13 stage or later. In an aspect, the corn plants of a corn field provided herein comprise an average height of less than or equal to 1.3 meters at V13 stage or later. In an aspect, the corn plants of a corn field provided herein comprise an average height of less than or equal to 1.2 meters at V13 stage or later. In an aspect, the corn plants of a corn field provided herein comprise an average height of less than or equal to 1.1 meters at V13 stage or later. In an aspect, the corn plants of a corn field provided herein comprise an average height of less than or equal to 1.0 meter at V13 stage or later. In an aspect, the corn plants of a corn field provided herein comprise an average height of less than or equal to 0.9 meters at V13 stage or later. In an aspect, the corn plants of a corn field provided herein comprise an average height of less than or equal to 0.8 meters at V13 stage or later. In an aspect, the corn plants of a corn field provided herein comprise an average height of less than or equal to 0.7 meters at V13 stage or later. In an aspect, the corn plants of a corn field provided herein comprise an average height of less than or equal to 0.6 meters at V13 stage or later. In an aspect, the corn plants of a corn field provided herein comprise an average height of less than or equal to 0.5 meters at V13 stage or later.

In an aspect, the corn plants of a corn field provided herein comprise an average height of less than or equal to 2.3 meters at V13 stage or later where the height is measured as the distance between the soil and the uppermost leaf surface of the leaf farthest from the soil. In an aspect, the corn plants of a corn field provided herein comprise an average height of less than or equal to 2.2 meters at V13 stage or later where the height is measured as the distance between the soil and the uppermost leaf surface of the leaf farthest from the soil. In an aspect, the corn plants of a corn field provided herein comprise an average height of less than or equal to 2.1 meters at V13 stage or later where the height is measured as the distance between the soil and the uppermost leaf surface of the leaf farthest from the soil. In an aspect, the corn plants of a corn field provided herein comprise an average height of less than or equal to 2.0 meters at V13 stage or later where the height is measured as the distance between the soil and the uppermost leaf surface of the leaf farthest from the soil. In an aspect, the corn plants of a corn field provided herein comprise an average height of less than or equal to 1.9 meters at V13 stage or later where the height is measured as the distance between the soil and the uppermost leaf surface of the leaf farthest from the soil. In an aspect, the corn plants of a corn field provided herein comprise an average height of less than or equal to 1.8 meters at V13 stage or later where the height is measured as the distance between the soil and the uppermost leaf surface of the leaf farthest from the soil. In an aspect, the corn plants of a corn field provided herein comprise an average height of less than or equal to 1.7 meters at V13 stage or later where the height is measured as the distance between the soil and the uppermost leaf surface of the leaf farthest from the soil. In an aspect, the corn plants of a corn field provided herein comprise an average height of less than or equal to 1.6 meters at V13 stage or later where the height is measured as the distance between the soil and the uppermost leaf surface of the leaf farthest from the soil. In an aspect, the corn plants of a corn field provided herein comprise an average height of less than or equal to 1.5 meters at V13 stage or later where the height is measured as the distance between the soil and the uppermost leaf surface of the leaf farthest from the soil. In an aspect, the corn plants of a corn field provided herein comprise an average height of less than or equal to 1.4 meters at V13 stage or later where the height is measured as the distance between the soil and the uppermost leaf surface of the leaf farthest from the soil. In an aspect, the corn plants of a corn field provided herein comprise an average height of less than or equal to 1.3 meters at V13 stage or later where the height is measured as the distance between the soil and the uppermost leaf surface of the leaf farthest from the soil. In an aspect, the corn plants of a corn field provided herein comprise an average height of less than or equal to 1.2 meters at V13 stage or later where the height is measured as the distance between the soil and the uppermost leaf surface of the leaf farthest from the soil. In an aspect, the corn plants of a corn field provided herein comprise an average height of less than or equal to 1.1 meters at V13 stage or later where the height is measured as the distance between the soil and the uppermost leaf surface of the leaf farthest from the soil. In an aspect, the corn plants of a corn field provided herein comprise an average height of less than or equal to 1.0 meter at V13 stage or later where the height is measured as the distance between the soil and the uppermost leaf surface of the leaf farthest from the soil.

In an aspect, the corn plants of a corn field provided herein comprise an average height of less than or equal to 1.8 meters at V13 stage or later where the height is measured as the distance between the soil and the ligule of the uppermost fully-expanded leaf. In an aspect, the corn plants of a corn field provided herein comprise an average height of less than or equal to 1.7 meters at V13 stage or later where the height is measured as the distance between the soil and the ligule of the uppermost fully-expanded leaf. In an aspect, the corn plants of a corn field provided herein comprise an average height of less than or equal to 1.6 meters at V13 stage or later where the height is measured as the distance between the soil and the ligule of the uppermost fully-expanded leaf. In an aspect, the corn plants of a corn field provided herein comprise an average height of less than or equal to 1.5 meters at V13 stage or later where the height is measured as the distance between the soil and the ligule of the uppermost fully-expanded leaf. In an aspect, the corn plants of a corn field provided herein comprise an average height of less than or equal to 1.4 meters at V13 stage or later where the height is measured as the distance between the soil and the ligule of the uppermost fully-expanded leaf. In an aspect, the corn plants of a corn field provided herein comprise an average height of less than or equal to 1.3 meters at V13 stage or later where the height is measured as the distance between the soil and the ligule of the uppermost fully-expanded leaf. In an aspect, the corn plants of a corn field provided herein comprise an average height of less than or equal to 1.2 meters at V13 stage or later where the height is measured as the distance between the soil and the ligule of the uppermost fully-expanded leaf. In an aspect, the corn plants of a corn field provided herein comprise an average height of less than or equal to 1.1 meters at V13 stage or later where the height is measured as the distance between the soil and the ligule of the uppermost fully-expanded leaf. In an aspect, the corn plants of a corn field provided herein comprise an average height of less than or equal to 1.0 meter at V13 stage or later where the height is measured as the distance between the soil and the ligule of the uppermost fully-expanded leaf. In an aspect, the corn plants of a corn field provided herein comprise an average height of less than or equal to 0.9 meters at V13 stage or later where the height is measured as the distance between the soil and the ligule of the uppermost fully-expanded leaf. In an aspect, the corn plants of a corn field provided herein comprise an average height of less than or equal to 0.8 meters at V13 stage or later where the height is measured as the distance between the soil and the ligule of the uppermost fully-expanded leaf. In an aspect, the corn plants of a corn field provided herein comprise an average height of less than or equal to 0.7 meters at V13 stage or later where the height is measured as the distance between the soil and the ligule of the uppermost fully-expanded leaf. In an aspect, the corn plants of a corn field provided herein comprise an average height of less than or equal to 0.6 meters at V13 stage or later where the height is measured as the distance between the soil and the ligule of the uppermost fully-expanded leaf. In an aspect, the corn plants of a corn field provided herein comprise an average height of less than or equal to 0.5 meters at V13 stage or later where the height is measured as the distance between the soil and the ligule of the uppermost fully-expanded leaf.

In an aspect, the corn plants of a corn field provided herein comprise an average height of less than or equal to 2.4 meters at V14 stage or later. In an aspect, the corn plants of a corn field provided herein comprise an average height of less than or equal to 2.3 meters at V14 stage or later. In an aspect, the corn plants of a corn field provided herein comprise an average height of less than or equal to 2.2 meters at V14 stage or later. In an aspect, the corn plants of a corn field provided herein comprise an average height of less than or equal to 2.1 meters at V14 stage or later. In an aspect, the corn plants of a corn field provided herein comprise an average height of less than or equal to 2.0 meters at V14 stage or later. In an aspect, the corn plants of a corn field provided herein comprise an average height of less than or equal to 1.9 meters at V14 stage or later. In an aspect, the corn plants of a corn field provided herein comprise an average height of less than or equal to 1.8 meters at V14 stage or later. In an aspect, the corn plants of a corn field provided herein comprise an average height of less than or equal to 1.7 meters at V14 stage or later. In an aspect, the corn plants of a corn field provided herein comprise an average height of less than or equal to 1.6 meters at V14 stage or later. In an aspect, the corn plants of a corn field provided herein comprise an average height of less than or equal to 1.5 meters at V14 stage or later. In an aspect, the corn plants of a corn field provided herein comprise an average height of less than or equal to 1.4 meters at V14 stage or later. In an aspect, the corn plants of a corn field provided herein comprise an average height of less than or equal to 1.3 meters at V14 stage or later. In an aspect, the corn plants of a corn field provided herein comprise an average height of less than or equal to 1.2 meters at V14 stage or later. In an aspect, the corn plants of a corn field provided herein comprise an average height of less than or equal to 1.1 meters at V14 stage or later. In an aspect, the corn plants of a corn field provided herein comprise an average height of less than or equal to 1.0 meter at V14 stage or later. In an aspect, the corn plants of a corn field provided herein comprise an average height of less than or equal to 0.9 meters at V14 stage or later. In an aspect, the corn plants of a corn field provided herein comprise an average height of less than or equal to 0.8 meters at V14 stage or later. In an aspect, the corn plants of a corn field provided herein comprise an average height of less than or equal to 0.7 meters at V14 stage or later. In an aspect, the corn plants of a corn field provided herein comprise an average height of less than or equal to 0.6 meters at V14 stage or later.

In an aspect, the corn plants of a corn field provided herein comprise an average height of less than or equal to 2.4 meters at V14 stage or later where the height is measured as the distance between the soil and the uppermost leaf surface of the leaf farthest from the soil. In an aspect, the corn plants of a corn field provided herein comprise an average height of less than or equal to 2.3 meters at V14 stage or later where the height is measured as the distance between the soil and the uppermost leaf surface of the leaf farthest from the soil. In an aspect, the corn plants of a corn field provided herein comprise an average height of less than or equal to 2.2 meters at V14 stage or later where the height is measured as the distance between the soil and the uppermost leaf surface of the leaf farthest from the soil. In an aspect, the corn plants of a corn field provided herein comprise an average height of less than or equal to 2.1 meters at V14 stage or later where the height is measured as the distance between the soil and the uppermost leaf surface of the leaf farthest from the soil. In an aspect, the corn plants of a corn field provided herein comprise an average height of less than or equal to 2.0 meters at V14 stage or later where the height is measured as the distance between the soil and the uppermost leaf surface of the leaf farthest from the soil. In an aspect, the corn plants of a corn field provided herein comprise an average height of less than or equal to 1.9 meters at V14 stage or later where the height is measured as the distance between the soil and the uppermost leaf surface of the leaf farthest from the soil. In an aspect, the corn plants of a corn field provided herein comprise an average height of less than or equal to 1.8 meters at V14 stage or later where the height is measured as the distance between the soil and the uppermost leaf surface of the leaf farthest from the soil. In an aspect, the corn plants of a corn field provided herein comprise an average height of less than or equal to 1.7 meters at V14 stage or later where the height is measured as the distance between the soil and the uppermost leaf surface of the leaf farthest from the soil. In an aspect, the corn plants of a corn field provided herein comprise an average height of less than or equal to 1.6 meters at V14 stage or later where the height is measured as the distance between the soil and the uppermost leaf surface of the leaf farthest from the soil. In an aspect, the corn plants of a corn field provided herein comprise an average height of less than or equal to 1.5 meters at V14 stage or later where the height is measured as the distance between the soil and the uppermost leaf surface of the leaf farthest from the soil. In an aspect, the corn plants of a corn field provided herein comprise an average height of less than or equal to 1.4 meters at V14 stage or later where the height is measured as the distance between the soil and the uppermost leaf surface of the leaf farthest from the soil. In an aspect, the corn plants of a corn field provided herein comprise an average height of less than or equal to 1.3 meters at V14 stage or later where the height is measured as the distance between the soil and the uppermost leaf surface of the leaf farthest from the soil. In an aspect, the corn plants of a corn field provided herein comprise an average height of less than or equal to 1.2 meters at V14 stage or later where the height is measured as the distance between the soil and the uppermost leaf surface of the leaf farthest from the soil.

In an aspect, the corn plants of a corn field provided herein comprise an average height of less than or equal to 1.9 meters at V14 stage or later where the height is measured as the distance between the soil and the ligule of the uppermost fully-expanded leaf. In an aspect, the corn plants of a corn field provided herein comprise an average height of less than or equal to 1.8 meters at V14 stage or later where the height is measured as the distance between the soil and the ligule of the uppermost fully-expanded leaf. In an aspect, the corn plants of a corn field provided herein comprise an average height of less than or equal to 1.7 meters at V14 stage or later where the height is measured as the distance between the soil and the ligule of the uppermost fully-expanded leaf. In an aspect, the corn plants of a corn field provided herein comprise an average height of less than or equal to 1.6 meters at V14 stage or later where the height is measured as the distance between the soil and the ligule of the uppermost fully-expanded leaf. In an aspect, the corn plants of a corn field provided herein comprise an average height of less than or equal to 1.5 meters at V14 stage or later where the height is measured as the distance between the soil and the ligule of the uppermost fully-expanded leaf. In an aspect, the corn plants of a corn field provided herein comprise an average height of less than or equal to 1.4 meters at V14 stage or later where the height is measured as the distance between the soil and the ligule of the uppermost fully-expanded leaf. In an aspect, the corn plants of a corn field provided herein comprise an average height of less than or equal to 1.3 meters at V14 stage or later where the height is measured as the distance between the soil and the ligule of the uppermost fully-expanded leaf. In an aspect, the corn plants of a corn field provided herein comprise an average height of less than or equal to 1.2 meters at V14 stage or later where the height is measured as the distance between the soil and the ligule of the uppermost fully-expanded leaf. In an aspect, the corn plants of a corn field provided herein comprise an average height of less than or equal to 1.1 meters at V14 stage or later where the height is measured as the distance between the soil and the ligule of the uppermost fully-expanded leaf. In an aspect, the corn plants of a corn field provided herein comprise an average height of less than or equal to 1.0 meter at V14 stage or later where the height is measured as the distance between the soil and the ligule of the uppermost fully-expanded leaf. In an aspect, the corn plants of a corn field provided herein comprise an average height of less than or equal to 0.9 meters at V14 stage or later where the height is measured as the distance between the soil and the ligule of the uppermost fully-expanded leaf. In an aspect, the corn plants of a corn field provided herein comprise an average height of less than or equal to 0.8 meters at V14 stage or later where the height is measured as the distance between the soil and the ligule of the uppermost fully-expanded leaf. In an aspect, the corn plants of a corn field provided herein comprise an average height of less than or equal to 0.7 meters at V14 stage or later where the height is measured as the distance between the soil and the ligule of the uppermost fully-expanded leaf. In an aspect, the corn plants of a corn field provided herein comprise an average height of less than or equal to 0.6 meters at V14 stage or later where the height is measured as the distance between the soil and the ligule of the uppermost fully-expanded leaf.

In an aspect, the corn plants of a corn field provided herein comprise an average height of less than or equal to 2.5 meters at V15 stage or later. In an aspect, the corn plants of a corn field provided herein comprise an average height of less than or equal to 2.4 meters at V15 stage or later. In an aspect, the corn plants of a corn field provided herein comprise an average height of less than or equal to 2.3 meters at V15 stage or later. In an aspect, the corn plants of a corn field provided herein comprise an average height of less than or equal to 2.2 meters at V15 stage or later. In an aspect, the corn plants of a corn field provided herein comprise an average height of less than or equal to 2.1 meters at V15 stage or later. In an aspect, the corn plants of a corn field provided herein comprise an average height of less than or equal to 2.0 meters at V15 stage or later. In an aspect, the corn plants of a corn field provided herein comprise an average height of less than or equal to 1.9 meters at V15 stage or later. In an aspect, the corn plants of a corn field provided herein comprise an average height of less than or equal to 1.8 meters at V15 stage or later. In an aspect, the corn plants of a corn field provided herein comprise an average height of less than or equal to 1.7 meters at V15 stage or later. In an aspect, the corn plants of a corn field provided herein comprise an average height of less than or equal to 1.6 meters at V15 stage or later. In an aspect, the corn plants of a corn field provided herein comprise an average height of less than or equal to 1.5 meters at V15 stage or later. In an aspect, the corn plants of a corn field provided herein comprise an average height of less than or equal to 1.4 meters at V15 stage or later. In an aspect, the corn plants of a corn field provided herein comprise an average height of less than or equal to 1.3 meters at V15 stage or later. In an aspect, the corn plants of a corn field provided herein comprise an average height of less than or equal to 1.2 meters at V15 stage or later. In an aspect, the corn plants of a corn field provided herein comprise an average height of less than or equal to 1.1 meters at V15 stage or later. In an aspect, the corn plants of a corn field provided herein comprise an average height of less than or equal to 1.0 meter at V15 stage or later. In an aspect, the corn plants of a corn field provided herein comprise an average height of less than or equal to 0.9 meters at V15 stage or later. In an aspect, the corn plants of a corn field provided herein comprise an average height of less than or equal to 0.8 meters at V15 stage or later.

In an aspect, the corn plants of a corn field provided herein comprise an average height of less than or equal to 2.5 meters at V15 stage or later where the height is measured as the distance between the soil and the uppermost leaf surface of the leaf farthest from the soil. In an aspect, the corn plants of a corn field provided herein comprise an average height of less than or equal to 2.4 meters at V15 stage or later where the height is measured as the distance between the soil and the uppermost leaf surface of the leaf farthest from the soil. In an aspect, the corn plants of a corn field provided herein comprise an average height of less than or equal to 2.3 meters at V15 stage or later where the height is measured as the distance between the soil and the uppermost leaf surface of the leaf farthest from the soil. In an aspect, the corn plants of a corn field provided herein comprise an average height of less than or equal to 2.2 meters at V15 stage or later where the height is measured as the distance between the soil and the uppermost leaf surface of the leaf farthest from the soil. In an aspect, the corn plants of a corn field provided herein comprise an average height of less than or equal to 2.1 meters at V15 stage or later where the height is measured as the distance between the soil and the uppermost leaf surface of the leaf farthest from the soil. In an aspect, the corn plants of a corn field provided herein comprise an average height of less than or equal to 2.0 meters at V15 stage or later where the height is measured as the distance between the soil and the uppermost leaf surface of the leaf farthest from the soil. In an aspect, the corn plants of a corn field provided herein comprise an average height of less than or equal to 1.9 meters at V15 stage or later where the height is measured as the distance between the soil and the uppermost leaf surface of the leaf farthest from the soil. In an aspect, the corn plants of a corn field provided herein comprise an average height of less than or equal to 1.8 meters at V15 stage or later where the height is measured as the distance between the soil and the uppermost leaf surface of the leaf farthest from the soil. In an aspect, the corn plants of a corn field provided herein comprise an average height of less than or equal to 1.7 meters at V15 stage or later where the height is measured as the distance between the soil and the uppermost leaf surface of the leaf farthest from the soil. In an aspect, the corn plants of a corn field provided herein comprise an average height of less than or equal to 1.6 meters at V15 stage or later where the height is measured as the distance between the soil and the uppermost leaf surface of the leaf farthest from the soil. In an aspect, the corn plants of a corn field provided herein comprise an average height of less than or equal to 1.5 meters at V15 stage or later where the height is measured as the distance between the soil and the uppermost leaf surface of the leaf farthest from the soil. In an aspect, the corn plants of a corn field provided herein comprise an average height of less than or equal to 1.4 meters at V15 stage or later where the height is measured as the distance between the soil and the uppermost leaf surface of the leaf farthest from the soil. In an aspect, the corn plants of a corn field provided herein comprise an average height of less than or equal to 1.3 meters at V15 stage or later where the height is measured as the distance between the soil and the uppermost leaf surface of the leaf farthest from the soil.

In an aspect, the corn plants of a corn field provided herein comprise an average height of less than or equal to 2.0 meters at V15 stage or later where the height is measured as the distance between the soil and the ligule of the uppermost fully-expanded leaf. In an aspect, the corn plants of a corn field provided herein comprise an average height of less than or equal to 1.9 meters at V15 stage or later where the height is measured as the distance between the soil and the ligule of the uppermost fully-expanded leaf. In an aspect, the corn plants of a corn field provided herein comprise an average height of less than or equal to 1.8 meters at V15 stage or later where the height is measured as the distance between the soil and the ligule of the uppermost fully-expanded leaf. In an aspect, the corn plants of a corn field provided herein comprise an average height of less than or equal to 1.7 meters at V15 stage or later where the height is measured as the distance between the soil and the ligule of the uppermost fully-expanded leaf. In an aspect, the corn plants of a corn field provided herein comprise an average height of less than or equal to 1.6 meters at V15 stage or later where the height is measured as the distance between the soil and the ligule of the uppermost fully-expanded leaf. In an aspect, the corn plants of a corn field provided herein comprise an average height of less than or equal to 1.5 meters at V15 stage or later where the height is measured as the distance between the soil and the ligule of the uppermost fully-expanded leaf. In an aspect, the corn plants of a corn field provided herein comprise an average height of less than or equal to 1.4 meters at V15 stage or later where the height is measured as the distance between the soil and the ligule of the uppermost fully-expanded leaf. In an aspect, the corn plants of a corn field provided herein comprise an average height of less than or equal to 1.3 meters at V15 stage or later where the height is measured as the distance between the soil and the ligule of the uppermost fully-expanded leaf. In an aspect, the corn plants of a corn field provided herein comprise an average height of less than or equal to 1.2 meters at V15 stage or later where the height is measured as the distance between the soil and the ligule of the uppermost fully-expanded leaf. In an aspect, the corn plants of a corn field provided herein comprise an average height of less than or equal to 1.1 meters at V15 stage or later where the height is measured as the distance between the soil and the ligule of the uppermost fully-expanded leaf. In an aspect, the corn plants of a corn field provided herein comprise an average height of less than or equal to 1.0 meter at V15 stage or later where the height is measured as the distance between the soil and the ligule of the uppermost fully-expanded leaf. In an aspect, the corn plants of a corn field provided herein comprise an average height of less than or equal to 0.9 meters at V15 stage or later where the height is measured as the distance between the soil and the ligule of the uppermost fully-expanded leaf. In an aspect, the corn plants of a corn field provided herein comprise an average height of less than or equal to 0.8 meters at V15 stage or later where the height is measured as the distance between the soil and the ligule of the uppermost fully-expanded leaf.

In an aspect, the corn plants of a corn field provided herein comprise an average height of less than or equal to 2.5 meters at VT stage or later. In an aspect, the corn plants of a corn field provided herein comprise an average height of less than or equal to 2.4 meters at VT stage or later. In an aspect, the corn plants of a corn field provided herein comprise an average height of less than or equal to 2.3 meters at VT stage or later. In an aspect, the corn plants of a corn field provided herein comprise an average height of less than or equal to 2.2 meters at VT stage or later. In an aspect, the corn plants of a corn field provided herein comprise an average height of less than or equal to 2.1 meters at VT stage or later. In an aspect, the corn plants of a corn field provided herein comprise an average height of less than or equal to 2.0 meters at VT stage or later. In an aspect, the corn plants of a corn field provided herein comprise an average height of less than or equal to 1.9 meters at VT stage or later. In an aspect, the corn plants of a corn field provided herein comprise an average height of less than or equal to 1.8 meters at VT stage or later. In an aspect, the corn plants of a corn field provided herein comprise an average height of less than or equal to 1.7 meters at VT stage or later. In an aspect, the corn plants of a corn field provided herein comprise an average height of less than or equal to 1.6 meters at VT stage or later. In an aspect, the corn plants of a corn field provided herein comprise an average height of less than or equal to 1.5 meters at VT stage or later. In an aspect, the corn plants of a corn field provided herein comprise an average height of less than or equal to 1.4 meters at VT stage or later. In an aspect, the corn plants of a corn field provided herein comprise an average height of less than or equal to 1.3 meters at VT stage or later. In an aspect, the corn plants of a corn field provided herein comprise an average height of less than or equal to 1.2 meters at VT stage or later. In an aspect, the corn plants of a corn field provided herein comprise an average height of less than or equal to 1.1 meters at VT stage or later.

In an aspect, the corn plants of a corn field provided herein comprise an average height of less than or equal to 2.5 meters at VT stage or later where the height is measured as the distance between the soil and the uppermost leaf surface of the leaf farthest from the soil. In an aspect, the corn plants of a corn field provided herein comprise an average height of less than or equal to 2.4 meters at VT stage or later where the height is measured as the distance between the soil and the uppermost leaf surface of the leaf farthest from the soil. In an aspect, the corn plants of a corn field provided herein comprise an average height of less than or equal to 2.3 meters at VT stage or later where the height is measured as the distance between the soil and the uppermost leaf surface of the leaf farthest from the soil. In an aspect, the corn plants of a corn field provided herein comprise an average height of less than or equal to 2.2 meters at VT stage or later where the height is measured as the distance between the soil and the uppermost leaf surface of the leaf farthest from the soil. In an aspect, the corn plants of a corn field provided herein comprise an average height of less than or equal to 2.1 meters at VT stage or later where the height is measured as the distance between the soil and the uppermost leaf surface of the leaf farthest from the soil. In an aspect, the corn plants of a corn field provided herein comprise an average height of less than or equal to 2.0 meters at VT stage or later where the height is measured as the distance between the soil and the uppermost leaf surface of the leaf farthest from the soil. In an aspect, the corn plants of a corn field provided herein comprise an average height of less than or equal to 1.9 meters at VT stage or later where the height is measured as the distance between the soil and the uppermost leaf surface of the leaf farthest from the soil. In an aspect, the corn plants of a corn field provided herein comprise an average height of less than or equal to 1.8 meters at VT stage or later where the height is measured as the distance between the soil and the uppermost leaf surface of the leaf farthest from the soil. In an aspect, the corn plants of a corn field provided herein comprise an average height of less than or equal to 1.7 meters at VT stage or later where the height is measured as the distance between the soil and the uppermost leaf surface of the leaf farthest from the soil. In an aspect, the corn plants of a corn field provided herein comprise an average height of less than or equal to 1.6 meters at VT stage or later where the height is measured as the distance between the soil and the uppermost leaf surface of the leaf farthest from the soil. In an aspect, the corn plants of a corn field provided herein comprise an average height of less than or equal to 1.5 meters at VT stage or later where the height is measured as the distance between the soil and the uppermost leaf surface of the leaf farthest from the soil. In an aspect, the corn plants of a corn field provided herein comprise an average height of less than or equal to 1.4 meters at VT stage or later where the height is measured as the distance between the soil and the uppermost leaf surface of the leaf farthest from the soil.

In an aspect, the corn plants of a corn field provided herein comprise an average height of less than or equal to 2.1 meters at VT stage or later where the height is measured as the distance between the soil and the ligule of the uppermost fully-expanded leaf. In an aspect, the corn plants of a corn field provided herein comprise an average height of less than or equal to 2.0 meters at VT stage or later where the height is measured as the distance between the soil and the ligule of the uppermost fully-expanded leaf. In an aspect, the corn plants of a corn field provided herein comprise an average height of less than or equal to 1.9 meters at VT stage or later where the height is measured as the distance between the soil and the ligule of the uppermost fully-expanded leaf. In an aspect, the corn plants of a corn field provided herein comprise an average height of less than or equal to 1.8 meters at VT stage or later where the height is measured as the distance between the soil and the ligule of the uppermost fully-expanded leaf. In an aspect, the corn plants of a corn field provided herein comprise an average height of less than or equal to 1.7 meters at VT stage or later where the height is measured as the distance between the soil and the ligule of the uppermost fully-expanded leaf. In an aspect, the corn plants of a corn field provided herein comprise an average height of less than or equal to 1.6 meters at VT stage or later where the height is measured as the distance between the soil and the ligule of the uppermost fully-expanded leaf. In an aspect, the corn plants of a corn field provided herein comprise an average height of less than or equal to 1.5 meters at VT stage or later where the height is measured as the distance between the soil and the ligule of the uppermost fully-expanded leaf. In an aspect, the corn plants of a corn field provided herein comprise an average height of less than or equal to 1.4 meters at VT stage or later where the height is measured as the distance between the soil and the ligule of the uppermost fully-expanded leaf. In an aspect, the corn plants of a corn field provided herein comprise an average height of less than or equal to 1.3 meters at VT stage or later where the height is measured as the distance between the soil and the ligule of the uppermost fully-expanded leaf. In an aspect, the corn plants of a corn field provided herein comprise an average height of less than or equal to 1.2 meters at VT stage or later where the height is measured as the distance between the soil and the ligule of the uppermost fully-expanded leaf. In an aspect, the corn plants of a corn field provided herein comprise an average height of less than or equal to 1.1 meters at VT stage or later where the height is measured as the distance between the soil and the ligule of the uppermost fully-expanded leaf.

In an aspect, the corn plants of a corn field provided herein comprise an average height of less than or equal to 2.5 meters at R1 stage or later. In an aspect, the corn plants of a corn field provided herein comprise an average height of less than or equal to 2.4 meters at R1 stage or later. In an aspect, the corn plants of a corn field provided herein comprise an average height of less than or equal to 2.3 meters at R1 stage or later. In an aspect, the corn plants of a corn field provided herein comprise an average height of less than or equal to 2.2 meters at R1 stage or later. In an aspect, the corn plants of a corn field provided herein comprise an average height of less than or equal to 2.1 meters at R1 stage or later. In an aspect, the corn plants of a corn field provided herein comprise an average height of less than or equal to 2.0 meters at R1 stage or later. In an aspect, the corn plants of a corn field provided herein comprise an average height of less than or equal to 1.9 meters at R1 stage or later. In an aspect, the corn plants of a corn field provided herein comprise an average height of less than or equal to 1.8 meters at R1 stage or later. In an aspect, the corn plants of a corn field provided herein comprise an average height of less than or equal to 1.7 meters at R1 stage or later. In an aspect, the corn plants of a corn field provided herein comprise an average height of less than or equal to 1.6 meters at R1 stage or later. In an aspect, the corn plants of a corn field provided herein comprise an average height of less than or equal to 1.5 meters at R1 stage or later. In an aspect, the corn plants of a corn field provided herein comprise an average height of less than or equal to 1.4 meters at R1 stage or later. In an aspect, the corn plants of a corn field provided herein comprise an average height of less than or equal to 1.3 meters at R1 stage or later. In an aspect, the corn plants of a corn field provided herein comprise an average height of less than or equal to 1.2 meters at R1 stage or later.

In an aspect, the corn plants of a corn field provided herein comprise an average height of less than or equal to 2.5 meters at R1 stage or later where the height is measured as the distance between the soil and the uppermost leaf surface of the leaf farthest from the soil. In an aspect, the corn plants of a corn field provided herein comprise an average height of less than or equal to 2.4 meters at R1 stage or later where the height is measured as the distance between the soil and the uppermost leaf surface of the leaf farthest from the soil. In an aspect, the corn plants of a corn field provided herein comprise an average height of less than or equal to 2.3 meters at R1 stage or later where the height is measured as the distance between the soil and the uppermost leaf surface of the leaf farthest from the soil. In an aspect, the corn plants of a corn field provided herein comprise an average height of less than or equal to 2.2 meters at R1 stage or later where the height is measured as the distance between the soil and the uppermost leaf surface of the leaf farthest from the soil. In an aspect, the corn plants of a corn field provided herein comprise an average height of less than or equal to 2.1 meters at R1 stage or later where the height is measured as the distance between the soil and the uppermost leaf surface of the leaf farthest from the soil. In an aspect, the corn plants of a corn field provided herein comprise an average height of less than or equal to 2.0 meters at R1 stage or later where the height is measured as the distance between the soil and the uppermost leaf surface of the leaf farthest from the soil. In an aspect, the corn plants of a corn field provided herein comprise an average height of less than or equal to 1.9 meters at R1 stage or later where the height is measured as the distance between the soil and the uppermost leaf surface of the leaf farthest from the soil. In an aspect, the corn plants of a corn field provided herein comprise an average height of less than or equal to 1.8 meters at R1 stage or later where the height is measured as the distance between the soil and the uppermost leaf surface of the leaf farthest from the soil. In an aspect, the corn plants of a corn field provided herein comprise an average height of less than or equal to 1.7 meters at R1 stage or later where the height is measured as the distance between the soil and the uppermost leaf surface of the leaf farthest from the soil. In an aspect, the corn plants of a corn field provided herein comprise an average height of less than or equal to 1.6 meters at R1 stage or later where the height is measured as the distance between the soil and the uppermost leaf surface of the leaf farthest from the soil. In an aspect, the corn plants of a corn field provided herein comprise an average height of less than or equal to 1.5 meters at R1 stage or later where the height is measured as the distance between the soil and the uppermost leaf surface of the leaf farthest from the soil.

In an aspect, the corn plants of a corn field provided herein comprise an average height of less than or equal to 2.1 meters at R1 stage or later where the height is measured as the distance between the soil and the ligule of the uppermost fully-expanded leaf. In an aspect, the corn plants of a corn field provided herein comprise an average height of less than or equal to 2.0 meters at R1 stage or later where the height is measured as the distance between the soil and the ligule of the uppermost fully-expanded leaf. In an aspect, the corn plants of a corn field provided herein comprise an average height of less than or equal to 1.9 meters at R1 stage or later where the height is measured as the distance between the soil and the ligule of the uppermost fully-expanded leaf. In an aspect, the corn plants of a corn field provided herein comprise an average height of less than or equal to 1.8 meters at R1 stage or later where the height is measured as the distance between the soil and the ligule of the uppermost fully-expanded leaf. In an aspect, the corn plants of a corn field provided herein comprise an average height of less than or equal to 1.7 meters at R1 stage or later where the height is measured as the distance between the soil and the ligule of the uppermost fully-expanded leaf. In an aspect, the corn plants of a corn field provided herein comprise an average height of less than or equal to 1.6 meters at R1 stage or later where the height is measured as the distance between the soil and the ligule of the uppermost fully-expanded leaf. In an aspect, the corn plants of a corn field provided herein comprise an average height of less than or equal to 1.5 meters at R1 stage or later where the height is measured as the distance between the soil and the ligule of the uppermost fully-expanded leaf. In an aspect, the corn plants of a corn field provided herein comprise an average height of less than or equal to 1.4 meters at R1 stage or later where the height is measured as the distance between the soil and the ligule of the uppermost fully-expanded leaf. In an aspect, the corn plants of a corn field provided herein comprise an average height of less than or equal to 1.3 meters at R1 stage or later where the height is measured as the distance between the soil and the ligule of the uppermost fully-expanded leaf. In an aspect, the corn plants of a corn field provided herein comprise an average height of less than or equal to 1.2 meters at R1 stage or later where the height is measured as the distance between the soil and the ligule of the uppermost fully-expanded leaf.

In an aspect, the corn plants of a corn field provided herein comprise an average height of between 0.2 meters and 2.2 meters, 0.2 meters and 2.1 meters, 0.2 meters and 2.0 meters, 0.2 meters and 1.9 meters, 0.2 meters and 1.8 meters, 0.2 meters and 1.7 meters, 0.2 meters and 1.6 meters, 0.2 meters and 1.5 meters, 0.2 meters and 1.4 meters, 0.2 meters and 1.3 meters, 0.2 meters and 1.2 meters, 0.2 meters and 1.1 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.2 meters, 0.3 meters and 2.1 meters, 0.3 meters and 2.0 meters, 0.3 meters and 1.9 meters, 0.3 meters and 1.8 meters, 0.3 meters and 1.7 meters, 0.3 meters and 1.6 meters, 0.3 meters and 1.5 meters, 0.3 meters and 1.4 meters, 0.3 meters and 1.3 meters, 0.3 meters and 1.2 meters, 0.3 meters and 1.1 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.2 meters, 0.4 meters and 2.1 meters, 0.4 meters and 2.0 meters, 0.4 meters and 1.9 meters, 0.4 meters and 1.8 meters, 0.4 meters and 1.7 meters, 0.4 meters and 1.6 meters, 0.4 meters and 1.5 meters, 0.4 meters and 1.4 meters, 0.4 meters and 1.3 meters, 0.4 meters and 1.2 meters, 0.4 meters and 1.1 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.2 meters, 0.5 meters and 2.1 meters, 0.5 meters and 2.0 meters, 0.5 meters and 1.9 meters, 0.5 meters and 1.8 meters, 0.5 meters and 1.7 meters, 0.5 meters and 1.6 meters, 0.5 meters and 1.5 meters, 0.5 meters and 1.4 meters, 0.5 meters and 1.3 meters, 0.5 meters and 1.2 meters, 0.5 meters and 1.1 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.2 meters, 0.6 meters and 2.1 meters, 0.6 meters and 2.0 meters, 0.6 meters and 1.9 meters, 0.6 meters and 1.8 meters, 0.6 meters and 1.7 meters, 0.6 meters and 1.6 meters, 0.6 meters and 1.5 meters, 0.6 meters and 1.4 meters, 0.6 meters and 1.3 meters, 0.6 meters and 1.2 meters, 0.6 meters and 1.1 meters, 0.6 meters and 1.0 meter, 0.6 meters and 0.9 meters, 0.6 meters and 0.8 meters, 0.6 meters and 0.7 meters, 0.7 meters and 2.2 meters, 0.7 meters and 2.1 meters, 0.7 meters and 2.0 meters, 0.7 meters and 1.9 meters, 0.7 meters and 1.8 meters, 0.7 meters and 1.7 meters, 0.7 meters and 1.6 meters, 0.7 meters and 1.5 meters, 0.7 meters and 1.4 meters, 0.7 meters and 1.3 meters, 0.7 meters and 1.2 meters, 0.7 meters and 1.1 meters, 0.7 meters and 1.0 meter, 0.7 meters and 0.9 meters, 0.7 meters and 0.8 meters, 0.8 meters and 2.2 meters, 0.8 meters and 2.1 meters, 0.8 meters and 2.0 meters, 0.8 meters and 1.9 meters, 0.8 meters and 1.8 meters, 0.8 meters and 1.7 meters, 0.8 meters and 1.6 meters, 0.8 meters and 1.5 meters, 0.8 meters and 1.4 meters, 0.8 meters and 1.3 meters, 0.8 meters and 1.2 meters, 0.8 meters and 1.1 meters, 0.8 meters and 1.0 meter, 0.8 meters and 0.9 meters, 0.9 meters and 2.2 meters, 0.9 meters and 2.1 meters, 0.9 meters and 2.0 meters, 0.9 meters and 1.9 meters, 0.9 meters and 1.8 meters, 0.9 meters and 1.7 meters, 0.9 meters and 1.6 meters, 0.9 meters and 1.5 meters, 0.9 meters and 1.4 meters, 0.9 meters and 1.3 meters, 0.9 meters and 1.2 meters, 0.9 meters and 1.1 meters, 0.9 meters and 1.0 meter, 1.0 meter and 2.2 meters, 1.0 meter and 2.1 meters, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, 1.2 meters and 1.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.2 meters, 1.7 meters and 2.1 meters, 1.7 meters and 2.0 meters, 1.7 meters and 1.9 meters, 1.7 meters and 1.8 meters, 1.8 meters and 2.2 meters, 1.8 meters and 2.1 meters, 1.8 meters and 2.0 meters, 1.8 meters and 1.9 meters, 1.9 meters and 2.2 meters, 1.9 meters and 2.1 meters, 1.9 meters and 2.0 meters, 2.0 meters and 2.2 meters, 2.0 meters and 2.1 meters, or 2.1 meters and 2.2 meters at V12 stage or later, V13 stage or later, V14 stage or later, V15 stage or later, VT stage or later, or R1 stage or later where the height is measured as the distance between the soil and the ligule (or collar) of the uppermost fully-expanded leaf.

In an aspect, the corn plants of a corn field provided herein comprise an average height of between 0.8 meters and 2.7 meters, 0.8 meters and 2.6 meters, 0.8 meters and 2.5 meters, 0.8 meters and 2.4 meters, 0.8 meters and 2.3 meters, 0.8 meters and 2.2 meters, 0.8 meters and 2.1 meters, 0.8 meters and 2.0 meters, 0.8 meters and 1.9 meters, 0.8 meters and 1.8 meters, 0.8 meters and 1.7 meters, 0.8 meters and 1.6 meters, 0.8 meters and 1.5 meters, 0.8 meters and 1.4 meters, 0.8 meters and 1.3 meters, 0.8 meters and 1.2 meters, 0.8 meters and 1.1 meters, 0.8 meters and 1.0 meter, 0.8 meters and 0.9 meters, 0.9 meters and 2.7 meters, 0.9 meters and 2.6 meters, 0.9 meters and 2.5 meters, 0.9 meters and 2.4 meters, 0.9 meters and 2.3 meters, 0.9 meters and 2.2 meters, 0.9 meters and 2.1 meters, 0.9 meters and 2.0 meters, 0.9 meters and 1.9 meters, 0.9 meters and 1.8 meters, 0.9 meters and 1.7 meters, 0.9 meters and 1.6 meters, 0.9 meters and 1.5 meters, 0.9 meters and 1.4 meters, 0.9 meters and 1.3 meters, 0.9 meters and 1.2 meters, 0.9 meters and 1.1 meters, 0.9 meters and 1.0 meter, 1.0 meter and 2.7 meters, 1.0 meter and 2.6 meters, 1.0 meter and 2.5 meters, 1.0 meter and 2.4 meters, 1.0 meter and 2.3 meters, 1.0 meter and 2.2 meters, 1.0 meter and 2.1 meters, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.7 meters, 1.1 meters and 2.6 meters, 1.1 meters and 2.5 meters, 1.1 meters and 2.4 meters, 1.1 meters and 2.3 meters, 1.1 meters and 2.2 meters, 1.1 meters and 2.1 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.7 meters, 1.2 meters and 2.6 meters, 1.2 meters and 2.5 meters, 1.2 meters and 2.4 meters, 1.2 meters and 2.3 meters, 1.2 meters and 2.2 meters, 1.2 meters and 2.1 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, 1.2 meters and 1.3 meters, 1.3 meters and 2.7 meters, 1.3 meters and 2.6 meters, 1.3 meters and 2.5 meters, 1.3 meters and 2.4 meters, 1.3 meters and 2.3 meters, 1.3 meters and 2.2 meters, 1.3 meters and 2.1 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.7 meters, 1.4 meters and 2.6 meters, 1.4 meters and 2.5 meters, 1.4 meters and 2.4 meters, 1.4 meters and 2.3 meters, 1.4 meters and 2.2 meters, 1.4 meters and 2.1 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.7 meters, 1.5 meters and 2.6 meters, 1.5 meters and 2.5 meters, 1.5 meters and 2.4 meters, 1.5 meters and 2.3 meters, 1.5 meters and 2.2 meters, 1.5 meters and 2.1 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.7 meters, 1.6 meters and 2.6 meters, 1.6 meters and 2.5 meters, 1.6 meters and 2.4 meters, 1.6 meters and 2.3 meters, 1.6 meters and 2.2 meters, 1.6 meters and 2.1 meters, 1.6 meters and 2.0 meters, 1.6 meters and 1.9 meters, 1.6 meters and 1.8 meters, 1.6 meters and 1.7 meters, 1.7 meters and 2.7 meters, 1.7 meters and 2.6 meters, 1.7 meters and 2.5 meters, 1.7 meters and 2.4 meters, 1.7 meters and 2.3 meters, 1.7 meters and 2.2 meters, 1.7 meters and 2.1 meters, 1.7 meters and 2.0 meters, 1.7 meters and 1.9 meters, 1.7 meters and 1.8 meters, 1.8 meters and 2.7 meters, 1.8 meters and 2.6 meters, 1.8 meters and 2.5 meters, 1.8 meters and 2.4 meters, 1.8 meters and 2.3 meters, 1.8 meters and 2.2 meters, 1.8 meters and 2.1 meters, 1.8 meters and 2.0 meters, 1.8 meters and 1.9 meters, 1.9 meters and 2.7 meters, 1.9 meters and 2.6 meters, 1.9 meters and 2.5 meters, 1.9 meters and 2.4 meters, 1.9 meters and 2.3 meters, 1.9 meters and 2.2 meters, 1.9 meters and 2.1 meters, 1.9 meters and 2.0 meters, 2.0 meters and 2.7 meters, 2.0 meters and 2.6 meters, 2.0 meters and 2.5 meters, 2.0 meters and 2.4 meters, 2.0 meters and 2.3 meters, 2.0 meters and 2.2 meters, 2.0 meters and 2.1 meters, 2.1 meters and 2.7 meters, 2.1 meters and 2.6 meters, 2.1 meters and 2.5 meters, 2.1 meters and 2.4 meters, 2.1 meters and 2.3 meters, 2.1 meters and 2.2 meters, 2.2 meters and 2.7 meters, 2.2 meters and 2.6 meters, 2.2 meters and 2.5 meters, 2.2 meters and 2.4 meters, 2.2 meters and 2.3 meters, 2.3 meters and 2.7 meters, 2.3 meters and 2.6 meters, 2.3 meters and 2.5 meters, 2.3 meters and 2.4 meters, 2.4 meters and 2.7 meters, 2.4 meters and 2.6 meters, 2.4 meters and 2.5 meters, 2.5 meters and 2.7 meters, 2.5 meters and 2.6 meters, or 2.6 meters and 2.7 meters at V12 stage or later, V13 stage or later, V14 stage or later, V15 stage or later, VT stage or later, or R1 stage or later where the height is measured as the distance between the soil and the uppermost leaf surface of the leaf farthest from the soil.

In an aspect, the corn plants of a corn field provided herein comprise an average height of less than or equal to 2.5 meters at R2 stage or later. In an aspect, the corn plants of a corn field provided herein comprise an average height of less than or equal to 2.4 meters at R2 stage or later. In an aspect, the corn plants of a corn field provided herein comprise an average height of less than or equal to 2.3 meters at R2 stage or later. In an aspect, the corn plants of a corn field provided herein comprise an average height of less than or equal to 2.2 meters at R2 stage or later. In an aspect, the corn plants of a corn field provided herein comprise an average height of less than or equal to 2.1 meters at R2 stage or later. In an aspect, the corn plants of a corn field provided herein comprise an average height of less than or equal to 2.0 meters at R2 stage or later. In an aspect, the corn plants of a corn field provided herein comprise an average height of less than or equal to 1.9 meters at R2 stage or later. In an aspect, the corn plants of a corn field provided herein comprise an average height of less than or equal to 1.8 meters at R2 stage or later. In an aspect, the corn plants of a corn field provided herein comprise an average height of less than or equal to 1.7 meters at R2 stage or later. In an aspect, the corn plants of a corn field provided herein comprise an average height of less than or equal to 1.6 meters at R2 stage or later. In an aspect, the corn plants of a corn field provided herein comprise an average height of less than or equal to 1.5 meters at R2 stage or later. In an aspect, the corn plants of a corn field provided herein comprise an average height of less than or equal to 1.4 meters at R2 stage or later. In an aspect, the corn plants of a corn field provided herein comprise an average height of less than or equal to 1.3 meters at R2 stage or later. In an aspect, the corn plants of a corn field provided herein comprise an average height of less than or equal to 1.2 meters at R2 stage or later.

In an aspect, the corn plants of a corn field provided herein comprise an average height of less than or equal to 2.5 meters at R2 stage or later where the height is measured as the distance between the soil and the uppermost leaf surface of the leaf farthest from the soil. In an aspect, the corn plants of a corn field provided herein comprise an average height of less than or equal to 2.4 meters at R2 stage or later where the height is measured as the distance between the soil and the uppermost leaf surface of the leaf farthest from the soil. In an aspect, the corn plants of a corn field provided herein comprise an average height of less than or equal to 2.3 meters at R2 stage or later where the height is measured as the distance between the soil and the uppermost leaf surface of the leaf farthest from the soil. In an aspect, the corn plants of a corn field provided herein comprise an average height of less than or equal to 2.2 meters at R2 stage or later where the height is measured as the distance between the soil and the uppermost leaf surface of the leaf farthest from the soil. In an aspect, the corn plants of a corn field provided herein comprise an average height of less than or equal to 2.1 meters at R2 stage or later where the height is measured as the distance between the soil and the uppermost leaf surface of the leaf farthest from the soil. In an aspect, the corn plants of a corn field provided herein comprise an average height of less than or equal to 2.0 meters at R2 stage or later where the height is measured as the distance between the soil and the uppermost leaf surface of the leaf farthest from the soil. In an aspect, the corn plants of a corn field provided herein comprise an average height of less than or equal to 1.9 meters at R2 stage or later where the height is measured as the distance between the soil and the uppermost leaf surface of the leaf farthest from the soil. In an aspect, the corn plants of a corn field provided herein comprise an average height of less than or equal to 1.8 meters at R2 stage or later where the height is measured as the distance between the soil and the uppermost leaf surface of the leaf farthest from the soil. In an aspect, the corn plants of a corn field provided herein comprise an average height of less than or equal to 1.7 meters at R2 stage or later where the height is measured as the distance between the soil and the uppermost leaf surface of the leaf farthest from the soil. In an aspect, the corn plants of a corn field provided herein comprise an average height of less than or equal to 1.6 meters at R2 stage or later where the height is measured as the distance between the soil and the uppermost leaf surface of the leaf farthest from the soil. In an aspect, the corn plants of a corn field provided herein comprise an average height of less than or equal to 1.5 meters at R2 stage or later where the height is measured as the distance between the soil and the uppermost leaf surface of the leaf farthest from the soil.

In an aspect, the corn plants of a corn field provided herein comprise an average height of less than or equal to 2.1 meters at R2 stage or later where the height is measured as the distance between the soil and the ligule of the uppermost fully-expanded leaf. In an aspect, the corn plants of a corn field provided herein comprise an average height of less than or equal to 2.0 meters at R2 stage or later where the height is measured as the distance between the soil and the ligule of the uppermost fully-expanded leaf. In an aspect, the corn plants of a corn field provided herein comprise an average height of less than or equal to 1.9 meters at R2 stage or later where the height is measured as the distance between the soil and the ligule of the uppermost fully-expanded leaf. In an aspect, the corn plants of a corn field provided herein comprise an average height of less than or equal to 1.8 meters at R2 stage or later where the height is measured as the distance between the soil and the ligule of the uppermost fully-expanded leaf. In an aspect, the corn plants of a corn field provided herein comprise an average height of less than or equal to 1.7 meters at R2 stage or later where the height is measured as the distance between the soil and the ligule of the uppermost fully-expanded leaf. In an aspect, the corn plants of a corn field provided herein comprise an average height of less than or equal to 1.6 meters at R2 stage or later where the height is measured as the distance between the soil and the ligule of the uppermost fully-expanded leaf. In an aspect, the corn plants of a corn field provided herein comprise an average height of less than or equal to 1.5 meters at R2 stage or later where the height is measured as the distance between the soil and the ligule of the uppermost fully-expanded leaf. In an aspect, the corn plants of a corn field provided herein comprise an average height of less than or equal to 1.4 meters at R2 stage or later where the height is measured as the distance between the soil and the ligule of the uppermost fully-expanded leaf. In an aspect, the corn plants of a corn field provided herein comprise an average height of less than or equal to 1.3 meters at R2 stage or later where the height is measured as the distance between the soil and the ligule of the uppermost fully-expanded leaf. In an aspect, the corn plants of a corn field provided herein comprise an average height of less than or equal to 1.2 meters at R2 stage or later where the height is measured as the distance between the soil and the ligule of the uppermost fully-expanded leaf.

In an aspect, the corn plants of a corn field provided herein comprise an average height of less than or equal to 2.5 meters at R3 stage or later. In an aspect, the corn plants of a corn field provided herein comprise an average height of less than or equal to 2.4 meters at R3 stage or later. In an aspect, the corn plants of a corn field provided herein comprise an average height of less than or equal to 2.3 meters at R3 stage or later. In an aspect, the corn plants of a corn field provided herein comprise an average height of less than or equal to 2.2 meters at R3 stage or later. In an aspect, the corn plants of a corn field provided herein comprise an average height of less than or equal to 2.1 meters at R3 stage or later. In an aspect, the corn plants of a corn field provided herein comprise an average height of less than or equal to 2.0 meters at R3 stage or later. In an aspect, the corn plants of a corn field provided herein comprise an average height of less than or equal to 1.9 meters at R3 stage or later. In an aspect, the corn plants of a corn field provided herein comprise an average height of less than or equal to 1.8 meters at R3 stage or later. In an aspect, the corn plants of a corn field provided herein comprise an average height of less than or equal to 1.7 meters at R3 stage or later. In an aspect, the corn plants of a corn field provided herein comprise an average height of less than or equal to 1.6 meters at R3 stage or later. In an aspect, the corn plants of a corn field provided herein comprise an average height of less than or equal to 1.5 meters at R3 stage or later. In an aspect, the corn plants of a corn field provided herein comprise an average height of less than or equal to 1.4 meters at R3 stage or later. In an aspect, the corn plants of a corn field provided herein comprise an average height of less than or equal to 1.3 meters at R3 stage or later. In an aspect, the corn plants of a corn field provided herein comprise an average height of less than or equal to 1.2 meters at R3 stage or later.

In an aspect, the corn plants of a corn field provided herein comprise an average height of less than or equal to 2.5 meters at R3 stage or later where the height is measured as the distance between the soil and the uppermost leaf surface of the leaf farthest from the soil. In an aspect, the corn plants of a corn field provided herein comprise an average height of less than or equal to 2.4 meters at R3 stage or later where the height is measured as the distance between the soil and the uppermost leaf surface of the leaf farthest from the soil. In an aspect, the corn plants of a corn field provided herein comprise an average height of less than or equal to 2.3 meters at R3 stage or later where the height is measured as the distance between the soil and the uppermost leaf surface of the leaf farthest from the soil. In an aspect, the corn plants of a corn field provided herein comprise an average height of less than or equal to 2.2 meters at R3 stage or later where the height is measured as the distance between the soil and the uppermost leaf surface of the leaf farthest from the soil. In an aspect, the corn plants of a corn field provided herein comprise an average height of less than or equal to 2.1 meters at R3 stage or later where the height is measured as the distance between the soil and the uppermost leaf surface of the leaf farthest from the soil. In an aspect, the corn plants of a corn field provided herein comprise an average height of less than or equal to 2.0 meters at R3 stage or later where the height is measured as the distance between the soil and the uppermost leaf surface of the leaf farthest from the soil. In an aspect, the corn plants of a corn field provided herein comprise an average height of less than or equal to 1.9 meters at R3 stage or later where the height is measured as the distance between the soil and the uppermost leaf surface of the leaf farthest from the soil. In an aspect, the corn plants of a corn field provided herein comprise an average height of less than or equal to 1.8 meters at R3 stage or later where the height is measured as the distance between the soil and the uppermost leaf surface of the leaf farthest from the soil. In an aspect, the corn plants of a corn field provided herein comprise an average height of less than or equal to 1.7 meters at R3 stage or later where the height is measured as the distance between the soil and the uppermost leaf surface of the leaf farthest from the soil. In an aspect, the corn plants of a corn field provided herein comprise an average height of less than or equal to 1.6 meters at R3 stage or later where the height is measured as the distance between the soil and the uppermost leaf surface of the leaf farthest from the soil.

In an aspect, the corn plants of a corn field provided herein comprise an average height of less than or equal to 1.5 meters at R3 stage or later where the height is measured as the distance between the soil and the uppermost leaf surface of the leaf farthest from the soil.

In an aspect, the corn plants of a corn field provided herein comprise an average height of less than or equal to 2.1 meters at R3 stage or later where the height is measured as the distance between the soil and the ligule of the uppermost fully-expanded leaf. In an aspect, the corn plants of a corn field provided herein comprise an average height of less than or equal to 2.0 meters at R3 stage or later where the height is measured as the distance between the soil and the ligule of the uppermost fully-expanded leaf. In an aspect, the corn plants of a corn field provided herein comprise an average height of less than or equal to 1.9 meters at R3 stage or later where the height is measured as the distance between the soil and the ligule of the uppermost fully-expanded leaf. In an aspect, the corn plants of a corn field provided herein comprise an average height of less than or equal to 1.8 meters at R3 stage or later where the height is measured as the distance between the soil and the ligule of the uppermost fully-expanded leaf. In an aspect, the corn plants of a corn field provided herein comprise an average height of less than or equal to 1.7 meters at R3 stage or later where the height is measured as the distance between the soil and the ligule of the uppermost fully-expanded leaf. In an aspect, the corn plants of a corn field provided herein comprise an average height of less than or equal to 1.6 meters at R3 stage or later where the height is measured as the distance between the soil and the ligule of the uppermost fully-expanded leaf. In an aspect, the corn plants of a corn field provided herein comprise an average height of less than or equal to 1.5 meters at R3 stage or later where the height is measured as the distance between the soil and the ligule of the uppermost fully-expanded leaf. In an aspect, the corn plants of a corn field provided herein comprise an average height of less than or equal to 1.4 meters at R3 stage or later where the height is measured as the distance between the soil and the ligule of the uppermost fully-expanded leaf. In an aspect, the corn plants of a corn field provided herein comprise an average height of less than or equal to 1.3 meters at R3 stage or later where the height is measured as the distance between the soil and the ligule of the uppermost fully-expanded leaf. In an aspect, the corn plants of a corn field provided herein comprise an average height of less than or equal to 1.2 meters at R3 stage or later where the height is measured as the distance between the soil and the ligule of the uppermost fully-expanded leaf.

In an aspect, the corn plants of a corn field provided herein comprise an average height of less than or equal to 2.5 meters at R4 stage or later. In an aspect, the corn plants of a corn field provided herein comprise an average height of less than or equal to 2.4 meters at R4 stage or later. In an aspect, the corn plants of a corn field provided herein comprise an average height of less than or equal to 2.3 meters at R4 stage or later. In an aspect, the corn plants of a corn field provided herein comprise an average height of less than or equal to 2.2 meters at R4 stage or later. In an aspect, the corn plants of a corn field provided herein comprise an average height of less than or equal to 2.1 meters at R4 stage or later. In an aspect, the corn plants of a corn field provided herein comprise an average height of less than or equal to 2.0 meters at R4 stage or later. In an aspect, the corn plants of a corn field provided herein comprise an average height of less than or equal to 1.9 meters at R4 stage or later. In an aspect, the corn plants of a corn field provided herein comprise an average height of less than or equal to 1.8 meters at R4 stage or later. In an aspect, the corn plants of a corn field provided herein comprise an average height of less than or equal to 1.7 meters at R4 stage or later. In an aspect, the corn plants of a corn field provided herein comprise an average height of less than or equal to 1.6 meters at R4 stage or later. In an aspect, the corn plants of a corn field provided herein comprise an average height of less than or equal to 1.5 meters at R4 stage or later. In an aspect, the corn plants of a corn field provided herein comprise an average height of less than or equal to 1.4 meters at R4 stage or later. In an aspect, the corn plants of a corn field provided herein comprise an average height of less than or equal to 1.3 meters at R4 stage or later. In an aspect, the corn plants of a corn field provided herein comprise an average height of less than or equal to 1.2 meters at R4 stage or later.

In an aspect, the corn plants of a corn field provided herein comprise an average height of less than or equal to 2.5 meters at R4 stage or later where the height is measured as the distance between the soil and the uppermost leaf surface of the leaf farthest from the soil. In an aspect, the corn plants of a corn field provided herein comprise an average height of less than or equal to 2.4 meters at R4 stage or later where the height is measured as the distance between the soil and the uppermost leaf surface of the leaf farthest from the soil. In an aspect, the corn plants of a corn field provided herein comprise an average height of less than or equal to 2.3 meters at R4 stage or later where the height is measured as the distance between the soil and the uppermost leaf surface of the leaf farthest from the soil. In an aspect, the corn plants of a corn field provided herein comprise an average height of less than or equal to 2.2 meters at R4 stage or later where the height is measured as the distance between the soil and the uppermost leaf surface of the leaf farthest from the soil. In an aspect, the corn plants of a corn field provided herein comprise an average height of less than or equal to 2.1 meters at R4 stage or later where the height is measured as the distance between the soil and the uppermost leaf surface of the leaf farthest from the soil. In an aspect, the corn plants of a corn field provided herein comprise an average height of less than or equal to 2.0 meters at R4 stage or later where the height is measured as the distance between the soil and the uppermost leaf surface of the leaf farthest from the soil. In an aspect, the corn plants of a corn field provided herein comprise an average height of less than or equal to 1.9 meters at R4 stage or later where the height is measured as the distance between the soil and the uppermost leaf surface of the leaf farthest from the soil. In an aspect, the corn plants of a corn field provided herein comprise an average height of less than or equal to 1.8 meters at R4 stage or later where the height is measured as the distance between the soil and the uppermost leaf surface of the leaf farthest from the soil. In an aspect, the corn plants of a corn field provided herein comprise an average height of less than or equal to 1.7 meters at R4 stage or later where the height is measured as the distance between the soil and the uppermost leaf surface of the leaf farthest from the soil. In an aspect, the corn plants of a corn field provided herein comprise an average height of less than or equal to 1.6 meters at R4 stage or later where the height is measured as the distance between the soil and the uppermost leaf surface of the leaf farthest from the soil. In an aspect, the corn plants of a corn field provided herein comprise an average height of less than or equal to 1.5 meters at R4 stage or later where the height is measured as the distance between the soil and the uppermost leaf surface of the leaf farthest from the soil.

In an aspect, the corn plants of a corn field provided herein comprise an average height of less than or equal to 2.1 meters at R4 stage or later where the height is measured as the distance between the soil and the ligule of the uppermost fully-expanded leaf. In an aspect, the corn plants of a corn field provided herein comprise an average height of less than or equal to 2.0 meters at R4 stage or later where the height is measured as the distance between the soil and the ligule of the uppermost fully-expanded leaf. In an aspect, the corn plants of a corn field provided herein comprise an average height of less than or equal to 1.9 meters at R4 stage or later where the height is measured as the distance between the soil and the ligule of the uppermost fully-expanded leaf. In an aspect, the corn plants of a corn field provided herein comprise an average height of less than or equal to 1.8 meters at R4 stage or later where the height is measured as the distance between the soil and the ligule of the uppermost fully-expanded leaf. In an aspect, the corn plants of a corn field provided herein comprise an average height of less than or equal to 1.7 meters at R4 stage or later where the height is measured as the distance between the soil and the ligule of the uppermost fully-expanded leaf. In an aspect, the corn plants of a corn field provided herein comprise an average height of less than or equal to 1.6 meters at R4 stage or later where the height is measured as the distance between the soil and the ligule of the uppermost fully-expanded leaf. In an aspect, the corn plants of a corn field provided herein comprise an average height of less than or equal to 1.5 meters at R4 stage or later where the height is measured as the distance between the soil and the ligule of the uppermost fully-expanded leaf. In an aspect, the corn plants of a corn field provided herein comprise an average height of less than or equal to 1.4 meters at R4 stage or later where the height is measured as the distance between the soil and the ligule of the uppermost fully-expanded leaf. In an aspect, the corn plants of a corn field provided herein comprise an average height of less than or equal to 1.3 meters at R4 stage or later where the height is measured as the distance between the soil and the ligule of the uppermost fully-expanded leaf. In an aspect, the corn plants of a corn field provided herein comprise an average height of less than or equal to 1.2 meters at R4 stage or later where the height is measured as the distance between the soil and the ligule of the uppermost fully-expanded leaf.

In an aspect, the corn plants of a corn field provided herein comprise an average height of less than or equal to 2.5 meters at R5 stage or later. In an aspect, the corn plants of a corn field provided herein comprise an average height of less than or equal to 2.4 meters at R5 stage or later. In an aspect, the corn plants of a corn field provided herein comprise an average height of less than or equal to 2.3 meters at R5 stage or later. In an aspect, the corn plants of a corn field provided herein comprise an average height of less than or equal to 2.2 meters at R5 stage or later. In an aspect, the corn plants of a corn field provided herein comprise an average height of less than or equal to 2.1 meters at R5 stage or later. In an aspect, the corn plants of a corn field provided herein comprise an average height of less than or equal to 2.0 meters at R5 stage or later. In an aspect, the corn plants of a corn field provided herein comprise an average height of less than or equal to 1.9 meters at R5 stage or later. In an aspect, the corn plants of a corn field provided herein comprise an average height of less than or equal to 1.8 meters at R5 stage or later. In an aspect, the corn plants of a corn field provided herein comprise an average height of less than or equal to 1.7 meters at R5 stage or later. In an aspect, the corn plants of a corn field provided herein comprise an average height of less than or equal to 1.6 meters at R5 stage or later. In an aspect, the corn plants of a corn field provided herein comprise an average height of less than or equal to 1.5 meters at R5 stage or later. In an aspect, the corn plants of a corn field provided herein comprise an average height of less than or equal to 1.4 meters at R5 stage or later. In an aspect, the corn plants of a corn field provided herein comprise an average height of less than or equal to 1.3 meters at R5 stage or later. In an aspect, the corn plants of a corn field provided herein comprise an average height of less than or equal to 1.2 meters at R5 stage or later.

In an aspect, the corn plants of a corn field provided herein comprise an average height of less than or equal to 2.5 meters at R5 stage or later where the height is measured as the distance between the soil and the uppermost leaf surface of the leaf farthest from the soil. In an aspect, the corn plants of a corn field provided herein comprise an average height of less than or equal to 2.4 meters at R5 stage or later where the height is measured as the distance between the soil and the uppermost leaf surface of the leaf farthest from the soil. In an aspect, the corn plants of a corn field provided herein comprise an average height of less than or equal to 2.3 meters at R5 stage or later where the height is measured as the distance between the soil and the uppermost leaf surface of the leaf farthest from the soil. In an aspect, the corn plants of a corn field provided herein comprise an average height of less than or equal to 2.2 meters at R5 stage or later where the height is measured as the distance between the soil and the uppermost leaf surface of the leaf farthest from the soil. In an aspect, the corn plants of a corn field provided herein comprise an average height of less than or equal to 2.1 meters at R5 stage or later where the height is measured as the distance between the soil and the uppermost leaf surface of the leaf farthest from the soil. In an aspect, the corn plants of a corn field provided herein comprise an average height of less than or equal to 2.0 meters at R5 stage or later where the height is measured as the distance between the soil and the uppermost leaf surface of the leaf farthest from the soil. In an aspect, the corn plants of a corn field provided herein comprise an average height of less than or equal to 1.9 meters at R5 stage or later where the height is measured as the distance between the soil and the uppermost leaf surface of the leaf farthest from the soil. In an aspect, the corn plants of a corn field provided herein comprise an average height of less than or equal to 1.8 meters at R5 stage or later where the height is measured as the distance between the soil and the uppermost leaf surface of the leaf farthest from the soil. In an aspect, the corn plants of a corn field provided herein comprise an average height of less than or equal to 1.7 meters at R5 stage or later where the height is measured as the distance between the soil and the uppermost leaf surface of the leaf farthest from the soil. In an aspect, the corn plants of a corn field provided herein comprise an average height of less than or equal to 1.6 meters at R5 stage or later where the height is measured as the distance between the soil and the uppermost leaf surface of the leaf farthest from the soil. In an aspect, the corn plants of a corn field provided herein comprise an average height of less than or equal to 1.5 meters at R5 stage or later where the height is measured as the distance between the soil and the uppermost leaf surface of the leaf farthest from the soil.

In an aspect, the corn plants of a corn field provided herein comprise an average height of less than or equal to 2.1 meters at R5 stage or later where the height is measured as the distance between the soil and the ligule of the uppermost fully-expanded leaf. In an aspect, the corn plants of a corn field provided herein comprise an average height of less than or equal to 2.0 meters at R5 stage or later where the height is measured as the distance between the soil and the ligule of the uppermost fully-expanded leaf. In an aspect, the corn plants of a corn field provided herein comprise an average height of less than or equal to 1.9 meters at R5 stage or later where the height is measured as the distance between the soil and the ligule of the uppermost fully-expanded leaf. In an aspect, the corn plants of a corn field provided herein comprise an average height of less than or equal to 1.8 meters at R5 stage or later where the height is measured as the distance between the soil and the ligule of the uppermost fully-expanded leaf. In an aspect, the corn plants of a corn field provided herein comprise an average height of less than or equal to 1.7 meters at R5 stage or later where the height is measured as the distance between the soil and the ligule of the uppermost fully-expanded leaf. In an aspect, the corn plants of a corn field provided herein comprise an average height of less than or equal to 1.6 meters at R5 stage or later where the height is measured as the distance between the soil and the ligule of the uppermost fully-expanded leaf. In an aspect, the corn plants of a corn field provided herein comprise an average height of less than or equal to 1.5 meters at R5 stage or later where the height is measured as the distance between the soil and the ligule of the uppermost fully-expanded leaf. In an aspect, the corn plants of a corn field provided herein comprise an average height of less than or equal to 1.4 meters at R5 stage or later where the height is measured as the distance between the soil and the ligule of the uppermost fully-expanded leaf. In an aspect, the corn plants of a corn field provided herein comprise an average height of less than or equal to 1.3 meters at R5 stage or later where the height is measured as the distance between the soil and the ligule of the uppermost fully-expanded leaf. In an aspect, the corn plants of a corn field provided herein comprise an average height of less than or equal to 1.2 meters at R5 stage or later where the height is measured as the distance between the soil and the ligule of the uppermost fully-expanded leaf.

In an aspect, the corn plants of a corn field provided herein comprise an average height of less than or equal to 2.5 meters at R6 stage or later. In an aspect, the corn plants of a corn field provided herein comprise an average height of less than or equal to 2.4 meters at R6 stage or later. In an aspect, the corn plants of a corn field provided herein comprise an average height of less than or equal to 2.3 meters at R6 stage or later. In an aspect, the corn plants of a corn field provided herein comprise an average height of less than or equal to 2.2 meters at R6 stage or later. In an aspect, the corn plants of a corn field provided herein comprise an average height of less than or equal to 2.1 meters at R6 stage or later. In an aspect, the corn plants of a corn field provided herein comprise an average height of less than or equal to 2.0 meters at R6 stage or later. In an aspect, the corn plants of a corn field provided herein comprise an average height of less than or equal to 1.9 meters at R6 stage or later. In an aspect, the corn plants of a corn field provided herein comprise an average height of less than or equal to 1.8 meters at R6 stage or later. In an aspect, the corn plants of a corn field provided herein comprise an average height of less than or equal to 1.7 meters at R6 stage or later. In an aspect, the corn plants of a corn field provided herein comprise an average height of less than or equal to 1.6 meters at R6 stage or later. In an aspect, the corn plants of a corn field provided herein comprise an average height of less than or equal to 1.5 meters at R6 stage or later. In an aspect, the corn plants of a corn field provided herein comprise an average height of less than or equal to 1.4 meters at R6 stage or later. In an aspect, the corn plants of a corn field provided herein comprise an average height of less than or equal to 1.3 meters at R6 stage or later. In an aspect, the corn plants of a corn field provided herein comprise an average height of less than or equal to 1.2 meters at R6 stage or later.

In an aspect, the corn plants of a corn field provided herein comprise an average height of less than or equal to 2.5 meters at R6 stage or later where the height is measured as the distance between the soil and the uppermost leaf surface of the leaf farthest from the soil. In an aspect, the corn plants of a corn field provided herein comprise an average height of less than or equal to 2.4 meters at R6 stage or later where the height is measured as the distance between the soil and the uppermost leaf surface of the leaf farthest from the soil. In an aspect, the corn plants of a corn field provided herein comprise an average height of less than or equal to 2.3 meters at R6 stage or later where the height is measured as the distance between the soil and the uppermost leaf surface of the leaf farthest from the soil. In an aspect, the corn plants of a corn field provided herein comprise an average height of less than or equal to 2.2 meters at R6 stage or later where the height is measured as the distance between the soil and the uppermost leaf surface of the leaf farthest from the soil. In an aspect, the corn plants of a corn field provided herein comprise an average height of less than or equal to 2.1 meters at R6 stage or later where the height is measured as the distance between the soil and the uppermost leaf surface of the leaf farthest from the soil. In an aspect, the corn plants of a corn field provided herein comprise an average height of less than or equal to 2.0 meters at R6 stage or later where the height is measured as the distance between the soil and the uppermost leaf surface of the leaf farthest from the soil. In an aspect, the corn plants of a corn field provided herein comprise an average height of less than or equal to 1.9 meters at R6 stage or later where the height is measured as the distance between the soil and the uppermost leaf surface of the leaf farthest from the soil. In an aspect, the corn plants of a corn field provided herein comprise an average height of less than or equal to 1.8 meters at R6 stage or later where the height is measured as the distance between the soil and the uppermost leaf surface of the leaf farthest from the soil. In an aspect, the corn plants of a corn field provided herein comprise an average height of less than or equal to 1.7 meters at R6 stage or later where the height is measured as the distance between the soil and the uppermost leaf surface of the leaf farthest from the soil. In an aspect, the corn plants of a corn field provided herein comprise an average height of less than or equal to 1.6 meters at R6 stage or later where the height is measured as the distance between the soil and the uppermost leaf surface of the leaf farthest from the soil. In an aspect, the corn plants of a corn field provided herein comprise an average height of less than or equal to 1.5 meters at R6 stage or later where the height is measured as the distance between the soil and the uppermost leaf surface of the leaf farthest from the soil.

In an aspect, the corn plants of a corn field provided herein comprise an average height of less than or equal to 2.1 meters at R6 stage or later where the height is measured as the distance between the soil and the ligule of the uppermost fully-expanded leaf. In an aspect, the corn plants of a corn field provided herein comprise an average height of less than or equal to 2.0 meters at R6 stage or later where the height is measured as the distance between the soil and the ligule of the uppermost fully-expanded leaf. In an aspect, the corn plants of a corn field provided herein comprise an average height of less than or equal to 1.9 meters at R6 stage or later where the height is measured as the distance between the soil and the ligule of the uppermost fully-expanded leaf. In an aspect, the corn plants of a corn field provided herein comprise an average height of less than or equal to 1.8 meters at R6 stage or later where the height is measured as the distance between the soil and the ligule of the uppermost fully-expanded leaf. In an aspect, the corn plants of a corn field provided herein comprise an average height of less than or equal to 1.7 meters at R6 stage or later where the height is measured as the distance between the soil and the ligule of the uppermost fully-expanded leaf. In an aspect, the corn plants of a corn field provided herein comprise an average height of less than or equal to 1.6 meters at R6 stage or later where the height is measured as the distance between the soil and the ligule of the uppermost fully-expanded leaf. In an aspect, the corn plants of a corn field provided herein comprise an average height of less than or equal to 1.5 meters at R6 stage or later where the height is measured as the distance between the soil and the ligule of the uppermost fully-expanded leaf. In an aspect, the corn plants of a corn field provided herein comprise an average height of less than or equal to 1.4 meters at R6 stage or later where the height is measured as the distance between the soil and the ligule of the uppermost fully-expanded leaf. In an aspect, the corn plants of a corn field provided herein comprise an average height of less than or equal to 1.3 meters at R6 stage or later where the height is measured as the distance between the soil and the ligule of the uppermost fully-expanded leaf. In an aspect, the corn plants of a corn field provided herein comprise an average height of less than or equal to 1.2 meters at R6 stage or later where the height is measured as the distance between the soil and the ligule of the uppermost fully-expanded leaf.

As used herein, "detasseled" corn refers to corn where the pollen-producing flowers, or tassel, has been removed. Detasseling is typically performed before the tassel can shed pollen. Detasseling can be accomplished via machine detasseling, manual detasseling, or a combination of both machine and manual detasseling. Detasseling often removes the uppermost leaves of the corn plant along with the developing tassel. Detasseled corn plants retain their female flowers, which eventually produce kernels on the ear.

In an aspect, at least 50% of the corn plants in a corn field provided herein have been detasseled. In another aspect, at least 60% of the corn plants in a corn field provided herein have been detasseled. In another aspect, at least 70% of the corn plants in a corn field provided herein have been detasseled. In another aspect, at least 80% of the corn plants in a corn field provided herein have been detasseled. In another aspect, at least 90% of the corn plants in a corn field provided herein have been detasseled. In another aspect, 100% of the corn plants in a corn field provided herein have been detasseled.

In another aspect, an agricultural composition is applied to a corn field where at least 50% of the corn plants have been detasseled. In another aspect, an agricultural composition is applied to a corn field where at least 60% of the corn plants have been detasseled. In another aspect, an agricultural composition is applied to a corn field where at least 70% of the corn plants have been detasseled. In another aspect, an agricultural composition is applied to a corn field where at least 80% of the corn plants have been detasseled. In another aspect, an agricultural composition is applied to a corn field where at least 90% of the corn plants have been detasseled. In another aspect, an agricultural composition is applied to a corn field where 100% of the corn plants have been detasseled.

In another aspect, a fertilizer is applied to a corn field where at least 50% of the corn plants have been detasseled. In another aspect, a fertilizer is applied to a corn field where at least 60% of the corn plants have been detasseled. In another aspect, a fertilizer is applied to a corn field where at least 70% of the corn plants have been detasseled. In another aspect, a fertilizer is applied to a corn field where at least 80% of the corn plants have been detasseled. In another aspect, a fertilizer is applied to a corn field where at least 90% of the corn plants have been detasseled. In another aspect, a fertilizer is applied to a corn field where 100% of the corn plants have been detasseled.

In another aspect, a pesticide is applied to a corn field where at least 50% of the corn plants have been detasseled. In another aspect, a pesticide is applied to a corn field where at least 60% of the corn plants have been detasseled. In another aspect, a pesticide is applied to a corn field where at least 70% of the corn plants have been detasseled. In another aspect, a pesticide is applied to a corn field where at least 80% of the corn plants have been detasseled. In another aspect, a pesticide is applied to a corn field where at least 90% of the corn plants have been detasseled. In another aspect, a pesticide is applied to a corn field where 100% of the corn plants have been detasseled.

In another aspect, a cover crop seed is applied to a corn field where at least 50% of the corn plants have been detasseled. In another aspect, a cover crop seed is applied to a corn field where at least 60% of the corn plants have been detasseled. In another aspect, a cover crop seed is applied to a corn field where at least 70% of the corn plants have been detasseled. In another aspect, a cover crop seed is applied to a corn field where at least 80% of the corn plants have been detasseled. In another aspect, a cover crop seed is applied to a corn field where at least 90% of the corn plants have been detasseled. In another aspect, a cover crop seed is applied to a corn field where 100% of the corn plants have been detasseled.

Female corn plants are often detasseled when a grower desires to produce hybrid corn seed. In an aspect, a corn plant provided herein is an inbred corn plant. As used herein, the term "inbred" means a line that has been bred for genetic homogeneity. In another aspect, a corn plant provided herein is a hybrid corn plant. As used herein, the term "hybrid" means a progeny of mating between at least two genetically dissimilar parents or inbreds. Without limitation, examples of mating schemes include single crosses, modified single cross, double modified single cross, three-way cross, modified three-way cross, and double cross wherein at least one parent in a modified cross is the progeny of a cross between sister lines.

As an alternative to detasseling, female corn plants can be treated with a chemical hybridizing agent or glyphosate (e.g., Roundup®) to cause male sterility as understood in the art. However, the shorter heights of female corn plants in a production field as provided herein are more accessible for the over-the-top treatment of the chemical hybridizing agent or glyphosate (or Roundup®) with standard farming equipment without damaging the female corn plants. In an aspect, methods are provided for planting and treating shorter female corn plants in a seed production field as described herein with a chemical hybridizing agent or glyphosate (or Roundup®) to induce male sterility, wherein the chemical hybridizing agent or glyphosate (or Roundup®) can be applied with standard farm equipment without damaging the plants. Thus, according to some embodiments, an agricultural composition as provided herein may be a chemical hybridizing agent, herbicide or glyphosate (e.g., Roundup®) to induce male sterility.

One system that can be employed to induce male sterility in female corn plants is the Roundup® hybridization system (RHS), wherein the male reproductive tissues or tassels are unable to produce pollen following treatment with glyphosate during an appropriate window of plant development. In one RHS system, corn plants (or female corn plants) in a seed production field have a Roundup® or glyphosate resistant 5-enolpyruvylshikimate-3-phosphate synthase (EPSPS) transgene, but due to the combination expression elements, the expression of the transgene in male reproductive tissues is low. As a result, when these corn plants (or female corn plants) are treated with glyphosate, their male reproductive structures or tassels do not develop to produce pollen. In a second generation RHS system (RHS2), the corn plants (or female corn plants) in a seed production field have a Roundup® or glyphosate resistant 5-enolpyruvylshikimate-3-phosphate synthase (EPSPS) transgene that further contains in its 3' untranslated region (UTR) a target site for an endogenous small interfering RNA (siRNA) expressed specifically in male tissues. Thus, expression of the transgene is suppressed in the male reproductive tissues to render those tissues susceptible to Roundup® or glyphosate treatment. Accordingly, corn plants (or female corn plants) containing this transgene can be made male sterile and unable to produce pollen by Roundup® or glyphosate treatment. According to some embodiments, corn plants (or female corn plants) comprise a RHS event, such as MON 87427 (see, e.g., U.S. Application Pub. No. 2011/0126310, the entire contents and disclosure of which is incorporated herein by reference) or MON 87429 (see, e.g., U.S. Provisional App. No. 62/625,537, the entire contents and disclosure of which is incorporated herein by reference). In addition to the RHS system, other chemical hybridizing agents (CHAs) known in the art could be used to make corn plants male sterile. As an additional alternative, shorter female corn plants in a seed production field have cytoplasmic male sterility without application of a chemical hybridizing agent or glyphosate (e.g., Roundup®).

As used herein, the term "cytoplasmic male sterility" or "CMS" refers to a condition where a corn plant is partially or fully incapable of producing functional pollen. As known in the art, cytoplasmic male sterility is a maternally inherited trait that is commonly associated with unusual open reading frames within the mitochondrial genome which cause cytoplasmic dysfunction. In an aspect, a corn plant or female corn plant provided herein is a cytoplasmic male sterile corn plant.

According to another set of embodiments, methods are provided for applying, spraying, distributing, casting, dropping, etc., pollen to one or more corn plants or "female" corn plants (e.g., a plurality of female corn plants) in a seed production field, wherein such (female) corn plants may be arranged in rows. Such application of pollen can be used to pollinate the female reproductive structures or ears of the (female) corn plants. Such methods for application of pollen may be used to augment or improve seed production and/or to reduce or eliminate the presence or number of "male" corn plants (or male corn plant rows) in the same production field. Due to the shorter plant height at later vegetative and reproductive stages of development, such application of pollen can be applied over-the-top by a ground-based agricultural vehicle to pollinate the female plants without the ground-based vehicle significantly or severely damaging the plants. Thus, according to some embodiments, an agricultural composition comprises pollen. According to another embodiment, a ground-based agricultural vehicle may be a pollinating device or vehicle that promotes or enhances the efficient release, distribution or spreading of pollen from male plants to female plants. Due to the shorter plant height at later vegetative and reproductive stages of development, such a ground-based pollination device or vehicle could be used without significantly or severely damaging the plants. See, e.g., PCT Application Publication No. WO 2018/129302, the entire contents and disclosure of which are incorporated herein by reference.

As used herein, "cultivar" and "variety" are used synonymously and mean a group of plants within a species (e.g., Z. mays L.) that share certain genetic traits that separate them from other possible varieties within that species. Corn cultivars can be inbreds or hybrids, though commercial corn cultivars are mostly hybrids to take advantage of hybrid vigor. Individuals within a corn hybrid cultivar are homogeneous, nearly genetically identical, with most loci in the heterozygous state.

A corn field is considered to be "harvested" when at least one ear has been removed from most, all, or a majority of the corn plants in the field. As such, an "unharvested" corn plant has not had any ears purposely removed. In an aspect, a corn field provided herein is an unharvested corn field. In an aspect, at least 50% of the corn plants in a corn field provided herein are unharvested. In an aspect, at least 60% of the corn plants in a corn field provided herein are unharvested. In an aspect, at least 70% of the corn plants in a corn field provided herein are unharvested. In an aspect, at least 80% of the corn plants in a corn field provided herein are unharvested. In an aspect, at least 90% of the corn plants in a corn field provided herein are unharvested. In an aspect, 100% of the corn plants in a corn field provided herein are unharvested.

Corn plant height varies depending on the line or variety grown, whether the plant is a hybrid or inbred, and environmental conditions. Although corn plants can reach a height of over 3.6 meters by maturity, a height of around 2.0-2.5 meters by maturity is more common. If corn plants can be made shorter, such as with a dwarf or semi-dwarf plant height and architecture, while preserving the agricultural benefits and uses of the crop plant, then improved methods would become available for accessing those corn plants with standard farm equipment at later stages of development without causing crop damage that would otherwise occur with standard corn plant heights at those stages.

Methods are thus provided herein for accessing shorter, dwarf or semi-dwarf corn plants and varieties at various stages of development (e.g., less than or equal to 2.0 meters, etc., at maturity) with standard farm equipment, possibly up to and including the time of harvest. Dwarf and semi-dwarf corn plants and varieties may also allow or permit an extended window for access with standard farm equipment at earlier stages of development (e.g., less than or equal to 1.6 meters, etc.). The reduction in the maximum plant height at maturity can be achieved in different ways. Shorter corn plant heights can also extend the time window until the crop plant reaches a given height, to enable and optimize in-season application of water, fertilizer, and control of pests and diseases at later stages, by farm equipment of limited height clearance. The ability to apply water, fungicide, herbicide, insecticide, pesticide, and/or fertilizer at later developmental stage(s) (e.g., during late vegetative and/or reproductive stage(s) of development) can have a significant impact on yield of the crop plant. Such applications can improve plant growth, leaf characteristics and the amount of nutrients available for the corn plant to devote or contribute to the developing ear.

In an aspect, a corn plant provided herein is a dwarf corn plant. As used herein, a "dwarf" plant refers to an atypically small plant. Generally, such a "dwarf plant" has a stature or height that is reduced from that of a control wild-type plant (e.g., a sibling plant comprising all other traits except the dwarf trait) by about 30%, 35%, 40%, 45%, 50%, 55%, 60% or greater.

In an aspect, a corn field provided herein comprises at least 50% dwarf corn plants. In an aspect, a corn field provided herein comprises at least 60% dwarf corn plants. a corn field provided herein comprises at least 70% dwarf corn plants. a corn field provided herein comprises at least 80% dwarf corn plants. a corn field provided herein comprises at least 90% dwarf corn plants. a corn field provided herein comprises 100% dwarf corn plants.

In another aspect, a corn plant provided herein is a semi-dwarf corn plant. As used herein, a "semi-dwarf plant" refers to a plant having a stature or height that is reduced relative to a control wild-type plant by about 5%, 10%, 15%, 20%, 25%, 30%, 35%, 40%, 45%, or less. Such a semi-dwarf plant can be characterized by a reduced stem, stalk, or trunk length when compared to the control wild-type plant under comparable growth conditions, which can result from fewer internodes or shorter average internode length. As used herein, an "internode" refers to the region between two nodes on a corn stalk, and a "node" refers to the point on the corn stalk (e.g., stem) where leaves and/or ears originate.

In an aspect, a corn field provided herein comprises at least 50% semi-dwarf corn plants. In an aspect, a corn field provided herein comprises at least 60% semi-dwarf corn plants. In an aspect, a corn field provided herein comprises at least 70% semi-dwarf corn plants. In an aspect, a corn field provided herein comprises at least 80% semi-dwarf corn plants. In an aspect, a corn field provided herein comprises at least 90% semi-dwarf corn plants. In an aspect, a corn field provided herein comprises at least 95% semi-dwarf corn plants. In an aspect, a corn field provided herein comprises 100% semi-dwarf corn plants.

According to another aspect of the present disclosure, it is proposed that, besides offering a longer time window for field access by standard farm equipment, shorter corn plants can also exhibit less root and stalk lodging and/or increased standability at or after the normal time of harvest, which may allow for more flexibility in how long corn is left in the field after drying down and/or allow for direct harvesting of hybrid seeds in a production field. In another aspect, shorter corn plants are left in a corn field post maturity and can afford a much longer time period for harvesting seeds without significantly jeopardizing the eventual seed yield. As used herein, "standability" refers to the ability of a plant to stand upright in a position that enables it to be harvested by standard farm equipment (e.g., a combine harvester). Corn plants with better standability, such as dwarf corn plants, semi-dwarf corn plants, and brachytic corn plants, are resistant to lodging. As used herein, "lodging" can refer to either "stalk lodging" or "root lodging." Stalk lodging occurs when the corn plant stalk is severely bent or broken below the ear. Root lodging occurs when the corn plant is leaning at an angle (e.g., greater than or equal to 45° relative to perpendicular from the ground, or at an angle less than 45° relative to the ground).

There are different ways in which a corn plant can be made to have a shorter semi-dwarf plant height. According to many aspects, a corn plant can be made shorter or semi-dwarf relative to a control plant by lowering the level(s) of active GAs in one or more tissue(s) of the plant, such as by suppressing, mutating or editing a GA oxidase gene in the corn plant. In an aspect, a corn plant or plurality of corn plants provided herein can each comprise a recombinant DNA construct or polynucleotide sequence, where the recombinant DNA construct or polynucleotide sequence comprises a transcribable DNA sequence encoding a non-coding RNA molecule that targets at least one endogenous GA20 or GA3 oxidase gene for suppression. In another aspect, a corn plant provided herein can comprise suppressed GA3 oxidase gene expression in one or more tissues as compared to a wild-type control plant. In another aspect, a corn plant provided herein can comprise suppressed GA20 oxidase gene expression in one or more tissues as compared to a wild-type control plant. In another aspect, a corn plant provided herein can comprise a mutation at or near an endogenous GA oxidase gene, where the expression level of the endogenous GA oxidase gene is reduced or eliminated in the corn plant, and where the corn plant has a shorter plant height as compared to a wild-type control plant. In an aspect, a corn plant provided herein comprises a recombinant polynucleotide capable of suppressing expression of one or more GA20 oxidase and/or GA3 oxidase gene(s) and/or mRNA(s) transcribed therefrom. Alternatively, a corn plant provided herein comprises one or more mutation(s) or edit(s) in one or more GA20 oxidase and/or GA3 oxidase gene(s). In an aspect, a female corn plant provided herein can comprise a mutation or edit in a GA20 oxidase locus or gene as compared to a wildtype GA20 oxidase locus or gene. In an aspect, a corn plant provided herein is homozygous (or biallelic) for one or more mutations and/or edits in one or more GA20 oxidase loci or genes as compared to a wildtype GA20 oxidase locus or gene. In another aspect, a corn plant provided herein is heterozygous for a mutation or edit in one or more GA20 oxidase loci or genes as compared to a wildtype GA20 oxidase locus or gene. In another aspect, a corn plant provided herein can comprise a mutation or edit in a GA3 oxidase locus or gene as compared to a wildtype GA3 oxidase locus or gene. In an aspect, a corn plant provided herein is homozygous (or biallelic) for one or more mutations and/or edits in one or more GA3 oxidase loci or genes as compared to a wildtype GA3 oxidase locus or gene. In another aspect, a corn plant provided herein is heterozygous for a mutation or edit in a one or more GA3 oxidase loci or genes as compared to a wildtype GA3 oxidase locus or gene. In another aspect, a corn plant provided herein can comprise a heterologous polynucleotide capable of suppressing expression of a GA20 oxidase gene or an mRNA transcribed therefrom.

According to other aspects, a corn plant(s) can have a mutation or edit in an auxin, brassinosteroid, jasmonic acid, cell cycle regulation, and/or other pathway gene(s) that are shown to affect plant height. According to yet further embodiments, a corn plant(s) can be made shorter by application of one or more chemistries, such as GA inhibitors, known to affect plant height. Additional information regarding chemistries, such as GA inhibitors, can be found in WO 2017/011791 and U.S. Patent Application Publication Nos. 2019/0014730 and 2019/0014731, which are incorporated herein by reference in their entireties. According to another aspect, a corn plant or plurality of corn plants provided herein can comprise a mutation, edit or mutant allele in one or more loci or genes, or a transgene targeting such one or more loci or genes, that have been associated with a short stature phenotype in corn, such as one or more of the following native corn genes: anther ear 1 (An1), brachytic 1 (Br1), brevis plant 1 (Bv1) or brachytic 3 (br3), crinkly 4 (Cr4), compact plant 2 (Ct2), dwarf plant 1 (dl), dwarf plant 8 (d8), dwarf plant 9 (d9), nana plant 1 (Na1), nana plant 2 (Na2), non-chromosomal stripe 3 (Nsc3), narrow leaf dwarf (Nld1), reduced plant 1 (Rd1), semi-dwarf/(Sdw1), semi-dwarf 2 (Sdw2), tangled 1 (Tan1), terminal ear 1 (Tel), and vanishing tassel 2 (Vt2). In an aspect, a corn plant(s) is heterozygous for a mutation or edit in one of the foregoing native corn genes. In an aspect, a corn plant(s) is homozygous for one or more mutation(s) and/or edit(s) in one of the foregoing native corn genes.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the $20^{th}$ century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro baciliform virus (RTBV) promoter, that drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), can be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this may be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

As introduced above, instead of suppressing one or more GA oxidase gene(s), active GA levels can also be reduced in a corn plant by mutation or editing of one or more GA20 and/or GA3 oxidase gene(s).

In an aspect, a corn plant provided herein is homozygous (or biallelic) for one or more mutation(s) and/or edit(s) in a GA20 oxidase_5 locus or gene as compared to a wildtype GA20 oxidase_5 locus or gene and homozygous (or biallelic) for one or more mutation(s) and/or edit(s) in a GA20 oxidase_3 locus or gene as compared to a wildtype GA20 oxidase_3 locus or gene. In an aspect, a corn plant provided herein is homozygous (or biallelic) for one or more mutation(s) and/or edit(s) in a GA20 oxidase_5 locus or gene as compared to a wildtype GA20 oxidase_5 locus or gene and heterozygous for a mutation or edit in a GA20 oxidase_3 locus or gene as compared to a wildtype GA20 oxidase_3 locus or gene. In an aspect, a corn plant provided herein is heterozygous for a mutation or an edit in a GA20 oxidase_5 locus or gene as compared to a wildtype GA20 oxidase_5 locus or gene and homozygous (or biallelic) for one or more mutation(s) and/or edit(s) in a GA20 oxidase_3 locus or gene as compared to a wildtype GA20 oxidase_3 locus or gene. See, e.g., U.S. Provisional Patent Application Nos. 62/631,412; 62/631,416; and 62/710,302; the contents and disclosures of which are incorporated herein by reference in their entireties.

Corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase 5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5'-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

In addition to phenotypic observations with targeting the GA20 oxidase_3 and/or GA20 oxidase_5 gene(s), or the GA3 oxidase_1 and/or GA3 oxidase_2 gene(s), for suppression, a semi-dwarf phenotype is also observed with suppression of the GA20 oxidase_4 gene. The genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

In an aspect, the present disclosure provides a corn plant or plurality of corn plants each comprising a recombinant DNA construct or polynucleotide sequence comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or corn cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, and/or 33, and wherein the transcribable DNA sequence is operably linked to a plant-expressible promoter, which can be heterologous with respect to the transcribable DNA sequence and/or the corn plant.

Recombinant DNA constructs and transgenic corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "transgene" refers to a recombinant DNA molecule, construct, or sequence comprising a gene and/or transcribable DNA sequence and integrated or inserted into a plant genome.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

As used herein, a "plant-expressible promoter" refers to a promoter that drives, causes or initiates expression of a transcribable DNA sequence or transgene operably linked to such promoter in one or more plant cells or tissues, such as one or more cells or tissues of a corn plant. In an aspect, a plant-expressible promoter is a constitutive promoter. In another aspect, a plant-expressible promoter is a vascular promoter. As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters. In another aspect, a plant-expressible promoter is a leaf promoter. As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

Promoters that drive enhanced expression in certain tissues of the plant relative to other plant tissues are referred to as "tissue-enhanced" or "tissue-preferred" promoters. Thus, a "tissue-preferred" promoter causes relatively higher or preferential or predominant expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters.

A non-limiting exemplary plant-expressible promoter is the RTBV promoter. In an aspect, a plant-expressible promoter is an RTBV promoter. In another aspect, a plant expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 39, SEQ ID NO: 40, or a functional portion thereof.

Non-limiting exemplary vascular promoters include a sucrose synthase promoter, a sucrose transporter promoter, a Sh1 promoter, Commelina yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, and a rice yellow stripe 2 (OsYSL2) promoter. In an aspect, a vascular promoter is selected from the group consisting of a sucrose synthase promoter, a sucrose transporter promoter, a Sh1 promoter, Commelina yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, a rice yellow stripe 2 (OsYSL2) promoter, and functional portions thereof. In an aspect, a vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 41, SEQ ID NO: 42, SEQ ID NO: 43, SEQ ID NO: 44, SEQ ID NO: 45, or a functional portion thereof.

Non-limiting exemplary leaf promoters include a RuBisCO promoter, a PPDK promoter, a FDA promoter, a Nadh-Gogat promoter, a chlorophyll a/b binding protein gene promoter, a phosphoenolpyruvate carboxylase (PEPC) promoter, and a Myb gene promoter. In an aspect, a leaf promoter is selected from the group consisting of a RuBisCO promoter, a PPDK promoter, a FDA promoter, a Nadh-Gogat promoter, a chlorophyll a/b binding protein gene promoter, a phosphoenolpyruvate carboxylase (PEPC) promoter, a Myb gene promoter, and functional portions thereof. In an aspect, a leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 46, SEQ ID NO: 47, SEQ ID NO: 48, or a functional portion thereof.

Non-limiting exemplary constitutive promoters include an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, and a maize alcohol dehydrogenase. In an aspect, a constitutive promoter is selected from the group consisting of an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, a maize alcohol dehydrogenase, or functional portions thereof. In an aspect, a constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, or a functional portion thereof.

In another aspect, the present disclosure provides a corn plant or plurality of corn plants each comprising a recombinant DNA construct or polynucleotide sequence comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase gene having at least 80%, at least 85%, at least 90%, at least 95%, at least 96%, at least 97%, at least 98%, at least 99%, at least 99.5%, or 100% identical to SEQ ID NO: 9, 12, 15, 30, and/or 33, and wherein the transcribable DNA sequence is operably linked to a plant-expressible promoter, which can be heterologous with respect to the transcribable DNA sequence and/or the corn plant.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to some embodiments, the first expression cassette comprises a first transcribable DNA sequence encoding a non-coding RNA targeting a GA20 oxidase_3 gene for suppression. According to other embodiments, the first expression cassette comprises a first transcribable DNA sequence encoding a non-coding RNA targeting a GA20 oxidase_5 gene for suppression. According to yet further embodiments, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

For suppression of a GA20 oxidase_3 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 7, SEQ ID NO: 8, and SEQ ID NO: 34.

For suppression of a GA20 oxidase_4 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 10, SEQ ID NO: 11, and SEQ ID NO: 38.

For suppression of a GA20 oxidase_5 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 13, SEQ ID NO: 14, and SEQ ID NO: 35.

For suppression of a GA20 oxidase_3 gene and a GA20 oxidase_5 gene, a transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 7, SEQ ID NO: 8, and SEQ ID NO: 34; and the transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 13, SEQ ID NO: 14, and SEQ ID NO: 35.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

For suppression of a GA3 oxidase_1 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 28, SEQ ID NO: 29, and SEQ ID NO: 36.

For suppression of a GA3 oxidase_2 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 31, SEQ ID NO: 32, and SEQ ID NO: 37.

For suppression of a GA3 oxidase_1 gene and a GA3 oxidase_2 gene, a transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 28, SEQ ID NO: 29, and SEQ ID NO: 36; and the transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 31, SEQ ID NO: 32 and SEQ ID NO: 37.

As used herein, a "gene" refers to a polynucleotide that can produce a functional unit (without being limiting, for example, a protein or a non-coding RNA molecule). A polynucleotide sequence encoding a non-coding RNA molecule can also be described as a transcribable DNA sequence. A non-coding RNA molecule can act as a suppression element that targets one or more gene(s) in a plant cell, such as one or more endogenous GA20 or GA3 oxidase gene(s), or as a RNA molecule, such as a guide RNA, etc., that guides a sequence-specific nuclease to cut and trigger a genome editing event at a target site in the genome. Non-limiting examples of a non-coding RNA molecules include a microRNA (miRNA), a miRNA precursor (pre-miRNA), a small interfering RNA (siRNA), a small RNA (18-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA). In an aspect, a non-coding RNA provided herein is selected from the group consisting of a microRNA, a small interfering RNA, a secondary small interfering RNA, a transfer RNA, a ribosomal RNA, a trans-acting small interfering RNA, a naturally occurring antisense small interfering RNA, a heterochromatic small interfering RNA, and precursors thereof. In another aspect, a non-coding RNA provided herein is selected from the group consisting of a miRNA, a pre-miRNA, a siRNA, a hc-siRNA, a piRNA, a hairpin dsRNA, a ta-siRNA, a nat-siRNA, a crRNA, a tracrRNA, a gRNA, and a sgRNA. In another aspect, a non-coding RNA provided herein is a miRNA. In another aspect, a non-coding RNA provided herein is an siRNA.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA interference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the corn plant, thereby suppressing the endogenous GA20 oxidase and/or GA3 oxidase gene(s).

According to an aspect, a corn plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control corn plant.

According to an aspect, a corn plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control corn plant.

According to an aspect, a corn plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control corn plant.

According to an aspect, a corn plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-'75%, 30%-80%, or 10%-75%, as compared to a control corn plant.

According to an aspect, the at least one tissue of a corn plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

The use of the terms "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. In an aspect, a polynucleotide provided herein is single-stranded. In another aspect, a polynucleotide provided herein is double-stranded.

As used herein, the term "heterologous" can refer to a combination of two or more DNA molecules or sequences, such as a promoter and an associated transcribable DNA sequence, coding sequence or gene, when such a combination is man-made and not normally found in nature. For example, a transcribable DNA sequence encoding a non-coding RNA molecule that targets one or more GA oxidase gene(s) for suppression can be operably linked to a heterologous plant-expressible promoter.

The term "suppression" as used herein, refers to a lowering, reduction or elimination of the expression level of an RNA and/or protein encoded by a gene in a plant, plant cell or plant tissue at one or more stage(s) of plant development, as compared to the expression level of such RNA and/or protein in a wild-type or control plant, cell or tissue at the same stage(s) of plant development.

As introduced above, a corn plant or plurality of corn plants provided herein can each comprise a recombinant DNA construct or polynucleotide sequence, where the recombinant DNA construct or polynucleotide sequence comprises a transcribable DNA sequence encoding a non-coding RNA molecule that targets at least one endogenous GA20 or GA3 oxidase gene for suppression. In an aspect, a corn plant provided herein comprises a GA3 oxidase or GA20 oxidase gene with suppressed expression in one or more tissues as compared to a wild-type control plant. In another aspect, a corn plant provided herein comprises a mutation at or near an endogenous GA oxidase gene, where the expression level of the endogenous GA oxidase gene is reduced or eliminated in the corn plant, and where the corn plant has a shorter plant height as compared to a wild-type control plant. In an aspect, a corn plant provided herein comprises a mutation in a GA20 oxidase locus or gene as compared to a wildtype GA20 oxidase locus or gene. In an aspect, a corn plant provided herein comprises a mutation in a GA3 oxidase locus or gene as compared to a wildtype GA3 oxidase locus or gene. Additional details about altering the expression of GA20 and/or GA3 oxidase gene(s) through suppression, mutation, or editing of those gene(s) can be found in PCT Application No. PCT/US2017/047405, the entire contents and disclosure of which is incorporated herein by reference.

As used herein, a "mutation" refers to an insertion, deletion, substitution, duplication, or inversion of one or more nucleotides and/or encoded amino acids as compared to a reference nucleotide or amino acid sequence, respectively, which can be introduced by any suitable mutagenesis or gene editing technique.

Certain mutations of brachytic genes have been shown to result in a short stature, semi-dwarf phenotype. Thus, in an aspect of the present disclosure, a corn plant is provided having a non-silent mutation or edit in a brachytic gene. See, e.g., PCT Application No. PCT/US2016/029492 and PCT/US2017/067888, the entire contents and disclosures of which are incorporated by reference. Thus, a shorter corn plant may comprise a mutation (or edit) in a brachytic gene, and may be homozygous (or biallelic) for a mutation (or edit) in a brachytic gene. As used herein, a "brachytic mutant plant" refers to a plant having a short semi-dwarf height and stature relative to a control plant (e.g., a wild-type sibling plant comprising all other traits except the brachytic trait) due to a shortening of the average internode length. Such a brachytic mutant plant can have a short semi-dwarf height and stature due to a shortening of the average internode length. As used herein, a "brachytic gene", "BR gene", "Br gene" or "br gene" refers to any brachytic gene in a corn plant that when mutated or edited to reduce its expression or function can result in a shorter, semi-dwarf corn plant and phenotype. In an aspect, an inbred or hybrid corn plant, or plurality of inbred or hybrid corn plants, is/are provided herein, each having a non-silent mutation or edit in a brachytic gene. In one aspect, the brachytic gene is a br1 mutant gene. In another aspect, the brachytic gene is a br2 mutant gene. In yet another aspect, the brachytic gene is a br3 mutant gene.

In maize, brachytic mutants have a short stature due to a shortening of the internode length without a corresponding reduction in the number of internodes or the number and size of other organs, including the leaves, ear and tassel. See Kempton *J. Hered.* 11:111-115 (1920); Pilu et al., *Molecular Breeding*, 20:83-91 (2007). Three brachytic mutants have been isolated in maize to date: brachytic1 (br1), brachytic2 (br2) and brachytic3 (br3). Both br1 and br3 mutations cause a reduction in corn plant height which has been thought too severe for commercial exploitation due to potential impacts on yield. In contrast, the br2 mutant has particular agronomic potential because of shortening of the internodes of the lower stalk without an obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with Gibberellins, auxins, brassinosteroids and cytokinins, suggesting that the biosynthesis of these hormones is not modified by the br2 mutation. Multani et al. identified the genomic sequence of the Br2 gene (SEQ ID NO: 58) and deposited it under GenBank Accession No. AY366085. See Multani et al., Science, 302:81-84 (2003). Br2 was annotated to encode a putative protein similar to adenosine triphosphate (ATP)-binding cassette transporters of the multidrug resistant (MDR) class of P-glycoproteins (PGPs). Pilu et al. reported a br2-23 allele having an 8-bp deletion in the 3' end of the Br2 gene and claimed a direct relationship between this deletion and the brachytic phenotype in their br2-23 plants. See Pilu et al., *Molecular Breeding*, 20:83-91 (2007). Nevertheless, the use of brachytic mutations in corn has not been exploited commercially partly because of the severity of the available brachytic mutant alleles.

As used herein, a "brachytic allele" is an allele at a particular genomic locus that confers, or contributes to, a brachytic or semi-dwarf phenotype, such as an allele of a brachytic gene that causes a brachytic or semi-dwarf phenotype, or alternatively, is an allele that allows for the identification of plants that comprise a brachytic phenotype or plants that can give rise to progenies with a brachytic phenotype. For example, a brachytic allele of a marker can be a marker allele that segregates with a brachytic phenotype.

In some aspects, a brachytic, dwarf, or semi-dwarf corn plant comprises a reduced level of Br2 mRNA and/or protein compared to a control corn plant not having the brachytic allele. In other aspects, the corn plants or seeds comprise reduced Br2 protein activity compared to a control plant not having the brachytic allele. In some aspects, the height of a brachytic, dwarf, or semi-dwarf plant comprising a brachytic allele at maturity is reduced by at least 10%, at least 20%, at least 30%, at least 40%, at least 50%, at least 60%, or at least 70% compared to a control plant not having a brachytic allele. In another aspect, the yield of a brachytic, dwarf, or semi-dwarf corn plant comprising a brachytic allele is equal to or more than the yield of a control plant not having the brachytic allele. In an aspect, a brachytic, dwarf, or semi-dwarf corn plant comprising a brachytic allele requires about 5%, 10%, 15%, 20%, or 25% fewer heat units than a control plant not having the brachytic allele to reach anthesis. In an aspect, a brachytic, dwarf, or semi-dwarf corn plant is homozygous for a brachytic allele. In another aspect, a brachytic, dwarf, or semi-dwarf corn plant is heterozygous for a brachytic allele. In an aspect, a brachytic, dwarf, or semi-dwarf corn plant is a hybrid. In another aspect, a brachytic, dwarf, or semi-dwarf corn plant is an inbred.

In an aspect, this disclosure provides brachytic, dwarf, or semi-dwarf corn plants comprising a brachytic allele comprising one or more sequences selected from the group consisting of SEQ ID Nos: 59-85. In another aspect, a brachytic, dwarf, or semi-dwarf corn plant comprises a single gene conversion of the Br2 genomic region.

In an aspect, a brachytic, dwarf, or semi-dwarf corn plant comprises a brachytic allele at a polymorphic locus, where the polymorphic locus is associated with, or linked to, a marker selected from the group consisting of SEQ ID NOs: 86-131. In another aspect, a brachytic allele at a polymorphic locus is within 20 cM (centimorgans), within 10 cM, within 5 cM, within 1 cM, or within 0.5 cM of a marker selected from the group consisting of SEQ ID NOs: 86-131. In another aspect, a brachytic allele is at a polymorphic locus within 20 cM, within 10 cM, within 5 cM, within 1 cM, or within 0.5 cM of a marker selected from the group consisting of SEQ ID NOs: 90-117. In another aspect, a brachytic allele is at a polymorphic locus within 20 cM, within 10 cM, within 5 cM, within 1 cM, or within 0.5 cM of a marker selected from the group consisting of SEQ ID NOs: 92 and 117.

In an aspect, a corn field provided herein comprises at least 50% brachytic corn plants. In an aspect, a corn field provided herein comprises at least 60% brachytic corn plants. a corn field provided herein comprises at least 70% brachytic corn plants. a corn field provided herein comprises at least 80% brachytic corn plants. a corn field provided herein comprises at least 90% brachytic corn plants. a corn field provided herein comprises 100% brachytic corn plants.

In an aspect, a corn plant provided herein comprises at least one non-natural brachytic mutation, where the corn plant exhibits a semi-dwarf phenotype compared to a control corn plant not comprising the at least one non-natural brachytic mutation when grown under comparable conditions. In another aspect, a corn plant provided herein comprises at least one non-natural brachytic mutation. In another aspect, a corn plant provided herein comprises at least one non-natural brachytic mutant allele. In another aspect, a corn plant provided herein comprises at least one non-natural brachytic mutation and exhibits a semi-dwarf phenotype. In an aspect, a corn plant provided herein comprises at least one non-natural brachytic mutant allele and exhibits a semi-dwarf phenotype. In an aspect, a corn plant provided herein comprises a non-naturally occurring mutation in a br gene reducing the activity of the br gene, where the mutation is not introduced via transposon. In another aspect, a corn plant provided herein can comprise a mutation in a br2 locus or gene as compared to a wildtype br2 locus or gene. In an aspect, a corn plant provided herein is homozygous for a mutation in a br2 locus or gene as compared to a wildtype br2 locus or gene. In another aspect, a corn plant provided herein is heterozygous for a mutation in a br2 locus or gene as compared to a wildtype br2 locus or gene. In another aspect, a corn plant provided herein comprises a modified br2 gene with reduced activity, where the corn plant does not comprise a br2-23 brachytic allele or SNP5259. In another aspect, a corn plant provided herein comprises a synthetic mutation in a br gene reducing the activity of the br gene. As used herein, the term "synthetic mutation" refers to non-spontaneous mutation and occurs as a result of exposure to mutagens.

In another aspect, a corn plant provided herein comprises a non-transgene or non-transposon mediated mutation in a br gene reducing the activity of the br gene. In a further aspect, a corn plant provided herein comprises a recessive, non-transgenic br mutant allele. In another aspect, a corn plant provided herein comprises a heterologous polynucleotide capable of suppressing expression of a br gene or an mRNA transcribed therefrom. In another aspect, a corn plant provided herein comprises a heterologous polynucleotide capable of suppressing expression of a br1 gene or an mRNA transcribed therefrom. In another aspect, a corn plant provided herein comprises a heterologous polynucleotide capable of suppressing expression of a br2 gene or an mRNA transcribed therefrom. In another aspect, a corn plant provided herein comprises a heterologous polynucleotide capable of suppressing expression of a br3 gene or an mRNA transcribed therefrom. Additional details about corn plants and altering the expression of BR genes can be found in PCT Application No. PCT/US2016/029492 and PCT/US2017/067888, which is incorporated by reference herein in its entirety.

Corn fields are often sprayed with a variety of compositions (e.g., fertilizer, pesticide, etc.) before, during, and after the growing season to provide essential nutrients and to combat pathogens and pests. Machinery, such as ground-based agricultural vehicles, are often used to apply these compositions to corn fields. As used herein, a "ground-based agricultural vehicle" refers to any vehicle or equipment capable of being driven, propelled, or pulled through a corn field while contacting the ground in some manner (e.g., wheels, tires, sleds, tracks, discs, etc.). In an aspect, a ground-based agricultural vehicle comprises at least one applicator. As used herein, an "applicator" refers to a piece of equipment or machinery that can provide or apply a liquid, gas, or solid composition (e.g., an agricultural composition) to a plant(s) or a field of plants, or to the soil or ground associated with such plants or field of plants. In an aspect, an applicator comprises an applicator arm or boom or other horizontal equipment, framework or support structure. In an aspect, an applicator comprises at least one drip line, at least one nozzle, or at least one wicker. In an aspect, a nozzle provided herein applies an agricultural composition in a downward direction. As used herein, a "downward direction" refers to pointing towards the ground or the base of a plant. In an aspect, a nozzle provided herein applies a fertilizer in a downward direction. In an aspect, a nozzle provided herein applies a pesticide in a downward direction. In an aspect, a nozzle provided herein applies a fungicide in a downward direction. In an aspect, a nozzle provided herein applies an insecticide in a downward direction. In an aspect, a nozzle provided herein applies an herbicide in a downward direction. In an aspect, a nozzle provided herein applies a nematicide in a downward direction. In an aspect, a nozzle provided herein applies water in a downward direction. In another aspect, an applicator comprises a spreader which may be used to apply a solid composition, such as seeds (e.g., cover crop seeds) or solid fertilizers or pesticides.

In an aspect, applying an agricultural composition comprises spraying, such as with at least one nozzle. In another aspect, applying an agricultural composition comprises dripping, such as with at least one drip line. In an aspect, a drip line may comprise a Y-drop. In another aspect, applying an agricultural composition comprises a spreader. In an aspect, applying a fertilizer comprises spraying. In another aspect, applying a fertilizer comprises dripping. In an aspect, applying a pesticide comprises spraying. In another aspect, applying a pesticide comprises dripping. In an aspect, applying an herbicide comprises spraying. In another aspect, applying an herbicide comprises dripping. In an aspect, applying an insecticide comprises spraying. In another aspect, applying an insecticide comprises dripping. In an aspect, applying a fungicide comprises spraying. In another aspect, applying a fungicide comprises dripping. In an aspect, applying a nematicide comprises spraying. In another aspect, applying a nematicide comprises dripping.

Ground-based agricultural vehicles can be powered by any method or energy source, for example, without being limiting, by hand, by electric power, by gasoline power, by diesel power, by natural gas power, by biodiesel power, by water power, or by solar power. Non-limiting exemplary ground-based agricultural vehicles include models such as the John Deere R4023, the John Deere R4030, the John Deere R4038, the John Deere R4045, the John Deere F4365, the Hagie™ DTS10, the Hagie™ STS10, the Hagie™ STS12, the Hagie™ STS14, the Hagie™ STS16, the RoGator® RG900C, the RoGator® RG1100C, and the RoGator® RG1300C, the John Deere 2410C Applicator, the John Deere 2510H Applicator, the John Deere 2510L Applicator, the RoGator® 300, and the AgSystems, Inc. NPX2800. The ground-based agricultural vehicle can be self-propelled or pulled by another vehicle, such as a tractor.

In an aspect, a ground-based agricultural vehicle provided herein comprises an irrigator, lateral irrigator or a center pivot irrigator, which may be capable of movement over a field. Center pivot irrigators are also referred to as watering pivots or water wheels in the art. An applicator of a center pivot irrigator, as understood in the art, typically comprises a longitudinal or outwardly extended portion (e.g., a pipe, such as segments of connected pipe, with sprinklers or applicators positioned along its length). Movement of the center pivot irrigator may be powered by a motor at the center of the pivot. The longitudinal or outwardly extended portion of the central pivot irrigator is often supported by trusses (e.g., a frame or scaffold) and wheels. A center pivot irrigator can move in a circular pattern to disperse liquids (e.g., water) supplied from the pivot point at the center of the circle. In an aspect, an applicator of a center pivot irrigator comprises at least one sprinkler head. In an aspect, an applicator of a center pivot irrigator comprises at least one nozzle, drip line or drip irrigator. An applicator of a lateral irrigator, as understood in the art, typically comprises a longitudinal portion (e.g., a pipe, such as segments of connected pipe, with sprinklers or applicators positioned along its length). Movement of the lateral irrigator may be powered by a motor at one or both ends of the applicator or longitudinal portion of the lateral irrigator. The longitudinal portion of the lateral irrigator is often supported by trusses and wheels. A lateral irrigator can move in a direction over a field to disperse liquids (e.g., water), which may be supplied at one end of the lateral irrigator. In an aspect, an applicator of a lateral irrigator comprises at least one sprinkler head. In an aspect, an applicator of a lateral irrigator comprises at least one nozzle, drip line or drip irrigator. As is known in the art, a "sprinkler head" is a component of a system capable of discharging and distributing a liquid, such as water.

In aspect, the irrigator, such as a lateral irrigator or central pivot irrigator, comprises a longitudinal portion, such as pipes and/or structural scaffold or framework, that has (or is positioned or adjusted to have) a lower exterior surface at a height above the ground and/or relative to the height of the corn plants as described herein for other types of ground based agricultural vehicles. For example, the lower exterior surface of the longitudinal portion of the irrigator may be equal to or less than 20 centimeters shorter or lower (i.e., no more than 20 centimeters shorter or lower) than the average height of the corn plants in a corn field (or a given percentage of corn plants in a corn field). The lower exterior surface of the applicator of a ground-based agricultural vehicle (whether fixed or adjustable) may be at a height that is equal to or less than 20 centimeters shorter or lower (i.e., no more than 20 centimeters shorter or lower) than the average height of the corn plants in a corn field (or a given percentage of corn plants in a corn field), or is equal to or less than 15 centimeters shorter or lower (i.e., no more than 15 centimeters shorter or lower) than the average height of corn plants in a corn field (or a given percentage of corn plants in a corn field), or is equal to or less than 10 centimeters shorter or lower (i.e., no more than 10 centimeters shorter or lower) than the average height of the corn plants in a corn field (or a given percentage of corn plants in a corn field). The lower exterior surface of the applicator of a ground-based agricultural vehicle (whether fixed or adjustable) may be at a height that is equal to or less than 10 centimeters shorter or lower (i.e., no more than 10 centimeters shorter or lower) than the average height of the corn plants in a corn field (or a given percentage of corn plants in a corn field), or is equal to or less than 5 centimeters shorter or lower (i.e., no more than 5 centimeters shorter or lower) than the average height of the corn plants in a corn field (or a given percentage of corn plants in a corn field), or is equal to or less than 1 centimeter shorter or lower (i.e., no more than 1 centimeters shorter or lower) than the average height of the corn plants in a corn field (or a given percentage of corn plants in a corn field).

In an aspect, the lower exterior surface of the longitudinal portion of the irrigator is at a height equal to or less than 2.5 meters, equal to or less than 2.4 meters, equal to or less than 2.3 meters, equal to or less than 2.2 meters, equal to or less than 2.1 meters, equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, or equal to or less than 0.4 meters above the top of the soil or ground level, and where the lower exterior surface of the longitudinal portion of the irrigator is equal to, or less than, 15 centimeters shorter or lower (i.e., no more than 15 centimeters shorter or lower) and/or equal to, or less than, 15 centimeters taller or higher (i.e., no more than 15 centimeters taller or higher) than the average height of the corn plants in a corn field (or a given percentage of corn plants in a corn field)—or within any other range therebetween, and where the corn plants are at V12 stage or later, V13 stage or later, V14 stage or later, V15 stage or later, VT stage or later, R1 stage or later, R2 stage or later, R3 stage or later, R4 stage or later, or R5 stage or later.

In an aspect, the lower exterior surface of the longitudinal portion of the irrigator is at a height equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, or equal to or less than 0.1 meter above the top of the soil or ground level, and wherein the lower exterior surface of the longitudinal portion of the irrigator is equal to, or less than, 15 centimeters shorter or lower (i.e., no more than 15 centimeters shorter or lower) and/or equal to, or less than, 15 centimeters taller or higher (i.e., no more than 15 centimeters taller or higher) than the average height of the corn plants in a corn field (or a given percentage of corn plants in a corn field)—or within any other range therebetween, and wherein the corn plants are at V6 stage or later, V7 stage or later, V8 stage or later, V9 stage or later, V10 stage or later, or V11 stage or later.

In an aspect, a lateral irrigator is at least 10 meters long. In another aspect, a lateral irrigator is at least 20 meters long. In another aspect, a lateral irrigator is at least 25 meters long. In another aspect, a lateral irrigator is at least 30 meters long. In another aspect, a lateral irrigator is at least 40 meters long. In another aspect, a lateral irrigator is at least 50 meters long. In another aspect, a lateral irrigator is at least 75 meters long. In another aspect, a lateral irrigator is at least 100 meters long. In another aspect, a lateral irrigator is at least 200 meters long. In another aspect, a lateral irrigator is at least 300 meters long. In another aspect, a lateral irrigator is at least 400 meters long. In another aspect, a lateral irrigator is at least 500 meters long. In another aspect, a lateral irrigator is at least 600 meters long. In another aspect, a lateral irrigator is at least 700 meters long. In another aspect, a lateral irrigator is at least 800 meters long. In another aspect, a lateral irrigator is at least 900 meters long. In another aspect, a lateral irrigator is at least 1000 meters long. In an aspect, a center pivot irrigator is at least 10 meters long. In another aspect, a center pivot irrigator is at least 20 meters long. In another aspect, a center pivot irrigator is at least 25 meters long. In another aspect, a center pivot irrigator is at least 30 meters long. In another aspect, a center pivot irrigator is at least 40 meters long. In another aspect, a center pivot irrigator is at least 50 meters long. In another aspect, a center pivot irrigator is at least 75 meters long. In another aspect, a center pivot irrigator is at least 100 meters long. In another aspect, a center pivot irrigator is at least 200 meters long. In another aspect, a center pivot irrigator is at least 300 meters long. In another aspect, a center pivot irrigator is at least 400 meters long. In another aspect, a center pivot irrigator is at least 500 meters long. In another aspect, a center pivot irrigator is at least 600 meters long. In another aspect, a center pivot irrigator is at least 700 meters long. In another aspect, a center pivot irrigator is at least 800 meters long. In another aspect, a center pivot irrigator is at least 900 meters long. In another aspect, a center pivot irrigator is at least 1000 meters long.

In an aspect, a ground-based agricultural vehicle provided herein applies an agricultural composition. In an aspect, a ground-based agricultural vehicle provided herein applies a fertilizer. In another aspect, a ground-based agricultural vehicle provided herein applies a pesticide. In another aspect, a ground-based agricultural vehicle provided herein applies an herbicide. In another aspect, a ground-based agricultural vehicle provided herein applies a fungicide. In another aspect, a ground-based agricultural vehicle provided herein applies an insecticide. In another aspect, a ground-based agricultural vehicle provided herein applies a nematicide. In another aspect, a ground-based agricultural vehicle provided herein applies water. In another aspect, a ground-based agricultural vehicle provided herein applies a cover crop seed.

In an aspect, a ground-based agricultural vehicle provided herein applies a solid composition. In another aspect, a ground-based agricultural vehicle provided herein applies a liquid composition. In a further aspect, a ground-based agricultural vehicle provided herein applies a gaseous composition. In an aspect, a ground-based agricultural vehicle provided herein applies a liquid agricultural composition. In an aspect, a ground-based agricultural vehicle provided herein applies a solid agricultural composition. In an aspect, a ground-based agricultural vehicle provided herein applies a gaseous agricultural composition. In an aspect, a ground-based agricultural vehicle provided herein applies a solid fertilizer. In another aspect, a ground-based agricultural vehicle provided herein applies a liquid fertilizer. In a further aspect, a ground-based agricultural vehicle provided herein applies a gaseous fertilizer. In an aspect, a ground-based agricultural vehicle provided herein applies a solid pesticide. In another aspect, a ground-based agricultural vehicle provided herein applies a liquid pesticide. In a further aspect, a ground-based agricultural vehicle provided herein applies a gaseous pesticide. In an aspect, a ground-based agricultural vehicle provided herein applies a solid herbicide. In another aspect, a ground-based agricultural vehicle provided herein applies a liquid herbicide. In a further aspect, a ground-based agricultural vehicle provided herein applies a gaseous herbicide. In an aspect, a ground-based agricultural vehicle provided herein applies a solid insecticide. In another aspect, a ground-based agricultural vehicle provided herein applies a liquid insecticide. In a further aspect, a ground-based agricultural vehicle provided herein applies a gaseous insecticide. In an aspect, a ground-based agricultural vehicle provided herein applies a solid fungicide. In another aspect, a ground-based agricultural vehicle provided herein applies a liquid fungicide. In a further aspect, a ground-based agricultural vehicle provided herein applies a gaseous fungicide. In an aspect, a ground-based agricultural vehicle provided herein applies a solid nematicide. In another aspect, a ground-based agricultural vehicle provided herein applies a liquid nematicide. In a further aspect, a ground-based agricultural vehicle provided herein applies a gaseous nematicide. In an aspect, a ground-based agricultural vehicle provided herein applies a cover crop seed. In another aspect, a ground-based agricultural vehicle provided herein applies water.

In an aspect, a ground-based agricultural vehicle provided herein comprises a self-propelled agricultural vehicle or agricultural sprayer. In another aspect, a ground-based agricultural vehicle provided herein comprises an agricultural vehicle or agricultural sprayer towed or pulled by a self-propelled vehicle. In an aspect, a self-propelled vehicle can tow one or more pieces of equipment. In another aspect, a self-propelled vehicle can tow two or more pieces of equipment. In a further aspect, a self-propelled vehicle can tow three or more pieces of equipment. Non-limiting examples of pieces of equipment capable of being towed by a self-propelled vehicle include agricultural sprayers, toolbars, planters, disc harrows, trailers, and plows. As used herein, an "agricultural sprayer" refers to any machine or equipment capable of providing or applying an agricultural composition to a corn field or a corn plant. In an aspect, an agricultural vehicle or agricultural sprayer comprises a main body and/or an applicator. In an aspect, an agricultural vehicle or agricultural sprayer is towed by a self-propelled vehicle, wherein the agricultural vehicle or agricultural sprayer comprises a main body and/or applicator and the self-propelled vehicle comprises a main body. In an aspect, an agricultural vehicle or agricultural sprayer provided herein comprises at least one applicator. In an aspect, an agricultural vehicle or agricultural sprayer provided herein is not capable of flight or movement without contact with the ground. In another aspect, an agricultural vehicle or agricultural sprayer provided herein is not an airplane. In a further aspect, an agricultural vehicle or agricultural sprayer provided herein is not a helicopter. In a further aspect, an agricultural vehicle or agricultural sprayer provided herein is not a drone. In an aspect, a self-propelled vehicle provided herein is a tractor. As used herein, a "tractor" refers to any vehicle that is capable of pulling an agricultural implement (e.g., an agricultural sprayer, a planter, a disc harrow) in a field. In an aspect, a tractor can tow one or more pieces of equipment. In another aspect, a tractor can tow two or more pieces of equipment. In a further aspect, a tractor can tow three or more pieces of equipment. A ground-based agricultural vehicle can comprise tires, treads, or both. In another aspect, a self-propelled vehicle provided herein is a truck. In an aspect, a self-propelled vehicle provided herein is an automobile.

In an aspect, a ground-based agricultural vehicle comprises a main body. As used herein, a "main body" refers to a central and/or motorized portion of a vehicle. In an aspect, a main body comprises a cabin capable of holding or seating at least one human or person. In an aspect, a main body comprises an engine. In an aspect, a main body comprises a pump. In an aspect, a main body comprises a steering wheel. In an aspect, a main body comprises one or more wheels, tires, sleds, discs, or tracks for contacting the ground, which may cause movement of the ground-based agricultural vehicle through its/their own movement. In an aspect, a main body comprises one or more axles. In an aspect, a main body comprises one or more control switches or panels for operating an agricultural vehicle, applicator or sprayer. In an aspect, a main body comprises a tow hitch. In an aspect, a ground-based agricultural vehicle comprises a main body and an applicator. In an aspect, a ground-based agricultural vehicle comprises a tandem applicator. In an aspect, an applicator of a ground-based agricultural vehicle comprises an applicator arm or boom. In a further aspect, a ground-based agricultural vehicle or a main body of a ground-based agricultural vehicle comprises at least one storage compartment or container capable of holding an agricultural composition. In an aspect, a storage compartment or container comprises a tank for storing a liquid. In an aspect, a ground-based agricultural vehicle comprises at least one anhydrous tank. In another aspect, a storage compartment or container comprises at least one anhydrous tank. In an aspect, a storage compartment or container comprises a tank for storing a fertilizer. In an aspect, a storage compartment or container comprises a tank for storing a pesticide. In an aspect, a storage compartment or container comprises a tank for storing an insecticide. In an aspect, a storage compartment or container comprises a tank for storing an herbicide. In an aspect, a storage compartment or container comprises a tank for storing a fungicide. In an aspect, a storage compartment or container comprises a tank for storing a nematicide. In an aspect, a storage compartment or container comprises a tank for storing cover crop seed. In an aspect, a storage compartment or container comprises a tank for storing water.

In an aspect, the lower exterior surface of the main body and/or applicator of a ground-based agricultural vehicle is equal to or less than 2.5 meters above soil level. In an aspect, the lower exterior surface of the main body and/or applicator of a ground-based agricultural vehicle is equal to or less than 2.4 meters above soil level. In an aspect, the lower exterior surface of the main body and/or applicator of a ground-based agricultural vehicle is equal to or less than 2.3 meters above soil level. In an aspect, the lower exterior surface of the main body and/or applicator of a ground-based agricultural vehicle is equal to or less than 2.2 meters above soil level. In an aspect, the lower exterior surface of the main body and/or applicator of a ground-based agricultural vehicle is equal to or less than 2.1 meters above soil level. In an aspect, the lower exterior surface of the main body and/or applicator of a ground-based agricultural vehicle is equal to or less than 2.0 meters above soil level. In an aspect, the lower exterior surface of the main body and/or applicator of a ground-based agricultural vehicle is equal to or less than 1.9 meters above soil level. In an aspect, the lower exterior surface of the main body and/or applicator of a ground-based agricultural vehicle is equal to or less than 1.8 meters above soil level. In an aspect, the lower exterior surface of the main body and/or applicator of a ground-based agricultural vehicle is equal to or less than 1.7 meters above soil level. In an aspect, the lower exterior surface of the main body and/or applicator of a ground-based agricultural vehicle is equal to or less than 1.6 meters above soil level. In an aspect, the lower exterior surface of the main body and/or applicator of a ground-based agricultural vehicle is equal to or less than 1.5 meters above soil level. In an aspect, the lower exterior surface of the main body and/or applicator of a ground-based agricultural vehicle is equal to or less than 1.4 meters above soil level. In an aspect, the lower exterior surface of the main body and/or applicator of a ground-based agricultural vehicle is equal to or less than 1.3 meters above soil level. In an aspect, the lower exterior surface of the main body and/or applicator of a ground-based agricultural vehicle is equal to or less than 1.2 meters above soil level. In an aspect, the lower exterior surface of the main body and/or applicator of a ground-based agricultural vehicle is equal to or less than 1.1 meters above soil level. In an aspect, the lower exterior surface of the main body and/or applicator of a ground-based agricultural vehicle is equal to or less than 1.0 meter above soil level. In an aspect, the lower exterior surface of the main body and/or applicator of a ground-based agricultural vehicle is equal to or less than 0.9 meters above soil level. In an aspect, the lower exterior surface of the main body and/or applicator of a ground-based agricultural vehicle is equal to or less than 0.8 meters above soil level. In an aspect, the lower exterior surface of the main body and/or applicator of a ground-based agricultural vehicle is equal to or less than 0.7 meters above soil level. In an aspect, the lower exterior surface of the main body and/or applicator of a ground-based agricultural vehicle is equal to or less than 0.6 meters above soil level. In an aspect, the lower exterior surface of the main body and/or applicator of a ground-based agricultural vehicle is equal to or less than 0.5 meters above soil level. In an aspect, the lower exterior surface of the main body and/or applicator of a ground-based agricultural vehicle is equal to or less than 0.4 meters above soil level. In an aspect, the lower exterior surface of the main body and/or applicator of a ground-based agricultural vehicle is equal to or less than 0.3 meters above soil level. In an aspect, the lower exterior surface of the main body and/or applicator of a ground-based agricultural vehicle is equal to or less than 0.2 meters above soil level. In an aspect, the lower exterior surface of the main body and/or applicator of a ground-based agricultural vehicle is equal to or less than 1.0 meters above soil level.

In an aspect, the lower exterior surface of the main body and/or applicator of a ground-based agricultural vehicle is between 0.1 meters and 2.5 meters, 0.1 meters and 2.3 meters, 0.1 meters and 2.0 meters, 0.1 meters and 1.8 meters, 0.1 meters and 1.5 meters, 0.1 meters and 1.0 meter, 0.1 meters and 0.9 meters, 0.1 meters and 0.8 meters, 0.1 meters and 0.7 meters, 0.1 meters and 0.6 meters, 0.1 meters and 0.5 meters, 0.1 meters and 0.4 meters, 0.1 meters and 0.3 meters, 0.1 meters and 0.2 meters, 0.2 meters and 2.5 meters, 0.2 meters and 2.3 meters, 0.2 meters and 2.0 meters, 0.2 meters and 1.8 meters, 0.2 meters and 1.5 meters, 0.2 meters and 1.0 meter, 0.2 meters and 0.9 meters, 0.2 meters and 0.8 meters, 0.2 meters and 0.7 meters, 0.2 meters and 0.6 meters, 0.2 meters and 0.5 meters, 0.2 meters and 0.4 meters, 0.2 meters and 0.3 meters, 0.3 meters and 2.5 meters, 0.3 meters and 2.3 meters, 0.3 meters and 2.0 meters, 0.3 meters and 1.8 meters, 0.3 meters and 1.5 meters, 0.3 meters and 1.0 meter, 0.3 meters and 0.9 meters, 0.3 meters and 0.8 meters, 0.3 meters and 0.7 meters, 0.3 meters and 0.6 meters, 0.3 meters and 0.5 meters, 0.3 meters and 0.4 meters, 0.4 meters and 2.5 meters, 0.4 meters and 2.3 meters, 0.4 meters and 2.0 meters, 0.4 meters and 1.8 meters, 0.4 meters and 1.5 meters, 0.4 meters and 1.0 meter, 0.4 meters and 0.9 meters, 0.4 meters and 0.8 meters, 0.4 meters and 0.7 meters, 0.4 meters and 0.6 meters, 0.4 meters and 0.5 meters, 0.5 meters and 2.5 meters, 0.5 meters and 2.3 meters, 0.5 meters and 2.0 meters, 0.5 meters and 1.8 meters, 0.5 meters and 1.5 meters, 0.5 meters and 1.0 meter, 0.5 meters and 0.9 meters, 0.5 meters and 0.8 meters, 0.5 meters and 0.7 meters, 0.5 meters and 0.6 meters, 0.6 meters and 2.5 meters, 0.6 meters and 2.3 meters, 0.6 meters and 2.0 meters, 0.6 meters and 1.8 meters, 0.6 meters and 1.5 meters, 0.6 meters and 1.0 meter, 0.6 meters and 0.9 meters, 0.6 meters and 0.8 meters, 0.6 meters and 0.7 meters, 0.7 meters and 2.5 meters, 0.7 meters and 2.3 meters, 0.7 meters and 2.0 meters, 0.7 meters and 1.8 meters, 0.7 meters and 1.5 meters, 0.7 meters and 1.0 meter, 0.7 meters and 0.9 meters, 0.7 meters and 0.8 meters, 0.8 meters and 2.5 meters, 0.8 meters and 2.3 meters, 0.8 meters and 2.0 meters, 0.8 meters and 1.8 meters, 0.8 meters and 1.5 meters, 0.8 meters and 1.0 meter, 0.8 meters and 0.9 meters, 0.9 meters and 2.5 meters, 0.9 meters and 2.3 meters, 0.9 meters and 2.0 meters, 0.9 meters and 1.8 meters, 0.9 meters and 1.5 meters, 0.9 meters and 1.0 meter, 1.0 meter and 2.5 meters, 1.0 meter and 2.3 meters, 1.0 meter and 2.0 meters, 1.0 meter and 1.9 meters, 1.0 meter and 1.8 meters, 1.0 meter and 1.7 meters, 1.0 meter and 1.6 meters, 1.0 meter and 1.5 meters, 1.0 meter and 1.4 meters, 1.0 meter and 1.3 meters, 1.0 meter and 1.2 meters, 1.0 meter and 1.1 meters, 1.1 meters and 2.5 meters, 1.1 meters and 2.3 meters, 1.1 meters and 2.0 meters, 1.1 meters and 1.9 meters, 1.1 meters and 1.8 meters, 1.1 meters and 1.7 meters, 1.1 meters and 1.6 meters, 1.1 meters and 1.5 meters, 1.1 meters and 1.4 meters, 1.1 meters and 1.3 meters, 1.1 meters and 1.2 meters, 1.2 meters and 2.5 meters, 1.2 meters and 2.3 meters, 1.2 meters and 2.0 meters, 1.2 meters and 1.9 meters, 1.2 meters and 1.8 meters, 1.2 meters and 1.7 meters, 1.2 meters and 1.6 meters, 1.2 meters and 1.5 meters, 1.2 meters and 1.4 meters, or 1.2 meters and 1.3 meters, 1.3 meters and 2.5 meters, 1.3 meters and 2.3 meters, 1.3 meters and 2.0 meters, 1.3 meters and 1.9 meters, 1.3 meters and 1.8 meters, 1.3 meters and 1.7 meters, 1.3 meters and 1.6 meters, 1.3 meters and 1.5 meters, 1.3 meters and 1.4 meters, 1.4 meters and 2.5 meters, 1.4 meters and 2.3 meters, 1.4 meters and 2.0 meters, 1.4 meters and 1.9 meters, 1.4 meters and 1.8 meters, 1.4 meters and 1.7 meters, 1.4 meters and 1.6 meters, 1.4 meters and 1.5 meters, 1.5 meters and 2.5 meters, 1.5 meters and 2.3 meters, 1.5 meters and 2.0 meters, 1.5 meters and 1.9 meters, 1.5 meters and 1.8 meters, 1.5 meters and 1.7 meters, 1.5 meters and 1.6 meters, 1.6 meters and 2.5 meters, 1.6 meters and 2.3 meters, 1.6 meters and 2.0 meters, 1.6 meters and 1.9 meters, 1.6 meters and 1.8 meters, 1.6 meters and 1.7 meters, 1.7 meters and 2.5 meters, 1.7 meters and 2.3 meters, 1.7 meters and 2.0 meters, 1.7 meters and 1.9 meters, 1.7 meters and 1.8 meters, 1.8 meters and 2.5 meters, 1.8 meters and 2.3 meters, 1.8 meters and 2.0 meters, 1.8 meters and 1.9 meters, 1.9 meters and 2.5 meters, 1.9 meters and 2.3 meters, 1.9 meters and 2.0 meters, 2.0 meters and 2.5 meters, 2.1 meters and 2.5 meters, 2.2 meters and 2.5 meters, 2.0 meters and 2.3 meters, 2.1 meters and 2.3 meters, 2.2 meters and 2.3 meters, 2.3 meters and 2.5 meters, or 2.4 meters and 2.5 meters above soil level.

In an aspect, a ground-based agricultural vehicle comprises a main body and an applicator, where the applicator comprises at least one applicator arm or boom attached to the main body. In an aspect, an applicator provided herein comprises at least one applicator arm or boom. Agricultural sprayers often comprise one or more applicator arms or booms. As used herein, an "applicator arm" or "boom" refers to any structure that comprises one or more applicators. Applicator arms and booms are typically elongated structures that are positioned or oriented in a horizontal, or mostly horizontal, direction when in use on one or both (opposite) sides relative to a central attachment or connection to the main body of a ground-based agricultural vehicle. In an aspect, an applicator arm or boom provided herein is positioned at a height that is vertically adjustable. In an aspect, an applicator arm or boom comprises multiple spray sections. In another aspect, an applicator arm or boom comprises one or more nozzles. In another aspect, an applicator arm or boom comprises one or more drip lines. As used herein, a "drip line" is a line, hose, or tube that hangs down (e.g., by gravity) or is oriented in a downward direction from the applicator arm or boom (e.g., in between rows of plants in the field). A drip line may allow for more focused and efficient applications of an agricultural composition to a desired or effective location(s) at or near the base of the plants or to the ground or soil at or near the base of the plants or between rows of plants. In another aspect, an applicator or arm comprises one or more wick applicators or "wickers." As used herein, a "wick applicator" or "wicker" includes any material saturated with an agricultural composition, where the agricultural composition can be absorbed, drawn off, or wicked away from the surface of the material (i.e., the wicker) to the surface of another object (e.g., a plant). Similar to a drip line, a wicker hangs down (e.g., by gravity) or is oriented in a downward direction from the applicator arm or boom (e.g., in between rows of plants in the field). Without being limiting, wicker material can comprise, for example, rope, nylon, canvas, pipe, sponge, or any combination thereof, which may be disposed within, or attached to, an applicator arm or boom. Indeed, a wicker may include an applicator arm or boom and a wicker material.

Applicator arms and booms provided herein can comprise multiple drip lines, nozzles, or wickers that can apply agricultural compositions (e.g., fertilizer, pesticide, water, etc.). The applicator arms or booms can be adjusted vertically so that they are positioned at a desired height above the soil level. Some applicator arms or booms comprise multiple sections that can be independently controlled (e.g., a first section can be positioned at a first vertical position, a second section can be positioned at a second vertical position, a third section can be positioned at a third vertical position, etc.). In an aspect, an agricultural sprayer comprises a horizontal or mostly horizontal applicator arm or boom. In an aspect, an agricultural sprayer comprises at least one horizontal or mostly horizontal applicator arm or boom. In another aspect, an agricultural sprayer comprises at least two horizontal or mostly horizontal applicator arms or booms. In an aspect, an agricultural sprayer comprises a vertically adjustable applicator arm or boom. In an aspect, an agricultural sprayer comprises at least one vertically adjustable applicator arm or boom. In another aspect, an agricultural sprayer comprises at least two vertically adjustable applicator arms or booms. In an aspect, a vertically adjustable applicator arm or boom comprises multiple sections. In an aspect, the multiple sections provided herein can be independently controlled.

In an aspect, nozzles provided herein are positioned on an applicator, applicator arm, or boom such that at least one nozzle is positioned between two rows of corn plants in a corn field. In an aspect, a plurality of nozzles on an applicator are positioned between at least two rows of corn plants in a corn field. In an aspect, a plurality of nozzles on an applicator arm or boom are positioned between at least two rows of corn plants in a corn field. In an aspect, drip lines provided herein are positioned on an applicator, applicator arm, or boom such that at least one drip line is positioned between two rows of corn plants in a corn field. In an aspect, a plurality of drip lines on an applicator are positioned between at least two rows of corn plants in a corn field. In an aspect, a plurality of drip lines on an applicator arm or boom are positioned between at least two rows of corn plants in a corn field. In an aspect, one or more wickers or wick applicators provided herein are positioned on (and/or in) an applicator, applicator arm, or boom such that at least one wicker or wick applicator is positioned at a desired height and/or between two rows of corn plants in a corn field. In an aspect, a plurality of wickers or wick applicators on an applicator are positioned between at least two rows of corn plants in a corn field. In an aspect, a plurality of wickers or wick applicators on an applicator arm or boom are positioned between at least two rows of corn plants in a corn field.

In an aspect, adjacent nozzles are positioned at least 5 centimeters apart. In an aspect, adjacent nozzles are positioned at least 10 centimeters apart. In an aspect, adjacent nozzles are positioned at least 15 centimeters apart. In an aspect, adjacent nozzles are positioned at least 30 centimeters apart. In an aspect, adjacent nozzles are positioned at least 45 centimeters apart. In an aspect, adjacent nozzles are positioned at least 60 centimeters apart. In an aspect, adjacent nozzles are positioned at least 75 centimeters apart. In an aspect, adjacent nozzles are positioned at least 100 centimeters apart. In an aspect, adjacent drip lines are positioned at least 5 centimeters apart. In an aspect, adjacent drip lines are positioned at least 10 centimeters apart. In an aspect, adjacent drip lines are positioned at least 15 centimeters apart. In an aspect, adjacent drip lines are positioned at least 30 centimeters apart. In an aspect, adjacent drip lines are positioned at least 45 centimeters apart. In an aspect, adjacent drip lines are positioned at least 60 centimeters apart. In an aspect, adjacent drip lines are positioned at least 75 centimeters apart. In an aspect, adjacent drip lines are positioned at least 100 centimeters apart. In an aspect, adjacent wickers or wick applicators are positioned at least 5 centimeters apart. In an aspect, a single continuous wicker is used for each applicator. In another aspect, two or more adjacent wickers or wick applicators are positioned at least 10 centimeters apart. In an aspect, adjacent wickers or wick applicators are positioned at least 15 centimeters apart. In an aspect, adjacent wickers or wick applicators are positioned at least 30 centimeters apart. In an aspect, adjacent wickers or wick applicators are positioned at least 45 centimeters apart. In an aspect, adjacent wickers or wick applicators are positioned at least 60 centimeters apart. In an aspect, adjacent wickers or wick applicators are positioned at least 75 centimeters apart. In an aspect, adjacent wickers or wick applicators are positioned at least 100 centimeters apart.

An applicator arm or boom can be positioned horizontal or at any angle above or below horizontal ("horizontal" being defined as parallel to the ground). In an aspect, an applicator arm or boom is in a horizontal position. In another aspect, an applicator arm or boom is positioned within 5° of horizontal. In another aspect, an applicator arm or boom is positioned within 10° of horizontal. In another aspect, an applicator arm or boom is positioned within 15° of horizontal. In another aspect, an applicator arm or boom is positioned within 20° of horizontal. In another aspect, an applicator arm or boom is positioned within 25° of horizontal. In another aspect, an applicator arm or boom is positioned within 30° of horizontal. In another aspect, an applicator arm or boom is positioned within 35° of horizontal. In another aspect, an applicator arm or boom is positioned within 40° of horizontal. In another aspect, an applicator arm or boom is positioned within 45° of horizontal. In another aspect, an applicator arm or boom is positioned within 60° of horizontal. In another aspect, an applicator arm or boom is positioned within 90° of horizontal. As used herein, "mostly horizontal" means more horizontal than vertical relative to the top of the soil or ground (e.g., less than 45° of horizontal). As used herein, "mostly horizontal" includes "nearly horizontal" which means within 30° of horizontal.

An applicator arm or boom can be of any length. In an aspect, an applicator arm or boom is self-supporting. In another aspect, an applicator arm or boom is supported by one or more wheels. In an aspect, an applicator arm or boom is supported by one or more cables. In an aspect, an applicator arm or boom is at least 0.5 meters long. In an aspect, an applicator arm or boom is at least 1 meter long. In another aspect, an applicator arm or boom is at least 2 meters long. In another aspect, an applicator arm or boom is at least 3 meters long. In another aspect, an applicator arm or boom is at least 4 meters long. In another aspect, an applicator arm or boom is at least 5 meters long. In another aspect, an applicator arm or boom is at least 6 meters long. In another aspect, an applicator arm or boom is at least 7 meters long. In another aspect, an applicator arm or boom is at least 8 meters long. In another aspect, an applicator arm or boom is at least 9 meters long. In another aspect, an applicator arm or boom is at least 10 meters long. In another aspect, an applicator arm or boom is at least 15 meters long. In another aspect, an applicator arm or boom is at least 20 meters long. In another aspect, an applicator arm or boom is at least 25 meters long. In another aspect, an applicator arm or boom is at least 30 meters long.

An applicator, applicator arm, or boom can comprise any number of drip lines, nozzles, wickers, or wick applicators. In an aspect, an applicator comprises between 1 and 500 nozzles. In another aspect, an applicator comprises between 1 and 400 nozzles. In another aspect, an applicator comprises between 1 and 300 nozzles. In another aspect, an applicator comprises between 1 and 200 nozzles. In another aspect, an applicator comprises between 1 and 100 nozzles. In another aspect, an applicator comprises between 25 and 250 nozzles. In an aspect, an applicator comprises between 50 and 300 nozzles. In another aspect, an applicator comprises between 1 and 5 nozzles. In another aspect, an applicator comprises between 1 and 10 nozzles. In another aspect, an applicator comprises between 1 and 15 nozzles. In another aspect, an applicator comprises between 1 and 20 nozzles. In another aspect, an applicator comprises between 1 and 25 nozzles. In another aspect, an applicator comprises between 1 and 50 nozzles. In another aspect, an applicator comprises between 5 and 15 nozzles. In another aspect, an applicator comprises between 5 and 25 nozzles. In an aspect, an applicator comprises at least 1 nozzle. In an aspect, an applicator comprises at least 5 nozzles. In another aspect, an applicator comprises at least 10 nozzles. In another aspect, an applicator comprises at least 25 nozzles. In another aspect, an applicator comprises at least 50 nozzles. In another aspect, an applicator comprises at least 75 nozzles. In another aspect, an applicator comprises at least 100 nozzles.

In an aspect, an applicator comprises between 1 and 500 drip lines. In another aspect, an applicator comprises between 1 and 400 drip lines. In another aspect, an applicator comprises between 1 and 300 drip lines. In another aspect, an applicator comprises between 1 and 200 drip lines. In another aspect, an applicator comprises between 1 and 100 drip lines. In another aspect, an applicator comprises between 25 and 250 drip lines. In another aspect, an applicator comprises between 50 and 300 drip lines. In another aspect, an applicator comprises between 1 and 5 drip lines. In another aspect, an applicator comprises between 1 and 10 drip lines. In another aspect, an applicator comprises between 1 and 15 drip lines. In another aspect, an applicator comprises between 1 and 20 drip lines. In another aspect, an applicator comprises between 1 and 25 drip lines. In another aspect, an applicator comprises between 1 and 50 drip lines. In another aspect, an applicator comprises between 5 and 15 drip lines. In another aspect, an applicator comprises between 5 and 25 drip lines. In an aspect, an applicator comprises at least 1 drip line. In an aspect, an applicator comprises at least 5 drip lines. In another aspect, an applicator comprises at least 10 drip lines. In another aspect, an applicator comprises at least 25 drip lines. In another aspect, an applicator comprises at least 50 drip lines. In another aspect, an applicator comprises at least 75 drip lines. In another aspect, an applicator comprises at least 100 drip lines.

In an aspect, an applicator comprises between 1 and 500 wickers or wick applicators. In another aspect, an applicator comprises between 1 and 400 wickers or wick applicators. In another aspect, an applicator comprises between 1 and 300 wickers or wick applicators. In another aspect, an applicator comprises between 1 and 200 wickers or wick applicators. In another aspect, an applicator comprises between 1 and 100 wickers or wick applicators. In another aspect, an applicator comprises between 25 and 250 wickers or wick applicators. In another aspect, an applicator comprises between 50 and 300 wickers or wick applicators. In another aspect, an applicator comprises between 1 and 5 wickers or wick applicators. In another aspect, an applicator comprises between 1 and 10 wickers or wick applicators. In another aspect, an applicator comprises between 1 and 15 wickers or wick applicators. In another aspect, an applicator comprises between 1 and 20 wickers or wick applicators. In another aspect, an applicator comprises between 1 and 25 wickers or wick applicators. In another aspect, an applicator comprises between 1 and 50 wickers or wick applicators. In another aspect, an applicator comprises between 5 and 15 wickers or wick applicators. In another aspect, an applicator comprises between 5 and 25 wickers or wick applicators. In an aspect, an applicator comprises at least 1 wicker or wick applicator. In another aspect, an applicator comprises at least 5 wickers or wick applicators. In another aspect, an applicator comprises at least 10 wickers or wick applicators. In another aspect, an applicator comprises at least 25 wickers or wick applicators. In another aspect, an applicator comprises at least 50 wickers or wick applicators. In another aspect, an applicator comprises at least 75 wickers or wick applicators. In another aspect, an applicator comprises at least 100 wickers or wick applicators.

In an aspect, an applicator arm or boom comprises between 1 and 500 nozzles. In another aspect, an applicator arm or boom comprises between 1 and 400 nozzles. In another aspect, an applicator arm or boom comprises between 1 and 300 nozzles. In another aspect, an applicator arm or boom comprises between 1 and 200 nozzles. In another aspect, an applicator arm or boom comprises between 1 and 100 nozzles. In another aspect, an applicator arm or boom comprises between 25 and 250 nozzles. In another aspect, an applicator arm or boom comprises between 50 and 300 nozzles. In another aspect, an applicator arm or boom comprises between 1 and 5 nozzles. In another aspect, an applicator arm or boom comprises between 1 and 10 nozzles. In another aspect, an applicator arm or boom comprises between 1 and 15 nozzles. In another aspect, an applicator arm or boom comprises between 1 and 20 nozzles. In another aspect, an applicator arm or boom comprises between 1 and 25 nozzles. In another aspect, an applicator arm or boom comprises between 1 and 50 nozzles. In another aspect, an applicator arm or boom comprises between 5 and 15 nozzles. In another aspect, an applicator arm or boom comprises between 5 and 25 nozzles. In an aspect, an applicator arm or boom comprises at least 1 nozzle. In another aspect, an applicator arm or boom comprises at least 5 nozzles. In another aspect, an applicator arm or boom comprises at least 10 nozzles. In another aspect, an applicator arm or boom comprises at least 25 nozzles. In another aspect, an applicator arm or boom comprises at least 50 nozzles. In another aspect, an applicator arm or boom comprises at least 75 nozzles. In another aspect, an applicator arm or boom comprises at least 100 nozzles.

In an aspect, an applicator arm or boom comprises between 1 and 500 drip lines. In another aspect, an applicator arm or boom comprises between 1 and 400 drip lines. In another aspect, an applicator arm or boom comprises between 1 and 300 drip lines. In another aspect, an applicator arm or boom comprises between 1 and 200 drip lines. In another aspect, an applicator arm or boom comprises between 1 and 100 drip lines. In another aspect, an applicator arm or boom comprises between 25 and 250 drip lines. In another aspect, an applicator arm or boom comprises between 50 and 300 drip lines. In another aspect, an applicator arm or boom comprises between 1 and 5 drip lines. In another aspect, an applicator arm or boom comprises between 1 and 10 drip lines. In another aspect, an applicator arm or boom comprises between 1 and 15 drip lines. In another aspect, an applicator arm or boom comprises between 1 and 20 drip lines. In another aspect, an applicator arm or boom comprises between 1 and 25 drip lines. In another aspect, an applicator arm or boom comprises between 1 and 50 drip lines. In another aspect, an applicator arm or boom comprises between 5 and 15 drip lines. In another aspect, an applicator arm or boom comprises between 5 and 25 drip lines. In an aspect, an applicator arm or boom comprises at least 1 drip line. In another aspect, an applicator arm or boom comprises at least 5 drip lines. In another aspect, an applicator arm or boom comprises at least 10 drip lines. In another aspect, an applicator arm or boom comprises at least 25 drip lines. In another aspect, an applicator arm or boom comprises at least 50 drip lines. In another aspect, an applicator arm or boom comprises at least 75 drip lines. In another aspect, an applicator arm or boom comprises at least 100 drip lines.

In an aspect, an applicator arm or boom comprises between 1 and 500 wickers or wick applicators. In another aspect, an applicator arm or boom comprises between 1 and 400 wickers or wick applicators. In another aspect, an applicator arm or boom comprises between 1 and 300 wickers or wick applicators. In another aspect, an applicator arm or boom comprises between 1 and 200 wickers or wick applicators. In another aspect, an applicator arm or boom comprises between 1 and 100 wickers or wick applicators. In another aspect, an applicator arm or boom comprises between 25 and 250 wickers or wick applicators. In another aspect, an applicator arm or boom comprises between 50 and 300 wickers or wick applicators. In another aspect, an applicator arm or boom comprises between 1 and 5 wickers or wick applicators. In another aspect, an applicator arm or boom comprises between 1 and 10 wickers or wick applicators. In another aspect, an applicator arm or boom comprises between 1 and 15 wickers or wick applicators. In another aspect, an applicator arm or boom comprises between 1 and 20 wickers or wick applicators. In another aspect, an applicator arm or boom comprises between 1 and 25 wickers or wick applicators. In another aspect, an applicator arm or boom comprises between 1 and 50 wickers or wick applicators. In another aspect, an applicator arm or boom comprises between 5 and 15 wickers or wick applicators. In another aspect, an applicator arm or boom comprises between 5 and 25 wickers or wick applicators. In an aspect, an applicator arm or boom comprises at least 1 wicker or wick applicator. In another aspect, an applicator arm or boom comprises at least 5 wickers or wick applicators. In another aspect, an applicator arm or boom comprises at least 10 wickers or wick applicators. In another aspect, an applicator arm or boom comprises at least 25 wickers or wick applicators. In another aspect, an applicator arm or boom comprises at least 50 wickers or wick applicators. In another aspect, an applicator arm or boom comprises at least 75 wickers or wick applicators. In another aspect, an applicator arm or boom comprises at least 100 wickers or wick applicators.

It is desirable for a main body and an applicator, such as an applicator arm or boom, of a ground-based agricultural vehicle to be positioned above the plants being sprayed so the applicator, applicator arm, or boom does not damage or destroy the plants. In an aspect, the lower surface of an applicator provided herein, such as an applicator arm or boom, is positioned equal to or less than 2.5 meters above soil level. In an aspect, the lower surface of an applicator provided herein is positioned equal to or less than 2.4 meters above soil level. In an aspect, the lower surface of an applicator provided herein is positioned equal to or less than 2.3 meters above soil level. In an aspect, the lower surface of an applicator provided herein is positioned equal to or less than 2.2 meters above soil level. In an aspect, the lower surface of an applicator provided herein is positioned equal to or less than 2.1 meters above soil level. In an aspect, the lower surface of an applicator provided herein is positioned equal to or less than 2.0 meters above soil level. In another aspect, the lower surface of an applicator provided herein is positioned equal to or less than 1.9 meters above soil level. In another aspect, the lower surface of an applicator provided herein is positioned equal to or less than 1.8 meters above soil level. In another aspect, the lower surface of an applicator provided herein is positioned equal to or less than 1.7 meters above soil level. In another aspect, the lower surface of an applicator provided herein is positioned equal to or less than 1.6 meters above soil level. In another aspect, the lower surface of an applicator provided herein is positioned equal to or less than 1.5 meters above soil level. In another aspect, the lower surface of an applicator provided herein is positioned equal to or less than 1.4 meters above soil level. In another aspect, the lower surface of an applicator provided herein is positioned equal to or less than 1.3 meters above soil level. In another aspect, the lower surface of an applicator provided herein is positioned equal to or less than 1.2 meters above soil level. In another aspect, the lower surface of an applicator provided herein is positioned equal to or less than 1.1 meters above soil level. In another aspect, the lower surface of an applicator provided herein is positioned equal to or less than 1.0 meter above soil level. In another aspect, the lower surface of an applicator provided herein is positioned equal to or less than 0.9 meters above soil level. In another aspect, the lower surface of an applicator provided herein is positioned equal to or less than 0.8 meters above soil level. In another aspect, the lower surface of an applicator provided herein is positioned equal to or less than 0.7 meters above soil level. In another aspect, the lower surface of an applicator provided herein is positioned equal to or less than 0.6 meters above soil level. In another aspect, the lower surface of an applicator provided herein is positioned equal to or less than 0.5 meters above soil level. In another aspect, the lower surface of an applicator provided herein is positioned equal to or less than 0.4 meters above soil level. In another aspect, the lower surface of an applicator provided herein is positioned equal to or less than 0.3 meters above soil level. In another aspect, the lower surface of an applicator provided herein is positioned equal to or less than 0.2 meters above soil level. In another aspect, the lower surface of an applicator provided herein is positioned equal to or less than 0.1 meters above soil level.

In an aspect, the lower surface of an applicator provided herein is positioned between 0.1 and 2.5 meters above soil level. In an aspect, the lower surface of an applicator provided herein is positioned between 0.2 and 2.5 meters above soil level. In an aspect, the lower surface of an applicator provided herein is positioned between 0.3 and 2.5 meters above soil level. In an aspect, the lower surface of an applicator provided herein is positioned between 0.4 and 2.5 meters above soil level. In an aspect, the lower surface of an applicator provided herein is positioned between 0.5 and 2.5 meters above soil level. In an aspect, the lower surface of an applicator provided herein is positioned between 0.6 and 2.5 meters above soil level. In an aspect, the lower surface of an applicator provided herein is positioned between 0.7 and 2.5 meters above soil level. In an aspect, the lower surface of an applicator provided herein is positioned between 0.8 and 2.5 meters above soil level. In an aspect, the lower surface of an applicator provided herein is positioned between 0.9 and 2.5 meters above soil level. In an aspect, the lower surface of an applicator provided herein is positioned between 1.0 and 2.5 meters above soil level. In an aspect, the lower surface of an applicator provided herein is positioned between 1.1 and 2.5 meters above soil level. In an aspect, the lower surface of an applicator provided herein is positioned between 1.2 and 2.5 meters above soil level. In an aspect, the lower surface of an applicator provided herein is positioned between 1.3 and 2.5 meters above soil level. In an aspect, the lower surface of an applicator provided herein is positioned between 1.4 and 2.5 meters above soil level. In an aspect, the lower surface of an applicator provided herein is positioned between 1.5 and 2.5 meters above soil level. In an aspect, the lower surface of an applicator provided herein is positioned between 1.6 and 2.5 meters above soil level. In an aspect, the lower surface of an applicator provided herein is positioned between 1.7 and 2.5 meters above soil level. In an aspect, the lower surface of an applicator provided herein is positioned between 1.8 and 2.5 meters above soil level. In an aspect, the lower surface of an applicator provided herein is positioned between 1.9 and 2.5 meters above soil level. In an aspect, the lower surface of an applicator provided herein is positioned between 2.0 and 2.5 meters above soil level. In an aspect, the lower surface of an applicator provided herein is positioned between 2.3 and 2.5 meters above soil level. In another aspect, the lower surface of an applicator provided herein is positioned between 0.1 and 2.0 meters above soil level. In another aspect, the lower surface of an applicator provided herein is positioned between 0.2 and 2.0 meters above soil level. In another aspect, the lower surface of an applicator provided herein is positioned between 0.3 and 2.0 meters above soil level. In another aspect, the lower surface of an applicator provided herein is positioned between 0.4 and 2.0 meters above soil level. In another aspect, the lower surface of an applicator provided herein is positioned between 0.5 and 2.0 meters above soil level. In another aspect, the lower surface of an applicator provided herein is positioned between 0.6 and 2.0 meters above soil level. In another aspect, the lower surface of an applicator provided herein is positioned between 0.7 and 2.0 meters above soil level. In another aspect, the lower surface of an applicator provided herein is positioned between 0.8 and 2.0 meters above soil level. In another aspect, the lower surface of an applicator provided herein is positioned between 0.9 and 2.0 meters above soil level. In a further aspect, the lower surface of an applicator provided herein is positioned between 1.0 and 2.0 meters above soil level. In another aspect, the lower surface of an applicator provided herein is positioned between 1.1 and 2.0 meters above soil level. In another aspect, the lower surface of an applicator provided herein is positioned between 1.2 and 2.0 meters above soil level. In another aspect, the lower surface of an applicator provided herein is positioned between 1.3 and 2.0 meters above soil level. In another aspect, the lower surface of an applicator provided herein is positioned between 1.4 and 2.0 meters above soil level. In another aspect, the lower surface of an applicator provided herein is positioned between 1.5 and 2.0 meters above soil level. In another aspect, the lower surface of an applicator provided herein is positioned between 1.6 and 2.0 meters above soil level. In another aspect, the lower surface of an applicator provided herein is positioned between 1.7 and 2.0 meters above soil level. In another aspect, the lower surface of an applicator provided herein is positioned between 1.8 and 2.0 meters above soil level. In another aspect, the lower surface of an applicator provided herein is positioned between 1.9 and 2.0 meters above soil level. In another aspect, the lower surface of an applicator provided herein is positioned between 0.1 and 1.5 meters above soil level. In another aspect, the lower surface of an applicator provided herein is positioned between 0.2 and 1.5 meters above soil level. In another aspect, the lower surface of an applicator provided herein is positioned between 0.3 and 1.5 meters above soil level. In another aspect, the lower surface of an applicator provided herein is positioned between 0.4 and 1.5 meters above soil level. In another aspect, the lower surface of an applicator provided herein is positioned between 0.5 and 1.5 meters above soil level. In another aspect, the lower surface of an applicator provided herein is positioned between 0.6 and 1.5 meters above soil level. In another aspect, the lower surface of an applicator provided herein is positioned between 0.7 and 1.5 meters above soil level. In another aspect, the lower surface of an applicator provided herein is positioned between 0.8 and 1.5 meters above soil level. In another aspect, the lower surface of an applicator provided herein is positioned between 0.9 and 1.5 meters above soil level. In a further aspect, the lower surface of an applicator provided herein is positioned between 1.0 and 1.5 meters above soil level. In another aspect, the lower surface of an applicator provided herein is positioned between 1.1 and 1.5 meters above soil level. In another aspect, the lower surface of an applicator provided herein is positioned between 1.2 and 1.5 meters above soil level. In another aspect, the lower surface of an applicator provided herein is positioned between 1.3 and 1.5 meters above soil level. In another aspect, the lower surface of an applicator provided herein is positioned between 1.4 and 1.5 meters above soil level. In another aspect, the lower surface of an applicator provided herein is positioned between 0.1 and 1.0 meter above soil level. In another aspect, the lower surface of an applicator provided herein is positioned between 0.2 and 1.0 meter above soil level. In another aspect, the lower surface of an applicator provided herein is positioned between 0.3 and 1.0 meter above soil level. In another aspect, the lower surface of an applicator provided herein is positioned between 0.4 and 1.0 meter above soil level. In another aspect, the lower surface of an applicator provided herein is positioned between 0.5 and 1.0 meter above soil level. In another aspect, the lower surface of an applicator provided herein is positioned between 0.6 and 1.0 meter above soil level. In another aspect, the lower surface of an applicator provided herein is positioned between 0.7 and 1.0 meter above soil level. In another aspect, the lower surface of an applicator provided herein is positioned between 0.8 and 1.0 meter above soil level. In another aspect, the lower surface of an applicator provided herein is positioned between 0.9 and 1.0 meter above soil level.

In an aspect, the lower surface of an applicator arm or boom provided herein is positioned equal to or less than 2.5 meters above soil level. In an aspect, the lower surface of an applicator arm or boom provided herein is positioned equal to or less than 2.4 meters above soil level. In an aspect, the lower surface of an applicator arm or boom provided herein is positioned equal to or less than 2.3 meters above soil level. In an aspect, the lower surface of an applicator arm or boom provided herein is positioned equal to or less than 2.2 meters above soil level. In an aspect, the lower surface of an applicator arm or boom provided herein is positioned equal to or less than 2.1 meters above soil level. In an aspect, the lower surface of an applicator arm or boom provided herein is positioned equal to or less than 2.0 meters above soil level. In another aspect, the lower surface of an applicator arm or boom provided herein is positioned equal to or less than 1.9 meters above soil level. In another aspect, the lower surface of an applicator arm or boom provided herein is positioned equal to or less than 1.8 meters above soil level. In another aspect, the lower surface of an applicator arm or boom provided herein is positioned equal to or less than 1.7 meters above soil level. In another aspect, the lower surface of an applicator arm or boom provided herein is positioned equal to or less than 1.6 meters above soil level. In another aspect, the lower surface of an applicator arm or boom provided herein is positioned equal to or less than 1.5 meters above soil level. In another aspect, the lower surface of an applicator arm or boom provided herein is positioned equal to or less than 1.4 meters above soil level. In another aspect, the lower surface of an applicator arm or boom provided herein is positioned equal to or less than 1.3 meters above soil level. In another aspect, the lower surface of an applicator arm or boom provided herein is positioned equal to or less than 1.2 meters above soil level. In another aspect, the lower surface of an applicator arm or boom provided herein is positioned equal to or less than 1.1 meters above soil level. In another aspect, the lower surface of an applicator arm or boom provided herein is positioned equal to or less than 1.0 meter above soil level. In another aspect, the lower surface of an applicator arm or boom provided herein is positioned equal to or less than 0.9 meters above soil level. In another aspect, the lower surface of an applicator arm or boom provided herein is positioned equal to or less than 0.8 meters above soil level. In another aspect, the lower surface of an applicator arm or boom provided herein is positioned equal to or less than 0.7 meters above soil level. In another aspect, the lower surface of an applicator arm or boom provided herein is positioned equal to or less than 0.6 meters above soil level. In another aspect, the lower surface of an applicator arm or boom provided herein is positioned equal to or less than 0.5 meters above soil level. In another aspect, the lower surface of an applicator arm or boom provided herein is positioned equal to or less than 0.4 meters above soil level. In another aspect, the lower surface of an applicator arm or boom provided herein is positioned equal to or less than 0.3 meters above soil level. In another aspect, the lower surface of an applicator arm or boom provided herein is positioned equal to or less than 0.2 meters above soil level. In another aspect, the lower surface of an applicator arm or boom provided herein is positioned equal to or less than 0.1 meters above soil level.

In an aspect, the lower surface of an applicator arm or boom provided herein is positioned between 0.1 and 2.5 meters above soil level. In an aspect, the lower surface of an applicator arm or boom provided herein is positioned between 0.2 and 2.5 meters above soil level. In an aspect, the lower surface of an applicator arm or boom provided herein is positioned between 0.3 and 2.5 meters above soil level. In an aspect, the lower surface of an applicator arm or boom provided herein is positioned between 0.4 and 2.5 meters above soil level. In an aspect, the lower surface of an applicator arm or boom provided herein is positioned between 0.5 and 2.5 meters above soil level. In an aspect, the lower surface of an applicator arm or boom provided herein is positioned between 0.6 and 2.5 meters above soil level. In an aspect, the lower surface of an applicator arm or boom provided herein is positioned between 0.7 and 2.5 meters above soil level. In an aspect, the lower surface of an applicator arm or boom provided herein is positioned between 0.8 and 2.5 meters above soil level. In an aspect, the lower surface of an applicator arm or boom provided herein is positioned between 0.9 and 2.5 meters above soil level. In an aspect, the lower surface of an applicator arm or boom provided herein is positioned between 1.0 and 2.5 meters above soil level. In an aspect, the lower surface of an applicator arm or boom provided herein is positioned between 1.1 and 2.5 meters above soil level. In an aspect, the lower surface of an applicator arm or boom provided herein is positioned between 1.2 and 2.5 meters above soil level. In an aspect, the lower surface of an applicator arm or boom provided herein is positioned between 1.3 and 2.5 meters above soil level. In an aspect, the lower surface of an applicator arm or boom provided herein is positioned between 1.4 and 2.5 meters above soil level. In an aspect, the lower surface of an applicator arm or boom provided herein is positioned between 1.5 and 2.5 meters above soil level. In an aspect, the lower surface of an applicator arm or boom provided herein is positioned between 1.6 and 2.5 meters above soil level. In an aspect, the lower surface of an applicator arm or boom provided herein is positioned between 1.7 and 2.5 meters above soil level. In an aspect, the lower surface of an applicator arm or boom provided herein is positioned between 1.8 and 2.5 meters above soil level. In an aspect, the lower surface of an applicator arm or boom provided herein is positioned between 1.9 and 2.5 meters above soil level. In an aspect, the lower surface of an applicator arm or boom provided herein is positioned between 2.0 and 2.5 meters above soil level. In an aspect, the lower surface of an applicator arm or boom provided herein is positioned between 2.3 and 2.5 meters above soil level. In another aspect, the lower surface of an applicator arm or boom provided herein is positioned between 0.1 and 2.0 meters above soil level. In another aspect, the lower surface of an applicator arm or boom provided herein is positioned between 0.2 and 2.0 meters above soil level. In another aspect, the lower surface of an applicator arm or boom provided herein is positioned between 0.3 and 2.0 meters above soil level. In another aspect, the lower surface of an applicator arm or boom provided herein is positioned between 0.4 and 2.0 meters above soil level. In another aspect, the lower surface of an applicator arm or boom provided herein is positioned between 0.5 and 2.0 meters above soil level. In another aspect, the lower surface of an applicator arm or boom provided herein is positioned between 0.6 and 2.0 meters above soil level. In another aspect, the lower surface of an applicator arm or boom provided herein is positioned between 0.7 and 2.0 meters above soil level. In another aspect, the lower surface of an applicator arm or boom provided herein is positioned between 0.8 and 2.0 meters above soil level. In another aspect, the lower surface of an applicator arm or boom provided herein is positioned between 0.9 and 2.0 meters above soil level. In a further aspect, the lower surface of an applicator arm or boom provided herein is positioned between 1.0 and 2.0 meters above soil level. In another aspect, the lower surface of an applicator arm or boom provided herein is positioned between 1.1 and 2.0 meters above soil level. In another aspect, the lower surface of an applicator arm or boom provided herein is positioned between 1.2 and 2.0 meters above soil level. In another aspect, the lower surface of an applicator arm or boom provided herein is positioned between 1.3 and 2.0 meters above soil level. In another aspect, the lower surface of an applicator arm or boom provided herein is positioned between 1.4 and 2.0 meters above soil level. In another aspect, the lower surface of an applicator arm or boom provided herein is positioned between 1.5 and 2.0 meters above soil level. In another aspect, the lower surface of an applicator arm or boom provided herein is positioned between 1.6 and 2.0 meters above soil level. In another aspect, the lower surface of an applicator arm or boom provided herein is positioned between 1.7 and 2.0 meters above soil level. In another aspect, the lower surface of an applicator arm or boom provided herein is positioned between 1.8 and 2.0 meters above soil level. In another aspect, the lower surface of an applicator arm or boom provided herein is positioned between 1.9 and 2.0 meters above soil level. In another aspect, the lower surface of an applicator arm or boom provided herein is positioned between 0.1 and 1.5 meters above soil level. In another aspect, the lower surface of an applicator arm or boom provided herein is positioned between 0.2 and 1.5 meters above soil level. In another aspect, the lower surface of an applicator arm or boom provided herein is positioned between 0.3 and 1.5 meters above soil level. In another aspect, the lower surface of an applicator arm or boom provided herein is positioned between 0.4 and 1.5 meters above soil level. In another aspect, the lower surface of an applicator arm or boom provided herein is positioned between 0.5 and 1.5 meters above soil level. In another aspect, the lower surface of an applicator arm or boom provided herein is positioned between 0.6 and 1.5 meters above soil level. In another aspect, the lower surface of an applicator arm or boom provided herein is positioned between 0.7 and 1.5 meters above soil level. In another aspect, the lower surface of an applicator arm or boom provided herein is positioned between 0.8 and 1.5 meters above soil level. In another aspect, the lower surface of an applicator arm or boom provided herein is positioned between 0.9 and 1.5 meters above soil level. In a further aspect, the lower surface of an applicator arm or boom provided herein is positioned between 1.0 and 1.5 meters above soil level. In another aspect, the lower surface of an applicator arm or boom provided herein is positioned between 1.1 and 1.5 meters above soil level. In another aspect, the lower surface of an applicator arm or boom provided herein is positioned between 1.2 and 1.5 meters above soil level. In another aspect, the lower surface of an applicator arm or boom provided herein is positioned between 1.3 and 1.5 meters above soil level. In another aspect, the lower surface of an applicator arm or boom provided herein is positioned between 1.4 and 1.5 meters above soil level. In another aspect, the lower surface of an applicator arm or boom provided herein is positioned between 0.1 and 1.0 meter above soil level. In another aspect, the lower surface of an applicator arm or boom provided herein is positioned between 0.2 and 1.0 meter above soil level. In another aspect, the lower surface of an applicator arm or boom provided herein is positioned between 0.3 and 1.0 meter above soil level. In another aspect, the lower surface of an applicator arm or boom provided herein is positioned between 0.4 and 1.0 meter above soil level. In another aspect, the lower surface of an applicator arm or boom provided herein is positioned between 0.5 and 1.0 meter above soil level. In another aspect, the lower surface of an applicator arm or boom provided herein is positioned between 0.6 and 1.0 meter above soil level. In another aspect, the lower surface of an applicator arm or boom provided herein is positioned between 0.7 and 1.0 meter above soil level. In another aspect, the lower surface of an applicator arm or boom provided herein is positioned between 0.8 and 1.0 meter above soil level. In another aspect, the lower surface of an applicator arm or boom provided herein is positioned between 0.9 and 1.0 meter above soil level.

If a ground-based agricultural vehicle, including for example a main body and/or an applicator, such as an applicator arm or boom, has a clearance height below (or significantly below) the height(s) of the corn plants to which it is spraying or applying an agricultural composition, the equipment or machinery can damage the corn plants. Damaged plants are more susceptible to disease than undamaged plants, and damage can significantly reduce yield. Damage to the top of plants may destroy tassels needed for pollen and fertilization. All parts of the corn plant could be susceptible to damage if the plant is contacted by any equipment or machinery. For example, damage can consist of torn, ripped, broken, or shredded leaves; torn, ripped, broken, or shredded tassels; torn, ripped, broken, or shredded stems; or torn, ripped, broken, or shredded ears. In extreme cases, damage can kill or lodge the entire plant.

In an aspect, at least 50% of the corn plants in a corn field provided herein are not damaged by a ground-based agricultural vehicle. In another aspect, at least 55% of the corn plants in a corn field provided herein are not damaged by a ground-based agricultural vehicle. In another aspect, at least 60% of the corn plants in a corn field provided herein are not damaged by a ground-based agricultural vehicle. In another aspect, at least 65% of the corn plants in a corn field provided herein are not damaged by a ground-based agricultural vehicle. In another aspect, at least 70% of the corn plants in a corn field provided herein are not damaged by a ground-based agricultural vehicle. In another aspect, at least 75% of the corn plants in a corn field provided herein are not damaged by a ground-based agricultural vehicle. In another aspect, at least 80% of the corn plants in a corn field provided herein are not damaged by a ground-based agricultural vehicle. In another aspect, at least 85% of the corn plants in a corn field provided herein are not damaged by a ground-based agricultural vehicle. In another aspect, at least 90% of the corn plants in a corn field provided herein are not damaged by a ground-based agricultural vehicle. In another aspect, at least 95% of the corn plants in a corn field provided herein are not damaged by a ground-based agricultural vehicle. In another aspect, 100% of the corn plants in a corn field provided herein are not damaged by a ground-based agricultural vehicle.

In an aspect, at least 50% of the corn plants in a corn field provided herein are not damaged by a main body and/or an applicator. In another aspect, at least 55% of the corn plants in a corn field provided herein are not damaged by a main body and/or an applicator. In another aspect, at least 60% of the corn plants in a corn field provided herein are not damaged by a main body and/or an applicator. In another aspect, at least 65% of the corn plants in a corn field provided herein are not damaged by a main body and/or an applicator. In another aspect, at least 70% of the corn plants in a corn field provided herein are not damaged by a main body and/or an applicator. In another aspect, at least 75% of the corn plants in a corn field provided herein are not damaged by a main body and/or an applicator. In another aspect, at least 80% of the corn plants in a corn field provided herein are not damaged by a main body and/or an applicator. In another aspect, at least 85% of the corn plants in a corn field provided herein are not damaged by a main body and/or an applicator. In another aspect, at least 90% of the corn plants in a corn field provided herein are not damaged by a main body and/or an applicator. In another aspect, at least 95% of the corn plants in a corn field provided herein are not damaged by a main body and/or an applicator. In another aspect, 100% of the corn plants in a corn field provided herein are not damaged by a main body and/or an applicator.

In an aspect, at least 50% of the corn plants in a corn field provided herein are not damaged by an applicator arm or boom. In another aspect, at least 55% of the corn plants in a corn field provided herein are not damaged by an applicator arm or boom. In another aspect, at least 60% of the corn plants in a corn field provided herein are not damaged by an applicator arm or boom. In another aspect, at least 65% of the corn plants in a corn field provided herein are not damaged by an applicator arm or boom. In another aspect, at least 70% of the corn plants in a corn field provided herein are not damaged by an applicator arm or boom. In another aspect, at least 75% of the corn plants in a corn field provided herein are not damaged by an applicator arm or boom. In another aspect, at least 80% of the corn plants in a corn field provided herein are not damaged by an applicator arm or boom. In another aspect, at least 85% of the corn plants in a corn field provided herein are not damaged by an applicator arm or boom. In another aspect, at least 90% of the corn plants in a corn field provided herein are not damaged by an applicator arm or boom. In another aspect, at least 95% of the corn plants in a corn field provided herein are not damaged by an applicator arm or boom. In another aspect, 100% of the corn plants in a corn field provided herein are not damaged by an applicator arm or boom.

In an aspect, at least 50% of the corn plants in a corn field provided herein are not damaged by application of an agricultural composition. In another aspect, at least 55% of the corn plants in a corn field provided herein are not damaged by application of an agricultural composition. In another aspect, at least 60% of the corn plants in a corn field provided herein are not damaged by application of an agricultural composition. In another aspect, at least 65% of the corn plants in a corn field provided herein are not damaged by application of an agricultural composition. In another aspect, at least 70% of the corn plants in a corn field provided herein are not damaged by application of an agricultural composition. In another aspect, at least 75% of the corn plants in a corn field provided herein are not damaged by application of an agricultural composition. In another aspect, at least 80% of the corn plants in a corn field provided herein are not damaged by application of an agricultural composition. In another aspect, at least 85% of the corn plants in a corn field provided herein are not damaged by application of an agricultural composition. In another aspect, at least 90% of the corn plants in a corn field provided herein are not damaged by application of an agricultural composition. In another aspect, at least 95% of the corn plants in a corn field provided herein are not damaged by application of an agricultural composition. In another aspect, 100% of the corn plants in a corn field provided herein are not damaged by application of an agricultural composition.

In an aspect, at least 50% of the corn plants in a corn field provided herein are not damaged by application of a fertilizer. In another aspect, at least 55% of the corn plants in a corn field provided herein are not damaged by application of a fertilizer. In another aspect, at least 60% of the corn plants in a corn field provided herein are not damaged by application of a fertilizer. In another aspect, at least 65% of the corn plants in a corn field provided herein are not damaged by application of a fertilizer. In another aspect, at least 70% of the corn plants in a corn field provided herein are not damaged by application of a fertilizer. In another aspect, at least 75% of the corn plants in a corn field provided herein are not damaged by application of a fertilizer. In another aspect, at least 80% of the corn plants in a corn field provided herein are not damaged by application of a fertilizer. In another aspect, at least 85% of the corn plants in a corn field provided herein are not damaged by application of a fertilizer. In another aspect, at least 90% of the corn plants in a corn field provided herein are not damaged by application of a fertilizer. In another aspect, at least 95% of the corn plants in a corn field provided herein are not damaged by application of a fertilizer. In another aspect, 100% of the corn plants in a corn field provided herein are not damaged by application of a fertilizer.

In an aspect, at least 50% of the corn plants in a corn field provided herein are not damaged by application of a pesticide. In another aspect, at least 55% of the corn plants in a corn field provided herein are not damaged by application of a pesticide. In another aspect, at least 60% of the corn plants in a corn field provided herein are not damaged by application of a pesticide. In another aspect, at least 65% of the corn plants in a corn field provided herein are not damaged by application of a pesticide. In another aspect, at least 70% of the corn plants in a corn field provided herein are not damaged by application of a pesticide. In another aspect, at least 75% of the corn plants in a corn field provided herein are not damaged by application of a pesticide. In another aspect, at least 80% of the corn plants in a corn field provided herein are not damaged by application of a pesticide. In another aspect, at least 85% of the corn plants in a corn field provided herein are not damaged by application of a pesticide. In another aspect, at least 90% of the corn plants in a corn field provided herein are not damaged by application of a pesticide. In another aspect, at least 95% of the corn plants in a corn field provided herein are not damaged by application of a pesticide. In another aspect, 100% of the corn plants in a corn field provided herein are not damaged by application of a pesticide.

In an aspect, at least 50% of the corn plants in a corn field provided herein are not damaged by application of a cover crop seed. In another aspect, at least 55% of the corn plants in a corn field provided herein are not damaged by application of a cover crop seed. In another aspect, at least 60% of the corn plants in a corn field provided herein are not damaged by application of a cover crop seed. In another aspect, at least 65% of the corn plants in a corn field provided herein are not damaged by application of a cover crop seed. In another aspect, at least 70% of the corn plants in a corn field provided herein are not damaged by application of a cover crop seed. In another aspect, at least 75% of the corn plants in a corn field provided herein are not damaged by application of a cover crop seed. In another aspect, at least 80% of the corn plants in a corn field provided herein are not damaged by application of a cover crop seed. In another aspect, at least 85% of the corn plants in a corn field provided herein are not damaged by application of a cover crop seed. In another aspect, at least 90% of the corn plants in a corn field provided herein are not damaged by application of a cover crop seed. In another aspect, at least 95% of the corn plants in a corn field provided herein are not damaged by application of a cover crop seed. In another aspect, 100% of the corn plants in a corn field provided herein are not damaged by application of a cover crop seed.

In some aspects, methods provided herein can comprise having, positioning, or adjusting the height of an applicator, such as an applicator arm or boom, of a ground-based agricultural vehicle such that the lower exterior surface of the applicator is within an acceptable distance or height at or below the average height of the corn plants in a corn field (or a given percentage of corn plants in a corn field), such that the applicator does not significantly damage the corn plants, even if the applicator touches or contacts an upper or top portion of the corn plants. In an aspect, methods provided herein can comprise having, positioning, or adjusting the height of an applicator, such as an applicator arm or boom, of a ground-based agricultural vehicle such that the lower exterior surface of the applicator is equal to or less than 20 centimeters shorter or lower (i.e., no more than 20 centimeters shorter or lower) than the average height of the corn plants in a corn field (or a given percentage of corn plants in a corn field). The lower exterior surface of the applicator of a ground-based agricultural vehicle (whether fixed or adjustable) may be at a height that is equal to or less than 20 centimeters shorter or lower (i.e., no more than 20 centimeters shorter or lower) than the average height of the corn plants in a corn field (or a given percentage of corn plants in a corn field). In an aspect, methods provided herein can comprise having, positioning, or adjusting the height of an applicator, such as an applicator arm or boom, of a ground-based agricultural vehicle such that the lower exterior surface of the applicator is equal to or less than 15 centimeters shorter or lower (i.e., no more than 15 centimeters shorter or lower) than the average height of corn plants in a corn field (or a given percentage of corn plants in a corn field). The lower exterior surface of the applicator of a ground-based agricultural vehicle (whether fixed or adjustable) may be at a height that is equal to or less than 15 centimeters shorter or lower (i.e., no more than 15 centimeters shorter or lower) than the average height of the corn plants in a corn field (or a given percentage of corn plants in a corn field). In another aspect, methods provided herein can comprise having, positioning, or adjusting the height of an applicator, such as an applicator arm or boom, of a ground-based agricultural vehicle such that the lower exterior surface of the applicator is equal to or less than 10 centimeters shorter or lower (i.e., no more than 10 centimeters shorter or lower) than the average height of the corn plants in a corn field (or a given percentage of corn plants in a corn field). The lower exterior surface of the applicator of a ground-based agricultural vehicle (whether fixed or adjustable) may be at a height that is equal to or less than 10 centimeters shorter or lower (i.e., no more than 10 centimeters shorter or lower) than the average height of the corn plants in a corn field (or a given percentage of corn plants in a corn field). In another aspect, methods provided herein can comprise having, positioning, or adjusting the height of an applicator, such as an applicator arm or boom, of a ground-based agricultural vehicle such that the lower exterior surface of the applicator is equal to or less than 5 centimeters shorter or lower (i.e., no more than 5 centimeters shorter or lower) than the average height of the corn plants in a corn field (or a given percentage of corn plants in a corn field). The lower exterior surface of the applicator of a ground-based agricultural vehicle (whether fixed or adjustable) may be at a height that is equal to or less than 5 centimeters shorter or lower (i.e., no more than 5 centimeters shorter or lower) than the average height of the corn plants in a corn field (or a given percentage of corn plants in a corn field). In another aspect, methods provided herein can comprise having, positioning, or adjusting the height of an applicator, such as an applicator arm or boom, of a ground-based agricultural vehicle such that the lower exterior surface of the applicator is equal to or less than 1 centimeter shorter or lower (i.e., no more than 1 centimeters shorter or lower) than the average height of the corn plants in a corn field (or a given percentage of corn plants in a corn field). The lower exterior surface of the applicator of a ground-based agricultural vehicle (whether fixed or adjustable) may be at a height that is equal to or less than 1 centimeters shorter or lower (i.e., no more than 1 centimeters shorter or lower) than the average height of the corn plants in a corn field (or a given percentage of corn plants in a corn field).

To avoid damaging a corn plant, the lowest part of equipment or machinery (e.g., a main body and/or applicator) may be at, or be positioned or adjusted to, a height that is equal to, above or higher than the average height of corn plants in a corn field (or a given percentage of corn plants in a corn field). In an aspect, the lower exterior surface of a main body of a ground-based agricultural vehicle is at, or positioned or adjusted to, a height that is above or higher than the average height of corn plants in a corn field (or a given percentage of corn plants in a corn field). In an aspect, the lower exterior surface of an applicator is at, or positioned or adjusted to, a height that is above or higher than the average height of corn plants in a corn field (or a given percentage of corn plants in a corn field). In an aspect, the lower exterior surface of an applicator arm or boom is at, or positioned or adjusted to, a height that is above or higher than the average height of corn plants in a corn field (or a given percentage of corn plants in a corn field). In an aspect, the lower exterior surface of a main body of a ground-based agricultural vehicle is at, or positioned or adjusted to, a height that is at least 1 centimeter above or higher than the average height of corn plants in a corn field (or a given percentage of corn plants in a corn field). In an aspect, the lower exterior surface of an applicator is at, or positioned or adjusted to, a height that is at least 1 centimeter above or higher than the average height of corn plants in a corn field (or a given percentage of corn plants in a corn field). In an aspect, the lower exterior surface of an applicator arm or boom is at, or positioned or adjusted to, a height that is at least 1 centimeter above or higher than the average height of corn plants in a corn field (or a given percentage of corn plants in a corn field). In an aspect, the lower exterior surface of a main body of a ground-based agricultural vehicle is at, or positioned or adjusted to, a height that is at least 5 centimeters above or higher than the average height of corn plants in a corn field (or a given percentage of corn plants in a corn field). In an aspect, the lower exterior surface of an applicator is at, or positioned or adjusted to, a height that is at least 5 centimeters above or higher than the average height of corn plants in a corn field (or a given percentage of corn plants in a corn field). In an aspect, the lower exterior surface of an applicator arm or boom is at, or positioned or adjusted to, a height that is at least 5 centimeters above or higher than the average height of corn plants in a corn field. In an aspect, the lower exterior surface of a main body of a ground-based agricultural vehicle is at, or positioned or adjusted to, a height that is at least 10 centimeters above or higher than the average height of corn plants in a corn field (or a given percentage of corn plants in a corn field). In an aspect, the lower exterior surface of an applicator is at, or positioned or adjusted to, a height that is at least 10 centimeters above or higher than the average height of corn plants in a corn field (or a given percentage of corn plants in a corn field). In an aspect, the lower exterior surface of an applicator arm or boom is at, or positioned or adjusted to, a height that is at least 10 centimeters above or higher than the average height of corn plants in a corn field (or a given percentage of corn plants in a corn field).

In an aspect, the lower exterior surface of a main body and/or applicator of a ground-based agricultural vehicle is positioned at a height that is equal to or above the average height of the corn plants in a corn field or a given percentage of corn plants in a corn field. In an aspect, the lower exterior surface of a main body and/or applicator of a ground-based agricultural vehicle is positioned at a height that is equal to or less than 20 centimeters taller or higher—i.e., no more 20 centimeters taller or higher—than the average height of the corn plants in a corn field or a given percentage of corn plants in a corn field. In an aspect, the lower exterior surface of a main body and/or applicator of a ground-based agricultural vehicle is positioned at a height that is equal to or less than 15 centimeters taller or higher—i.e., no more 15 centimeters taller or higher—than the average height of the corn plants in a corn field or a given percentage of corn plants in a corn field. In an aspect, the lower exterior surface of a main body and/or applicator of a ground-based agricultural vehicle is positioned at a height that is equal to or less than 10 centimeters taller or higher—i.e., no more 10 centimeters taller or higher—than the average height of the corn plants in a corn field or a given percentage of corn plants in a corn field. In an aspect, the lower exterior surface of a main body and/or applicator of a ground-based agricultural vehicle is positioned at a height that is equal to or less than 5 centimeters taller or higher—i.e., no more 5 centimeters taller or higher—than the average height of the corn plants in a corn field or a given percentage of corn plants in a corn field. In an aspect, the lower exterior surface of a main body and/or applicator of a ground-based agricultural vehicle is positioned at a height that is equal to or less than 1 centimeter taller or higher—i.e., no more 1 centimeter taller or higher—than the average height of the corn plants in a corn field or a given percentage of corn plants in a corn field.

In an aspect, the lower exterior surface of a main body and/or an applicator, such as an applicator arm or boom, of a ground-based agricultural vehicle is/are at a height that is within a range from a height that is 20 centimeters shorter or lower than the average height of the corn plants in a corn field (or a given percentage of corn plants in a corn field) to a height that is 20 centimeters taller or higher than the average height of the corn plants in a corn field (or the given percentage of corn plants in a corn field)—i.e., within a range from 20 centimeters shorter or lower to 20 centimeters taller or higher than the average height of the corn plants in a corn field, the tallest corn plant in a corn field, or a given percentage of corn plants in a corn field. In an aspect, the lower exterior surface of a main body and/or an applicator, such as an applicator arm or boom, of a ground-based agricultural vehicle is/are at a height that is within a range from a height that is 15 centimeters shorter or lower than the average height of the corn plants in a corn field (or a given percentage of corn plants in a corn field) to a height that is 15 centimeters taller or higher than the average height of the corn plants in a corn field (or the given percentage of corn plants in a corn field)—i.e., within a range from 15 centimeters shorter or lower to 15 centimeters taller or higher than the average height of the corn plants in a corn field, the tallest corn plant in a corn field, or a given percentage of corn plants in a corn field. In an aspect, the lower exterior surface of a main body and/or an applicator, such as an applicator arm or boom, of a ground-based agricultural vehicle is/are at a height that is within a range from a height that is 15 centimeters shorter or lower than the average height of the corn plants in a corn field (or a given percentage of corn plants in a corn field) to a height that is 10 centimeters taller or higher than the average height of the corn plants in a corn field (or the given percentage of corn plants in a corn field)—i.e., within a range from 15 centimeters shorter or lower to 10 centimeters taller or higher than the average height of the corn plants in a corn field, the tallest corn plant in a corn field, or a given percentage of corn plants in a corn field. In an aspect, the lower exterior surface of a main body and/or an applicator, such as an applicator arm or boom, of a ground-based agricultural vehicle is/are at a height that is within a range from a height that is 15 centimeters shorter or lower than the average height of the corn plants in a corn field (or a given percentage of corn plants in a corn field) to a height that is 5 centimeters taller or higher than the average height of the corn plants in a corn field (or the given percentage of corn plants in a corn field)—i.e., within a range from 15 centimeters shorter or lower to 5 centimeters taller or higher than the average height of the corn plants in a corn field, the tallest corn plant in a corn field, or a given percentage of corn plants in a corn field. In an aspect, the lower exterior surface of a main body and/or an applicator, such as an applicator arm or boom, of a ground-based agricultural vehicle is/are at a height that is within a range from a height that is 10 centimeters shorter or lower than the average height of the corn plants in a corn field (or a given percentage of corn plants in a corn field) to a height that is 5 centimeters taller or higher than the average height of the corn plants in a corn field (or the given percentage of corn plants in a corn field)—i.e., within a range from 10 centimeters shorter or lower to 5 centimeters taller or higher than the average height of the corn plants in a corn field, the tallest corn plant in a corn field, or a given percentage of corn plants in a corn field. Any other ranges of heights that are no more than 20 centimeters shorter or lower than the average height of the corn plants in a corn field (or the given percentage of corn plants in a corn field) are also contemplated.

In another aspect, methods provided herein can comprise having, positioning, or adjusting the height of a main body and/or an applicator of a ground-based agricultural vehicle, such that the lower exterior surface of the main body and/or applicator is equal to or greater than 1 centimeter taller or higher than the average height of the corn plants in a corn field (or a given percentage of corn plants in a corn field). In another aspect, methods provided herein can comprise having, positioning, or adjusting the height of main body and/or an applicator of a ground-based agricultural vehicle, such that the lower exterior surface of the applicator arm or boom is equal to or greater than 5 centimeters taller or higher than the average height of the corn plants in a corn field (or a given percentage of corn plants in a corn field). In another aspect, methods provided herein can comprise having, positioning, or adjusting the height of a main body and/or an applicator of a ground-based agricultural vehicle, such that the lower exterior surface of the main body and/or applicator is equal to or greater than 10 centimeters taller or higher than the average height of the corn plants in a corn field (or a given percentage of corn plants in a corn field). In another aspect, methods provided herein can comprise having, positioning, or adjusting the height of a main body and/or an applicator of a ground-based agricultural vehicle such that the lower exterior surface of the applicator is equal to or greater than 15 centimeters taller than the average height of the corn plants in a corn field (or a given percentage of corn plants in a corn field). In another aspect, methods provided herein can comprise having, positioning, or adjusting the height of a main body and/or an applicator of a ground-based agricultural vehicle, such that the lower exterior surface of the main body and/or applicator is equal to or greater than 20 centimeters taller than the average height of the corn plants in a corn field (or a given percentage of corn plants in a corn field).

Although it is preferred to avoid contact between equipment or machinery and a corn plant, it is also possible as stated above for equipment or machinery to graze the top of a corn plant without damaging it. In an aspect, the lower exterior surface of a main body of a ground-based agricultural vehicle is positioned at a height that is equal to or less than 15 centimeters lower than the average height of corn plants in a corn field. In an aspect, the lower exterior surface of a main body of a ground-based agricultural vehicle is positioned at a height that is equal to or less than 10 centimeters lower than the average height of corn plants in a corn field. In an aspect, the lower exterior surface of a main body of a ground-based agricultural vehicle is positioned at a height that is equal to or less than 5 centimeters lower than the average height of corn plants in a corn field. In an aspect, the lower exterior surface of a main body of a ground-based agricultural vehicle is positioned at a height that is equal to or less than 4 centimeters lower than the average height of corn plants in a corn field. In an aspect, the lower exterior surface of a main body of a ground-based agricultural vehicle is positioned at a height that is equal to or less than 3 centimeters lower than the average height of corn plants in a corn field. In an aspect, the lower exterior surface of a main body of a ground-based agricultural vehicle is positioned at a height that is equal to or less than 2 centimeters lower than the average height of corn plants in a corn field. In an aspect, the lower exterior surface of a main body of a ground-based agricultural vehicle is positioned at a height that is equal to or less than 1 centimeter lower than the average height of corn plants in a corn field.

In an aspect, the lower exterior surface of an applicator is positioned at a height that is equal to or less than 15 centimeters lower than the average height of corn plants in a corn field. In an aspect, the lower exterior surface of an applicator is positioned at a height that is equal to or less than 10 centimeters lower than the average height of corn plants in a corn field. In an aspect, the lower exterior surface of an applicator is positioned at a height that is equal to or less than 5 centimeters lower than the average height of corn plants in a corn field. In an aspect, the lower exterior surface of an applicator is positioned at a height that is equal to or less than 4 centimeters lower than the average height of corn plants in a corn field. In an aspect, the lower exterior surface of an applicator is positioned at a height that is equal to or less than 3 centimeters lower than the average height of corn plants in a corn field. In an aspect, the lower exterior surface of an applicator is positioned at a height that is equal to or less than 2 centimeters lower than the average height of corn plants in a corn field. In an aspect, the lower exterior surface of an applicator is positioned at a height that is equal to or less than 1 centimeter lower than the average height of corn plants in a corn field.

In an aspect, the lower exterior surface of an applicator arm or boom is positioned at a height that is equal to or less than 15 centimeters lower than the average height of corn plants in a corn field. In an aspect, the lower exterior surface of an applicator arm or boom is positioned at a height that is equal to or less than 10 centimeters lower than the average height of corn plants in a corn field. In an aspect, the lower exterior surface of an applicator arm or boom is positioned at a height that is equal to or less than 5 centimeters lower than the average height of corn plants in a corn field. In an aspect, the lower exterior surface of an applicator arm or boom is positioned at a height that is equal to or less than 4 centimeters lower than the average height of corn plants in a corn field. In an aspect, the lower exterior surface of an applicator arm or boom is positioned at a height that is equal to or less than 3 centimeters lower than the average height of corn plants in a corn field. In an aspect, the lower exterior surface of an applicator arm or boom is positioned at a height that is equal to or less than 2 centimeters lower than the average height of corn plants in a corn field. In an aspect, the lower exterior surface of an applicator arm or boom is positioned at a height that is equal to or less than 1 centimeter lower than the average height of corn plants in a corn field.

In an aspect, the lower exterior surface of a main body of a ground-based agricultural vehicle provided herein is between 0 and 15 centimeters lower than the average height of corn plants in a corn field. In an aspect, the lower exterior surface of a main body of a ground-based agricultural vehicle provided herein is between 0 and 10 centimeters lower than the average height of corn plants in a corn field. In an aspect, the lower exterior surface of a main body of a ground-based agricultural vehicle provided herein is between 0 and 5 centimeters lower than the average height of corn plants in a corn field. In an aspect, the lower exterior surface of a main body of a ground-based agricultural vehicle provided herein is between 0 and 4 centimeters lower than the average height of corn plants in a corn field. In an aspect, the lower exterior surface of a main body of a ground-based agricultural vehicle provided herein is between 0 and 3 centimeters lower than the average height of corn plants in a corn field. In an aspect, the lower exterior surface of a main body of a ground-based agricultural vehicle provided herein is between 0 and 2 centimeters lower than the average height of corn plants in a corn field. In an aspect, the lower exterior surface of a main body of a ground-based agricultural vehicle provided herein is between 1 and 15 centimeters lower than the average height of corn plants in a corn field. In an aspect, the lower exterior surface of a main body of a ground-based agricultural vehicle provided herein is between 2 and 15 centimeters lower than the average height of corn plants in a corn field. In an aspect, the lower exterior surface of a main body of a ground-based agricultural vehicle provided herein is between 3 and 15 centimeters lower than the average height of corn plants in a corn field. In an aspect, the lower exterior surface of a main body of a ground-based agricultural vehicle provided herein is between 4 and 15 centimeters lower than the average height of corn plants in a corn field. In an aspect, the lower exterior surface of a main body of a ground-based agricultural vehicle provided herein is between 5 and 15 centimeters lower than the average height of corn plants in a corn field. In an aspect, the lower exterior surface of a main body of a ground-based agricultural vehicle provided herein is between 10 and 15 centimeters lower than the average height of corn plants in a corn field. In an aspect, the lower exterior surface of a main body of a ground-based agricultural vehicle provided herein is between 1 and 10 centimeters lower than the average height of corn plants in a corn field.

In an aspect, the lower exterior surface of a main body of an applicator provided herein is between 0 and 15 centimeters lower than the average height of corn plants in a corn field. In an aspect, the lower exterior surface of a main body of an applicator provided herein is between 0 and 10 centimeters lower than the average height of corn plants in a corn field. In an aspect, the lower exterior surface of a main body of an applicator provided herein is between 0 and 5 centimeters lower than the average height of corn plants in a corn field. In an aspect, the lower exterior surface of a main body of an applicator provided herein is between 0 and 4 centimeters lower than the average height of corn plants in a corn field. In an aspect, the lower exterior surface of a main body of an applicator provided herein is between 0 and 3 centimeters lower than the average height of corn plants in a corn field. In an aspect, the lower exterior surface of a main body of an applicator provided herein is between 0 and 2 centimeters lower than the average height of corn plants in a corn field. In an aspect, the lower exterior surface of a main body of an applicator provided herein is between 1 and 15 centimeters lower than the average height of corn plants in a corn field. In an aspect, the lower exterior surface of a main body of an applicator provided herein is between 2 and 15 centimeters lower than the average height of corn plants in a corn field. In an aspect, the lower exterior surface of a main body of an applicator provided herein is between 3 and 15 centimeters lower than the average height of corn plants in a corn field. In an aspect, the lower exterior surface of a main body of an applicator provided herein is between 4 and 15 centimeters lower than the average height of corn plants in a corn field. In an aspect, the lower exterior surface of a main body of an applicator provided herein is between 5 and 15 centimeters lower than the average height of corn plants in a corn field. In an aspect, the lower exterior surface of a main body of an applicator provided herein is between 10 and 15 centimeters lower than the average height of corn plants in a corn field. In an aspect, the lower exterior surface of a main body of an applicator provided herein is between 1 and 10 centimeters lower than the average height of corn plants in a corn field.

In an aspect, the lower exterior surface of a main body of an applicator arm or boom provided herein is between 0 and 15 centimeters lower than the average height of corn plants in a corn field. In an aspect, the lower exterior surface of a main body of an applicator arm or boom provided herein is between 0 and 10 centimeters lower than the average height of corn plants in a corn field. In an aspect, the lower exterior surface of a main body of an applicator arm or boom provided herein is between 0 and 5 centimeters lower than the average height of corn plants in a corn field. In an aspect, the lower exterior surface of a main body of an applicator arm or boom provided herein is between 0 and 4 centimeters lower than the average height of corn plants in a corn field. In an aspect, the lower exterior surface of a main body of an applicator arm or boom provided herein is between 0 and 3 centimeters lower than the average height of corn plants in a corn field. In an aspect, the lower exterior surface of a main body of an applicator arm or boom provided herein is between 0 and 2 centimeters lower than the average height of corn plants in a corn field. In an aspect, the lower exterior surface of a main body of an applicator arm or boom provided herein is between 1 and 15 centimeters lower than the average height of corn plants in a corn field. In an aspect, the lower exterior surface of a main body of an applicator arm or boom provided herein is between 2 and 15 centimeters lower than the average height of corn plants in a corn field. In an aspect, the lower exterior surface of a main body of an applicator arm or boom provided herein is between 3 and 15 centimeters lower than the average height of corn plants in a corn field. In an aspect, the lower exterior surface of a main body of an applicator arm or boom provided herein is between 4 and 15 centimeters lower than the average height of corn plants in a corn field. In an aspect, the lower exterior surface of a main body of an applicator arm or boom provided herein is between 5 and 15 centimeters lower than the average height of corn plants in a corn field. In an aspect, the lower exterior surface of a main body of an applicator arm or boom provided herein is between 10 and 15 centimeters lower than the average height of corn plants in a corn field. In an aspect, the lower exterior surface of a main body of an applicator arm or boom provided herein is between 1 and 10 centimeters lower than the average height of corn plants in a corn field.

In an aspect, this disclosure provides a method of providing an agricultural composition to a plurality of corn plants in a corn field, comprising applying the agricultural composition to the corn plants of the corn field from above using a ground-based agricultural vehicle comprising an applicator arm or boom for applying the agricultural composition, where the lower exterior surface of the applicator arm or boom is at a height equal to or less than 2.5 meters, equal to or less than 2.4 meters, equal to or less than 2.3 meters, equal to or less than 2.2 meters, equal to or less than 2.1 meters, equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.5 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, or equal to or less than 0.1 meters above the top of the soil or ground level, and is and is equal to, or less than 15 centimeters shorter or lower (i.e., no more than 15 centimeters shorter or lower) than the highest point of the corn plants, and where the corn plants are at V6 stage or later, V7 stage or later, V8 stage or later, V9 stage or later, V10 stage or later, V11 stage or later, V12 stage or later, V13 stage or later, V14 stage or later, V15 stage or later, R1 stage or later, R2 stage or later, R3 stage or later, R4 stage or later, or R5 stage or later.

In an aspect, this disclosure provides a method of providing an agricultural composition, such as water and/or a fertilizer, pesticide, insecticide, herbicide, fungicide, or cover crop seed, to a plurality of corn plants in a corn field, comprising applying the agricultural composition to the corn plants of the corn field from above using a ground-based agricultural vehicle comprising a main body and/or an applicator for applying the agricultural composition, where the lower exterior surface or side of the main body and/or applicator is at a height equal to or less than 2.5 meters, equal to or less than 2.4 meters, equal to or less than 2.3 meters, equal to or less than 2.2 meters, equal to or less than 2.1 meters, equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, or equal to or less than 0.4 meters above the top of the soil or ground level, and where the lower exterior surface or side of the main body and/or applicator is equal to, or less than, 15 centimeters shorter or lower (i.e., no more than 15 centimeters shorter or lower) and/or equal to, or less than, 15 centimeters taller or higher (i.e., no more than 15 centimeters taller or higher) than the average height of the corn plants in a corn field (or a given percentage of corn plants in a corn field)—or within any other range therebetween, and where the corn plants are at V12 stage or later, V13 stage or later, V14 stage or later, V15 stage or later, VT stage or later, R1 stage or later, R2 stage or later, R3 stage or later, R4 stage or later, or R5 stage or later.

In an aspect, this disclosure provides a method of providing an agricultural composition, such as water and/or a fertilizer, pesticide, insecticide, herbicide, fungicide, or cover crop seed, to a plurality of corn plants in a corn field, comprising applying the agricultural composition to the corn plants of the corn field from above using a ground-based agricultural vehicle comprising a main body and/or an applicator for applying the agricultural composition, where the lower exterior surface or side of the main body and/or applicator is at a height equal to or less than 2.0 meters, equal to or less than 1.9 meters, equal to or less than 1.8 meters, equal to or less than 1.7 meters, equal to or less than 1.6 meters, equal to or less than 1.5 meters, equal to or less than 1.4 meters, equal to or less than 1.3 meters, equal to or less than 1.2 meters, equal to or less than 1.1 meters, equal to or less than 1.0 meter, equal to or less than 0.9 meters, equal to or less than 0.8 meters, equal to or less than 0.7 meters, equal to or less than 0.6 meters, equal to or less than 0.5 meters, equal to or less than 0.4 meters, equal to or less than 0.3 meters, equal to or less than 0.2 meters, or equal to or less than 0.1 meters above the top of the soil or ground level, and wherein the lower exterior surface or side of the main body and/or applicator is equal to, or less than, 15 centimeters shorter or lower (i.e., no more than 15 centimeters shorter or lower) and/or equal to, or less than, 15 centimeters taller or higher (i.e., no more than 15 centimeters taller or higher) than the average height of the corn plants in a corn field (or a given percentage of corn plants in a corn field)—or within any other range therebetween, and wherein the corn plants are at V6 stage or later, V7 stage or later, V8 stage or later, V9 stage or later, V10 stage or later, or V11 stage or later.

For each of the embodiments described herein, the extent to which a plant, or a plurality of plants, has likely developed is dependent on, and may be described in terms of, the number of growing degree units (GDUs) measured from the date of planting, which may be used instead of, or in addition to, developmental stage to describe the embodiments herein. With respect to each of the embodiments provided herein, the following ranges of growing degree units (GDUs) from planting may be used in place of developmental stages as approximate conversions. Although the number of GDUs at a given location provides a better indication of the likely developmental stage of a corn plant, as compared to days from planting, the actual correlation between GDUs and developmental stage is still somewhat dependent on a number of factors, such as corn plant germplasm, environment and latitude. However, a range of about 350 to 525 GDUs may correspond to, and be used in place of, V4 stage, a range of about 400 to 575 GDUs may correspond to, and be used in place of, V5 stage, a range of about 450 to 625 GDUs may correspond to, and be used in place of, V6 stage, a range of about 525 to 700 GDUs may correspond to, and be used in place of, V7 stage, a range of about 575 to 800 GDUs may correspond to, and be used in place of, V8 stage, a range of about 650 to 850 GDUs may correspond to, and be used in place of, V9 stage, a range of about 700 to 900 GDUs may correspond to, and be used in place of, V10 stage, a range of about 750 to 1000 GDUs may correspond to, and be used in place of, V11 stage, a range of about 800 to 1050 GDUs may correspond to, and be used in place of, V12 stage, a range of about 900 to 1100 GDUs may correspond to, and be used in place of, V13 stage, a range of about 950 to 1200 GDUs may correspond to, and be used in place of, V14 stage, a range of about 1050 to 1250 GDUs may correspond to, and be used in place of, V15 stage, a range of about 1100 to 1450 GDUs may correspond to, and be used in place of, VT stage, a range of about 1250 to 1800 GDUs may correspond to, and be used in place of, R1 stage, a range of about 1600 to 2000 GDUs may correspond to, and be used in place of, R2 stage, a range of about 1850 to 2300 GDUs may correspond to, and be used in place of, R3 stage, a range of about 1900 to 2400 GDUs may correspond to, and be used in place of, R4 stage, a range of about 2000 to 2750 GDUs may correspond to, and be used in place of, R5 stage, and a range of about 2300 to 3000 GDUs may correspond to, and be used in place of, R6 stage. Thus, any description provided herein in reference to a certain developmental stage may also be described in terms of a number or range of GDUs equal to or within these corresponding ranges of GDUs for the developmental stage. The numbers of GDUs (or range of GDUs) for a particular corn germplasm, planting location, and growing season corresponding to each developmental stage can be known and/or determined via routine experimentation.

As used herein, a "fertilizer" refers to any composition that is applied to soil or a plant tissue to supply at least one nutrient essential to plant growth. A fertilizer can be of natural (e.g., manure) or synthetic origin. In an aspect, a fertilizer is a liquid fertilizer. In another aspect, a fertilizer is a solid fertilizer. In an aspect, a fertilizer comprises nitrogen. In another aspect, a fertilizer comprises phosphorous. In a further aspect, a fertilizer comprises potassium. In another aspect, a fertilizer comprises sulfur. In an aspect, a fertilizer comprises sulfur. In another aspect, a fertilizer comprises calcium. In an aspect, a fertilizer comprises magnesium. In still another aspect, a fertilizer comprises boron. In an aspect, a fertilizer comprises zinc. In another aspect, a fertilizer comprises copper. In a further aspect, a fertilizer comprises iron. In still a further aspect, a fertilizer comprises chloride. In an aspect, a fertilizer comprises manganese. In another aspect, a fertilizer comprises molybdenum. In an aspect, a fertilizer comprises cobalt. In yet another aspect, a fertilizer comprises an element selected from the group consisting of nitrogen, phosphorus, potassium, sulfur, calcium, magnesium, boron, zinc, copper, iron, chloride, manganese, molybdenum, cobalt, or any combination thereof.

As used herein, a "pesticide" refers to any composition that can be used to control a pest. Non-limiting examples of pests include weeds, insects, arachnids, nematodes, molluscs, bacteria, viruses, and fungi. In an aspect, a pesticide provided herein is an herbicide. In another aspect, a pesticide provided herein is an insecticide. In a further aspect, a pesticide provided herein is a fungicide. In an aspect, a pesticide provided herein is a nematicide. In an aspect, a pesticide is a liquid pesticide. In another aspect, a pesticide is a solid pesticide. In another aspect, a pesticide is a gaseous pesticide.

In an aspect, a pesticide provided herein comprises glyphosate. In another aspect, a pesticide provided herein comprises atrazine. In a further aspect, a pesticide provided herein comprises lambda-chalothrin. In another aspect, a pesticide provided herein comprises acetochlor. In another aspect, a pesticide provided herein comprises dicamba. In another aspect, a pesticide provided herein comprises clyphosate. In another aspect, a pesticide provided herein comprises 2,4-D. In another aspect, a pesticide provided herein comprises isoxaflutole. In another aspect, a pesticide provided herein comprises mesotrione. In another aspect, a pesticide provided herein comprises nicosulfuron. In another aspect, a pesticide provided herein comprises paraquat. In another aspect, a pesticide provided herein comprises pendimethalin. In another aspect, a pesticide provided herein comprises primisulfuron. In another aspect, a pesticide provided herein comprises rimsulfuron. In another aspect, a pesticide provided herein comprises S-metolachlor. In another aspect, a pesticide provided herein comprises chlorpyrifos. In another aspect, a pesticide provided herein comprises tefluthrin. In another aspect, a pesticide provided herein comprises metolachlor. In an aspect, a pesticide provided herein comprises one or more double-stranded RNA molecules complementary to a messenger RNA of a corn pest.

As used herein, a "cover crop" is a crop that is grown for the protection of soil, enrichment of soil, or both. Farmers rely on cover crops to suppress weeds, control pests and diseases, prevent soil erosion, improve soil fertility, improve soil quality, and to improve soil water retention. In an aspect, a cover crop provided herein is a grass species. In another aspect, a cover crop provided herein is a legume species. In still another aspect, a cover crop provided herein is a brassica species. In a further aspect, a cover crop provided herein is selected from the group consisting of a grass species, a legume species, and a brassica species. In an aspect, a cover crop provided herein is a monocotyledonous species. In another aspect, a cover crop provided herein is a dicotyledonous species. In an aspect, seeds of a cover crop are applied to an unharvested corn field. As used herein, "cover crop seed" is one or more seeds of a cover crop.

In an aspect, a grass species provided herein is rye. In another aspect, a grass species provided herein is wheat. In another aspect, a grass species provided herein is barley. In still another aspect, a grass species provided herein is triticale. In a further aspect, a grass species provided herein is selected from the group consisting of rye, wheat, barley, and triticale.

In an aspect, a legume species provided herein is alfalfa. In another aspect, a legume species provided herein is hairy vetch. In another aspect, a legume species provided herein is cahaba vetch. In another aspect, a legume species provided herein is field pea. In another aspect, a legume species provided herein is lentil. In another aspect, a legume species provided herein is crimson clover. In another aspect, a legume species provided herein is red clover. In another aspect, a legume species provided herein is berseem clover. In another aspect, a legume species provided herein is selected from the group consisting of alfalfa, hairy vetch, cahaba vetch, field pea, lentil, crimson clover, red clover, and berseem clover.

In another aspect, a brassica species provided herein is canola. In another aspect, a brassica species provided herein is mustard. In another aspect, a brassica species provided herein is forage radish. In another aspect, a brassica species provided herein is turnip. In another aspect, a brassica species provided herein is selected from the group consisting of canola, mustard, forage radish, and turnip.

The following are non-limiting exemplary embodiments of the present disclosure:

1. A method of providing an agricultural composition to a corn field comprising applying the agricultural composition on the corn field from above using a ground-based agricultural vehicle comprising an applicator for applying the agricultural composition, where the corn plants of the corn field comprise an average height of less than or equal to 1.8 meters, and where at least 50% of the corn plants are at V12 stage or later.
2. A method of providing an agricultural composition to a corn field, comprising applying the agricultural composition to the corn field from above using a ground-based agricultural vehicle with an applicator for applying the agricultural composition, where the ground-based agricultural vehicle comprises a main body, and where the applicator is attached to the main body, where the lower exterior surface of the main body and/or applicator is positioned at a height equal to or less than 1.8 meters above soil level, and where at least 50% of the corn plants are at V12 stage or later.
3. A method of providing an agricultural composition to a plurality of corn plants in a corn field, comprising applying the agricultural composition to the corn plants of the corn field from above using a ground-based agricultural vehicle comprising an applicator arm or boom for applying the agricultural composition, where the lower surface of the applicator arm or boom is at a height equal to or less than 1.8 meters above the soil level and is equal to or less than 15 centimeters shorter than average height of the corn plants, and where the corn plants are at V12 stage or later.
4. A method of providing an agricultural composition to a corn plant comprising applying the agricultural composition on the corn plant from above using a ground-based agricultural vehicle, where the corn plant is not damaged by the ground-based agricultural vehicle, where the corn plant comprises a height of equal to or less than 1.8 meters, and where the corn plant is at V12 stage or later.
5. The method of embodiments 1 or 2, where at least 50% of the corn plants are not damaged by the applicator.
6. The method of any one of embodiments 1, 2, or 5, where at least 70% of the corn plants are not damaged by the applicator.
7. The method of any one of embodiments 1-6, where the agricultural composition comprises a fertilizer.
8. The method of embodiment 7, where the fertilizer comprises an element selected from the group consisting of nitrogen, phosphorus, potassium, sulfur, calcium, magnesium, boron, zinc, copper, iron, chloride, manganese, molybdenum, cobalt, or any combination thereof
9. The method of any one of embodiments 1-6, where the agricultural composition comprises a pesticide.
10. The method of embodiment 9, where the pesticide is selected from the group consisting of an herbicide, a fungicide, a nematicide, and an insecticide.
11. The method of embodiment 9 or 10, where the pesticide is selected from the group consisting of glyphosate, lambda-chalothrin, acetochlor, dicamba, clyphosate, 2,4-D, isoxaflutole, mesotrione, nicosulfuron, paraquat, pendimethalin, primisulfuron, rimsulfuron, S-metolachlor, chlorpyrifos, tefluthrin, metolachlor, and one or more double-stranded RNA molecules complementary to a messenger RNA of a corn pest.
12. The method of any one of embodiments 1-6, where the agricultural composition comprises a cover crop seed.
13. The method of embodiment 12, where the cover crop is selected from the group consisting of a grass species, a legume species, and a brassica species.
14. The method of embodiment 13, where the grass species is selected from the group consisting of rye, wheat, barley, and triticale.
15. The method of embodiment 13, where the legume species is selected from the group consisting of alfalfa, hairy vetch, cahaba vetch, field pea, lentil, crimson clover, red clover, and berseem clover.
16. The method of embodiment 13, where the brassica species is selected from the group consisting of canola, mustard, forage radish, and turnip.
17. The method of any one of embodiments 1-16, where the corn plants are inbred corn plants.
18. The method of any one of embodiments 1-16, where the corn plants are hybrid corn plants.
19. The method of any one of embodiments 1-18, where at least 50% of the corn plants are semi-dwarf corn plants.
20. The method of any one of embodiments 1-18, where at least 50% of the corn plants are dwarf corn plants.
21. The method of any one of embodiments 1-18, where at least 50% of the corn plants are brachytic corn plants.
22. The method of any one of embodiments 1-21, where at least 60% of the corn plants are at V15 stage or later.
23. The method of any one of embodiments 1-22, where at least 60% of the corn plants are at R1 stage or later.
24. The method of any one of embodiments 1-3 or 5-23, where at least 50% of the corn plants have been detasseled.
25. The method of any one of embodiments 1-24, where the height is measured as the distance between the soil and the ligule of the uppermost fully-expanded leaf
26. The method of any one of embodiments 1-24, where the height is measured as the distance between the soil and the uppermost leaf surface of the leaf farthest from the soil.
27. The method of any one of embodiments 1-24, where the height is measured as the distance between the soil and the arch of the highest corn leaf that is at least 50% developed.
28. The method of any one of embodiments 1, 2, or 5, where at least 60% of the corn plants are not damaged by the applying.
29. The method of any one of embodiments 1-28, where the corn plants comprise an average height of less than or equal to 1.7 meters.
30. The method of any one of embodiments 1-29, where the ground-based agricultural vehicle comprises a self-propelled agricultural sprayer.
31. The method of any one of embodiments 1-29, where the ground-based agricultural vehicle comprises an agricultural sprayer towed by a self-propelled vehicle.
32. The method of embodiment 31, where the self-propelled vehicle is a tractor.
33. The method of any one of embodiments 1-32, where the agricultural sprayer comprises an applicator arm or boom.

34. The method of embodiment 33, where the lower surface of the applicator arm or boom is positioned equal to or less than 2.0 meters above soil level.
35. The method of embodiment 33, where the lower surface of the applicator arm or boom is positioned between 0.5 meters and 2.0 meters above soil level.
36. The method of any one of embodiments 33-35, where the boom comprises multiple sections
37. The method of embodiment 36, where the multiple sections can be independently controlled.
38. The method of any one of embodiments 33-37, where the applicator arm or boom is positioned within 30° of horizontal.
39. The method of any one of embodiments 1-38, where the ground-based agricultural vehicle comprises a main body.
40. The method of embodiment 39, where the ground-based agricultural vehicle comprises at least one applicator arm or boom attached to the main body.
41. The method of embodiment 39 or 40, where the lower exterior surface of the main body is equal to or less than 2.0 meters above soil level.
42. The method of any one of embodiments 39-41, where the lower exterior surface of the main body is equal to or less than 2.0 meters above soil level.
43. The method of any one of embodiments 39-42, where the lower exterior surface of the main body is between 0.5 meters and 2.0 meters above soil level.
44. The method of any one of embodiments 1, 2, or 5-43, where the lower surface of the applicator is positioned equal to or less than 2.0 meters above soil level.
45. The method of any one of embodiments 1, 2, or 5-44, where the lower surface of the applicator is positioned between 0.5 and 2.0 meters above soil level.
46. The method of any one of embodiments 1, 2, or 5-45, where the lower surface of the applicator is positioned higher the average height of the corn plants.
47. The method of any one of embodiments 1, 2, or 5-46, where the lower surface of the applicator is positioned at least one centimeter higher than the average height of the corn plants.
48. The method of any one of embodiments 1, 2, or 5-45, where the lower surface of the applicator is positioned equal to or less than 15 centimeters lower than the average height of the corn plants in the corn field.
49. The method of any one of embodiments 1, 2, or 5-45, where the lower surface of the applicator is positioned between 0 centimeters and 15 centimeters lower than the average height of the corn plants in the corn field.
50. The method of any one of embodiments 1, 2, or 5-49, where the applicator comprises at least one nozzle.
51. The method of embodiment 50, where the at least one nozzle applies the agricultural composition in a downward direction.
52. The method of embodiment 50 or 51, where the at least one nozzle is positioned between two corn rows of the corn field.
53. The method of any one of embodiments 1, 2, or 5-52, where the applicator comprises at least one drip line.
54. The method of embodiment 53, where the at least one drip line is positioned between two corn rows of the corn field.
55. The method of any one of embodiments 1, 2, or 5-54, where the applicator comprises at least one wicker.
56. The method of embodiment 55, where the at least one wicker is positioned between two corn rows of the corn field.
57. The method of any one of embodiments 1-56, where at least 50%, at least 60%, at least 70%, at least 75%, at least 80%, at least 85%, at least 90%, at least 95%, or 100% of the corn plants comprise a mutation in a br2 locus as compared to a wildtype br2 locus.
58. The method of any one of embodiments 1-57, where at least 50%, at least 60%, at least 70%, at least 75%, at least 80%, at least 85%, at least 90%, at least 95%, or 100% of the corn plants comprise a heterologous polynucleotide capable of suppressing expression of a br2 gene or an mRNA transcribed therefrom.
59. The method of any one of embodiments 1-58, where at least 50%, at least 60%, at least 70%, at least 75%, at least 80%, at least 85%, at least 90%, at least 95%, or 100% of the corn plants comprise a mutation in a GA20ox locus as compared to a wildtype GA20ox locus.
60. The method of any one of embodiments 1-59, where at least 50%, at least 60%, at least 70%, at least 75%, at least 80%, at least 85%, at least 90%, at least 95%, or 100% of the corn plants comprise a heterologous polynucleotide capable of suppressing expression of a GA20ox gene or an mRNA transcribed therefrom.
61. The method of any one of embodiments 1-60, where the applying comprises applying a liquid agricultural composition.
62. The method of any one of embodiments 1-60, where the applying comprises applying a solid agricultural composition.
63. The method of any one of embodiments 1-60, where the applying comprises applying a gaseous agricultural composition.
64. The method of any one of embodiments 1-63, where the applying comprises spraying.
65. The method of any one of embodiments 1-62, where the applying comprises dripping.
66. The method of any one of embodiments 1-3 or 5-65, where the corn field comprises a planting density of at least 10,000 corn plants per acre.
67. The method of any one of embodiments 1-3 or 5-65, where the corn field comprises a planting density of between 10,000 corn plants per acre and 50,000 corn plants per acre.
68. The method of any one of embodiments 33-67, where the method further comprises adjusting the height of the applicator arm or boom of the ground-based agricultural vehicle such that the lower surface of the applicator arm or boom is equal to or less than 15 centimeters shorter than the average height the corn plants in the corn field.
69. The method of embodiment 4, where the corn plant is planted in a field.
70. A method of providing an agricultural composition to a corn field comprising applying the agricultural composition on the corn field from above using a ground-based agricultural vehicle comprising an applicator for applying the agricultural composition, where the corn plants of the corn field comprise an average height of less than or equal to 1.0 meter, and where at least 50% of the corn plants are at V6 stage or later.
71. A method of providing an agricultural composition to a corn field, comprising applying the agricultural composition to the corn field from above using a ground-based agricultural vehicle with an applicator for applying the agricultural composition, where the ground-based agricultural vehicle comprises a main body, and where the applicator is attached to the main body, where the lower exterior surface of the main body and/or applicator is positioned at a height equal to or less than 1.5 meters above soil level, and where at least 50% of the corn plants of the corn field are at V8 stage or later.

72. A method of providing an agricultural composition to a plurality of corn plants in a corn field, comprising applying the agricultural composition to the corn plants of the corn field from above using a ground-based agricultural vehicle comprising an applicator arm or boom for applying the agricultural composition, where the lower exterior surface of the applicator arm or boom is at a height equal to or less than 1.5 meters above the soil level and is equal to or less than 15 centimeters shorter than average height of the corn plants, and where the corn plants are at V8 stage or later.

73. A method of providing an agricultural composition to a corn plant comprising applying the agricultural composition on the corn plant from above using a ground-based agricultural vehicle, where the corn plant is not damaged by the ground-based agricultural vehicle, where the corn plant comprises a height of equal to or less than 1.5 meters, and where the corn plant is at V8 stage or later.

74. The method of embodiments 70 or 71, where at least 50% of the corn plants are not damaged by the applicator.

75. The method of any one of embodiments 70, 71, or 74, where at least 70% of the corn plants are not damaged by the applicator.

76. The method of any one of embodiments 70-75, where the agricultural composition comprises a fertilizer.

77. The method of embodiment 76, where the fertilizer comprises an element selected from the group consisting of nitrogen, phosphorus, potassium, sulfur, calcium, magnesium, boron, zinc, copper, iron, chloride, manganese, molybdenum, cobalt, or any combination thereof 78. The method of any one of embodiments 70-75, where the agricultural composition comprises a pesticide.

79. The method of embodiment 78, where the pesticide is selected from the group consisting of an herbicide, a fungicide, a nematicide, and an insecticide.

80. The method of embodiment 78 or 79, where the pesticide is selected from the group consisting of glyphosate, lambda-chalothrin, acetochlor, dicamba, clyphosate, 2,4-D, isoxaflutole, mesotrione, nicosulfuron, paraquat, pendimethalin, primisulfuron, rimsulfuron, S-metolachlor, chlorpyrifos, tefluthrin, metolachlor, and one or more double-stranded RNA molecules complementary to a messenger RNA of a corn pest.

81. The method of any one of embodiments 70-75, where the agricultural composition comprises a cover crop seed.

82. The method of embodiment 81, where the cover crop is selected from the group consisting of a grass species, a legume species, and a brassica species.

83. The method of embodiment 82, where the grass species is selected from the group consisting of rye, wheat, barley, and triticale.

84. The method of embodiment 82, where the legume species is selected from the group consisting of alfalfa, hairy vetch, cahaba vetch, field pea, lentil, crimson clover, red clover, and berseem clover.

85. The method of embodiment 82, where the brassica species is selected from the group consisting of canola, mustard, forage radish, and turnip.

86. The method of any one of embodiments 70-85, where the corn plants are inbred corn plants.

87. The method of any one of embodiments 70-85, where the corn plants are hybrid corn plants.

88. The method of any one of embodiments 70-87, where at least 50% of the corn plants are semi-dwarf corn plants.

89. The method of any one of embodiments 70-87, where at least 50% of the corn plants are dwarf corn plants.

90. The method of any one of embodiments 70-87, where at least 50% of the corn plants are brachytic corn plants.

91. The method of any one of embodiments 70-90, where at least 60% of the corn plants are at V15 stage or later.

92. The method of any one of embodiments 70-91, where at least 60% of the corn plants are at R1 stage or later.

93. The method of any one of embodiments 70-72 or 74-92, where at least 50% of the corn plants have been detasseled.

94. The method of any one of embodiments 70-93, where the height is measured as the distance between the soil and the ligule of the uppermost fully-expanded leaf 95. The method of any one of embodiments 70-93, where the height is measured as the distance between the soil and the uppermost leaf surface of the leaf farthest from the soil.

96. The method of any one of embodiments 70-93, where the height is measured as the distance between the soil and the arch of the highest corn leaf that is at least 50% developed.

97. The method of any one of embodiments 70, 71, or 74, where at least 60% of the corn plants are not damaged by the applying.

98. The method of any one of embodiments 70-97, where the corn plants comprise an average height of less than or equal to 1.5 meters.

99. The method of any one of embodiments 70-98, where the ground-based agricultural vehicle comprises a self-propelled agricultural sprayer.

100. The method of any one of embodiments 70-98, where the ground-based agricultural vehicle comprises an agricultural sprayer towed by a self-propelled vehicle.

101. The method of embodiment 31, where the self-propelled vehicle is a tractor.

102. The method of any one of embodiments 70-101, where the agricultural sprayer comprises an applicator arm or boom.

103. The method of embodiment 102, where the lower surface of the applicator arm or boom is positioned equal to or less than 1.9 meters above soil level.

104. The method of embodiment 102, where the lower surface of the applicator arm or boom is positioned between 0.5 meters and 1.9 meters above soil level.

105. The method of any one of embodiments 102-104, where the boom comprises multiple sections.

106. The method of embodiment 105, where the multiple sections can be independently controlled.

107. The method of any one of embodiments 102-106, where the applicator arm or boom is positioned within 30° of horizontal.

108. The method of any one of embodiments 70-107, where the ground-based agricultural vehicle comprises a main body.

109. The method of embodiment 108, where the ground-based agricultural vehicle comprises at least one applicator arm or boom attached to the main body.

110. The method of embodiment 108 or 109, where the lower exterior surface of the main body is equal to or less than 1.9 meters above soil level.

111. The method of any one of embodiments 108-110, where the lower exterior surface of the main body is equal to or less than 1.9 meters above soil level.

112. The method of any one of embodiments 108-111, where the lower exterior surface of the main body is between 0.5 meters and 1.9 meters above soil level.

113. The method of any one of embodiments 70, 71, or 74-112, where the lower exterior surface of the applicator is positioned equal to or less than 1.9 meters above soil level.
114. The method of any one of embodiments 70, 71, or 74-113, where the lower exterior surface of the applicator is positioned between 0.5 and 1.9 meters above soil level.
115. The method of any one of embodiments 70, 71, or 74-114, where the lower exterior surface of the applicator is positioned higher the average height of the corn plants.
116. The method of any one of embodiments 70, 71, or 74-115, where the lower exterior surface of the applicator is positioned at least one centimeter higher than the average height of the corn plants.
117. The method of any one of embodiments 70, 71, or 74-116, where the lower exterior surface of the applicator is positioned equal to or less than 15 centimeters lower than the average height of the corn plants in the corn field.
118. The method of any one of embodiments 70, 71, or 74-117, where the lower exterior surface of the applicator is positioned between 0 centimeters and 15 centimeters lower than the average height of the corn plants in the corn field.
119. The method of any one of embodiments 70, 71, or 74-118, where the applicator comprises at least one nozzle.
120. The method of embodiment 119, where the at least one nozzle applies the agricultural composition in a downward direction.
121. The method of embodiment 119 or 120, where the at least one nozzle is positioned between two corn rows of the corn field.
122. The method of any one of embodiments 70, 71, or 74-121, where the applicator comprises at least one drip line.
123. The method of embodiment 122, where the at least one drip line is positioned between two corn rows of the corn field.
124. The method of any one of embodiments 70, 71, or 74-121, where the applicator comprises at least one wicker.
125. The method of embodiment 124, where the at least one wicker is positioned between two corn rows of the corn field.
126. The method of any one of embodiments 70-125, where at least 50%, at least 60%, at least 70%, at least 75%, at least 80%, at least 85%, at least 90%, at least 95%, or 100% of the corn plants comprise a mutation in a br2 locus as compared to a wildtype br2 locus.
127. The method of any one of embodiments 70-126, where at least 50%, at least 60%, at least 70%, at least 75%, at least 80%, at least 85%, at least 90%, at least 95%, or 100% of the corn plants comprise a heterologous polynucleotide capable of suppressing expression of a br2 gene or an mRNA transcribed therefrom.
128. The method of any one of embodiments 70-127, where at least 50%, at least 60%, at least 70%, at least 75%, at least 80%, at least 85%, at least 90%, at least 95%, or 100% of the corn plants comprise a mutation in a GA20ox locus as compared to a wildtype GA20ox locus.
129. The method of any one of embodiments 70-128, where at least 50%, at least 60%, at least 70%, at least 75%, at least 80%, at least 85%, at least 90%, at least 95%, or 100% of the corn plants comprise a heterologous polynucleotide capable of suppressing expression of a GA20ox gene or an mRNA transcribed therefrom.
130. The method of any one of embodiments 70-129, where the applying comprises applying a liquid agricultural composition.
131. The method of any one of embodiments 70-129, where the applying comprises applying a solid agricultural composition.
132. The method of any one of embodiments 70-129, where the applying comprises applying a gaseous agricultural composition.
133. The method of any one of embodiments 70-132, where the applying comprises spraying.
134. The method of any one of embodiments 70-132, where the applying comprises dripping.
135. The method of any one of embodiments 70-72 or 74-134, where the corn field comprises a planting density of at least 10,000 corn plants per acre.
136. The method of any one of embodiments 70-72 or 74-135, where the corn field comprises a planting density of between 10,000 corn plants per acre and 50,000 corn plants per acre.
137. The method of any one of embodiments 102-136, where the method further comprises adjusting the height of the applicator arm or boom of the ground-based agricultural vehicle such that the lower surface of the applicator arm or boom is equal to or less than 15 centimeters shorter than the average height the corn plants in the corn field.
138. The method of embodiment 73, where the corn plant is planted in a field.
139. The method of any one of embodiments 1, 2, or 5-45, where the lower surface of the applicator is positioned equal to or less than 15 centimeters taller than the average height of the corn plants in the corn field.
140. The method of any one of embodiments 1, 2, or 5-45, where the lower surface of the applicator is positioned between 0 centimeters and 15 centimeters taller than the average height of the corn plants in the corn field.
141. The method of any one of embodiments 1-24 or 28-69, wherein said average height is between 0.8 meters and 2.1 meters, between 0.9 meters and 2.1 meters, or between 0.9 meters and 1.5 meters when said height is measured as the distance between the soil and the uppermost leaf surface of the leaf farthest from the soil.
142. The method of any one of embodiment 1-24 or 28-69, wherein said average height is between 0.4 meters and 1.6 meters, between 0.4 meters and 0.9 meters, or between 0.4 meters and 1.0 meter when said height is measured as the distance between the soil and the ligule of the uppermost fully-expanded leaf.
143. The method of any one of embodiments 70, 74-93, or 97-138 wherein said average height is between 0.1 meters and 1.0 meter, between 0.2 meters and 1.0 meter, or between 0.2 meters and 0.4 meters when said height is measured as the distance between the soil and the uppermost leaf surface of the leaf farthest from the soil.
144. The method of any one of embodiments 71-93 or 97-138, wherein said average height is between 0.1 meters and 0.5 meters, between 0.09 meters and 0.3 meters, or between 0.09 meters and 0.5 meters when said height is measured as the distance between the soil and the ligule of the uppermost fully-expanded leaf.

EXAMPLES

Example 1. Comparing Semi-Dwarf and Control Plant Height at Different Times and Growth Stages Using Time-Lapse Imagery Hybrid semi-dwarf corn plants comprising a GA20 oxidase suppression construct (SUP_GA20 oxidase) were produced by crossing a first parental line comprising the GA20 oxidase suppression construct with a second parental line that lacked the construct. The SUP_GA20 oxidase plant comprised a microRNA (miRNA) encoding transcribable DNA sequence operably linked to a rice tungro bacilliform virus (RTBV) promoter, wherein the miRNA targets GA20 oxidase gene(s) for suppression. The hybrid SUP_GA20 oxidase corn plants were grown in a corn field next to wild-type control hybrid plants lacking the GA20 oxidase suppression construct. The hybrid corn plants were grown in rows with 30-inch spacing and at a planting density of approximately 34,500 plants per acre.

A height standard was installed adjacent to the plots. Time-lapse images of the plants in each plot were taken every two hours from V4 stage until harvest. Plant height was measured as the distance from the ground to the highest point of the uppermost leave surface in the image using the image processing and analysis software ImageJ, which was calibrated using the height standard. Images were visually inspected to determine plant height measurements.

SUP_GA20 oxidase plants obtained a maximum height of approximately 6 feet (1.83 meters), while the wild-type control plants reached a height of approximately 8 feet (2.44 meters). See FIG. 1. In addition, SUP_GA20 oxidase plants exhibited a significant delay in growth after V11 stage. SUP_GA20 oxidase plants reached an average height of 5 feet (1.52 meters) approximately 10 days later than the wild-type control plants.

Example 2. Comparing Semi-Dwarf and Control Plant Heights at Different Times and Growth Stages Using Direct Measurement In addition to the time-lapse imaging performed in Example 1, direct measurement of individual plant heights was conducted using several germplasm backgrounds and larger sample sizes to measure the average height and variation in plant populations.

Ten different transgenic hybrids having the GA20 oxidase suppression element of Example 1 were made from different parental lines and grown as a population of corn plants. Corresponding wild-type control hybrids from the same parental lines but lacking the GA20 oxidase suppression element were also produced for comparison. Each SUP_GA20 oxidase transgenic or wild-type control hybrid was grown as a population under standard agronomic practice in four plots. Ten plants from each plot were randomly selected for height measurements. Plant height was measured as the distance from the ground to the ligule (collar) of the uppermost fully expanded leaf. In this experiment, measurements were taken at V4, V8, V12 and R1 stages of growth. See Table 3.

The semi-dwarf SUP_GA20 oxidase plants reached a height of between 4.12 feet (1.26 meters) and 5.37 feet (1.64 meters) at maturity (R1 stage), which was significantly shorter than the range of 6.16 feet (1.88 meters) to 8.34 feet (2.54 meters) observed in wild-type control plants. SUP_GA20 oxidase plants reached V4, V8, V12, and R1 growth stages on the same number of days after planting, but they exhibited a reduced height at every growth stage. Note the heights in Table 3 are lower than those presented in FIG. 1 at an equivalent growth stage since the height measurements are different—the ligule or collar of the uppermost fully expanded leaf is lower than the highest point of the uppermost leaf surface.

TABLE 3

Height of semi-dwarf SUP_GA20 oxidase corn plants and wild-type control plants

| | Days After Planting | Growth Stage | Height (feet) | | |
|---|---|---|---|---|---|
| | | | Average | Minimum | Maximum |
| WT Control | 32 | V4 | 0.28 | 0.19 | 0.35 |
| SUP_GA20 oxidase | 32 | V4 | 0.2 | 0.14 | 0.27 |
| WT Control | 46 | V8 | 1.04 | 0.79 | 1.35 |
| SUP_GA20 oxidase | 46 | V8 | 0.71 | 0.58 | 0.83 |
| WT Control | 56 | V12 | 3.32 | 2.41 | 3.87 |
| SUP_GA20 oxidase | 56 | V12 | 1.53 | 1.21 | 1.83 |
| WT Control | 66 | R1 | 7.48 | 6.16 | 8.34 |
| SUP_GA20 oxidase | 66 | R1 | 4.76 | 4.12 | 5.37 |

Example 3. Comparing Semi-Dwarf Brachytic Plant Height at Different Times and Growth Stages Using Time-Lapse Imagery Hybrid semi-dwarf corn plants comprising a recessive brachytic allele (BR; described in PCT Patent Application No. PCT/US2016/029492) were produced by crossing a first parental line comprising the recessive BR mutant allele with a second parental line that also comprised the recessive BR mutant allele. The hybrid BR corn plants were grown in a corn field next to wild-type control hybrid plants using standard agronomic practices with planting in 30-inch rows at a planting density of approximately 34,500 plants per acre. The control hybrid plants were created by crossing the two parental lines, where neither parental line comprised the BR mutant allele.

A height standard was installed adjacent to the plots. Time-lapse images of the plants in each plot were taken every two hours from V4 stage until harvest. Plant height was measured as the distance from the ground to the highest point of the uppermost leaf surface in the image using the image processing and analysis software ImageJ, which was calibrated using the height standard. Images were visually inspected to determine plant height measurements. See Table 4.

TABLE 4

Height of semi-dwarf brachytic (BR) corn plants and wild-type control plants in feet.

| Stage | Wild-type Control | Semi-dwarf BR |
|---|---|---|
| V8 | 2.6 | 2.5 |
| V10 | 4.5 | 3.8 |
| V12 | 5.6 | 4.6 |
| R1 | 8.2 | 5.5 |

In this experiment, the semi-dwarf BR corn plants reached a height of 5.5 feet (1.68 meters) at maturity (R1 stage) as compared to a height of 8.2 feet (2.5 meters) for the wild-type control. Additionally, semi-dwarf BR plants exhibit delayed growth after the V8 growth stage. For example, wild-type control plants reached a height of 4.5 feet (1.37 meters) at V10 stage, but semi-dwarf BR plants did not reach 4.6 feet (1.4 meters) until V12 stage.

Figure 2:
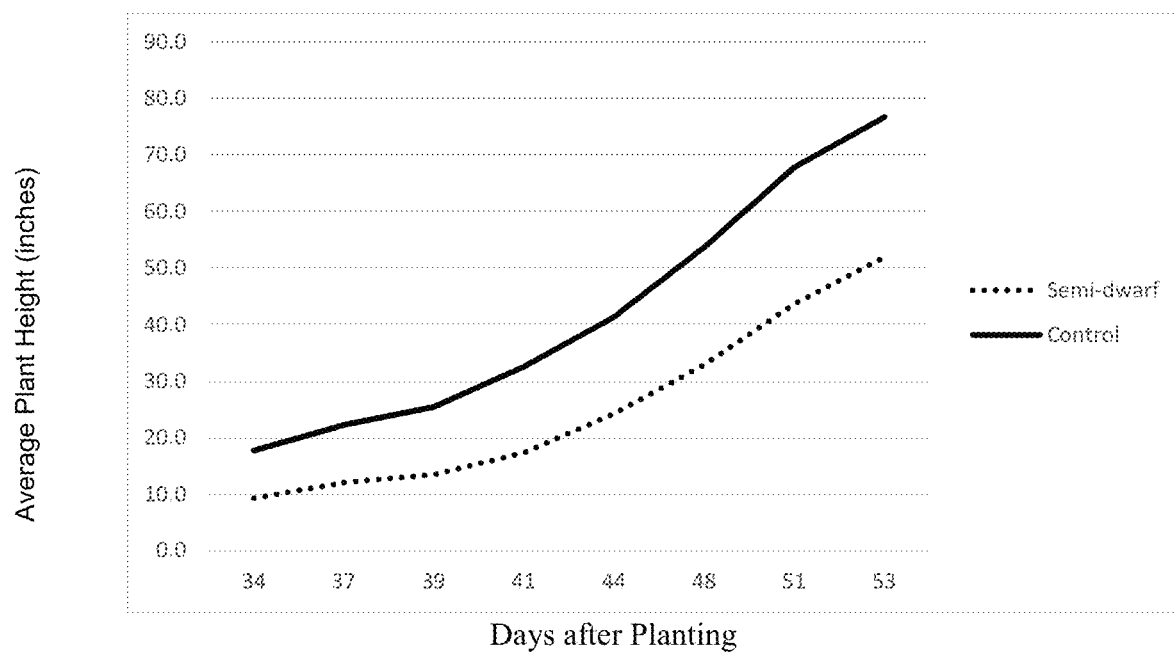
FIG. 2 depicts plant heights (in inches) of semi-dwarf BR hybrid corn plants, where plant height was measured as the distance from the ground to the collar of the uppermost fully expanded leaf.

In a separate time-course experiment, two fields containing both tall control and semi-dwarf corn plants were used to take measurements. One representative semi-dwarf plant and one representative tall control plant were selected in each field and marked with a neighboring stake. A blank colored stake was put next to the plant and in the front of the plot as a marker to ensure that the time-course measurements were taken from the same corn plant. Every other day during the week measurements were taken at both fields. The date, plant height from the ground to the top visible leaf collar (i.e., to the ligule or collar of the uppermost fully expanded leaf), and growth stage were recorded. Each height measurement was taken using a yard stick until the top leaf collar reached 36 inches, and subsequently measurements were taken with a taller plant height stick with 2-inch increments. Measurements taken from around V5/V6 stage until the plants started tasseling (i.e., at VT/R1 stage). The results for the average height of semi-dwarf BR corn plants and tall wild-type hybrid corn plants (in inches) are provided in Table 5 and FIG. 2.

The semi-dwarf BR corn plants reached a height of 51.9 inches at maturity as compared to a height of 76.7 inches for the taller wild-type control. Additionally, semi-dwarf BR plants exhibit delayed growth after the V5 growth stage. For example, wild-type control plants reached a height of 40 inches between V9 and V10 stage, but semi-dwarf BR plants did not reach 40 inches until between V12 and V13 stage. Note the heights in Table 5 are lower than those presented in Table 4 and FIG. 2 at an equivalent growth stage since the height measurements are different—the ligule or collar of the uppermost fully expanded leaf is lower than the highest point of the uppermost leaf surface.

TABLE 5

Height of semi-dwarf brachytic (BR) corn plants and wild-type control plants

| Days from Planting | Range of Stages | Average or Dominant Stage | Average Height of Semi-Dwarf Plants (inches) | Average Height of Control Plants (inches) |
|---|---|---|---|---|
| 34 | V5-7 | V6 | 9.3 | 17.7 |
| 37 | V6-8 | V7 | 12.1 | 22.3 |
| 39 | V7-9 | V8 | 13.5 | 25.4 |
| 41 | V7-10 | V9 | 17.3 | 32.6 |
| 44 | V9-11 | V10 | 24.2 | 41.3 |
| 48 | V10-12 | V12 | 32.9 | 53.7 |
| 51 | V13-VT | V13 | 43.7 | 67.8 |
| 53 | V13-R1 | VT | 51.9 | 76.7 |

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

The invention claimed is:

1. A method of providing an agricultural composition to a corn field comprising applying said agricultural composition on said corn field from above using a ground-based agricultural vehicle comprising an applicator for applying said agricultural composition, wherein at least 50% of the corn plants of said corn field comprise a recombinant polynucleotide encoding an RNA molecule that suppresses expression of an endogenous GA20 oxidase_3 gene and an endogenous GA20 oxidase_5 gene and have an average height of less than or equal to 1.8 meters at R1 stage or later.

2. The method of claim 1, wherein said average height is between 0.9 meters and 1.5 meters.

3. The method of claim 1, wherein said corn plants comprising the recombinant polynucleotide are not significantly damaged by said applicator.

4. The method of claim 1, wherein said agricultural composition comprises a composition selected from the group consisting of a fertilizer, a pesticide, and a cover crop seed.

5. The method of claim 1, wherein said corn plants are semi-dwarf corn plants or dwarf corn plants.

6. The method of claim 1, wherein said ground-based agricultural vehicle comprises a self-propelled agricultural sprayer.

7. The method of claim 1, wherein said agricultural sprayer comprises an applicator arm or boom, wherein the lower surface of said applicator arm or boom is positioned equal to or less than 1.8 meters above soil level.

8. The method of claim 1, wherein said ground-based agricultural vehicle comprises a main body, wherein the lower exterior surface of said main body is equal to or less than 1.8 meters above soil level.

9. The method of claim 1, wherein the lower surface of said applicator is positioned equal to or less than 1.8 meters above soil level.

10. The method of claim 1, wherein said applicator comprises a component selected from the group consisting of at least one nozzle and at least one drip line.

11. The method of claim 1, wherein at least 75% of said corn plants comprise said recombinant polynucleotide.

12. The method of claim 1, wherein at least 90% of said corn plants comprise said recombinant polynucleotide.

13. The method of claim 1, wherein said applying comprises applying a composition selected from the group consisting of a liquid agricultural composition, a solid agricultural composition, and a gaseous agricultural composition.

14. A method of providing an agricultural composition to a corn field comprising applying the agricultural composition on the corn field from above using a ground-based agricultural vehicle comprising an applicator for applying the agricultural composition, where at least 50% of the corn plants of the corn field comprise a recombinant polynucleotide encoding an RNA molecule that suppresses expression of an endogenous GA20 oxidase_3 gene and an endogenous GA20 oxidase_5 gene, wherein the at least 50% of the corn plants have reached a V12 growth stage and have an average height of less than or equal to 0.7 meters.

15. The method of claim 14, wherein the ground-based agricultural vehicle comprises a main body, wherein the applicator is attached to the main body, and wherein the lower exterior surface of the main body and/or applicator is positioned at a height equal to or less than 0.7 meters above soil level.

16. The method of claim 14, wherein said average height is between 0.4 meters and 0.7 meters.

17. The method of claim 14, wherein said agricultural composition comprises a composition selected from the group consisting of a fertilizer, a pesticide, and a cover crop seed.

18. The method of claim 14, wherein said corn plants are semi-dwarf corn plants or dwarf corn plants.

19. The method of claim 14, wherein the lower exterior surface of said applicator is positioned at least one centimeter higher than the average height of said corn plants.

20. The method of claim 14, wherein the lower exterior surface of said applicator is positioned equal to or less than 20 centimeters lower than the average height of the corn plants in the corn field.

21. The method of claim 14, wherein the lower exterior surface of said applicator is positioned between 0 centimeters and 15 centimeters lower than the average height of the corn plants in the corn field.

22. The method of claim 14, wherein the lower exterior surface of said applicator is positioned between 1 centimeter and 10 centimeters lower than the average height of the corn plants in the corn field.

23. The method of claim 14, wherein the lower exterior surface of said applicator is positioned between 0.5 meters and 0.7 meters above the ground.

24. The method of claim 14, wherein at least 75% of said corn plants comprise said recombinant polynucleotide.

25. The method of claim 14, wherein at least 90% of said corn plants comprise said recombinant polynucleotide.

26. The method of claim 14, wherein at least 95% of said corn plants comprise said recombinant polynucleotide.

27. The method of claim 14, wherein said corn plants comprising the recombinant polynucleotide are not significantly damaged by said applicator.

28. The method of claim 14, wherein said average height is between 0.3 meters and 0.7 meters.

29. The method of claim 14, wherein said average height is between 0.3 meters and 0.6 meters.

30. The method of claim 1, wherein at least 95% of said corn plants comprise said recombinant polynucleotide.

31. The method of claim 1, wherein a lower surface of said applicator is positioned at least one centimeter higher than the average height of the corn plants.

32. The method of claim 1, wherein a lower surface of said applicator is positioned equal to or less than 20 centimeters lower than the average height of the corn plants.

33. The method of claim 1, wherein a lower surface of said applicator is positioned between 0 centimeters and 15 centimeters lower than the average height of the corn plants.

34. The method of claim 1, wherein a lower surface of said applicator is positioned between 1 centimeter and 10 centimeters lower than the average height of the corn plants.

35. The method of claim 7, wherein the lower exterior surface of said applicator arm or boom is positioned between 1.4 meters and 1.8 meters above the ground.

36. The method of claim 1, wherein said average height is between 1.1 meters and 1.4 meters.

37. The method of claim 1, wherein said average height is between 1.2 meters and 1.5 meters.

* * * * *